(12) United States Patent
Youd et al.

(10) Patent No.: US 9,765,144 B2
(45) Date of Patent: Sep. 19, 2017

(54) NUCLEIC ACIDS ENCODING ANTI-CXCR3 ANTIBODIES

(71) Applicant: GENZYME CORPORATION, Cambridge, MA (US)

(72) Inventors: Michele Youd, Lexington, MA (US); Jennifer Tedstone, Hopkinton, MA (US); Tracey Lodie, Northbridge, MA (US); Karen B. Carter, Fiskdale, MA (US); Timothy D. Connors, Shrewsbury, MA (US); Jason Robert Pinckney, Marlborough, MA (US); Elizabeth Masterjohn, Hudson, MA (US); Ruiyin Chu, Belle Mead, NJ (US)

(73) Assignee: GENZYME CORPORATION, Cambridge, MA (US)

( * ) Notice: Subject to any disclaimer, the term of this patent is extended or adjusted under 35 U.S.C. 154(b) by 0 days.

(21) Appl. No.: 14/480,052

(22) Filed: Sep. 8, 2014

(65) Prior Publication Data

US 2014/0377806 A1    Dec. 25, 2014

Related U.S. Application Data

(62) Division of application No. 13/745,377, filed on Jan. 18, 2013, now Pat. No. 8,865,870.

(60) Provisional application No. 61/588,936, filed on Jan. 20, 2012.

(51) Int. Cl.
| | |
|---|---|
| *C07K 16/28* | (2006.01) |
| *A61K 39/395* | (2006.01) |
| *A61K 45/06* | (2006.01) |
| *A61K 39/00* | (2006.01) |

(52) U.S. Cl.
CPC ...... *C07K 16/2866* (2013.01); *A61K 39/3955* (2013.01); *A61K 45/06* (2013.01); *A61K 2039/505* (2013.01); *C07K 2317/24* (2013.01); *C07K 2317/34* (2013.01); *C07K 2317/565* (2013.01); *C07K 2317/76* (2013.01); *C07K 2317/92* (2013.01)

(58) Field of Classification Search
CPC ............... A61K 39/3955; A61K 45/06; A61K 2039/505; C07K 16/2866; C07K 2317/24; C07K 2317/34; C07K 2317/505; C07K 2317/565; C07K 2317/76; C07K 2317/92
See application file for complete search history.

(56) References Cited

U.S. PATENT DOCUMENTS

| | | | |
|---|---|---|---|
| 4,376,110 A | 3/1983 | David et al. | |
| 4,816,567 A | 3/1989 | Cabilly et al. | |
| 5,225,539 A | 7/1993 | Winter et al. | |
| 5,530,101 A | 6/1996 | Queen et al. | |
| 5,565,332 A | 10/1996 | Hoogenboom et al. | |
| 5,585,089 A | 12/1996 | Queen et al. | |
| 5,589,205 A | 12/1996 | Ishikawa et al. | |
| 5,693,762 A | 12/1997 | Queen et al. | |
| 5,714,352 A | 2/1998 | Jakobovits | |
| 5,723,323 A | 3/1998 | Kauffman et al. | |
| 5,763,192 A | 6/1998 | Kauffman et al. | |
| 5,766,886 A | 6/1998 | Studnicka et al. | |
| 5,800,988 A | 9/1998 | Casterman et al. | |
| 5,814,476 A | 9/1998 | Kauffman et al. | |
| 5,817,483 A | 10/1998 | Kauffman et al. | |
| 5,824,514 A | 10/1998 | Kauffman et al. | |
| 5,976,862 A | 11/1999 | Kauffman et al. | |
| 6,005,079 A | 12/1999 | Casterman et al. | |
| 6,180,370 B1 | 1/2001 | Queen et al. | |
| 6,184,358 B1 | 2/2001 | Loetscher et al. | |
| 6,204,023 B1 | 3/2001 | Robinson et al. | |
| 6,632,927 B2 | 10/2003 | Adair et al. | |
| 6,686,175 B1 | 2/2004 | Loetscher et al. | |
| 7,241,877 B2 | 7/2007 | Adair et al. | |
| 7,244,615 B2 | 7/2007 | Adair et al. | |
| 7,244,832 B2 | 7/2007 | Adair et al. | |
| 7,262,050 B2 | 8/2007 | Adair et al. | |
| 7,405,275 B2 | 7/2008 | Qin et al. | |
| 7,407,655 B2 | 8/2008 | Loetscher et al. | |
| 2004/0236078 A1 | 11/2004 | Carter et al. | |
| 2007/0082365 A1 | 4/2007 | Lipovsek et al. | |
| 2008/0181892 A1 | 7/2008 | Ledbetter et al. | |
| 2008/0227958 A1 | 9/2008 | Thompson et al. | |
| 2010/0061983 A1 | 3/2010 | Loetscher et al. | |

FOREIGN PATENT DOCUMENTS

| | | |
|---|---|---|
| EP | 239400 A2 | 9/1987 |
| EP | 592106 A1 | 4/1994 |
| WO | 91/09967 | 7/1991 |
| WO | 94/04678 | 3/1994 |
| WO | 94/25591 | 11/1994 |
| WO | 0172334 | 10/2001 |
| WO | 2005030793 | 4/2005 |

(Continued)

OTHER PUBLICATIONS

PCT/US2013/022280 International Search Report & Written Opinion mailed Sep. 23, 2013, 27 pages.
Clark-Lewis, I. et al., Structure-Function Relationship between the Human Chemokine Receptor CXCR3 and Its Ligands; Journal of Biologicial Chemistry, vol. 278, No. 1, pp. 289-295, issue of Jan. 3, 2003.
PCT/US2013/022280 Response to Written Opinion filed Dec. 19, 2013, 135 pages.
PCT/US2013/022280 Written Opinion of the International Preliminary Examining Authority mailed Mar. 13, 2014, 8 pages.

(Continued)

*Primary Examiner* — Robert Landsman
(74) *Attorney, Agent, or Firm* — Lathrop Gage LLP; James H. Velema, Esq.

(57) ABSTRACT

The present disclosure provides anti-CXCR3 antibodies and methods of using the antibodies to diagnose and/or treat CXCR3-associated disorders such as diabetes mellitus type I (T1D), particularly new-onset T1D. In certain embodiments, disclosed herein are CXCR3 neutralizing antibodies.

37 Claims, 94 Drawing Sheets

(56) References Cited

FOREIGN PATENT DOCUMENTS

| WO | 2008094942 | 8/2008 |
|---|---|---|
| WO | 2009032661 | 3/2009 |
| WO | 2010103517 | 9/2010 |

OTHER PUBLICATIONS

PCT/US2013/022280 Notification Concerning Informal Communications With the Applicatn Mar. 13, 2014, 7 pages.
Paul, W.E., Fundamental Immunology, 3rd Edition, Raven Press, New York, Chapt. 8, pp. 292-295, 1993.
Rudikoff S. et al., Proc. Natl. Acad. Sci. USA, 79(6):1979-1983, Mar. 1982.
Colman P. M., Research in Immunology, 145:33-36, 1994.

Clone 12.0 - VH amino acid sequence
- CDRs in bold and underlined

```
1         10        20        30        40        50
EVQLEESGGGLVQPKGSLKLSCAASGISFNDAAMNWIRQAPGEGLEWVAR 60        70        80        90        100
IRSKINDYGTHYAASVKDRFTISRDDSQNILFLQMNNLKTEDTGMYYCVI

110
DGYGSLAYWGQGTLVTVSA    (SEQ ID NO: 2)
```

Clone 12.0 - VL amino acid sequence
- CDRs in bold and underlined

```
1         10        20        30        40        50
DIVLTQSPAIMSSSPGEKVTMTCRASSSVISSYLHWYQQRSGASPKLWIY 60        70        80        90        100
STSSLASGVPARFSGSGSGTSFSLTISSVEAEDAATYYCQQYSGYPLTFG
```

AGTKLELK    (SEQ ID NO: 3)

| SEQ ID NO | Region | Sequence |
|---|---|---|
| Heavy Chain ||| 
| 115 | FR1 | EVQLEESGGGLVQPKGSLKLSCAAS |
| 116 | CDR1 | GISFNDAA |
| 117 | FR2 | MNWIRQAPGEGLEWVAR |
| 118 | CDR2 | IRSKINDYGT |
| 119 | FR3 | HYAASVKDRFTISRDDSQNILFLQMNNLKTEDTGMYYC |
| 120 | CDR3 | VIDGYGSLAY |
| 121 | FR4 | WGQGTLVTVSA |
| Light Chain ||| 
| 122 | FR1 | DIVLTQSPAIMSSSPGEKVTMTCRAS |
| 123 | CDR1 | SSVISSY |
| 124 | FR2 | LHWYQQRSGASPKLWIY |
| 125 | CDR2 | STS |
| 126 | FR3 | SLASGVPARFSGSGSGTSFSLTISSVEAEDAATYYC |
| 127 | CDR3 | QQYSGYPLT |
| 128 | FR4 | FGAGTKLELK |

Fig. 23A

Clone 12.1 - VH amino acid sequence - CDRs in bold and underlined

```
1         10        20        30        40        50
EVQLVESGGGLVQPGGSLKLSCAASGISFNDAAMHWVRQASGKGLEWVAR 60        70        80        90        100
IRSKINDYGTAYAASVKGRFTISRDDSQNTLYLQMNSLKTEDTAVYYCVI

110
DGYGSLAYWGQGTLVTVSS    (SEQ ID NO: 4)
```

Clone 12.1 - VL amino acid sequence - CDRs in bold and underlined

```
1         10        20        30        40        50
EIVLTQSPATLSLSPGERATLSCRASSSVISSYLAWYQQKPGQAPRLWIY 60        70        80        90        100
STSNRATGIPARFSGSGSGTDFTLTISSLEPEDFATYYCQQYSGYPLTFG

GGTKVEIK    (SEQ ID NO: 5)
```

| SEQ ID NO | Region | Sequence |
|---|---|---|
| Heavy Chain ||| 
| 129 | FR1 | EVQLVESGGGLVQPGGSLKLSCAAS |
| 130 | CDR1 | GISFNDAA |
| 131 | FR2 | MHWVRQASGKGLEWVAR |
| 132 | CDR2 | IRSKINDYGT |
| 133 | FR3 | AYAASVKGRFTISRDDSQNTLYLQMNSLKTEDTAVYYC |
| 134 | CDR3 | VIDGYGSLAY |
| 135 | FR4 | WGQGTLVTVSS |
| Light Chain |||
| 136 | FR1 | EIVLTQSPATLSLSPGERATLSCRAS |
| 137 | CDR1 | SSVISSY |
| 138 | FR2 | LAWYQQKPGQAPRLWIY |
| 139 | CDR2 | STS |
| 140 | FR3 | NRATGIPARFSGSGSGTDFTLTISSLEPEDFATYYC |
| 141 | CDR3 | QQYSGYPLT |
| 142 | FR4 | FGGGTKVEIK |

Fig. 23B

Clone 12.2 - VH amino acid sequence - CDRs in bold and underlined

```
1         10        20        30        40        50
EVQLVESGGGLVQPGGSLKLSCAASGISFNDAAMNWIRQASGKGLEWVAR 60        70        80        90        100
IRSKINDYGTHYAASVKGRFTISRDDSQNTLYLQMNSLKTEDTAMYYCVI

110
DGYGSLAYWGQGTLVTVSS   (SEQ ID NO: 6)
```

Clone 12.2 - VL amino acid sequence - CDRs in bold and underlined

```
1         10        20        30        40        50
EIVLTQSPATLSLSPGERATLSCRASSSVISSYLHWYQQKPGQAPRLWIY 60        70        80        90        100
STSSLASGIPARFSGSGSGTDFTLTISSLEPEDFATYYCQQYSGYPLTFG

AGTKVEIK   (SEQ ID NO: 7)
```

| SEQ ID NO | Region | Sequence |
|---|---|---|
| Heavy Chain ||| 
| 143 | FR1 | EVQLVESGGGLVQPGGSLKLSCAAS |
| 144 | CDR1 | GISFNDAA |
| 145 | FR2 | MNWIRQASGKGLEWVAR |
| 146 | CDR2 | IRSKINDYGT |
| 147 | FR3 | HYAASVKGRFTISRDDSQNTLYLQMNSLKTEDTAMYYC |
| 148 | CDR3 | VIDGYGSLAY |
| 149 | FR4 | WGQGTLVTVSS |
| Light Chain ||| 
| 150 | FR1 | EIVLTQSPATLSLSPGERATLSCRAS |
| 151 | CDR1 | SSVISSY |
| 152 | FR2 | LHWYQQKPGQAPRLWIY |
| 153 | CDR2 | STS |
| 154 | FR3 | SLASGIPARFSGSGSGTDFTLTISSLEPEDFATYYC |
| 155 | CDR3 | QQYSGYPLT |
| 156 | FR4 | FGAGTKVEIK |

Fig. 23C

Clone 12.3 - VH amino acid sequence - CDRs in bold and underlined

```
1         10        20        30        40        50
EVQLVESGGGLVQPKGSLKLSCAASGISFNDAAMNWIRQASGKGLEWVAR 60        70        80        90        100
IRSKINDYGTHYAASVKDRFTISRDDSQNILYLQMNNLKTEDTAMYYCVI

110
DGYGSLAYWGQGTLVTVSS    (SEQ ID NO: 8)
```

Clone 12.3 - VL amino acid sequence - CDRs in bold and underlined

```
1         10        20        30        40        50
EIVLTQSPAILSSSPGERATLSCRASSSVISSYLHWYQQKPGAAPRLWIY 60        70        80        90        100
STSSLASGIPARFSGSGSGTSFTLTISSLEAEDFATYYCQQYSGYPLTFG
```

AGTKVEIK    (SEQ ID NO: 9)

| SEQ ID NO | Region | Sequence |
|---|---|---|
| Heavy Chain ||| 
| 157 | FR1 | EVQLVESGGGLVQPKGSLKLSCAAS |
| 158 | CDR1 | GISFNDAA |
| 159 | FR2 | MNWIRQASGKGLEWVAR |
| 160 | CDR2 | IRSKINDYGT |
| 161 | FR3 | HYAASVKDRFTISRDDSQNILYLQMNNLKTEDTAMYYC |
| 162 | CDR3 | VIDGYGSLAY |
| 163 | FR4 | WGQGTLVTVSS |
| Light Chain |||
| 164 | FR1 | EIVLTQSPAILSSSPGERATLSCRAS |
| 165 | CDR1 | SSVISSY |
| 166 | FR2 | LHWYQQKPGAAPRLWIY |
| 167 | CDR2 | STS |
| 168 | FR3 | SLASGIPARFSGSGSGTSFTLTISSLEAEDFATYYC |
| 169 | CDR3 | QQYSGYPLT |
| 170 | FR4 | FGAGTKVEIK |

Fig. 23D

Clone 135.0 - VH amino acid sequence - CDRs in bold and underlined

```
1         10        20        30        40        50
EVKLEESGGGLVKPGGSLKLSCAASGFTFTSYALSWVRQTPEKRLEWVAT 60        70        80        90        100
ISHGGSYTYYPDSVKGRFTISRDNAKNTLNLQMSSLRSEDTAMYYCARHP

110       120
FYSGNYQGYFDYWGQGTLLTVSS     (SEQ ID NO: 10)
```

Clone 135.0 - VL amino acid sequence - CDRs in bold and underlined

```
1         10        20        30        40        50
DIVLTQSPAIMSASLGEKVTMNCRANSGVNYMYWYQQKSDASPKLWIYFT

60        70        80        90        100
SNLAPGVPARFSGSGSGNSYSLTISSMEGDAATYYCQQFTSSPYTFGGG

TKLEIK    (SEQ ID NO: 11)
```

| SEQ ID NO | Region | Sequence |
|---|---|---|
| Heavy Chain ||| 
| 171 | FR1 | EVKLEESGGGLVKPGGSLKLSCAAS |
| 172 | CDR1 | GFTFTSYA |
| 173 | FR2 | LSWVRQTPEKRLEWVAT |
| 174 | CDR2 | ISHGGSYT |
| 175 | FR3 | YYPDSVKGRFTISRDNAKNTLNLQMSSLRSEDTAMYYC |
| 176 | CDR3 | ARHPFYSGNYQGYFDY |
| 177 | FR4 | WGQGTLLTVSS |
| Light Chain |||
| 178 | FR1 | DIVLTQSPAIMSASLGEKVTMNCRAN |
| 179 | CDR1 | SGVNY |
| 180 | FR2 | MYWYQQKSDASPKLWIY |
| 181 | CDR2 | FTS |
| 182 | FR3 | NLAPGVPARFSGSGSGNSYSLTISSMEGEDAATYYC |
| 183 | CDR3 | QQFTSSPYT |
| 184 | FR4 | FGGGTKLEIK |

Fig. 24A

Clone 135.1 - VH amino acid sequence - CDRs in bold and underlined

```
1         10        20        30        40        50
EVQLEESGGGLVQPGGSLRLSCAASGFTFTSYAMSWVRQAPGKGLEWVAV 60        70        80        90        100
ISHGGSYTYYADSVKGRFTISRDNSKNTLYLQMNSLRAEDTAVYYCARHP

110       120
FYSGNYQGYFDYWGQGTLVTVSS    (SEQ ID NO: 12)
```

Clone 135.1 - VL amino acid sequence - CDRs in bold and underlined

```
1         10        20        30        40        50
DIQLTQSPSFLSASVGDRVTITCRASSGVNYLAWYQQKPGKAPKLWIYFT

60        70        80        90        100
STLQSGVPSRFSGSGSGNEYTLTISSLQFEDFATYYCQQFTSSPYTFGQG

TKLEIK    (SEQ ID NO: 13)
```

| SEQ ID NO | Region | Sequence |
|---|---|---|
| Heavy Chain | | |
| 185 | FR1 | EVQLEESGGGLVQPGGSLRLSCAAS |
| 186 | CDR1 | GFTFTSYA |
| 187 | FR2 | MSWVRQAPGKGLEWVAV |
| 188 | CDR2 | ISHGGSYT |
| 189 | FR3 | YYADSVKGRFTISRDNSKNTLYLQMNSLRAEDTAVYYC |
| 190 | CDR3 | ARHPFYSGNYQGYFDY |
| 191 | FR4 | WGQGTLVTVSS |
| Light Chain | | |
| 192 | FR1 | DIQLTQSPSFLSASVGDRVTITCRAS |
| 193 | CDR1 | SGVNY |
| 194 | FR2 | LAWYQQKPGKAPKLWIY |
| 195 | CDR2 | FTS |
| 196 | FR3 | TLQSGVPSRFSGSGSGNEYTLTISSLQFEDFATYYC |
| 197 | CDR3 | QQFTSSPYT |
| 198 | FR4 | FGQGTKLEIK |

Fig. 24B

Clone 135.2 - VH amino acid sequence - CDRs in bold and underlined

```
1         10        20        30        40        50
EVQLEESGGGLVQPGGSLRLSCAASGFTFTSYALSWVRQAPGKGLEWVAT 60        70        80        90        100
ISHGGSYTYYPDSVKGRFTISRDNSKNTLYLQMNSLRAEDTAVYYCARHP

110       120
FYSGNYQGYFDYWGQGTLVTVSS     (SEQ ID NO: 14)
```

Clone 135.2 - VL amino acid sequence - CDRs in bold and underlined

```
1         10        20        30        40        50
DIQLTQSPSFLSASVGDRVTITCRANSGVNYMYWYQQKPGKAPKLWIYFT

60        70        80        90        100
SNLAPGVPSRFSGSGSGNEYTLTISSLQFEDFATYYCQQFTSSPYTFGGG

TKLEIK    (SEQ ID NO: 15)
```

| SEQ ID NO | Region | Sequence |
|---|---|---|
| Heavy Chain ||| 
| 199 | FR1 | EVQLEESGGGLVQPGGSLRLSCAAS |
| 200 | CDR1 | GFTFTSYA |
| 201 | FR2 | LSWVRQAPGKGLEWVAT |
| 202 | CDR2 | ISHGGSYT |
| 203 | FR3 | YYPDSVKGRFTISRDNSKNTLYLQMNSLRAEDTAVYYC |
| 204 | CDR3 | ARHPFYSGNYQGYFDY |
| 205 | FR4 | WGQGTLVTVSS |
| Light Chain ||| 
| 206 | FR1 | DIQLTQSPSFLSASVGDRVTITCRAN |
| 207 | CDR1 | SGVNY |
| 208 | FR2 | MYWYQQKPGKAPKLWIY |
| 209 | CDR2 | FTS |
| 210 | FR3 | NLAPGVPSRFSGSGSGNEYTLTISSLQFEDFATYYC |
| 211 | CDR3 | QQFTSSPYT |
| 212 | FR4 | FGGGTKLEIK |

Fig. 24C

Clone 135.3 - VH amino acid sequence - CDRs in bold and underlined

```
1         10        20        30        40        50
EVQLLESGGGLVQPGGSLRLSCAASGFTFTSYALSWVRQTPEKRLEWVAT 60        70        80        90        100
ISHGGSYTYYPDSVKGRFTISRDNSKNTLNLQMSSLRAEDTAVYYCARHP

110       120
FYSGNYQGYFDYWGQGTLVTVSS      (SEQ ID NO: 16)
```

Clone 135.3 - VL amino acid sequence - CDRs in bold and underlined

```
1         10        20        30        40        50
DIQLTQSPSFLSASVGDRVTITCRANSGVNYMYWYQQKPDAAPKLWIYFT

60        70        80        90        100
SNLAPGVPSRFSGSGSGNSYTLTISSLQFEDFATYYCQQFTSSPYTFGGG

TKLEIK      (SEQ ID NO: 17)
```

| SEQ ID NO | Region | Sequence |
|---|---|---|
| Heavy Chain | | |
| 213 | FR1 | EVQLLESGGGLVQPGGSLRLSCAAS |
| 214 | CDR1 | GFTFTSYA |
| 215 | FR2 | LSWVRQTPEKRLEWVAT |
| 216 | CDR2 | ISHGGSYT |
| 217 | FR3 | YYPDSVKGRFTISRDNSKNTLNLQMSSLRAEDTAVYYC |
| 218 | CDR3 | ARHPFYSGNYQGYFDY |
| 219 | FR4 | WGQGTLVTVSS |
| Light Chain | | |
| 220 | FR1 | DIQLTQSPSFLSASVGDRVTITCRAN |
| 221 | CDR1 | SGVNY |
| 222 | FR2 | MYWYQQKPDAAPKLWIY |
| 223 | CDR2 | FTS |
| 224 | FR3 | NLAPGVPSRFSGSGSGNSYTLTISSLQFEDFATYYC |
| 225 | CDR3 | QQFTSSPYT |
| 226 | FR4 | FGGGTKLEIK |

Fig. 24D

Clone 4.0 - VH amino acid sequence - CDRs in bold and underlined

```
1         10        20        30        40        50
EVQLEESGGGLVKPGGSLKLSCAASGFTFSNYAMSWVRQTPDKRLEWVAT 60        70        80        90        100
ISNGGSYTYYPDTVKGRFTISRDNAKNTLSLQMSSLRSEDTAMYYCSRPS

110       120
ERSHYYATSQFAYWGQGTLVTVSA      (SEQ ID NO: 18)
```

Clone 4.0 - VL amino acid sequence - CDRs in bold and underlined

```
1         10        20        30        40        50
DIVLTQSPGIMSASPGEKVTMTCSASSSVSYMHWYQQKSGTSPKRWIYDT

60        70        80        90        100
SKLASGVPARFSGSGSGTSYSLTISSMEAEDAATYYCQQWSSSPLTFGAG

TKVELK    (SEQ ID NO: 19)
```

| SEQ ID NO | Region | Sequence |
|---|---|---|
| colspan="3" | Heavy Chain | |
| 227 | FR1 | EVQLEESGGGLVKPGGSLKLSCAAS |
| 228 | CDR1 | GFTFSNYA |
| 229 | FR2 | MSWVRQTPDKRLEWVAT |
| 230 | CDR2 | ISNGGSYT |
| 231 | FR3 | YYPDTVKGRFTISRDNAKNTLSLQMSSLRSEDTAMYYC |
| 232 | CDR3 | SRPSERSHYYATSQFAY |
| 233 | FR4 | WGQGTLVTVSA |
| colspan="3" | Light Chain | |
| 234 | FR1 | DIVLTQSPGIMSASPGEKVTMTCSAS |
| 235 | CDR1 | SSVSY |
| 236 | FR2 | MHWYQQKSGTSPKRWIY |
| 237 | CDR2 | DTS |
| 238 | FR3 | KLASGVPARFSGSGSGTSYSLTISSMEAEDAATYYC |
| 239 | CDR3 | QQWSSSPLT |
| 240 | FR4 | FGAGTKVELK |

Fig. 25A

Clone 4.1 - VH amino acid sequence - CDRs in bold and underlined

```
1         10        20        30        40        50
EVQLLESGGGLVQPGGSLRLSCAASGFTFSNYAMSWVRQAPGKGLEWVAV 60        70        80        90        100
ISNGGSYTYYADSVKGRFTISRDNSKNTLYLQMNSLRAEDTAVYYCSRPS

110       120
ERSHYYATSQFAYWGQGTLVTVSS      (SEQ ID NO: 20)
```

Clone 4.1 - VL amino acid sequence - CDRs in bold and underlined

```
1         10        20        30        40        50
EIVLTQSPATLSLSPGERATLSCRASSSVSYLAWYQQKPGQAPRRWIYDT

60        70        80        90        100
SNRATGIPARFSGSGSGTDYTLTISSLEPEDFAVYYCQQWSSSPLTFGGG

TKVEIK    (SEQ ID NO: 21)
```

| SEQ ID NO | Region | Sequence |
|---|---|---|
| Heavy Chain | | |
| 241 | FR1 | EVQLLESGGGLVQPGGSLRLSCAAS |
| 242 | CDR1 | GFTFSNYA |
| 243 | FR2 | MSWVRQAPGKGLEWVAV |
| 244 | CDR2 | ISNGGSYT |
| 245 | FR3 | YYADSVKGRFTISRDNSKNTLYLQMNSLRAEDTAVYYC |
| 246 | CDR3 | SRPSERSHYYATSQFAY |
| 247 | FR4 | WGQGTLVTVSS |
| Light Chain | | |
| 248 | FR1 | EIVLTQSPATLSLSPGERATLSCRAS |
| 249 | CDR1 | SSVSY |
| 250 | FR2 | LAWYQQKPGQAPRRWIY |
| 251 | CDR2 | DTS |
| 252 | FR3 | NRATGIPARFSGSGSGTDYTLTISSLEPEDFAVYYC |
| 253 | CDR3 | QQWSSSPLT |
| 254 | FR4 | FGGGTKVEIK |

Fig. 25B

Clone 4.2 - VH amino acid sequence - CDRs in bold and underlined

```
1        10        20        30        40        50
EVQLLESGGGLVQPGGSLRLSCAASGFTFSNYAMSWVRQAPGKGLEWVAT 60        70        80        90        100
ISNGGSYTYYPDSVKGRFTISRDNSKNTLYLQMNSLRAEDTAVYYCSRPS

110       120
ERSHYYATSQFAYWGQGTLVTVSS    (SEQ ID NO: 22)
```

Clone 4.2 - VL amino acid sequence - CDRs in bold and underlined

```
1        10        20        30        40        50
EIVLTQSPATLSLSPGERATLSCSASSSVSYMHWYQQKPGTAPRRWIYDT

60        70        80        90        100
SKLASGIPARFSGSGSGTDYTLTISSLEPEDFATYYCQQWSSSPLTFGAG

TKVEIK    (SEQ ID NO: 23)
```

| SEQ ID NO | Region | Sequence |
|---|---|---|
| Heavy Chain ||| 
| 255 | FR1 | EVQLLESGGGLVQPGGSLRLSCAAS |
| 256 | CDR1 | GFTFSNYA |
| 257 | FR2 | MSWVRQAPGKGLEWVAT |
| 258 | CDR2 | ISNGGSYT |
| 259 | FR3 | YYPDSVKGRFTISRDNSKNTLYLQMNSLRAEDTAVYYC |
| 260 | CDR3 | SRPSERSHYYATSQFAY |
| 261 | FR4 | WGQGTLVTVSS |
| Light Chain |||
| 262 | FR1 | EIVLTQSPATLSLSPGERATLSCSAS |
| 263 | CDR1 | SSVSY |
| 264 | FR2 | MHWYQQKPGTAPRRWIY |
| 265 | CDR2 | DTS |
| 266 | FR3 | KLASGIPARFSGSGSGTDYTLTISSLEPEDFATYYC |
| 267 | CDR3 | QQWSSSPLT |
| 268 | FR4 | FGAGTKVEIK |

Fig. 25C

Clone 4.3 – VH amino acid sequence – CDRs in bold and underlined

```
1         10        20        30        40        50
EVQLEESGGGLVQPGGSLRLSCAASGFTFSNYAMSWVRQTPDKRLEWVAT 60        70        80        90       100
ISNGGSYTYYPDSVKGRFTISRDNSKNTLYLQMSSLRAEDTAVYYCSRPS

110       120
ERSHYYATSQFAYWGQGTLVTVSS    (SEQ ID NO: 24)
```

Clone 4.3 – VL amino acid sequence – CDRs in bold and underlined

```
1         10        20        30        40        50
EIVLTQSPAILSLSPGERATLSCSASSSVSYMHWYQQKPGQAPRRWIYDT

60        70        80        90       100
SKLASGIPARFSGSGSGTSYTLTISSLEAEDFATYYCQQWSSSPLTFGAG

TKVEIK    (SEQ ID NO: 25)
```

| SEQ ID NO | Region | Sequence |
|---|---|---|
| Heavy Chain | | |
| 269 | FR1 | EVQLEESGGGLVQPGGSLRLSCAAS |
| 270 | CDR1 | GFTFSNYA |
| 271 | FR2 | MSWVRQTPDKRLEWVAT |
| 272 | CDR2 | ISNGGSYT |
| 273 | FR3 | YYPDSVKGRFTISRDNSKNTLYLQMSSLRAEDTAVYYC |
| 274 | CDR3 | SRPSERSHYYATSQFAY |
| 275 | FR4 | WGQGTLVTVSS |
| Light Chain | | |
| 276 | FR1 | EIVLTQSPAILSLSPGERATLSCSAS |
| 277 | CDR1 | SSVSY |
| 278 | FR2 | MHWYQQKPGQAPRRWIY |
| 279 | CDR2 | DTS |
| 280 | FR3 | KLASGIPARFSGSGSGTSYTLTISSLEAEDFATYYC |
| 281 | CDR3 | QQWSSSPLT |
| 282 | FR4 | FGAGTKVEIK |

Fig. 25D

Clone 4.4 - VH amino acid sequence - CDRs in bold and underlined

```
1         10        20        30        40        50
EVQLVESGGGVKKPGGSLKLSCAASGFTFSNYAMSWVRQTPGKGLEWVAT 60        70        80        90        100
ISNGGSYTYYPDSFQGRFTISRDNAKSTLSLQMSSLKSEDTAMYYCSRPS

110       120
ERSHYYATSQFAYWGQGTLVTVSA     (SEQ ID NO: 26)
```

| SEQ ID NO | Region | Sequence |
|---|---|---|
| Heavy Chain ||| 
| 283 | FR1 | EVQLVESGGGVKKPGGSLKLSCAAS |
| 284 | CDR1 | GFTFSNYA |
| 285 | FR2 | MSWVRQTPGKGLEWVAT |
| 286 | CDR2 | ISNGGSYT |
| 287 | FR3 | YYPDSFQGRFTISRDNAKSTLSLQMSSLKSEDTAMYYC |
| 288 | CDR3 | SRPSERSHYYATSQFAY |
| 289 | FR4 | WGQGTLVTVSA |

Fig. 25E

Clone 4.5 - VH amino acid sequence - CDRs in bold and underlined

```
1         10        20        30        40        50
EVQLVESGGGVKKPGGSLKLSCAASGFTFSNYAMSWVRQTPGKGLEWVAT 60        70        80        90       100
ISNGGSYTYYPDSFQGRFTISRDNAKSTLSLQMSSLKAEDTAMYYCSRPS

110       120
ERSHYYATSQFAYWGQGTLVTVSS    (SEQ ID NO: 27)
```

| SEQ ID NO | Region | Sequence |
|---|---|---|
| Heavy Chain | | |
| 290 | FR1 | EVQLVESGGGVKKPGGSLKLSCAAS |
| 291 | CDR1 | GFTFSNYA |
| 292 | FR2 | MSWVRQTPGKGLEWVAT |
| 293 | CDR2 | ISNGGSYT |
| 294 | FR3 | YYPDSFQGRFTISRDNAKSTLSLQMSSLKAEDTAMYYC |
| 295 | CDR3 | SRPSERSHYYATSQFAY |
| 296 | FR4 | WGQGTLVTVSS |

Fig. 25F

Clone 4.6 - VH amino acid sequence - CDRs in bold and underlined

```
1         10        20        30        40        50
EVQLVESGGGVKKPGGSLKLSCAASGFTFSNYAMSWVRQTPGKGLEWVAT 60        70        80        90        100
ISQGGSYTYYPESFQGRFTISRDQAKSTLSLQMSSLKSEDTAMYYCSRPS

110       120
ERSHYYATSQFAYWGQGTLVTVSA     (SEQ ID NO: 28)
```

| SEQ ID NO | Region | Sequence |
|---|---|---|
| Heavy Chain ||| 
| 297 | FR1 | EVQLVESGGGVKKPGGSLKLSCAAS |
| 298 | CDR1 | GFTFSNYA |
| 299 | FR2 | MSWVRQTPGKGLEWVAT |
| 300 | CDR2 | ISQGGSYT |
| 301 | FR3 | YYPESFQGRFTISRDQAKSTLSLQMSSLKSEDTAMYYC |
| 302 | CDR3 | SRPSERSHYYATSQFAY |
| 303 | FR4 | WGQGTLVTVSA |

Fig. 25G

Clone 4.7 - VH amino acid sequence - CDRs in bold and underlined

```
1         10        20        30        40        50
EVQLLESGGGLVQPGGSLRLSCAASGFTFSNYAMSWVRQAPGKGLEWVAT 60        70        80        90        100
ISQGGSYTYYPDSVKGRFTISRDNSKNTLYLQMNSLRAEDTAVYYCSRPS

110       120
ERSHYYATSQFAYWGQGTLVTVSS        (SEQ ID NO: 29)
```

| SEQ ID NO | Region | Sequence |
|---|---|---|
| Heavy Chain | | |
| 304 | FR1 | EVQLLESGGGLVQPGGSLRLSCAAS |
| 305 | CDR1 | GFTFSNYA |
| 306 | FR2 | MSWVRQAPGKGLEWVAT |
| 307 | CDR2 | ISQGGSYT |
| 308 | FR3 | YYPDSVKGRFTISRDNSKNTLYLQMNSLRAEDTAVYYC |
| 309 | CDR3 | SRPSERSHYYATSQFAY |
| 310 | FR4 | WGQGTLVTVSS |

Fig. 25H

Clone 4.8 - VH amino acid sequence - CDRs in bold and underlined

```
1         10        20        30        40        50
EVQLLESGGGLVQPGGSLRLSCAASGFTFSNYAMSWVRQAPGKGLEWVAT 60        70        80        90        100
ISNLGSYTYYPDSVKGRFTISRDNSKNTLYLQMNSLRAEDTAVYYCSRPS

110       120
ERSHYYATSQFAYWGQGTLVTVSS        (SEQ ID NO: 30)
```

| SEQ ID NO | Region | Sequence |
|---|---|---|
| | | Heavy Chain |
| 311 | FR1 | EVQLLESGGGLVQPGGSLRLSCAAS |
| 312 | CDR1 | GFTFSNYA |
| 313 | FR2 | MSWVRQAPGKGLEWVAT |
| 314 | CDR2 | ISNLGSYT |
| 315 | FR3 | YYPDSVKGRFTISRDNSKNTLYLQMNSLRAEDTAVYYC |
| 316 | CDR3 | SRPSERSHYYATSQFAY |
| 317 | FR4 | WGQGTLVTVSS |

Fig. 25I

Clone 4.9 - VH amino acid sequence - CDRs in bold and underlined

```
1         10        20        30        40        50
EVQLLESGGGLVQPGGSLRLSCAASGFTFSNYAMSWVRQAPGKGLEWVAT 60        70        80        90       100
ISNSGSYTYYPDSVKGRFTISRDNSKNTLYLQMNSLRAEDTAVYYCSRPS

110       120
ERSHYYATSQFAYWGQGTLVTVSS    (SEQ ID NO: 31)
```

| SEQ ID NO | Region | Sequence |
|---|---|---|
| Heavy Chain | | |
| 318 | FR1 | EVQLLESGGGLVQPGGSLRLSCAAS |
| 319 | CDR1 | GFTFSNYA |
| 320 | FR2 | MSWVRQAPGKGLEWVAT |
| 321 | CDR2 | ISNSGSYT |
| 322 | FR3 | YYPDSVKGRFTISRDNSKNTLYLQMNSLRAEDTAVYYC |
| 323 | CDR3 | SRPSERSHYYATSQFAY |
| 324 | FR4 | WGQGTLVTVSS |

Fig. 25J

Clone 4.10 - VH amino acid sequence - CDRs in bold and underlined

```
1         10        20        30        40        50
EVQLLESGGGLVQPGGSLRLSCAASGFTFSNYAMSWVRQAPGKGLEWVAT 60        70        80        90        100
ISDGGSYTYYPDSVKGRFTISRDNSKNTLYLQMNSLRAEDTAVYYCSRPS

110       120
ERSHYYATSQFAYWGQGTLVTVSS    (SEQ ID NO: 32)
```

| SEQ ID NO | Region | Sequence |
|---|---|---|
| Heavy Chain ||||
| 325 | FR1 | EVQLLESGGGLVQPGGSLRLSCAAS |
| 326 | CDR1 | GFTFSNYA |
| 327 | FR2 | MSWVRQAPGKGLEWVAT |
| 328 | CDR2 | ISDGGSYT |
| 329 | FR3 | YYPDSVKGRFTISRDNSKNTLYLQMNSLRAEDTAVYYC |
| 330 | CDR3 | SRPSERSHYYATSQFAY |
| 331 | FR4 | WGQGTLVTVSS |

Fig. 25K

Clone 4.11 - VH amino acid sequence - CDRs in bold and underlined

```
1         10        20        30        40        50
EVQLLESGGGLVQPGGSLRLSCAASGFTFSNYAMSWVRQAPGKGLEWVAT 60        70        80        90        100
ISNVGSYTYYPDSVKGRFTISRDNSKNTLYLQMNSLRAEDTAVYYCSRPS

110       120
ERSHYYATSQFAYWGQGTLVTVSS     (SEQ ID NO: 33)
```

| SEQ ID NO | Region | Sequence |
|---|---|---|
| Heavy Chain |||
| 332 | FR1 | EVQLLESGGGLVQPGGSLRLSCAAS |
| 333 | CDR1 | GFTFSNYA |
| 334 | FR2 | MSWVRQAPGKGLEWVAT |
| 335 | CDR2 | ISNVGSYT |
| 336 | FR3 | YYPDSVKGRFTISRDNSKNTLYLQMNSLRAEDTAVYYC |
| 337 | CDR3 | SRPSERSHYYATSQFAY |
| 338 | FR4 | WGQGTLVTVSS |

Fig. 25L

Clone 4.4 - VL amino acid sequence - CDRs in bold and underlined

```
1         10        20        30        40        50
DIVLTQSPGSLSASVGDRVTMCSASSSVSYMHWYQQKPGTSPKRWIYDT

60        70        80        90        100
SKLASGVPARFSGSGSGTSYSLTISSLQPEDAATYYCQQWSSSPLTFGAG
```

TKVELK    (SEQ ID NO: 34)

| SEQ ID NO | Region | Sequence |
|---|---|---|
| | | Light Chain |
| 339 | FR1 | DIVLTQSPGSLSASVGDRVTMCSAS |
| 340 | CDR1 | SSVSY |
| 341 | FR2 | MHWYQQKPGTSPKRWIY |
| 342 | CDR2 | DTS |
| 343 | FR3 | KLASGVPARFSGSGSGTSYSLTISSLQPEDAATYYC |
| 344 | CDR3 | QQWSSSPLT |
| 345 | FR4 | FGAGTKVELK |

Fig. 25M

Clone 4.5 - VL amino acid sequence - CDRs in bold and underlined

```
1         10        20        30        40        50
DIVLTQSPSSLSASVGDRVTITCSASSSVSYMHWYQQKPGTSPKRWIYDT

60        70        80        90        100
SKLASGVPARFSGSGSGTSYSLTISSLQPEDAATYYCQQWSSSPLTFGAG
```

TKVEIK       (SEQ ID NO: 35)

| SEQ ID NO | Region | Sequence |
|---|---|---|
| Light Chain ||| 
| 346 | FR1 | DIVLTQSPSSLSASVGDRVTITCSAS |
| 347 | CDR1 | SSVSY |
| 348 | FR2 | MHWYQQKPGTSPKRWIY |
| 349 | CDR2 | DTS |
| 350 | FR3 | KLASGVPARFSGSGSGTSYSLTISSLQPEDAATYYC |
| 351 | CDR3 | QQWSSSPLT |
| 352 | FR4 | FGAGTKVEIK |

Fig. 25N

Clone 4.6 - VL amino acid sequence - CDRs in bold and underlined

```
1         10        20        30        40        50
DIVLTQSPSSLSASVGDRVTITCSASSSVSYMHWYQQKPGQSPKRWIYDT

60        70        80        90        100
SKLASGVPARFSGSGSGTSYSLTISSLQPEDAATYYCQQWSSSPLTFGAG
```

TKVEIK    (SEQ ID NO: 36)

| SEQ ID NO | Region | Sequence |
|---|---|---|
| Light Chain ||| 
| 353 | FR1 | DIVLTQSPSSLSASVGDRVTITCSAS |
| 354 | CDR1 | SSVSY |
| 355 | FR2 | MHWYQQKPGQSPKRWIY |
| 356 | CDR2 | DTS |
| 357 | FR3 | KLASGVPARFSGSGSGTSYSLTISSLQPEDAATYYC |
| 358 | CDR3 | QQWSSSPLT |
| 359 | FR4 | FGAGTKVEIK |

Fig. 25O

Clone 4.7 - VL amino acid sequence - CDRs in bold and underlined

```
1         10        20        30        40        50
DIQLTQSPGSLSASVGDRVTMTCSASSSVSYMHWYQQKPGTSPKRWIYDT

60        70        80        90        100
SKLASGVPARFSGSGSGTSYSLTISSLQPEDAATYYCQQWSSSPLTFGAG

TKVELK    (SEQ ID NO: 37)
```

| SEQ ID NO | Region | Sequence |
|---|---|---|
| Light Chain ||| 
| 360 | FR1 | DIQLTQSPGSLSASVGDRVTMTCSAS |
| 361 | CDR1 | SSVSY |
| 362 | FR2 | MHWYQQKPGTSPKRWIY |
| 363 | CDR2 | DTS |
| 364 | FR3 | KLASGVPARFSGSGSGTSYSLTISSLQPEDAATYYC |
| 365 | CDR3 | QQWSSSPLT |
| 366 | FR4 | FGAGTKVELK |

Fig. 25P

Clone 53.0 - VH amino acid sequence - CDRs in bold and underlined

```
1         10        20        30        40        50
EVQLEESGGGLVKPGGSLKLSCAAS GFTFTSYA MSWVRQTPEKRLEWVAT 60        70        80        90        100
ISHGGTYT YYPDSVKGRFTISRDNAKNTLYLQMSSLRSEDTAMYYC ARHP 110       120
IYSGNYQGYFDY WGQGTTLTVSS    (SEQ ID NO: 38)
```

Clone 53.0 - VL amino acid sequence - CDRs in bold and underlined

```
1         10        20        30        40        50
DIVLTQSPAIMSASLGEKVTMSCRAS SGVNY IYWYQQKSDASPKLWIY FT 60        70        80        90        100
SNLAPGVPARFSGSGSGNSYSLTISSMEGEDAATYYC QQFTSSPYT FGGG

TKLEIK     (SEQ ID NO: 39)
```

| SEQ ID NO | Region | Sequence |
|---|---|---|
| Heavy Chain |||
| 367 | FR1 | EVQLEESGGGLVKPGGSLKLSCAAS |
| 368 | CDR1 | GFTFTSYA |
| 369 | FR2 | MSWVRQTPEKRLEWVAT |
| 370 | CDR2 | ISHGGTYT |
| 371 | FR3 | YYPDSVKGRFTISRDNAKNTLYLQMSSLRSEDTAMYYC |
| 372 | CDR3 | ARHPIYSGNYQGYFDY |
| 373 | FR4 | WGQGTTLTVSS |
| Light Chain |||
| 374 | FR1 | DIVLTQSPAIMSASLGEKVTMSCRAS |
| 375 | CDR1 | SGVNY |
| 376 | FR2 | IYWYQQKSDASPKLWIY |
| 377 | CDR2 | FTS |
| 378 | FR3 | NLAPGVPARFSGSGSGNSYSLTISSMEGEDAATYYC |
| 379 | CDR3 | QQFTSSPYT |
| 380 | FR4 | FGGGTKLEIK |

Fig. 26A

Clone 53.1 - VH amino acid sequence - CDRs in bold and underlined

```
1         10        20        30        40        50
EVQLLESGGGLVQPGGSLRLSCAASGFTFTSYAMSWVRQAPGKGLEWVAV 60        70        80        90        100
ISHGGTYTYYADSVKGRFTISRDNAKNTLYLQMNSLRAEDTAVYYCARHP

110       120
IYSGNYQGYFDYWGQGTLVTVSS    (SEQ ID NO: 40)
```

Clone 53.1 - VL amino acid sequence - CDRs in bold and underlined

```
1         10        20        30        40        50
DIQLTQSPSFLSASVGDRVTITCRASSGVNYLAWYQQKPGKAPKLWIYFT

60        70        80        90        100
STLQSGVPSRFSGSGSGNEYTLTISSLQPEDFATYYCQQFTSSPYTFGQG

TKLEIK    (SEQ ID NO: 41)
```

| SEQ ID NO | Region | Sequence |
|---|---|---|
| Heavy Chain | | |
| 381 | FR1 | EVQLLESGGGLVQPGGSLRLSCAAS |
| 382 | CDR1 | GFTFTSYA |
| 383 | FR2 | MSWVRQAPGKGLEWVAV |
| 384 | CDR2 | ISHGGTYT |
| 385 | FR3 | YYADSVKGRFTISRDNAKNTLYLQMNSLRAEDTAVYYC |
| 386 | CDR3 | ARHPIYSGNYQGYFDY |
| 387 | FR4 | WGQGTLVTVSS |
| Light Chain | | |
| 388 | FR1 | DIQLTQSPSFLSASVGDRVTITCRAS |
| 389 | CDR1 | SGVNY |
| 390 | FR2 | LAWYQQKPGKAPKLWIY |
| 391 | CDR2 | FTS |
| 392 | FR3 | TLQSGVPSRFSGSGSGNEYTLTISSLQPEDFATYYC |
| 393 | CDR3 | QQFTSSPYT |
| 394 | FR4 | FGQGTKLEIK |

Fig. 26B

Clone 53.2 - VH amino acid sequence - CDRs in bold and underlined

```
1         10        20        30        40        50
EVQLLESGGGLVQPGGSLRLSCAASGFTFTSYAMSWVRQAPGKGLEWVAT 60        70        80        90       100
ISHGGTYTYYPDSVKGRFTISRDNAKNTLYLQMNSLRAEDTAMYYCARHP

110       120
IYSGNYQGYFDYWGQGTLVTVSS    (SEQ ID NO: 42)
```

Clone 53.2 - VL amino acid sequence - CDRs in bold and underlined

```
1         10        20        30        40        50
DIQLTQSPSFLSASVGDRVTITCRASSGVNYIYWYQQKPGKAPKLWIYFT

60        70        80        90       100
SNLAPGVPSRFSGSGSGNEYTLTISSLQPEDFATYYCQQFTSSPYTFGGG

TKLEIK    (SEQ ID NO: 43)
```

| SEQ ID NO | Region | Sequence |
|---|---|---|
| Heavy Chain | | |
| 395 | FR1 | EVQLLESGGGLVQPGGSLRLSCAAS |
| 396 | CDR1 | GFTFTSYA |
| 397 | FR2 | MSWVRQAPGKGLEWVAT |
| 398 | CDR2 | ISHGGTYT |
| 399 | FR3 | YYPDSVKGRFTISRDNAKNTLYLQMNSLRAEDTAMYYC |
| 400 | CDR3 | ARHPIYSGNYQGYFDY |
| 401 | FR4 | WGQGTLVTVSS |
| Light Chain | | |
| 402 | FR1 | DIQLTQSPSFLSASVGDRVTITCRAS |
| 403 | CDR1 | SGVNY |
| 404 | FR2 | IYWYQQKPGKAPKLWIY |
| 405 | CDR2 | FTS |
| 406 | FR3 | NLAPGVPSRFSGSGSGNEYTLTISSLQPEDFATYYC |
| 407 | CDR3 | QQFTSSPYT |
| 408 | FR4 | FGGGTKLEIK |

Fig. 26C

Clone 53.3 - VH amino acid sequence - CDRs in bold and underlined

```
1         10        20        30        40        50
EVQLEESGGGLVQPGGSLRLSCAASGFTFTSYAMSWVRQTPEKRLEWVAT 60        70        80        90        100
ISHGGTYTYYPDSVKGRFTISRDNAKNTLYLQMNSLRAEDTAMYYCARHP

110       120
IYSGNYQGYFDYWGQGTTVTVSS    (SEQ ID NO: 44)
```

Clone 53.3 - VL amino acid sequence - CDRs in bold and underlined

```
1         10        20        30        40        50
DIQLTQSPSFLSASVGDRVTITCRASSGVNYIYWYQQKPDAAPKLWIYFT

60        70        80        90        100
SNLAPGVPSRFSGSGSGNSYTLTISSLQPEDFATYYCQQFTSSPYTFGGG
```

TKLEIK    (SEQ ID NO: 45)

| SEQ ID NO | Region | Sequence |
|---|---|---|
| Heavy Chain ||||
| 409 | FR1 | EVQLEESGGGLVQPGGSLRLSCAAS |
| 410 | CDR1 | GFTFTSYA |
| 411 | FR2 | MSWVRQTPEKRLEWVAT |
| 412 | CDR2 | ISHGGTYT |
| 413 | FR3 | YYPDSVKGRFTISRDNAKNTLYLQMNSLRAEDTAMYYC |
| 414 | CDR3 | ARHPIYSGNYQGYFDY |
| 415 | FR4 | WGQGTTVTVSS |
| Light Chain ||||
| 416 | FR1 | DIQLTQSPSFLSASVGDRVTITCRAS |
| 417 | CDR1 | SGVNY |
| 418 | FR2 | IYWYQQKPDAAPKLWIY |
| 419 | CDR2 | FTS |
| 420 | FR3 | NLAPGVPSRFSGSGSGNSYTLTISSLQPEDFATYYC |
| 421 | CDR3 | QQFTSSPYT |
| 422 | FR4 | FGGGTKLEIK |

Fig. 26D

Clone 53.4 - VH amino acid sequence - CDRs in bold and underlined

```
1         10        20        30        40        50
EVQLLESGGGLVQPGGSLRLSCAASGFTFTSYAMSWVRQAPGKGLEWVAV 60        70        80        90        100
ISHGGTYTYYPDSVKGRFTISRDNAKNTLYLQMNSLRAEDTAMYYCARHP

110       120
IYSGNYQGYFDYWGQGTLVTVSS      (SEQ ID NO: 46)
```

| SEQ ID NO | Region | Sequence |
|---|---|---|
| Heavy Chain ||| 
| 423 | FR1 | EVQLLESGGGLVQPGGSLRLSCAAS |
| 424 | CDR1 | GFTFTSYA |
| 425 | FR2 | MSWVRQAPGKGLEWVAV |
| 426 | CDR2 | ISHGGTYT |
| 427 | FR3 | YYPDSVKGRFTISRDNAKNTLYLQMNSLRAEDTAMYYC |
| 428 | CDR3 | ARHPIYSGNYQGYFDY |
| 429 | FR4 | WGQGTLVTVSS |

Fig. 26E

Clone 53.5 - VH amino acid sequence - CDRs in bold and underlined

```
1         10        20        30        40        50
EVQLLESGGGLVQPGGSLRLSCAASGFTFTSYAMSWVRQAPGKGLEWVAT 60        70        80        90        100
ISHGGTYTYYADSVKGRFTISRDNAKNTLYLQMNSLRAEDTAMYYCARHP

110       120
IYSGNYQGYFDYWGQGTLVTVSS     (SEQ ID NO: 47)
```

| SEQ ID NO | Region | Sequence |
|---|---|---|
| | | Heavy Chain |
| 430 | FR1 | EVQLLESGGGLVQPGGSLRLSCAAS |
| 431 | CDR1 | GFTFTSYA |
| 432 | FR2 | MSWVRQAPGKGLEWVAT |
| 433 | CDR2 | ISHGGTYT |
| 434 | FR3 | YYADSVKGRFTISRDNAKNTLYLQMNSLRAEDTAMYYC |
| 435 | CDR3 | ARHPIYSGNYQGYFDY |
| 436 | FR4 | WGQGTLVTVSS |

Fig. 26F

Clone 53.6 - VH amino acid sequence - CDRs in bold and underlined

```
1         10        20        30        40        50
EVQLLESGGGLVQPGGSLRLSCAASGFTFTSYAMSWVRQAPGKGLEWVAT 60        70        80        90        100
ISHGGTYTYYPDSVKGRFTISRDNAKNTLYLQMNSLRAEDTAVYYCARHP

110       120
IYSGNYQGYFDYWGQGTLVTVSS     (SEQ ID NO: 48)
```

| SEQ ID NO | Region | Sequence |
|---|---|---|
| Heavy Chain | | |
| 437 | FR1 | EVQLLESGGGLVQPGGSLRLSCAAS |
| 438 | CDR1 | GFTFTSYA |
| 439 | FR2 | MSWVRQAPGKGLEWVAT |
| 440 | CDR2 | ISHGGTYT |
| 441 | FR3 | YYPDSVKGRFTISRDNAKNTLYLQMNSLRAEDTAVYYC |
| 442 | CDR3 | ARHPIYSGNYQGYFDY |
| 443 | FR4 | WGQGTLVTVSS |

Fig. 26G

Clone 53.4 - VL amino acid sequence - CDRs in bold and underlined

```
1         10        20        30        40        50
DIQLTQSPSFLSASVGDRVTITCRASSGVNYLYWYQQKPGKAPKLWIYFT

60        70        80        90        100
SNLAPGVPSRFSGSGSGNEYTLTISSLQPEDFATYYCQQFTSSPYTFGGG
```

TKLEIK    (SEQ ID NO: 49)

| SEQ ID NO | Region | Sequence |
|---|---|---|
| Light Chain ||| 
| 444 | FR1 | DIQLTQSPSFLSASVGDRVTITCRAS |
| 445 | CDR1 | SGVNY |
| 446 | FR2 | LYWYQQKPGKAPKLWIY |
| 447 | CDR2 | FTS |
| 448 | FR3 | NLAPGVPSRFSGSGSGNEYTLTISSLQPEDFATYYC |
| 449 | CDR3 | QQFTSSPYT |
| 450 | FR4 | FGGGTKLEIK |

Fig. 26H

Clone 53.5 - VL amino acid sequence - CDRs in bold and underlined

```
1         10        20        30        40        50
DIQLTQSPSFLSASVGDRVTITCRASSGVNYIAWYQQKPGKAPKLWIYFT

60        70        80        90        100
SNLAPGVPSRFSGSGSGNEYTLTISSLQPEDFATYYCQQFTSSPYTFGGG

TKLEIK    (SEQ ID NO: 50)
```

| SEQ ID NO | Region | Sequence |
|---|---|---|
| | | Light Chain |
| 451 | FR1 | DIQLTQSPSFLSASVGDRVTITCRAS |
| 452 | CDR1 | SGVNY |
| 453 | FR2 | IAWYQQKPGKAPKLWIY |
| 454 | CDR2 | FTS |
| 455 | FR3 | NLAPGVPSRFSGSGSGNEYTLTISSLQPEDFATYYC |
| 456 | CDR3 | QQFTSSPYT |
| 457 | FR4 | FGGGTKLEIK |

Fig. 26I

Clone 53.6 - VL amino acid sequence - CDRs in bold and underlined

```
1         10        20        30        40        50
DIQLTQSPSFLSASVGDRVTITCRASSGVNYIYWYQQKPGKAPKLWIYFT

60        70        80        90        100
STLAPGVPSRFSGSGSGNEYTLTISSLQPEDFATYYCQQFTSSPYTFGGG
```

TKLEIK  (SEQ ID NO: 51)

| SEQ ID NO | Region | Sequence |
|---|---|---|
| Light Chain ||| 
| 458 | FR1 | DIQLTQSPSFLSASVGDRVTITCRAS |
| 459 | CDR1 | SGVNY |
| 460 | FR2 | IYWYQQKPGKAPKLWIY |
| 461 | CDR2 | FTS |
| 462 | FR3 | TLAPGVPSRFSGSGSGNEYTLTISSLQPEDFATYYC |
| 463 | CDR3 | QQFTSSPYT |
| 464 | FR4 | FGGGTKLEIK |

Fig. 26J

Clone 53.7 - VL amino acid sequence - CDRs in bold and underlined

```
1         10        20        30        40        50
DIQLTQSPSFLSASVGDRVTITCRASSGVNYIYWYQQKPGKAPKLWIYFT

60        70        80        90        100
SNLQPGVPSRFSGSGSGNEYTLTISSLQPEDFATYYCQQFTSSPYTFGGG

TKLEIK    (SEQ ID NO: 52)
```

| SEQ ID NO | Region | Sequence |
|---|---|---|
| Light Chain ||| 
| 465 | FR1 | DIQLTQSPSFLSASVGDRVTITCRAS |
| 466 | CDR1 | SGVNY |
| 467 | FR2 | IYWYQQKPGKAPKLWIY |
| 468 | CDR2 | FTS |
| 469 | FR3 | NLQPGVPSRFSGSGSGNEYTLTISSLQPEDFATYYC |
| 470 | CDR3 | QQFTSSPYT |
| 471 | FR4 | FGGGTKLEIK |

Fig. 26K

Clone 53.8 - VL amino acid sequence - CDRs in bold and underlined

```
1         10        20        30        40        50
DIQLTQSPSFLSASVGDRVTITCRASSGVNYIYWYQQKPGKAPKLWIYFT

60        70        80        90        100
SNLASGVPSRFSGSGSGNEYTLTISSLQPEDFATYYCQQFTSSPYTFGGG

TKLEIK    (SEQ ID NO: 53)
```

| SEQ ID NO | Region | Sequence |
|---|---|---|
| Light Chain ||| 
| 472 | FR1 | DIQLTQSPSFLSASVGDRVTITCRAS |
| 473 | CDR1 | SGVNY |
| 474 | FR2 | IYWYQQKPGKAPKLWIY |
| 475 | CDR2 | FTS |
| 476 | FR3 | NLASGVPSRFSGSGSGNEYTLTISSLQPEDFATYYC |
| 477 | CDR3 | QQFTSSPYT |
| 478 | FR4 | FGGGTKLEIK |

Fig. 26L

Clone 53.9 - VL amino acid sequence - CDRs in bold and underlined

```
1         10        20        30        40        50
DIQLTQSPSFLSASVGDRVTITCRASSGVNYIYWYQQKPGKAPKLWIYFT

60        70        80        90        100
SNLAPGVPSRFSGSGSGNEYTLTISSLQPEDFATYYCQQFTSSPYTFGQG
```

TKLEIK  (SEQ ID NO: 54)

| SEQ ID NO | Region | Sequence |
|---|---|---|
| Light Chain | | |
| 479 | FR1 | DIQLTQSPSFLSASVGDRVTITCRAS |
| 480 | CDR1 | SGVNY |
| 481 | FR2 | IYWYQQKPGKAPKLWIY |
| 482 | CDR2 | FTS |
| 483 | FR3 | NLAPGVPSRFSGSGSGNEYTLTISSLQPEDFATYYC |
| 484 | CDR3 | QQFTSSPYT |
| 485 | FR4 | FGQGTKLEIK |

Fig. 26M

Clone 53.7 - VH amino acid sequence - CDRs in bold and underlined

```
1         10        20        30        40        50
EVQLLESGGGLVQPGGSLKLSCAASGFTFTSYAMSWVRQTPGKRLEWVAT 60        70        80        90        100
ISHGGTYTYYPDSVKGRFTISRDNSKNTLYLQMSSLRSEDTAMYYCARHP

110       120
IYSGNYQGYFDYWGQGTTLTVSS      (SEQ ID NO: 63)
```

| SEQ ID NO | Region | Sequence |
|---|---|---|
| Heavy Chain | | |
| 486 | FR1 | EVQLLESGGGLVQPGGSLKLSCAAS |
| 487 | CDR1 | GFTFTSYA |
| 488 | FR2 | MSWVRQTPGKRLEWVAT |
| 489 | CDR2 | ISHGGTYT |
| 490 | FR3 | YYPDSVKGRFTISRDNSKNTLYLQMSSLRSEDTAMYYC |
| 491 | CDR3 | ARHPIYSGNYQGYFDY |
| 492 | FR4 | WGQGTTLTVSS |

Fig. 26N

Clone 53.8 - VH amino acid sequence - CDRs in bold and underlined

```
1         10        20        30        40        50
EVQLLESGGGLVQPGGSLKLSCAASGFTFTSYAMSWVRQAPGKGLEWVAT 60        70        80        90        100
ISHGGTYTYYPDSVKGRFTISRDNSKNTLYLQMSSLRAEDTAVYYCARHP

110       120
IYSGNYQGYFDYWGQGTLVTVSS     (SEQ ID NO: 64)
```

| SEQ ID NO | Region | Sequence |
|---|---|---|
| Heavy Chain ||| 
| 493 | FR1 | EVQLLESGGGLVQPGGSLKLSCAAS |
| 494 | CDR1 | GFTFTSYA |
| 495 | FR2 | MSWVRQAPGKGLEWVAT |
| 496 | CDR2 | ISHGGTYT |
| 497 | FR3 | YYPDSVKGRFTISRDNSKNTLYLQMSSLRAEDTAVYYC |
| 498 | CDR3 | ARHPIYSGNYQGYFDY |
| 499 | FR4 | WGQGTLVTVSS |

Fig. 26O

Clone 53.9 - VH amino acid sequence - CDRs in bold and underlined

```
1         10        20        30        40        50
EVQLLESGGGLVQPGGSLKLSCAASGFTFTSYAMSWVRQTPGKRLEWVAT 60        70        80        90        100
ISHGGTYTYYPESVKGRFTISRDSKNTLYLQMSSLRSEDTAVYYCARHP

110       120
IYSGNYQGYFDYWGQGTTLTVSS     (SEQ ID NO: 65)
```

| SEQ ID NO | Region | Sequence |
|---|---|---|
| Heavy Chain | | |
| 500 | FR1 | EVQLLESGGGLVQPGGSLKLSCAAS |
| 501 | CDR1 | GFTFTSYA |
| 502 | FR2 | MSWVRQTPGKRLEWVAT |
| 503 | CDR2 | ISHGGTYT |
| 504 | FR3 | YYPESVKGRFTISRDSKNTLYLQMSSLRSEDTAVYYC |
| 505 | CDR3 | ARHPIYSGNYQGYFDY |
| 506 | FR4 | WGQGTTLTVSS |

Fig. 26P

Clone 53.10 - VH amino acid sequence - CDRs in bold and underlined

```
1         10        20        30        40        50
EVQLLESGGGLVQPGGSLKLSCAASGFTFTSYAMSWVRQAPGKGLEWVAT 60        70        80        90        100
ISHGGTYTYYPESVKGRFTISRDQSKNTLYLQMSSLRAEDTAVYYCARHP

110       120
IYSGNYQGYFDYWGQGTLVTVSS    (SEQ ID NO: 66)
```

| SEQ ID NO | Region | Sequence |
|---|---|---|
| Heavy Chain ||| 
| 507 | FR1 | EVQLLESGGGLVQPGGSLKLSCAAS |
| 508 | CDR1 | GFTFTSYA |
| 509 | FR2 | MSWVRQAPGKGLEWVAT |
| 510 | CDR2 | ISHGGTYT |
| 511 | FR3 | YYPESVKGRFTISRDQSKNTLYLQMSSLRAEDTAVYYC |
| 512 | CDR3 | ARHPIYSGNYQGYFDY |
| 513 | FR4 | WGQGTLVTVSS |

Fig. 26Q

Clone 53.10 – VL amino acid sequence – CDRs in bold and underlined

```
1         10        20        30        40        50
DIQLTQSPAIMSASVGDRVTMSCRASSGVNYIYWYQQKPGASPKLWIYFT

60        70        80        90        100
SNLAPGVPARFSGSGSGNSYSLTISSMQGEDAATYYCQQFTSSPYTFGGG
```

TKLEIK    (SEQ ID NO: 67)

| SEQ ID NO | Region | Sequence |
|---|---|---|
| Light Chain ||| 
| 514 | FR1 | DIQLTQSPAIMSASVGDRVTMSCRAS |
| 515 | CDR1 | SGVNY |
| 516 | FR2 | IYWYQQKPGASPKLWIY |
| 517 | CDR2 | FTS |
| 518 | FR3 | NLAPGVPARFSGSGSGNSYSLTISSMQGEDAATYYC |
| 519 | CDR3 | QQFTSSPYT |
| 520 | FR4 | FGGGTKLEIK |

Fig. 26R

Clone 53.11 - VL amino acid sequence - CDRs in bold and underlined

```
1         10        20        30        40        50
DIQLTQSPAILSASVGDRVTISCRASSGVNYIYWYQQKPGQSPKLWIYFT

60        70        80        90        100
SNLAPGVPARFSGSGSGNSYSLTISSMQGEDAATYYCQQFTSSPYTFGGG

TKLEIK    (SEQ ID NO: 68)
```

| SEQ ID NO | Region | Sequence |
|---|---|---|
| Light Chain ||| 
| 521 | FR1 | DIQLTQSPAILSASVGDRVTISCRAS |
| 522 | CDR1 | SGVNY |
| 523 | FR2 | IYWYQQKPGQSPKLWIY |
| 524 | CDR2 | FTS |
| 525 | FR3 | NLAPGVPARFSGSGSGNSYSLTISSMQGEDAATYYC |
| 526 | CDR3 | QQFTSSPYT |
| 527 | FR4 | FGGGTKLEIK |

Fig. 26S

Clone 53.12 - VL amino acid sequence - CDRs in bold and underlined

```
1         10        20        30        40        50
DIQLTQSPAILSASVGDRVTMSCRASSGVNYIYWYQQKPGASPKLWIYFT

60        70        80        90        100
SNLAPGVPARFSGSGSGNSYSLTISSMQGEDAATYYCQQFTSSPYTFGGG
```

TKLEIK    (SEQ ID NO: 69)

| SEQ ID NO | Region | Sequence |
|---|---|---|
| Light Chain ||| 
| 528 | FR1 | DIQLTQSPAILSASVGDRVTMSCRAS |
| 529 | CDR1 | SGVNY |
| 530 | FR2 | IYWYQQKPGASPKLWIY |
| 531 | CDR2 | FTS |
| 532 | FR3 | NLAPGVPARFSGSGSGNSYSLTISSMQGEDAATYYC |
| 533 | CDR3 | QQFTSSPYT |
| 534 | FR4 | FGGGTKLEIK |

Fig. 26T

Clone 53.13 - VL amino acid sequence - CDRs in bold and underlined

```
1         10        20        30        40        50
DIQLTQSPAILSASVGDRVTISCRASSGVNYIYWYQQKPGQSPKLWIYFT

60        70        80        90        100
SNLAPGVPARFSGSGSGNSYSLTISSMQGEDAATYYCQQFTSSPYTFGGG
```

TKLEIK    (SEQ ID NO: 70)

| SEQ ID NO | Region | Sequence |
|---|---|---|
| Light Chain | | |
| 535 | FR1 | DIQLTQSPAILSASVGDRVTISCRAS |
| 536 | CDR1 | SGVNY |
| 537 | FR2 | IYWYQQKPGQSPKLWIY |
| 538 | CDR2 | FTS |
| 539 | FR3 | NLAPGVPARFSGSGSGNSYSLTISSMQGEDAATYYC |
| 540 | CDR3 | QQFTSSPYT |
| 541 | FR4 | FGGGTKLEIK |

Fig. 26U

Clone 82.0 - VH amino acid sequence - CDRs in bold and underlined

```
1         10        20        30        40        50
EVKLEESGPEVVRPGVSVKISCKGSGYTFTDYAMHWVKQSHAKSLEWIGV 60        70        80        90       100
ISTYNGNTKYNQKFKGKATMTVDKSSSTAYMELARLTSEDSAIYYCARFL

110
SLRYFDVWGAGTTVTVSS     (SEQ ID NO: 55)
```

Clone 82.0 - VL amino acid sequence - CDRs in bold and underlined

```
1         10        20        30        40        50
DIVLTQSPAILSAPPGEKVTMTCRASSSVIYMYWYQQKPGSSPKPWIYAT 60        70        80        90       100
SKLASGVPVRFSGSGSGTSYSLTISRVEAEDVATYYCQQWSSEPLTFGAG

TKLELK    (SEQ ID NO: 56)
```

| SEQ ID NO | Region | Sequence |
|---|---|---|
| Heavy Chain | | |
| 542 | FR1 | EVKLEESGPEVVRPGVSVKISCKGS |
| 543 | CDR1 | GYTFTDYA |
| 544 | FR2 | MHWVKQSHAKSLEWIGV |
| 545 | CDR2 | ISTYNGNT |
| 546 | FR3 | KYNQKFKGKATMTVDKSSSTAYMELARLTSEDSAIYYC |
| 547 | CDR3 | ARFLSLRYFDV |
| 548 | FR4 | WGAGTTVTVSS |
| Light Chain | | |
| 549 | FR1 | DIVLTQSPAILSAPPGEKVTMTCRAS |
| 550 | CDR1 | SSVIY |
| 551 | FR2 | MYWYQQKPGSSPKPWIY |
| 552 | CDR2 | ATS |
| 553 | FR3 | KLASGVPVRFSGSGSGTSYSLTISRVEAEDVATYYC |
| 554 | CDR3 | QQWSSEPLT |
| 555 | FR4 | FGAGTKLELK |

Fig. 27A

Clone 82.1 - VH amino acid sequence - CDRs in bold and underlined

```
1         10        20        30        40        50
QVKLVQSGAEVKKPGASVKVSCKASGYTFTDYAMHWVRQAPGQRLEWIGW 60        70        80        90        100
ISTYNGNTKYSQKFQGRATMTVDKSASTAYMELSSLRSEDTAVYYCARFL

110
SLRYFDVWGKGTTVTVSS      (SEQ ID NO: 57)
```

Clone 82.1 - VL amino acid sequence - CDRs in bold and underlined

```
1         10        20        30        40        50
DIQLTQSPSFLSASVGDRVTITCRASSSVIYLAWYQQKPGKAPKPWIYAT

60        70        80        90        100
STLQSGVPSRFSGSGSGTEYTLTISSLQPEDFATYYCQQWSSEPLTFGGG

TKVEIK    (SEQ ID NO: 58)
```

| SEQ ID NO | Region | Sequence |
|---|---|---|
| Heavy Chain | | |
| 556 | FR1 | QVKLVQSGAEVKKPGASVKVSCKAS |
| 557 | CDR1 | GYTFTDYA |
| 558 | FR2 | MHWVRQAPGQRLEWIGW |
| 559 | CDR2 | ISTYNGNT |
| 560 | FR3 | KYSQKFQGRATMTVDKSASTAYMELSSLRSEDTAVYYC |
| 561 | CDR3 | ARFLSLRYFDV |
| 562 | FR4 | WGKGTTVTVSS |
| Light Chain | | |
| 563 | FR1 | DIQLTQSPSFLSASVGDRVTITCRAS |
| 564 | CDR1 | SSVIY |
| 565 | FR2 | LAWYQQKPGKAPKPWIY |
| 566 | CDR2 | ATS |
| 567 | FR3 | TLQSGVPSRFSGSGSGTEYTLTISSLQPEDFATYYC |
| 568 | CDR3 | QQWSSEPLT |
| 569 | FR4 | FGGGTKVEIK |

Fig. 27B

Clone 82.2 - VH amino acid sequence - CDRs in bold and underlined

```
1         10        20        30        40        50
QVKLVQSGAEVKKPGASVKVSCKGSGYTFTDYAMHWVRQAPGQRLEWIGV 60        70        80        90        100
ISTYNGNTKYNQKFQGRATMTVDKSASTAYMELSSLRSEDTAIYYCARFL

110
SLRYFDVWGAGTTVTVSS    (SEQ ID NO: 59)
```

Clone 82.2 - VL amino acid sequence - CDRs in bold and underlined

```
1         10        20        30        40        50
DIQLTQSPSFLSASVGDRVTITCRASSSVIYMYWYQQKPGKAPKPWIYAT 60        70        80        90        100
SKLASGVPSRFSGSGSGTEYTLTISSLQPEDFATYYCQQWSSEPLTFGAG

TKVEIK    (SEQ ID NO: 60)
```

| SEQ ID NO | Region | Sequence |
|---|---|---|
| Heavy Chain ||| 
| 570 | FR1 | QVKLVQSGAEVKKPGASVKVSCKGS |
| 571 | CDR1 | GYTFTDYA |
| 572 | FR2 | MHWVRQAPGQRLEWIGV |
| 573 | CDR2 | ISTYNGNT |
| 574 | FR3 | KYNQKFQGRATMTVDKSASTAYMELSSLRSEDTAIYYC |
| 575 | CDR3 | ARFLSLRYFDV |
| 576 | FR4 | WGAGTTVTVSS |
| Light Chain |||
| 577 | FR1 | DIQLTQSPSFLSASVGDRVTITCRAS |
| 578 | CDR1 | SSVIY |
| 579 | FR2 | MYWYQQKPGKAPKPWIY |
| 580 | CDR2 | ATS |
| 581 | FR3 | KLASGVPSRFSGSGSGTEYTLTISSLQPEDFATYYC |
| 582 | CDR3 | QQWSSEPLT |
| 583 | FR4 | FGAGTKVEIK |

Fig. 27C

Clone 82.3 - VH amino acid sequence - CDRs in bold and underlined

```
1         10        20        30        40        50
QVKLVQSGPEVKVPGASVKVSCKGSGYTFTDYAMHWVRQAPGQSLEWIGV 60        70        80        90        100
ISTYNGNTKYNQKFQGRATMTVDKSASTAYMELSRLSEDTAIYYCARFL

110
SLRYFDVWGAGTTVTVSS       (SEQ ID NO: 61)
```

Clone 82.3 - VL amino acid sequence - CDRs in bold and underlined

```
1         10        20        30        40        50
DIQLTQSPSFLSASPGDRVTITCRASSSVIYMYWYQQKPGSAPKPWIYAT 60        70        80        90        100
SKLASGVPVRFSGSGSGTSYTLTISRLQAEDFATYYCQQWSSEPLTFGAG

TKVEIK    (SEQ ID NO: 62)
```

| SEQ ID NO | Region | Sequence |
|---|---|---|
| Heavy Chain | | |
| 584 | FR1 | QVKLVQSGPEVKVPGASVKVSCKGS |
| 585 | CDR1 | GYTFTDYA |
| 586 | FR2 | MHWVRQAPGQSLEWIGV |
| 587 | CDR2 | ISTYNGNT |
| 588 | FR3 | KYNQKFQGRATMTVDKSASTAYMELSRLSEDTAIYYC |
| 589 | CDR3 | ARFLSLRYFDV |
| 590 | FR4 | WGAGTTVTVSS |
| Light Chain | | |
| 591 | FR1 | DIQLTQSPSFLSASPGDRVTITCRAS |
| 592 | CDR1 | SSVIY |
| 593 | FR2 | MYWYQQKPGSAPKPWIY |
| 594 | CDR2 | ATS |
| 595 | FR3 | KLASGVPVRFSGSGSGTSYTLTISRLQAEDFATYYC |
| 596 | CDR3 | QQWSSEPLT |
| 597 | FR4 | FGAGTKVEIK |

Fig. 27D

| SEQ ID NO | Antibody | Sequence |
|---|---|---|
| 598 | 12.0 VH | 5'GAGGTGCAGCTGGAAGAGTCCGGCGGAGGCCTGGTGCAGCCCAAGGGCAGCCTGAAGCTGAGCTGTGCCGCCAGCGGCATCAGCTTCAACGACGCCGCCATGAACTGGATCCGGCAGGCCCCTGGCGAGGGCCTGGAATGGGTGGCCCGGATCAGAAGCAAGATCAACGACTACGGCACCCACTACGCCGCCAGCGTGAAGGACCGGTTCACCATCAGCCGGGACGACAGCCAGAATATCCTGTTCCTGCAGATGAACAACCTGAAAACCGAGGACACCGGCATGTACTACTGCGTGATCGACGGCTACGGCAGCCTGGCCTACTGGGGCCAGGGAACCCTGGTGACAGTGTCCGCC3' |
| 599 | 12.0 VL | 5'GACATCGTGCTGACCCAGAGCCCCGCCATCATGAGCAGCAGCCCTGGCGAGAAAGTGACCATGACCTGCCGGGCCAGCAGCAGCGTGATCAGCAGCTACCTGCACTGGTATCAGCAGCGGAGCGGCGCCAGCCCCAAGCTGTGGATCTACAGCACCAGCAGCCTGGCCAGCGGCGTGCCAGCCAGATTTTCTGGCAGCGGCAGCGGCACCTCCTTCAGCCTGACCATCAGCAGCGTGGAAGCCGAGGACGCCGCCACCTACTACTGCCAGCAGTACAGCGGCTACCCCCTGACCTTCGGAGCCGGCACCAAGCTGGAACTGAAG3' |
| 600 | 12.1 VH | 5'GAGGTGCAGCTGGTGGAAAGCGGCGGAGGACTGGTGCAGCCTGGCGGCAGCCTGAAGCTGTCTTGTGCCGCCAGCGGCATCAGCTTCAACGACGCCGCCATGCACTGGGTGCGCCAGGCCTCTGGCAAGGGCCTGGAATGGGTGGCCCGGATCAGAAGCAAGATCAACGACTACGGCACCGCCTACGCCGCCAGCGTGAAGGGCAGATTCACCATCAGCCGGGACGACAGCCAGAACACCCTGTACCTGCAGATGAACAGCCTGAAAACCGAGGACACCGCCGTGTACTACTGCGTGATCGACGGCTACGGCAGCCTGGCCTACTGGGGCCAGGGAACCCTGGTGACAGTGTCCAGC3' |
| 601 | 12.1 VL | 5'GAGATCGTGCTGACCCAGAGCCCCGCCACCCTGTCTCTGAGCCCTGGCGAGAGAGCCACCCTGAGCTGCAGAGCCAGCAGCAGCGTGATCAGCAGCTACCTGGCCTGGTATCAGCAGAAGCCCGGCCAGGCCCCCAGACTGTGGATCTACAGCACCAGCAACCGGGCCACCGGCATCCCCGCCAGATTTTCTGGCAGCGGCAGCGGCACCGACTTCACCCTGACCATCAGCAGCCTGGAACCCGAGGACTTCGCCACCTACTACTGCCAGCAGTACAGCGGCTACCCCCTGACCTTCGGCGGAGGCACCAAGGTGGAAATCAAG3' |

Fig. 28A

| SEQ ID NO | Antibody | Sequence |
|---|---|---|
| 602 | 12.2 VH | 5'GAGGTGCAGCTGGTGGAAAGCGGCGGAGGACTGGTGCAGCCTGGC GGCAGCCTGAAGCTGTCTTGTGCCGCCAGCGGCATCAGCTTCAACGA CGCCGCCATGAACTGGATCCGGCAGGCCAGCGGCAAGGGCCTGGAAT GGGTGGCCCGGATCAGAAGCAAGATCAACGACTACGGCACCCACTAC GCCGCCAGCGTGAAGGGCCGGTTCACCATCAGCCGGGACGACAGCCA GAACACCCTGTACCTGCAGATGAACAGCCTGAAAACCGAGGACACCG CCATGTACTACTGCGTGATCGACGGCTACGGCAGCCTGGCCTACTGG GGCCAGGGAACCCTGGTGACAGTGTCCAGC3' |
| 603 | 12.2 VL | 5'GAGATCGTGCTGACCCAGAGCCCCGCCACCCTGTCTCTGAGCCCT GGCGAGAGAGCCACCCTGAGCTGCAGAGCCAGCAGCAGCGTGATCAG CAGCTACCTGCACTGGTATCAGCAGAAGCCCGGCCAGGCCCCCAGAC TGTGGATCTACAGCACCAGCAGCCTGGCCAGCGGCATCCCCGCCAGA TTTTCTGGCAGCGGCAGCGGCACCGACTTCACCCTGACCATCAGCTC CCTGGAACCCGAGGACTTCGCCACCTACTACTGCCAGCAGTACAGCG GCTACCCCCTGACCTTCGGAGCCGGCACCAAGGTGGAAATCAAG3' |
| 604 | 12.3 VH | 5'GAGGTGCAGCTGGTGGAAAGCGGCGGAGGCCTGGTGCAGCCCAAG GGCAGCCTGAAGCTGAGCTGTGCCGCCAGCGGCATCAGCTTCAACGA CGCCGCCATGAACTGGATCCGGCAGGCCAGCGGCAAGGGCCTGGAAT GGGTGGCCCGGATCAGAAGCAAGATCAACGACTACGGCACCCACTAC GCCGCCAGCGTGAAGGACCGGTTCACCATCAGCCGGGACGACAGCCA GAACATCCTGTACCTGCAGATGAACAACCTGAAAACCGAGGACACCG CCATGTACTACTGCGTGATCGACGGCTACGGCAGCCTGGCCTACTGG GGCCAGGGAACCCTGGTGACAGTGTCCAGC3' |
| 605 | 12.3 VL | 5'GAGATCGTGCTGACCCAGAGCCCCGCCATCCTGAGCAGCTCTCCA GGCGAGAGAGCCACCCTGAGCTGCAGAGCCAGCAGCAGCGTGATCAG CAGCTACCTGCACTGGTATCAGCAGAAGCCTGGCGCCGCTCCCCGGC TGTGGATCTACAGCACAAGCAGCCTGGCCAGCGGCATCCCCGCCAGA TTTTCTGGCAGCGGCAGCGGCACCAGCTTCACCCTGACCATCAGCAG CCTGGAAGCCGAGGACTTCGCCACCTACTACTGCCAGCAGTACAGCG GCTACCCCCTGACCTTCGGAGCCGGCACCAAGGTGGAAATCAAG3' |

Fig. 28B

| SEQ ID NO | Antibody | Sequence |
|---|---|---|
| 606 | 135.0 VH | 5'GAAGTGAAGCTGGAAGAGTCCGGCGGAGGCCTGGTGAAACCTGGCGGCA GCCTGAAGCTGAGCTGCGCCGCCAGCGGCTTCACCTTCACCAGCTACGCCC TGAGCTGGGTGCGCCAGACCCCCGAGAAGAGACTGGAATGGGTGGCCACCA TCAGCCACGGCGGCAGCTACACCTACTACCCCGACAGCGTGAAGGGCCGGT TCACCATCAGCAGAGACAACGCCAAGAACACCCTGAACCTGCAGATGAGCA GCCTGCGGAGCGAGGACACCGCCATGTACTACTGCGCCAGGCACCCCTTCT ACAGCGGCAACTACCAGGGCTACTTCGACTACTGGGGCCAGGGCACCCTGC TGACCGTGTCCTCT3' |
| 607 | 135.0 VL | 5'GACATCGTGCTGACCCAGAGCCCCGCCATCATGAGCGCCAGCCTGGGCG AGAAAGTGACCATGAACTGCCGGGCCAACAGCGGCGTGAACTACATGTACT GGTATCAGCAGAAGTCCGACGCCAGCCCCAAGCTGTGGATCTACTTCACCA GCAACCTGGCCCCTGGCGTGCCCGCCAGATTTTCTGGCAGCGGCAGCGGCA ACAGCTACAGCCTGACCATCAGCAGCATGGAAGGCGAGGACGCCGCCACCT ACTACTGCCAGCAGTTCACCAGCAGCCCCTACACCTTCGGCGGAGGCACCA AGCTGGAAATCAAG3' |
| 608 | 135.1 VH | 5'GAGGTGCAGCTGGAAGAGTCCGGCGGAGGACTGGTGCAGCCTGGCGGCA GCCTGAGACTGTCTTGCGCCGCCAGCGGCTTCACCTTCACCAGCTACGCCA TGAGCTGGGTGCGCCAGGCCCCTGGCAAGGGACTGGAATGGGTGGCCGTGA TCAGCCACGGCGGCAGCTACACCTACTACGCCGACAGCGTGAAGGGCCGGT TCACCATCAGCCGGGACAACAGCAAGAACACCCTGTACCTGCAGATGAACA GCCTGCGGGCCGAGGACACCGCCGTGTACTACTGCGCCAGACACCCCTTCT ACAGCGGCAACTACCAGGGCTACTTCGACTACTGGGGCCAGGGCACCCTGG TGACAGTGTCCAGC3' |
| 609 | 135.1 VL | 5'GACATCCAGCTGACCCAGAGCCCCAGCTTCCTGAGCGCCAGCGTGGGCG ACAGAGTGACCATCACCTGTCGGGCCAGCAGCGGCGTGAACTACCTGGCCT GGTATCAGCAGAAGCCCGGCAAGGCCCCCAAGCTGTGGATCTACTTCACCA GCACCCTGCAGAGCGGCGTGCCCAGCAGATTTCTGGCAGCGGCAGCGGCA ACGAGTACACCCTGACCATCAGCAGCCTGCAGTTCGAGGACTTCGCCACCT ACTACTGCCAGCAGTTCACCAGCAGCCCCTACACCTTCGGCCAGGGCACCA AGCTGGAAATCAAG3' |

Fig. 28C

| SEQ ID NO | Antibody | Sequence |
|---|---|---|
| 610 | 135.2 VH | 5'GAGGTGCAGCTGGAAGAGTCCGGCGGAGGACTGGTGCAGCCTGGCGGCA GCCTGAGACTGTCTTGCGCCGCCAGCGGCTTCACCTTCACCAGCTACGCCC TGAGCTGGGTGCGCCAGGCCCCTGGCAAAGGACTGGAATGGGTGGCCACCA TCAGCCACGGCGGCAGCTACACCTACTACCCCGACAGCGTGAAGGGCCGGT TCACCATCAGCAGAGACAACAGCAAGAACACCCTGTACCTGCAGATGAACA GCCTGCGGGCCGAGGACACCGCCGTGTACTACTGCGCCAGACACCCCTTCT ACAGCGGCAACTACCAGGGCTACTTCGACTACGGGGCCAGGGCACCCTGG TGACAGTGTCCAGC3' |
| 611 | 135.2 VL | 5'GACATCCAGCTGACCCAGAGCCCCAGCTTCCTGAGCGCCAGCGTGGGCG ACAGAGTGACCATCACCTGTCGGGCCAACAGCGGCGTGAACTACATGTACT GGTATCAGCAGAAGCCCGGCAAGGCCCCCAAGCTGTGGATCTACTTCACCA GCAACCTGGCCCCTGGCGTGCCCAGCAGATTTCTGGCAGCGGCAGCGGCA ACGAGTACACCCTGACCATCAGCAGCCTGCAGTTCGAGGACTTCGCCACCT ACTACTGCCAGCAGTTCACCAGCAGCCCCTACACCTTCGGCGGAGGCACCA AGCTGGAAATCAAG3' |
| 612 | 135.3 VH | 5'GAGGTGCAGCTGCTGGAAAGCGGCGGAGGACTGGTGCAGCCTGGCGGCA GCCTGAGACTGTCTTGCGCCGCCAGCGGCTTCACCTTCACCAGCTACGCCC TGAGCTGGGTGCGCCAGACCCCCGAGAAGAGACTGGAATGGGTGGCCACCA TCAGCCACGGCGGCAGCTACACCTACTACCCCGACAGCGTGAAGGGCCGGT TCACCATCAGCAGAGACAACAGCAAGAACACCCTGAACCTGCAGATGAGCA GCCTGCGGGCCGAGGACACCGCCGTGTACTACTGCGCCAGGCACCCCTTCT ACAGCGGCAACTACCAGGGCTACTTCGACTACGGGGCCAGGGCACCCTGG TGACAGTGTCCAGC3' |
| 613 | 135.3 VL | 5'GACATCCAGCTGACCCAGAGCCCCAGCTTCCTGAGCGCCAGCGTGGGCG ACAGAGTGACCATCACCTGTCGGGCCAACAGCGGCGTGAACTACATGTACT GGTATCAGCAGAAGCCCGACGCCGCTCCCAAGCTGTGGATCTACTTCACCA GCAACCTGGCCCCTGGCGTGCCCAGCAGATTTCTGGCAGCGGCAGCGGCA ACAGCTACACCCTGACCATCAGCAGCCTGCAGTTCGAGGACTTCGCCACCT ACTACTGCCAGCAGTTCACCAGCAGCCCCTACACCTTCGGCGGAGGCACCA AGCTGGAAATCAAG3' |

Fig. 28D

| SEQ ID NO | Antibody | Sequence |
|---|---|---|
| 614 | 4.0 VH | 5'GAAGTGCAGCTGGAGGAGTCAGGGGGAGGCTTAGTGAAGCCTGGAGGGT CCCTAAAACTCTCCTGTGCAGCCTCTGGATTCACTTTCAGTAATTATGCCA TGTCTTGGGTTCGCCAGACTCCGGATAAGCGGCTGGAGTGGGTCGCAACCA TTAGTAATGGTGGTAGTTACACCTACTATCCAGACACTGTGAAGGGTCGCT TCACCATCTCCAGAGACAATGCCAAGAACACCCTGTCTCTGCAAATGAGCA GTCTGAGGTCTGAGGACACGGCCATGTATTACTGTTCAAGACCCTCTGAGA GATCCCATTACTACGCTACTAGCCAGTTTGCTTACTG GGGCCAAGGGACTCTGGTCACTGTCTCTGCA3' |
| 615 | 4.0 VL | 5'GACATTGTGCTGACCCAGTCTCCAGGAATCATGTCTGCATCTCCAGGGG AGAAAGTCACCATGACCTGCAGTGCCAGCTCAAGTGTAAGTTACATGCATT GGTACCAGCAGAAGTCAGGCACCTCCCCCAAAAGATGGATTTATGACACAT CCAAACTGGCTTCTGGAGTCCCTGCTCGCTTCAGTGGCAGTGGGTCTGGGA CCTCTTACTCTCTCACAATCAGCAGCATGGAGGCTGAAGATGCTGCCACTT ATTACTGCCAGCAGTGGAGTAGTAGCCCGCTCACGTTCGGTGCTGGGACCA AGGTGGAGCTGAAA3' |
| 616 | 4.1 VH | 5'GAGGTGCAGCTGCTGGAAAGCGGCGGAGGACTGGTGCAGCCTGGCGGCA GCCTGAGACTGTCTTGCGCCGCCAGCGGCTTCACCTTCAGCAACTACGCCA TGAGCTGGGTGCGCCAGGCCCCTGGCAAGGGACTGGAATGGGTGGCCGTGA TCAGCAACGGCGGCAGCTACACCTACTACGCCGACAGCGTGAAGGGCCGGT TCACCATCAGCCGGGACAACAGCAAGAACACCCTGTACCTGCAGATGAACA GCCTGCGGGCCGAGGACACCGCCGTGTACTACTGCAGCCGGCCCAGCGAGC GGAGCCACTACTACGCCACCAGCCAGTTCGCCTACTGGGGCCAGGGCACCC TGGTGACAGTGTCCAGC3' |
| 617 | 4.1 VL | 5'GAGATCGTGCTGACCCAGAGCCCCGCCACCCTGTCTCTGAGCCCTGGCG AGAGAGCCACCCTGAGCTGCAGAGCCAGCAGCAGCGTGTCCTACCTGGCCT GGTATCAGCAGAAGCCCGGCCAGGCCCCCAGACGGTGGATCTACGACACCA GCAACCGGGCCACCGGCATCCCCGCCAGATTTTCTGGCAGCGGCAGCGGCA CCGACTACACCCTGACCATCAGCAGCCTGGAACCCGAGGACTTCGCCGTGT ACTACTGCCAGCAGTGGTCCAGCAGCCCCCTGACCTTCGGCGGAGGCACCA AGGTGGAAATCAAG3' |

Fig. 28E

| SEQ ID NO | Antibody | Sequence |
|---|---|---|
| 618 | 4.2 VH | 5'GAGGTGCAGCTGCTGGAAAGCGGCGGAGGACTGGTGCAGCCTGGCGGCA GCCTGAGACTGTCTTGCGCCGCCAGCGGCTTCACCTTCAGCAACTACGCCA TGAGCTGGGTGCGCCAGGCCCCTGGCAAGGGACTGGAATGGGTGGCCACCA TCAGCAACGGCGGCAGCTACACCTACTACCCCGACAGCGTGAAGGGCCGGT TCACCATCAGCCGGGACAACAGCAAGAACACCCTGTACCTGCAGATGAACA GCCTGCGGGCCGAGGACACCGCCGTGTACTACTGCAGCGGCCCAGCGAGC GGAGCCACTACTACGCCACCAGCCAGTTCGCCTACTGGGGCCAGGGCACCC TGGTGACAGTGTCCAGC3' |
| 619 | 4.2 VL | 5'GAGATCGTGCTGACCCAGAGCCCCGCCACCCTGTCTCTGAGCCCTGGCG AGAGAGCCACCCTGAGCTGTAGCGCCAGCAGCAGCGTGTCCTACATGCACT GGTATCAGCAGAAGCCCGGCACCGCCCCAGACGGTGGATCTACGATACCA GCAAGCTGGCCAGCGGCATCCCCGCCAGATTTTCTGGCAGCGGCAGCGGCA CCGACTACACCCTGACCATCAGCAGCCTGGAACCCGAGGACTTCGCCACCT ACTACTGCCAGCAGTGGTCCAGCAGCCCCCTGACCTTCGGAGCCGGCACCA AGGTGGAAATCAAG3' |
| 620 | 4.3 VH | 5'GAGGTGCAGCTGGAAGAGTCCGGCGGAGGACTGGTGCAGCCTGGCGGCA GCCTGAGACTGTCTTGCGCCGCCAGCGGCTTCACCTTCAGCAACTACGCCA TGAGCTGGGTGCGCCAGACCCCCGACAAGCGGCTGGAATGGGTGGCCACCA TCAGCAACGGCGGCAGCTACACCTACTACCCCGACAGCGTGAAGGGCCGGT TCACCATCAGCCGGGACAACAGCAAGAACACCCTGTACCTGCAGATGAGCA GCCTGCGGGCCGAGGACACCGCCGTGTACTACTGCAGCGGCCCAGCGAGC GGAGCCACTACTACGCCACCAGCCAGTTCGCCTACTGGGGCCAGGGCACCC TGGTGACAGTGTCCAGC3' |
| 621 | 4.3 VL | 5'GAGATCGTGCTGACCCAGAGCCCCGCCATCCTGAGCCTGTCTCCAGGCG AGAGAGCCACCCTGAGCTGCAGCGCCAGCAGCAGCGTGTCCTACATGCACT GGTATCAGCAGAAGCCCGGCCAGGCCCCAGACGGTGGATCTACGATACCA GCAAGCTGGCCAGCGGCATCCCCGCCAGATTTTCTGGCAGCGGCAGCGGCA CCAGCTACACCCTGACCATCAGCAGCCTGGAAGCCGAGGACTTCGCCACCT ACTACTGCCAGCAGTGGTCCAGCAGCCCCCTGACCTTCGGAGCCGGCACCA AGGTGGAAATCAAG3' |

Fig. 28F

| SEQ ID NO | Antibody | Sequence |
|---|---|---|
| 622 | 4.4 VH | 5'GAGGTGCAGCTGGTGGAAAGCGGCGGAGGCGTGAAGAAGCCTGGCGGCAGCCTGAAGCTGAGCTGTGCCGCCAGCGGCTTCACCTTCAGCAACTACGCCATGAGCTGGGTCCGACAGACCCCCGGCAAGGGCCTGGAATGGGTGGCCACCATCAGCAACGGCGGCAGCTACACCTACTACCCCGACAGCTTCCAGGGCCGGTTCACCATCAGCCGGGACAACGCCAAGAGCACCCTGAGCCTGCAGATGTCCAGCCTGAAGTCCGAGGACACCGCCATGTACTACTGCAGCCGGCCCAGCGAGCGGAGCCACTACTACGCCACCAGCCAGTTCGCCTACTGGGGCCAGGGCACCCTGGTCACCGTGTCTGCT3' |
| 623 | 4.5 VH | 5'GAGGTGCAGCTGGTGGAAAGCGGCGGAGGCGTGAAGAAGCCTGGCGGCAGCCTGAAGCTGAGCTGTGCCGCCAGCGGCTTCACCTTCAGCAACTACGCCATGAGCTGGGTCCGACAGACCCCCGGCAAGGGCCTGGAATGGGTGGCCACCATCAGCAACGGCGGCAGCTACACCTACTACCCCGACAGCTTCCAGGGCCGGTTCACCATCAGCCGGGACAACGCCAACAGCACCCTGAGCCTGCAGATGTCCAGCCTGAAGGCCGAGGACACCGCCATGTACTACTGCAGCCGGCCCAGCGAGCGGAGCCACTACTACGCCACCAGCCAGTTCGCCTACTGGGGCCAGGGCACCCTGGTCACCGTGTCCTCT3' |
| 624 | 4.6 VH | 5'GAGGTGCAGCTGGTGGAAAGCGGCGGAGGCGTGAAGAAGCCTGGCGGCAGCCTGAAGCTGAGCTGTGCCGCCAGCGGCTTCACCTTCAGCAACTACGCCATGAGCTGGGTCCGACAGACCCCCGGCAAGGGCCTGGAATGGGTGGCCACAATCAGCCAGGGCGGCAGCTACACCTACTACCCCGAGAGCTTCCAGGGCCGGTTCACCATCAGCCGGGACCAGGCCAAGAGCACCCTGAGCCTGCAGATGTCCAGCCTGAAGTCCGAGGACACCGCCATGTACTACTGCAGCCGGCCCAGCGAGCGGAGCCACTACTACGCCACCAGCCAGTTCGCCTACTGGGGCCAGGGCACCCTGGTCACCGTGTCTGCT3' |
| 625 | 4.7 VH | 5'GAGGTGCAGCTGCTGGAAAGCGGCGGAGGACTGGTGCAGCCTGGCGGCAGCCTGAGACTGTCTTGCGCCGCCAGCGGCTTCACCTTCAGCAACTACGCCATGAGCTGGGTGCGCCAGGCCCCTGGCAAGGGACTGGAATGGGTGGCCACCATCAGCCAGGGTGGCAGCTACACCTACTACCCCGACAGCGTGAAGGGCCGGTTCACCATCAGCCGGGACAACAGCAAGAACACCCTGTACCTGCAGATGAACAGCCTGCGGGCCGAGGACACCGCCGTGTACTACTGCAGCCGGCCCAGCGAGCGGAGCCACTACTACGCCACCAGCCAGTTCGCCTACTGGGGCCAGGGCACCCTGGTGACAGTGTCCAGC3' |

Fig. 28G

| SEQ ID NO | Antibody | Sequence |
|---|---|---|
| 626 | 4.8 VH | 5'GAGGTGCAGCTGCTGGAAAGCGGCGGAGGACTGGTGCAGCCTGGCGGCA GCCTGAGACTGTCTTGCGCCGCCAGCGGCTTCACCTTCAGCAACTACGCCA TGAGCTGGGTGCGCCAGGCCCCTGGCAAGGGACTGGAATGGGTGGCCACCA TCAGCAATCTGGGCAGCTACACCTACTACCCCGACAGCGTGAAGGGCCGGT TCACCATCAGCCGGGACAACAGCAAGAACACCCTGTACCTGCAGATGAACA GCCTGCGGGCCGAGGACACCGCCGTGTACTACTGCAGCCGGCCCAGCGAGC GGAGCCACTACTACGCCACCAGCCAGTTCGCCTACTGGGGCCAGGGCACCC TGGTGACAGTGTCCAGC3' |
| 627 | 4.9 VH | 5'GAGGTGCAGCTGCTGGAAAGCGGCGGAGGACTGGTGCAGCCTGGCGGCA GCCTGAGACTGTCTTGCGCCGCCAGCGGCTTCACCTTCAGCAACTACGCCA TGAGCTGGGTGCGCCAGGCCCCTGGCAAGGGACTGGAATGGGTGGCCACCA TCAGCAATTCAGGCAGCTACACCTACTACCCCGACAGCGTGAAGGGCCGGT TCACCATCAGCCGGGACAACAGCAAGAACACCCTGTACCTGCAGATGAACA GCCTGCGGGCCGAGGACACCGCCGTGTACTACTGCAGCCGGCCCAGCGAGC GGAGCCACTACTACGCCACCAGCCAGTTCGCCTACTGGGGCCAGGGCACCC TGGTGACAGTGTCCAGC3' |
| 628 | 4.10 VH | 5'GAGGTGCAGCTGCTGGAAAGCGGCGGAGGACTGGTGCAGCCTGGCGGCA GCCTGAGACTGTCTTGCGCCGCCAGCGGCTTCACCTTCAGCAACTACGCCA TGAGCTGGGTGCGCCAGGCCCCTGGCAAGGGACTGGAATGGGTGGCCACCA TCAGCGACGGTGGCAGCTACACCTACTACCCCGACAGCGTGAAGGGCCGGT TCACCATCAGCCGGGACAACAGCAAGAACACCCTGTACCTGCAGATGAACA GCCTGCGGGCCGAGGACACCGCCGTGTACTACTGCAGCCGGCCCAGCGAGC GGAGCCACTACTACGCCACCAGCCAGTTCGCCTACTGGGGCCAGGGCACCC TGGTGACAGTGTCCAGC3' |
| 629 | 4.11 VH | 5'GAGGTGCAGCTGCTGGAAAGCGGCGGAGGACTGGTGCAGCCTGGCGGCA GCCTGAGACTGTCTTGCGCCGCCAGCGGCTTCACCTTCAGCAACTACGCCA TGAGCTGGGTGCGCCAGGCCCCTGGCAAGGGACTGGAATGGGTGGCCACCA TCAGCAATGTCGGCAGCTACACCTACTACCCCGACAGCGTGAAGGGCCGGT TCACCATCAGCCGGGACAACAGCAAGAACACCCTGTACCTGCAGATGAACA GCCTGCGGGCCGAGGACACCGCCGTGTACTACTGCAGCCGGCCCAGCGAGC GGAGCCACTACTACGCCACCAGCCAGTTCGCCTACTGGGGCCAGGGCACCC TGGTGACAGTGTCCAGC3' |

Fig. 28H

| SEQ ID NO | Antibody | Sequence |
|---|---|---|
| 630 | 4.4 VL | 5'GACATCGTGCTGACCCAGAGCCCCGGCAGCCTGTCTGCCAGCGTGGGCG ACAGAGTGACCATGACCTGCAGCGCCAGCAGCAGCGTGTCCTACATGCACT GGTATCAGCAGAAGCCCGGCACCAGCCCCAAGCGGTGGATCTACGACACCA GCAAGCTGGCCAGCGGCGTGCCCGCCAGATTTTCTGGCAGCGGCAGCGGCA CCAGCTACAGCCTGACCATCAGCAGCCTGCAGCCCGAGGACGCCGCCACCT ACTACTGCCAGCAGTGGTCCAGCAGCCCCCTGACCTTTGGAGCCGGCACCA AGGTGGAACTGAAG3' |
| 631 | 4.5 VL | 5'GACATCGTGCTGACCCAGAGCCCCAGCAGCCTGAGCGCCAGCGTGGGCG ACAGAGTGACCATCACCTGTAGCGCCAGCAGCAGCGTGTCCTACATGCACT GGTATCAGCAGAAGCCCGGCACCAGCCCCAAGCGGTGGATCTACGACACCA GCAAGCTGGCCAGCGGCGTGCCCGCCAGATTTTCTGGCAGCGGCAGCGGCA CCAGCTACAGCCTGACCATCAGCAGCCTGCAGCCCGAGGACGCCGCCACCT ACTACTGCCAGCAGTGGTCCAGCAGCCCCCTGACCTTTGGAGCCGGCACCA AGGTGGAAATCAAG3' |
| 632 | 4.6 VL | 5'GACATCGTGCTGACCCAGAGCCCCAGCAGCCTGAGCGCCAGCGTGGGCG ACAGAGTGACCATCACCTGTAGCGCCAGCAGCAGCGTGTCCTACATGCACT GGTATCAGCAGAAGCCCGGCCAGTCCCCCAAGCGGTGGATCTACGACACCA GCAAGCTGGCCAGCGGCGTGCCCGCCAGATTTTCTGGCAGCGGCAGCGGCA CCAGCTACAGCCTGACCATCAGCAGCCTGCAGCCCGAGGACGCCGCCACCT ACTACTGCCAGCAGTGGTCCAGCAGCCCCCTGACCTTTGGAGCCGGCACCA AGGTGGAAATCAAG3' |
| 633 | 4.7 VL | 5'GACATCCAGCTGACCCAGAGCCCCGGCAGCCTGTCTGCCAGCGTGGGCG ACAGAGTGACCATGACCTGCAGCGCCAGCAGCAGCGTGTCCTACATGCACT GGTATCAGCAGAAGCCCGGCACCAGCCCCAAGCGGTGGATCTACGACACCA GCAAGCTGGCCAGCGGCGTGCCCGCCAGATTTTCTGGCAGCGGCAGCGGCA CCAGCTACAGCCTGACCATCAGCAGCCTGCAGCCCGAGGACGCCGCCACCT ACTACTGCCAGCAGTGGTCCAGCAGCCCCCTGACCTTTGGAGCCGGCACCA AGGTGGAACTGAAG3' |

Fig. 28I

| SEQ ID NO | Antibody | Sequence |
|---|---|---|
| 634 | 53.0 VH | 5'GAGGTTCAGCTGGAGGAGTCAGGGGGAGGCTTAGTGAAGCCTGGAGGGT CCCTGAAACTCTCCTGTGCAGCCTCTGGATTCACTTTCACTAGCTATGCCA TGTCTTGGGTTCGCCAGACTCCGGAGAAGAGGCTGGAGTGGGTCGCAACCA TTAGTCATGGTGGTACTTACACCTACTATCCAGACAGTGTGAAGGGACGAT TCACCATCTCCAGAGACAATGCCAAGAACACCCTGTACCTGCAAATGAGCA GTCTGAGGTCTGAGGACACGGCCATGTATTACTGTGCAAGACATCCTATCT ACTCTGGTAACTACCAGGGATACTTTGACTACTGG GGCCAAGGCACCACTCTCACAGTCTCCTCA3' |
| 635 | 53.0 VL | 5'GACATTGTGCTCACCCAGTCTCCAGCAATCATGTCTGCATCTCTAGGGG AGAAGGTCACCATGAGCTGCAGGGCCAGCTCAGGTGTAAATTACATATACT GGTACCAGCAGAAGTCAGATGCCTCCCCCAAACTATGGATTTATTTCACAT CCAACCTGGCTCCTGGAGTCCCAGCTCGCTTCAGTGGCAGTGGGTCTGGGA ACTCTTATTCTCTCACAATCAGCAGCATGGAGGGTGAAGATGCTGCCACTT ATTACTGCCAGCAGTTTACTAGTTCCCCGTACACGTTCGGAGGGGGGACCA AGCTGGAAATAAAA3' |
| 636 | 53.1 VH | 5'GAGGTGCAGCTGCTGGAAAGCGGCGGAGGACTGGTGCAGCCTGGCGGCA GCCTGAGACTGTCTTGCGCCGCCAGCGGCTTCACCTTCACCAGCTACGCCA TGAGCTGGGTGCGCCAGGCCCCTGGCAAGGGACTGGAATGGGTGGCCGTGA TCAGCCACGGCGGCACCTACACCTACTACGCCGACAGCGTGAAGGGCCGGT TCACCATCAGCCGGGACAACGCCAAGAACACCCTGTACCTGCAGATGAACA GCCTGCGGGCCGAGGACACCGCCGTGTACTACTGCGCCAGACACCCCATCT ACAGCGGCAACTACCAGGGCTACTTCGACTACTGGGGCCAGGGCACCCTGG TGACAGTGTCCAGC3' |
| 637 | 53.1 VL | 5'GACATCCAGCTGACCCAGAGCCCCAGCTTCCTGAGCGCCAGCGTGGGCG ACAGAGTGACCATCACCTGTCGGGCCAGCAGCGGCGTGAACTACCTGGCCT GGTATCAGCAGAAGCCCGGCAAGGCCCCCAAGCTGTGGATCTACTTCACCA GCACCCTGCAGAGCGGCGTGCCCAGCAGATTTTCTGGCAGCGGCAGCGGCA ACGAGTACACCCTGACCATCAGCAGCCTGCAGCCCGAGGACTTCGCCACCT ACTACTGCCAGCAGTTCACCAGCAGCCCCTACACCTTCGGCCAGGGCACCA AGCTGGAAATCAAG3' |

Fig. 28J

| SEQ ID NO | Antibody | Sequence |
|---|---|---|
| 638 | 53.2 VH | 5'GAGGTGCAGCTGCTGGAAAGCGGCGGAGGACTGGTGCAGCCTGGCGGCA GCCTGAGACTGTCTTGCGCCGCCAGCGGCTTCACCTTCACCAGCTACGCCA TGAGCTGGGTGCGCCAGGCCCCTGGCAAGGGACTGGAATGGGTGGCCACAA TCAGCCACGGCGGCACCTACACCTACTACCCCGACAGCGTGAAGGGCCGGT TCACCATCAGCCGGGACAACGCCAAGAACACCCTGTACCTGCAGATGAACA GCCTGCGGGCCGAGGACACCGCCATGTACTACTGCGCCAGACACCCCATCT ACAGCGGCAACTACCAGGGCTACTTCGACTACTGGGGCCAGGGCACCCTGG TGACAGTGTCCAGC3' |
| 639 | 53.2 VL | 5'GACATCCAGCTGACCCAGAGCCCCAGCTTCCTGAGCGCCAGCGTGGGCG ACAGAGTGACCATCACCTGTCGGGCCAGCAGCGGCGTGAACTACATCTACT GGTATCAGCAGAAGCCCGGCAAGGCCCCCAAGCTGTGGATCTACTTCACCA GCAACCTGGCCCCTGGCGTGCCCAGCAGATTTCTGGCAGCGGCAGCGGCA ACGAGTACACCCTGACCATCAGCAGCCTGCAGCCCGAGGACTTCGCCACCT ACTACTGCCAGCAGTTCACCAGCAGCCCCTACACCTTCGGCGGAGGCACCA AGCTGGAAATCAAG3' |
| 640 | 53.3 VH | 5'GAGGTGCAGCTGGAAGAGTCCGGCGGAGGACTGGTGCAGCCTGGCGGCA GCCTGAGACTGTCTTGCGCCGCCAGCGGCTTCACCTTCACCAGCTACGCCA TGAGCTGGGTGCGCCAGACCCCCGAGAAGCGGCTGGAATGGGTGGCCACAA TCAGCCACGGCGGCACCTACACCTACTACCCCGACAGCGTGAAGGGCCGGT TCACCATCAGCCGGGACAACGCCAAGAACACCCTGTACCTGCAGATGAACA GCCTGCGGGCCGAGGACACCGCCATGTACTACTGCGCCAGGCACCCCATCT ACAGCGGCAACTACCAGGGCTACTTCGACTACTGGGGCCAGGGCACCACCG TGACCGTGTCCTCT3' |
| 641 | 53.3 VL | 5'GACATCCAGCTGACCCAGAGCCCCAGCTTCCTGAGCGCCAGCGTGGGCG ACAGAGTGACCATCACCTGTCGGGCCAGCAGCGGCGTGAACTACATCTACT GGTATCAGCAGAAGCCCGACGCCGCTCCCAAGCTGTGGATCTACTTCACCA GCAACCTGGCCCCTGGCGTGCCCAGCAGATTTCTGGCAGCGGCAGCGGCA ACAGCTACACCCTGACCATCAGCAGCCTGCAGCCCGAGGACTTCGCCACCT ACTACTGCCAGCAGTTCACCAGCAGCCCCTACACCTTCGGCGGAGGCACCA AGCTGGAAATCAAG3' |

Fig. 28K

| SEQ ID NO | Antibody | Sequence |
|---|---|---|
| 642 | 53.4 VH | 5'GAGGTGCAGCTGCTGGAAAGCGGCGGAGGACTGGTGCAGCCTGGCGGCA GCCTGAGACTGTCTTGCGCCGCCAGCGGCTTCACCTTCACCAGCTACGCCA TGAGCTGGGTGCGCCAGGCCCCTGGCAAGGGACTGGAATGGGTGGCCGTAA TCAGCCACGGCGGCACCTACACCTACTACCCCGACAGCGTGAAGGGCCGGT TCACCATCAGCCGGGACAACGCCAAGAACACCCTGTACCTGCAGATGAACA GCCTGCGGGCCGAGGACACCGCCATGTACTACTGCGCCAGACACCCCATCT ACAGCGGCAACTACCAGGGCTACTTCGACTACTGGGGCCAGGGCACCCTGG TGACAGTGTCCAGC3' |
| 643 | 53.5 VH | 5'GAGGTGCAGCTGCTGGAAAGCGGCGGAGGACTGGTGCAGCCTGGCGGCA GCCTGAGACTGTCTTGCGCCGCCAGCGGCTTCACCTTCACCAGCTACGCCA TGAGCTGGGTGCGCCAGGCCCCTGGCAAGGGACTGGAATGGGTGGCCACAA TCAGCCACGGCGGCACCTACACCTACTACGCCGACAGCGTGAAGGGCCGGT TCACCATCAGCCGGGACAACGCCAAGAACACCCTGTACCTGCAGATGAACA GCCTGCGGGCCGAGGACACCGCCATGTACTACTGCGCCAGACACCCCATCT ACAGCGGCAACTACCAGGGCTACTTCGACTACTGGGGCCAGGGCACCCTGG TGACAGTGTCCAGC3' |
| 644 | 53.6 VH | 5'GAGGTGCAGCTGCTGGAAAGCGGCGGAGGACTGGTGCAGCCTGGCGGCA GCCTGAGACTGTCTTGCGCCGCCAGCGGCTTCACCTTCACCAGCTACGCCA TGAGCTGGGTGCGCCAGGCCCCTGGCAAGGGACTGGAATGGGTGGCCACAA TCAGCCACGGCGGCACCTACACCTACTACCCCGACAGCGTGAAGGGCCGGT TCACCATCAGCCGGGACAACGCCAAGAACACCCTGTACCTGCAGGTGAACA GCCTGCGGGCCGAGGACACCGCCATGTACTACTGCGCCAGACACCCCATCT ACAGCGGCAACTACCAGGGCTACTTCGACTACTGGGGCCAGGGCACCCTGG TGACAGTGTCCAGC3' |

Fig. 28L

| SEQ ID NO | Antibody | Sequence |
|---|---|---|
| 645 | 53.4 VL | 5'GACATCCAGCTGACCCAGAGCCCCAGCTTCCTGAGCGCCAGCGTGGGCGACAGAGTGACCATCACCTGTCGGGCCAGCAGCGGCGTGAACTACCTCTACTGGTATCAGCAGAAGCCCGGCAAGGCCCCCAAGCTGTGGATCTACTTCACCAGCAACCTGGCCCCTGGCGTGCCCAGCAGATTTTCTGGCAGCGGCAGCGGCACGAGTACACCCTGACCATCAGCAGCCTGCAGCCCGAGGACTTCGCCACCTACTACTGCCAGCAGTTCACCAGCAGCCCTACACCTTCGGCGGAGGCACCAAGCTGGAAATCAAG3' |
| 646 | 53.5 VL | 5'GACATCCAGCTGACCCAGAGCCCCAGCTTCCTGAGCGCCAGCGTGGGCGACAGAGTGACCATCACCTGTCGGGCCAGCAGCGGCGTGAACTACATCGCCTGGTATCAGCAGAAGCCCGGCAAGGCCCCCAAGCTGTGGATCTACTTCACCAGCAACCTGGCCCCTGGCGTGCCCAGCAGATTTTCTGGCAGCGGCAGCGGCACGAGTACACCCTGACCATCAGCAGCCTGCAGCCCGAGGACTTCGCCACCTACTACTGCCAGCAGTTCACCAGCAGCCCTACACCTTCGGCGGAGGCACCAAGCTGGAAATCAAG3' |
| 647 | 53.6 VL | 5'GACATCCAGCTGACCCAGAGCCCCAGCTTCCTGAGCGCCAGCGTGGGCGACAGAGTGACCATCACCTGTCGGGCCAGCAGCGGCGTGAACTACATCTACTGGTATCAGCAGAAGCCCGGCAAGGCCCCCAAGCTGTGGATCTACTTCACCAGCACCCTGGCCCCTGGCGTGCCCAGCAGATTTTCTGGCAGCGGCAGCGGCACGAGTACACCCTGACCATCAGCAGCCTGCAGCCCGAGGACTTCGCCACCTACTACTGCCAGCAGTTCACCAGCAGCCCTACACCTTCGGCGGAGGCACCAAGCTGGAAATCAAG3' |
| 648 | 53.7 VL | 5'GACATCCAGCTGACCCAGAGCCCCAGCTTCCTGAGCGCCAGCGTGGGCGACAGAGTGACCATCACCTGTCGGGCCAGCAGCGGCGTGAACTACATCTACTGGTATCAGCAGAAGCCCGGCAAGGCCCCCAAGCTGTGGATCTACTTCACCAGCAACCTGCAACCTGGCGTGCCCAGCAGATTTTCTGGCAGCGGCAGCGGCACGAGTACACCCTGACCATCAGCAGCCTGCAGCCCGAGGACTTCGCCACCTACTACTGCCAGCAGTTCACCAGCAGCCCTACACCTTCGGCGGAGGCACCAAGCTGGAAATCAAG3' |

Fig. 28M

| SEQ ID NO | Antibody | Sequence |
|---|---|---|
| 649 | 53.8 VL | 5'GACATCCAGCTGACCCAGAGCCCCAGCTTCCTGAGCGCCAGCGTGGGCG<br>ACAGAGTGACCATCACCTGTCGGGCCAGCAGCGGCGTGAACTACATCTACT<br>GGTATCAGCAGAAGCCCGGCAAGGCCCCCAAGCTGTGGATCTACTTCACCA<br>GCAACCTGGCCTCTGGCGTGCCCAGCAGATTTTCTGGCAGCGGCAGCGGCA<br>ACGAGTACACCCTGACCATCAGCAGCCTGCAGCCCGAGGACTTCGCCACCT<br>ACTACTGCCAGCAGTTCACCAGCAGCCCCTACACCTTCGGCGGAGGCACCA<br>AGCTGGAAATCAAG3' |
| 650 | 53.9 VL | 5'GACATCCAGCTGACCCAGAGCCCCAGCTTCCTGAGCGCCAGCGTGGGCG<br>ACAGAGTGACCATCACCTGTCGGGCCAGCAGCGGCGTGAACTACATCTACT<br>GGTATCAGCAGAAGCCCGGCAAGGCCCCCAAGCTGTGGATCTACTTCACCA<br>GCAACCTGGCCCCTGGCGTGCCCAGCAGATTTTCTGGCAGCGGCAGCGGCA<br>ACGAGTACACCCTGACCATCAGCAGCCTGCAGCCCGAGGACTTCGCCACCT<br>ACTACTGCCAGCAGTTCACCAGCAGCCCCTACACCTTCGGCCAAGGCACCA<br>AGCTGGAAATCAAG3' |

Fig. 28N

| SEQ ID NO | Antibody | Sequence |
|---|---|---|
| 651 | 82.0 VH | 5'GAAGTGAAGCTGGAAGAGTCCGGCCCTGAGGTGGTGCGCCCTGGCGTGT CCGTGAAGATCAGCTGCAAGGGCAGCGGCTACACCTTCACCGACTACGCCA TGCACTGGGTGAAACAGAGCCACGCCAAGAGCCTGGAATGGATCGGCGTGA TCAGCACCTACAACGGCAACACCAAGTACAACCAGAAGTTCAAGGGCAAGG CCACCATGACCGTGGACAAGAGCAGCAGCACCGCCTACATGGAACTGGCCC GGCTGACCAGCGAGGACAGCGCCATCTACTACTGCGCCCGGTTCCTGAGCC TGCGGTACTTCGATGTGTGGGGAGCCGGCACCACCGTGACCGTGTCTAGC3 ' |
| 652 | 82.0 VL | 5'GACATCGTGCTGACCCAGAGCCCCGCCATCCTGTCTGCCCCCCCTGGCG AGAAAGTGACCATGACCTGCCGGGCCAGCAGCAGCGTGATCTACATGTACT GGTATCAGCAGAAGCCCGGCAGCAGCCCCAAGCCCTGGATCTACGCCACCA GCAAGCTGGCCAGCGGCGTGCCAGTGCGGTTTAGCGGCAGCGGCTCTGGCA CCAGCTACAGCCTGACCATCAGCCGGGTGGAAGCCGAGGACGTGGCCACCT ACTACTGCCAGCAGTGGTCCAGCGAGCCCCTGACCTTCGGAGCCGGCACCA AGCTGGAACTGAAG3' |
| 653 | 82.1 VH | 5'CAGGTGAAACTGGTGCAGTCTGGCGCCGAAGTGAAGAAACCTGGCGCCA GCGTGAAGGTGTCCTGCAAGGCCAGCGGCTACACCTTCACCGACTACGCCA TGCACTGGGTGCGCCAGGCCCCTGGCCAGAGACTGGAATGGATCGGCTGGA TCAGCACCTACAACGGCAACACCAAGTACAGCCAGAAGTTCCAGGGCAGAG CCACCATGACCGTGGACAAGAGCGCCAGCACCGCCTACATGGAACTGAGCA GCCTGCGGAGCGAGGACACCGCCGTGTACTACTGCGCCCGGTTCCTGAGCC TGCGGTACTTCGACGTGTGGGGCAAGGGCACCACCGTGACCGTGTCCAGC3 ' |
| 654 | 82.1 VL | 5'GACATCCAGCTGACCCAGAGCCCCAGCTTCCTGAGCGCCAGCGTGGGCG ACAGAGTGACCATCACCTGTCGGGCCAGCAGCAGCGTGATCTACCTGGCCT GGTATCAGCAGAAGCCCGGCAAGGCCCCCAAGCCCTGGATCTACGCCACCA GCACACTGCAGAGCGGCGTGCCCAGCAGATTCAGCGGCAGCGGCTCTGGCA CCGAGTACACCCTGACCATCAGCAGCCTGCAGCCCGAGGACTTCGCCACCT ACTACTGCCAGCAGTGGTCCAGCGAGCCCCTGACCTTCGGCGGAGGCACCA AGGTGGAAATCAAG3' |

Fig. 28O

| SEQ ID NO | Antibody | Sequence |
|---|---|---|
| 655 | 82.2 VH | 5'CAGGTGAAACTGGTGCAGTCTGGCGCCGAAGTGAAGAAACCTGGCGCCA GCGTGAAGGTGTCCTGCAAGGGCAGCGGCTACACCTTCACCGACTACGCCA TGCACTGGGTGCGCCAGGCCCCTGGCCAGAGACTGGAATGGATCGGCGTGA TCAGCACCTACAACGGCAACACCAAGTACAACCAGAAGTTCCAGGGCAGAG CCACCATGACCGTGGACAAGAGCGCCAGCACCGCCTACATGGAACTGAGCA GCCTGCGGAGCGAGGACACCGCCATCTACTACTGCGCCCGGTTCCTGAGCC TGCGGTACTTCGATGTGTGGGGAGCCGGCACCACCGTGACCGTGTCTAGC3' |
| 656 | 82.2 VL | 5'GACATCCAGCTGACCCAGAGCCCCAGCTTCCTGAGCGCCAGCGTGGGCG ACAGAGTGACCATCACCTGTCGGGCCAGCAGCAGCGTGATCTACATGTACT GGTATCAGCAGAAGCCCGGCAAGGCCCCCAAGCCCTGGATCTACGCCACCA GCAAGCTGGCCAGCGGCGTGCCCAGCAGATTTTCTGGCAGCGGCAGCGGCA CCGAGTACACCCTGACCATCAGCAGCCTGCAGCCCGAGGACTTCGCCACCT ACTACTGCCAGCAGTGGTCCAGCGAGCCCCTGACCTTCGGAGCCGGCACCA AGGTGGAAATCAAG3' |
| 657 | 82.3 VH | 5'CAGGTGAAACTGGTGCAGAGCGGCCCTGAAGTGAAGGTGCCAGGCGCCA GCGTGAAGGTGTCCTGCAAGGGCAGCGGCTACACCTTCACCGACTACGCCA TGCACTGGGTGCGCCAGGCCCCTGGCCAGAGCCTGGAATGGATCGGCGTGA TCAGCACCTACAACGGCAACACCAAGTACAACCAGAAGTTCCAGGGCAGAG CCACCATGACCGTGGACAAGAGCGCCAGCACCGCCTACATGGAACTGAGCC GGCTGCGGAGCGAGGACACCGCCATCTACTACTGCGCCCGGTTCCTGAGCC TGCGGTACTTCGATGTGTGGGGAGCCGGCACCACCGTGACCGTGTCTAGC3' |
| 658 | 82.3 VL | 5'GACATCCAGCTGACCCAGAGCCCCAGCTTCCTGAGCGCCAGCCCTGGCG ACAGAGTGACCATCACCTGTCGGGCCAGCAGCAGCGTGATCTACATGTACT GGTATCAGCAGAAGCCCGGCAGCGCCCCCAAGCCCTGGATCTACGCCACAA GCAAGCTGGCCAGCGGCGTGCCCGTGCGGTTTAGCGGCTCTGGCAGCGGCA CCAGCTACACCCTGACCATCAGCCGGCTGCAGGCCGAGGACTTCGCCACCT ACTACTGCCAGCAGTGGTCCAGCGAGCCCCTGACCTTCGGAGCCGGCACCA AGGTGGAAATCAAG3' |

Fig. 28P

NUCLEIC ACIDS ENCODING ANTI-CXCR3 ANTIBODIES

RELATED APPLICATIONS

This application is a division of U.S. application Ser. No. 13/745,377, now U.S. Pat. No. 8,865,870, filed Jan. 18, 2013 which claims the benefit of priority under 35 U.S.C. §119 of United States Provisional Application No. 61/588,936, filed Jan. 20, 2012. Both of the aforementioned applications are incorporated herein by reference in their entirety.

SEQUENCE LISTING

The instant application contains a Sequence Listing which has been submitted in ASCII format via EFS-Web and is hereby incorporated by reference in its entirety.

BACKGROUND

The invention relates to antibodies and methods of using antibodies to treat disorders associated with CXCR3 signaling such as diabetes mellitus type 1 (type I diabetes; T1D).

Diabetes is characterized by chronic hyperglycemia resulting from a lack of insulin action, along with various characteristic metabolic abnormalities. Diabetes can be broadly divided into type I and type II. T1D is characterized by the loss of pancreatic β-cells of the Langerhans' islets, while type II diabetes is characterized by reductions in both insulin secretion and insulin sensitivity (insulin resistance). In the United States, the prevalence of diabetes is about 2 to 4 percent of the population, with type I diabetes (also known as insulin-dependent or IDDM) making up about 7 to 10 percent of all cases.

Type I diabetes is characterized by the failure to produce sufficient insulin to maintain glucose homeostasis. This disorder is believed to be caused by autoimmune-mediated destruction of the pancreatic β-cells. Autoimmunity associated with type I diabetes involves the participation of both B and T autoreactive lymphocytes. Indeed, up to 98% of type I diabetes patients have antibodies against one or more of their own β-cell antigens, including insulin, glutamic acid decarboxylase (GAD), insulinoma antigen-2 and insulinoma antigen-2b (IA-2 and IA-2 β), and heterogeneous islet cell cytoplasmic antigens (ICAs). Although it may not always be determinative, the level of one or more autoantibodies generally correlates with the state of β-cell destruction. Irvine, et al., Diabetes, 26:138-47 (1997); Riley, et al., N. Engl. J. Med., 323:1167-72 (1990). Accordingly, autoantibodies can serve as indicators of the development of autoimmune diabetes and together with metabolic changes can predict the risk of developing diabetes in relatives of T1D patients The development of type I diabetes may be mediated by autoreactive T cells, as evidenced by tissue biopsies obtained near the time of T1D diagnosis that show the islets infiltrated with activated T cells. Bottazzo et al., N. Engl. J. Med., 313:353-60 (1985); Hanninen et al., J. Clin. Invest., 90:1901-10 (1992); Itoh et al., J. Clin. Invest., 92:2313-22 (1993); Imagawa, et al., Diabetes, 50:1269-73 (2001).

Chemokine (C-X-C motif) receptor 3 (CXCR3), also known as G protein-coupled receptor 9 (GPR9), CD183, IP-10 receptor, and Mig receptor, is a chemokine receptor expressed on autoreactive T cells that have been implicated in a range of physiological processes and related disorders, such as T1D. CXCR3 is largely absent from naïve T cells but is upregulated upon activation with antigen and recruits activated cells to sites of tissue inflammation in response to its primary ligands: CXCL9, CXCL10, and CXCL11. β cells have been shown to predominately express CXCL10, with lower levels of CXCL9, in mouse models of T1D (Christen et al The Journal of Immunology, 2003, 171: 6838-6845; Morimoto et al. J Immunol 2004; 173; 7017-7024; Sarkar et al. Diabetes. 2012 February; 61(2):436-46); and in islets from T1D patients having insulitis (Uno et al 2010; Roep et al Clinical and Experimental Immunology, 2003, 159: 338-343; Sarkar et al. Diabetes. 2012 February; 61(2):436-46). In addition, T cells that have infiltrated the pancreas have been shown to express CXCR3 in T1D mice models and type 1 diabetes patient pancreas samples (Christen et al, The Journal of Immunology, 2003, 171: 6838-6845; Van Halteren et al., Diabetologia 48:75-82 (2005); Uno et al 2010; Roep et al., Clinical and Experimental Immunology, 2003, 159: 338-343; Sarkar et al., Diabetes. 2012 February; 61(2): 436-46). Furthermore, knockout mice deficient in CXCR3 demonstrate a significant delay in onset and a reduction in incidence of T1D (Frigerio et al., Nature Medicine 8:1414-1420 (2002)), while overexpression of CXCL10 in the islets of transgenic mice promotes T cell infiltration and accelerates the onset of T1D (Rhode et al., J. Immunol. 175(6): 3516-24 (2005)). Neutralization of CXCL10 by antibody treatment has been shown to be protective (Christen et al., The Journal of Immunology, 2003, 171: 6838-6845).

There are three isoforms of CXCR3, denoted A, B, and Alt., that have been identified in humans (Lasagni et al. J. Exp. Med. 2003 197:1537; Ehlert et al J. Immunol. 2004; 173; 6234-6240), CXCR3-A binds to the CXC chemokines CXCL9 (MIG), CXCL10 (IP-10), and CXCL11 (I-TAC); CXCR3-B also binds to these targets but also binds CXCL4; CXCR3-Alt appears to interact with CXCL11. Although alternative splicing leads to the generation of several protein isoforms of CXCR3, CXCR3-A is the predominant form in vivo as the CXCR3-B and CXCR3-Alt are expressed at much lower levels at the protein levels. Lasagni et al. J. Exp. Med. 2003 197:1537; Ehlert et al J. Immunol. 2004; 173; 6234-6240.

Efforts to disrupt the CXCR3 pathway using small molecule inhibitors of CXCR3 have not proved fully effective. Christen et al., Clin Exp. Immunol. 165: 318-328 (2011). Accordingly, research has focused on antibodies and other methods of disrupting CXCL10, primarily before the onset of diabetes. Morimoto et al., J. Immun. 173: 7017-7024 (2004); Oikawa et al., Rev. Diabet. Stud. 7: 209-224 (2010).

In view of the prevalence of T1D and other disorders in which CXCR3 has been implicated, a need exists for additional methods that target CXCR3 signaling, e.g., to treat or reduce the progression of a disorder such as T1D in a patient.

Disclosed herein are antibodies and methods of using antibodies that are capable of binding to CXCR3. In some embodiments, the antibodies can be used to prevent, treat or reduce the early progression of T1D in a subject by targeting the CXCR3 pathway. The antibodies and methods rely, at least in part, on the surprising result that neutralizing antibodies directed to CXCR3 can prevent onset of T1D in NOD mice when administered prior to disease onset, or can reverse the course of disease when administered in the new-onset stage of T1D in NOD mice. Furthermore, neutralization of CXCR3 activity is not associated with a significant impairment of the normal operation of the patient's immune system, thereby reducing the undesirable side effects of antibody therapy.

Accordingly, in one aspect, disclosed herein are antibodies and antigen binding fragments capable of neutralizing the activity of CXCR3. In certain embodiments, CXCR3 neutralizing antibodies may be characterized by the ability to bind to a peptide selected from residues 1-58, 1-16, or 1-37 of SEQ ID NO:1. In some embodiments, the antibodies comprise all or portions of antibody clones (Cl) designated Cl 12, Cl 135, Cl 82, Cl 53 and/or Cl 4. In certain embodiments, variants of antibodies Cl 12, Cl 135, Cl 82, Cl 53 and/or Cl 4 are provided, including CDR-grafted, humanized, back mutated, and fully human variants of the disclosed antibodies. In particular embodiments, the antibody comprises one or more complementarity determining regions (CDRs), e.g., one or more of heavy chain CDR1, CDR2, and CDR3, and/or one or more of light chain CDR1, CDR2, and CDR3, from clones Cl 12, Cl 135, Cl 82, Cl 53 and/or Cl 4 or any of the variants of clones 4, 12, 53, 82, and 135 disclosed herein. In some embodiments, the antibodies from Cl 12, Cl 135, Cl 82, Cl 53 and/or Cl 4, or the chimeric and humanized versions thereof, exhibit certain beneficial properties, as compared to anti-CXCR3 clones 5H7, 7H5, V44D7, 1C6, and/or 49801. For example, the antibodies disclosed herein can exhibit increased binding affinity as compared to the anti-hCXCR3 clones 5H7, 7H5, V44D7, 1C6, and 49801. For example, the antibody may exhibit 1, 2, 3, 4, 5, or more fold better affinity (or any value in between) over anti-CXCR3 antibodies such as 1C6, e.g., as measured by surface Plasmon resonance (e.g., using a BIA-CORE™ assay). The humanized antibodies disclosed herein also have a predicted reduction in immunogenicity as compared to the mouse anti-hCXCR3 clones 5H7, 7H5, V44D7, 1C6, and 49801. In addition, heavy chain clones 4.7-4.11 disclosed herein have been optimized to remove a deamidation site at positions 58 and 59 (using IMGT numbering) and thereby enhance stability over the initial mouse anti-hCXCR3 heavy chain variable domain (VH) CDR2 sequence.

In another aspect, the present disclosure provides methods of prophylaxis prior to T1D onset, as well as methods of treating or reducing the progression of new onset T1D in a subject by administering an effective amount of a CXCR3 neutralizing antibody. In particular embodiments, the subject is a mammal, such as a human.

In certain embodiments, the subject having new onset T1D is treated by the methods disclosed herein within 6 months of clinical diagnosis. In other embodiments, the subject is treated more than 6 months after clinical diagnosis, wherein the subject retains residual fasting integrated serum C-peptide levels of at least about 0.2 nmol/L.

In some embodiments, subjects may be characterized by elevated fasting blood glucose levels in the absence of exogenous insulin above 120 mg/dL or an abnormally low fasting integrated serum C-peptide level of about 0.033 to 1.0 nmol/L×min during C-peptide stimulation. In particular embodiments the CXCR3 neutralizing antibody is administered at a dose of about 0.03-3.7 mg/kg/dose. In some embodiments, the subject is administered at least one dose of antibody. In certain embodiments, the subject is administered repeat doses of antibody (e.g., at least yearly, quarterly, bimonthly, monthly, biweekly, weekly, or daily). In further embodiments, the methods described above may further comprise the step of administering an immunosuppressant and/or β-cell stimulating agent concurrently or sequentially (before or after) administering the CXCR3 neutralizing antibody.

In various embodiments, the anti-CXCR3 antibodies disclosed herein are administered to treat a condition characterized by abnormal CXCR3 expression. In some embodiments, the anti-CXCR3 antibodies are administered to treat any condition that can benefit from the downregulation and/or neutralization of CXCR3 activity. In some embodiments, the anti-CXCR3 antibodies disclosed herein are administered to treat T1D.

Additional embodiments and advantages of the invention will be set forth in part in the description which follows, and in part will be obvious from the description, or may be learned by practice of the invention. The embodiments and advantages of the invention will be realized and attained by means of the elements and combinations particularly pointed out in the appended claims.

It is to be understood that both the foregoing general description and the following detailed description are exemplary and explanatory only and are not restrictive of the invention, as claimed.

The accompanying drawings, which are incorporated in and constitute a part of this specification, illustrate one (several) embodiment(s) of the invention and together with the description, serve to explain the principles of the invention.

BRIEF DESCRIPTION OF THE DRAWINGS

Figure 17B:
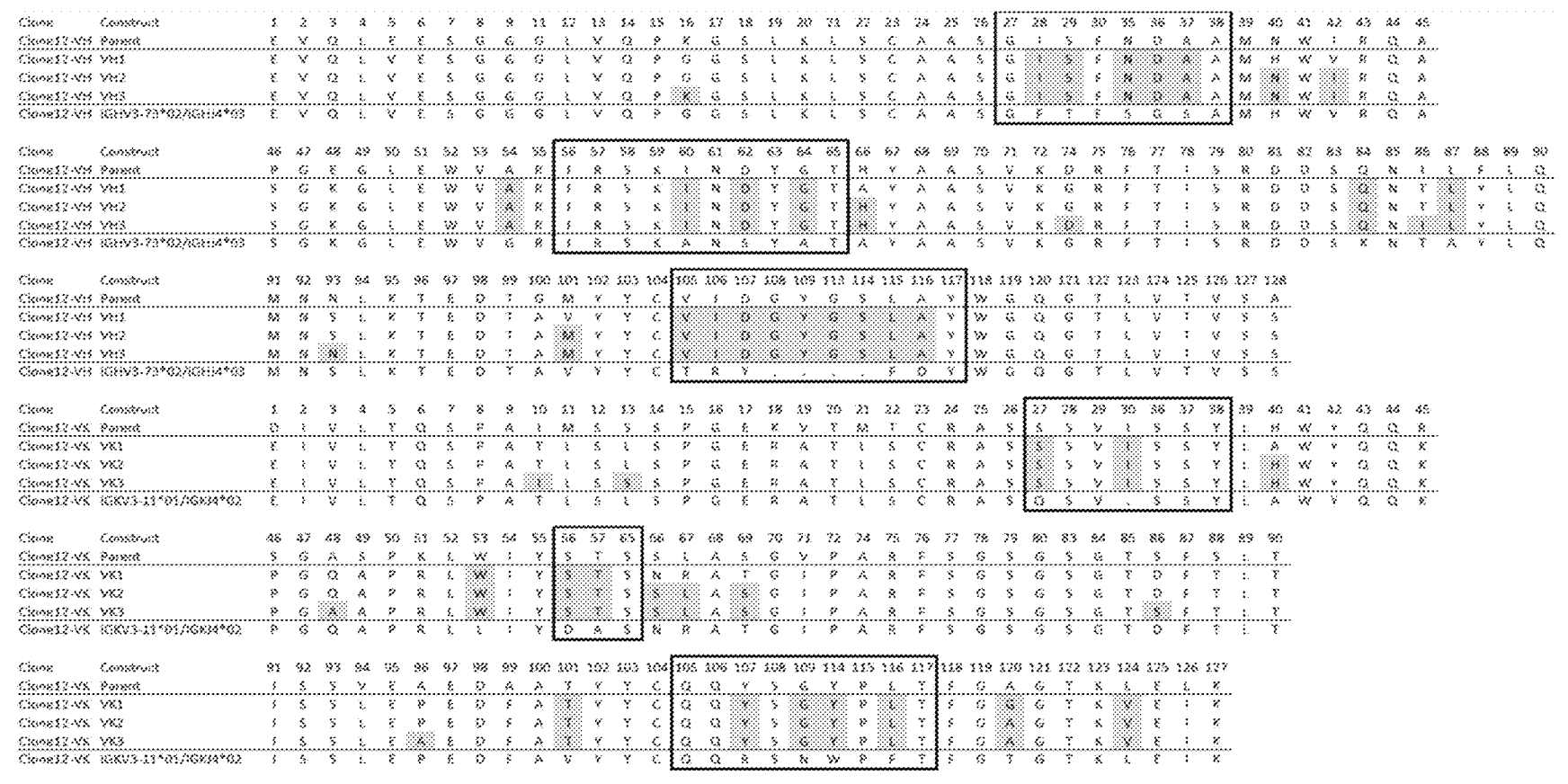
Figure 17D:
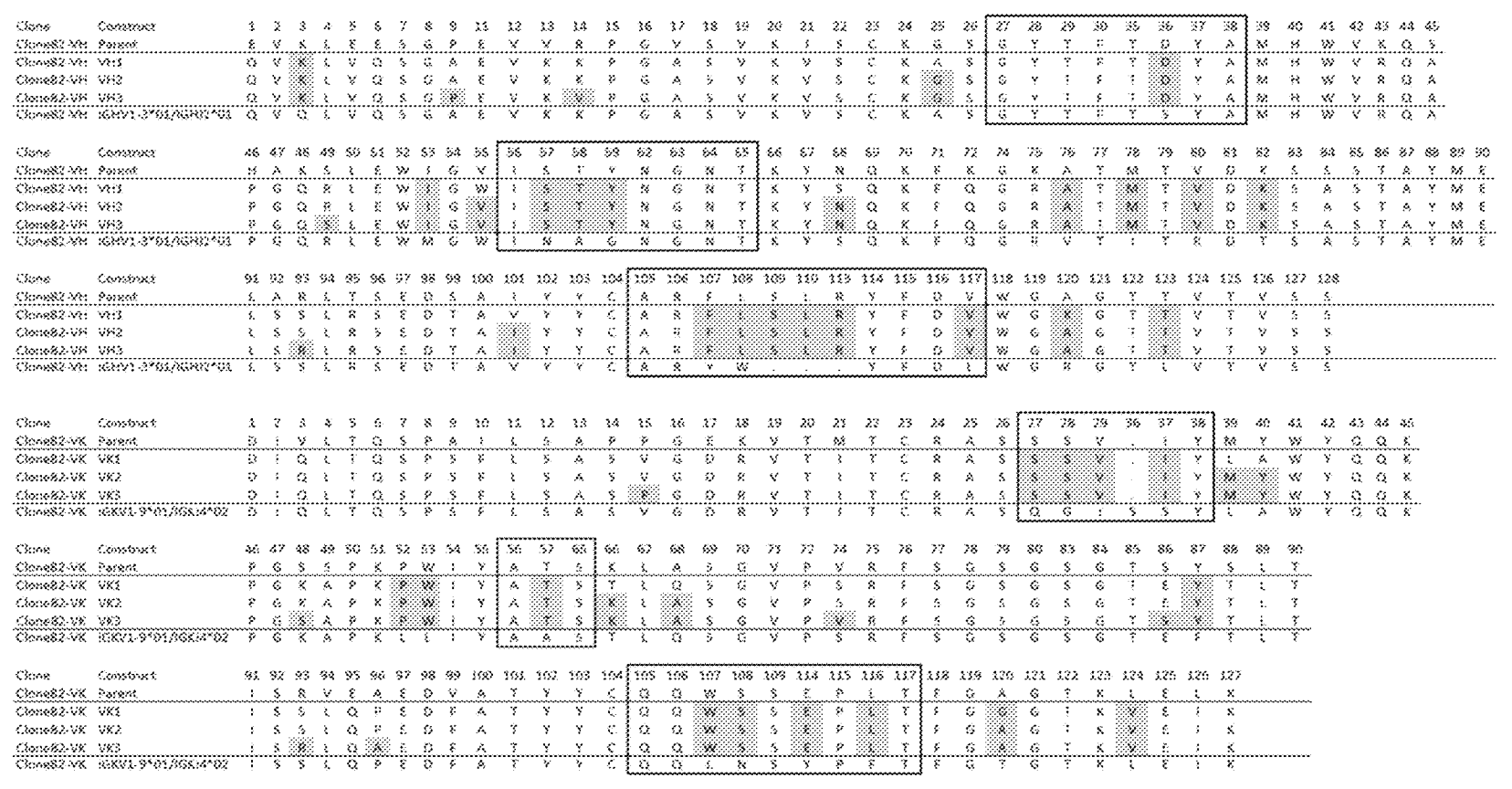
Figure 17E:
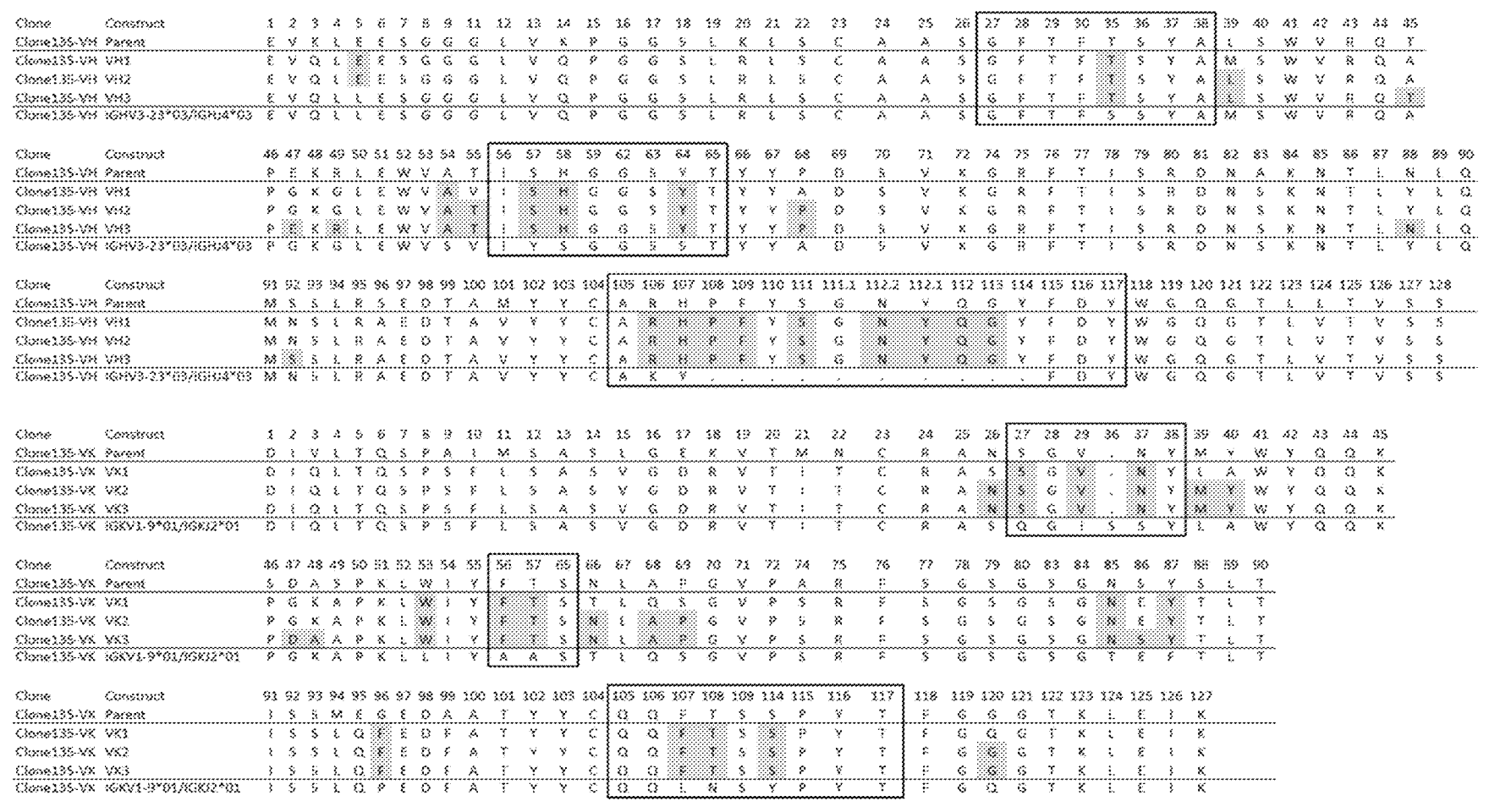

FIG. 17A discloses heavy chain sequences as SEQ ID NOS 18, 20, 22, 24, 29-33, and 659, and light chain sequences as SEQ ID NOS 19, 25, 21, 23, and 660, all respectively, in order of appearance in the alignment. FIG. 17B shows an alignment of the heavy (VH) and light (VK) chain variable domains for clone 12.0 (labeled "parent") and certain humanized variants (labeled VH1-3 and VK 1-3). FIG. 17B discloses heavy chain sequences as SEQ ID NOS 2, 4, 6, 8, and 661, and light chain sequences as SEQ ID NOS 3, 5, 7, 9, and 662, all respectively, in order of appearance in the alignment. FIG. 17C discloses heavy chain sequences as SEQ ID NOS 38, 40, 42, 44, 46-48, and 663, and light chain sequences as SEQ ID NOS 39, 41, 43, 45, 49-54, and 664, all respectively, in order of appearance in the alignment. FIG. 17D shows an alignment of the heavy (VH) and light (VK) chain variable domains for clone 82.0 (labeled "parent") and certain humanized variants (labeled VH1-3 and VK 1-3). FIG. 17D discloses heavy chain sequences as SEQ ID NOS 55, 57, 59, 61, and 665, and light chain sequences as SEQ ID NOS 56, 58, 60, 62, and 666, all respectively, in order of appearance in the alignment. FIG. 17E shows an alignment of the heavy (VH) and light (VK) chain variable domains for clone 135.0 (labeled "parent") and certain humanized variants (labeled VH1-3 and VK 1-3). FIG. 17E discloses heavy chain sequences as SEQ ID NOS 10, 12, 14, 16, and 667, and light chain sequences as SEQ ID NOS 11, 13, 15, 17, and 668, all respectively, in order of appearance in the alignment. FIG. 17F discloses light chain sequences as SEQ ID NOS 19, 34-37, and 669, and heavy chain sequences as SEQ ID NOS 18, 27, 28, and 26, all respectively, in order of appearance in the alignment. FIG. 17G discloses heavy chain sequences as SEQ ID NOS 38, 63-66, and 663, and light chain sequences as SEQ ID NOS 39, 67-70, and 664, all respectively, in order of appearance in the alignment. The bottom sequence in each alignment in FIG. 17A-G represent the closest human germline sequences. Black boxes indicate CDR domains, shaded residues vary in sequence from the corresponding germline residue (FIG. 17A-E) or the corresponding parent residue (FIG. 17F-G), IMGT numbering and CDR delimitation is used. FIG. 17H discloses heavy chain sequences as SEQ ID NOS 18, 2, 38, 55, 10, and 670-671, and light chain sequences as SEQ ID NOS 19, 3, 39, 56, 11, and 672-673, all respectively, in order of appearance in the alignment. Black boxes indicate CDR domains, shaded residues vary in sequence from the previous sequence in the alignment, IMGT numbering is used.

FIG. 18 discloses SEQ ID NO: 81.

FIG. 23A depicts the amino acid sequences for heavy and light chain clones 12.0. FIG. 23B depicts the amino acid sequences for heavy and light chain clones 12.1. FIG. 23C depicts the amino acid sequences for heavy and light chain clones 12.2. FIG. 23D depicts the amino acid sequences for heavy and light chain clones 12.3.

FIG. 24A depicts the amino acid sequences for heavy and light chain clones 135.0. FIG. 24B depicts the amino acid sequences for heavy and light chain clones 135.1. FIG. 24C depicts the amino acid sequences for heavy and light chain clones 135.2. FIG. 24D depicts the amino acid sequences for heavy and light chain clones 135.3.

FIG. 25A depicts the amino acid sequences for heavy and light chain clones 4.0. FIG. 25B depicts the amino acid sequences for heavy and light chain clones 4.1. FIG. 25C depicts the amino acid sequences for heavy and light chain clones 4.2. FIG. 25D depicts the amino acid sequences for heavy and light chain clones 4.3. FIG. 25E depicts the amino acid sequences for heavy chain clone 4.4. FIG. 25F depicts the amino acid sequences for heavy chain clone 4.5. FIG. 25G depicts the amino acid sequences for heavy chain clone 4.6. FIG. 25H depicts the amino acid sequences for heavy chain clone 4.7. FIG. 25I depicts the amino acid sequences for heavy chain clone 4.8. FIG. 25J depicts the amino acid sequences for heavy chain clone 4.9. FIG. 25K depicts the amino acid sequences for heavy chain clone 4.10. FIG. 25L depicts the amino acid sequences for heavy chain clone 4.11. FIG. 25M depicts the amino acid sequences for light chain clone 4.4. FIG. 25N depicts the amino acid sequences for light chain clone 4.5. FIG. 25O depicts the amino acid sequences for light chain clone 4.6. FIG. 25P depicts the amino acid sequences for light chain clone 4.7.

FIG. 26A depicts the amino acid sequences for heavy and light chain clones 53.0. FIG. 26B depicts the amino acid sequences for heavy and light chain clones 53.1. FIG. 26C depicts the amino acid sequences for heavy and light chain clones 53.2. FIG. 26D depicts the amino acid sequences for heavy and light chain clones 53.3. FIG. 26E depicts the amino acid sequences for heavy chain clone 53.4. FIG. 26F depicts the amino acid sequences for heavy chain clone 53.5. FIG. 26G depicts the amino acid sequences for heavy chain clone 53.6. FIG. 26H depicts the amino acid sequences for light chain clone 53.4. FIG. 26I depicts the amino acid sequences for light chain clone 53.5. FIG. 26J depicts the amino acid sequences for light chain clone 53.6. FIG. 26K depicts the amino acid sequences for light chain clone 53.7. FIG. 26L depicts the amino acid sequences for light chain clone 53.8. FIG. 26M depicts the amino acid sequences for light chain clone 53.9. FIG. 26N depicts the amino acid sequences for heavy chain clone 53.7. FIG. 26O depicts the amino acid sequences for heavy chain clone 53.8. FIG. 26P depicts the amino acid sequences for heavy chain clone 53.9. FIG. 26Q depicts the amino acid sequences for heavy chain clone 53.10. FIG. 26R depicts the amino acid sequences for light chain clone 53.10. FIG. 26S depicts the amino acid sequences for light chain clone 53.11. FIG. 26T depicts the amino acid sequences for light chain clone 53.12. FIG. 26U depicts the amino acid sequences for light chain clone 53.13.

FIG. 27A depicts the amino acid sequences for heavy and light chain clones 82.0. FIG. 27B depicts the amino acid sequences for heavy and light chain clones 82.1. FIG. 27C depicts the amino acid sequences for heavy and light chain clones 82.2. FIG. 27D depicts the amino acid sequences for heavy and light chain clones 82.3.

FIG. 28A-P show the nucleic acid sequences for heavy chain clones 12.0-12.3 and light chain clones 12.0-12.3, heavy chain clones 135.0-135.3 and light chain clones 135.0-135.3, heavy chain clones 4.0-4.11 and light chain clones 4.0-4.7, heavy chain clones 53.0-53.6 and light chain clones 53.0-53.9, and heavy chain clones 82.0-82.3 and light chain clones 82.0-82.3.

EXEMPLARY EMBODIMENTS

Figure 1:
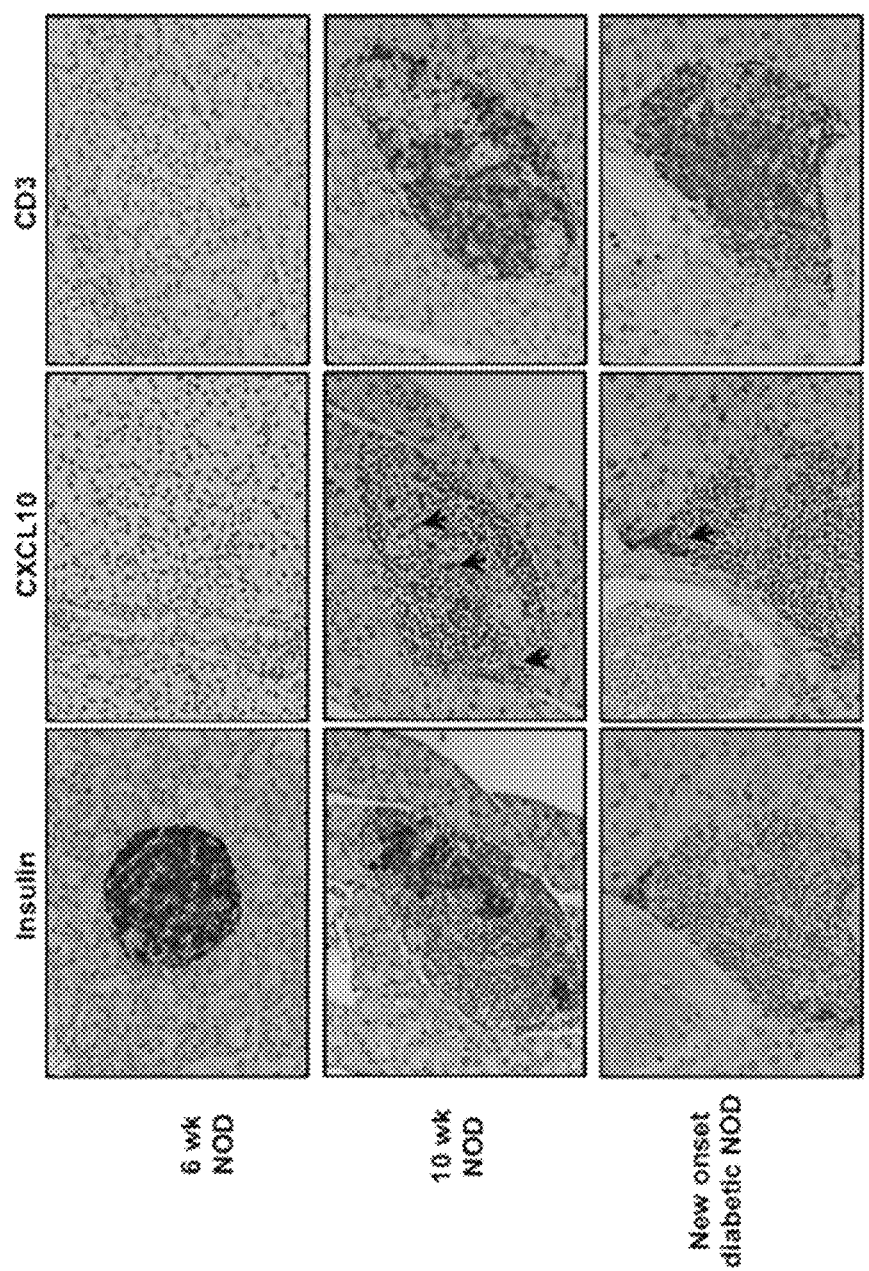
FIG. 1 shows expression of insulin (left panel), CXCL10 (center panel), and CD3 (right panel) in pancreas sections from 6 week old female NOD mice (first row), 10 week old female NOD mice (second row) and new onset diabetic female NOD mice (third row).

Reference will now be made in detail to certain exemplary embodiments according to the present disclosure, certain examples of which are illustrated in the accompanying drawings.

CXCR3

CXCR3 (MIM: 300574, human GeneID: 2833, chemokine (C-X-C motif) receptor 3; also known as CD182, CD183, CKR-L2, CMKAR3, GPR9, IP10-R, Mig-R, MigR, G protein-coupled receptor 9, IP-10 receptor, IP10 receptor, Mig receptor, chemokine (C-X-C) receptor 3, interferon-inducible protein 10 receptor) is a chemokine receptor that is largely absent from naïve T cells but is upregulated upon activation with antigen and recruits these cells to sites of tissue inflammation in response to its primary ligands: CXCL9 (human GeneID: 4283), CXCL10 (human GeneID: 3627), and CXCL11 (human GeneID: 6373). β cells in the islet of Langerhans express CXCL9 and CXCL10 (Frigerio et al., *Nature Medicine* 8:1414-1420 (2002) and T cells that have infiltrated the pancreas express CXCR3 (Christen et al, *The Journal of Immunology*, 2003, 171: 6838-6845; Van Halteren et al., *Diabetologia* 48:75-82 (2005); Uno et al 2010; Roep et al., *Clinical and Experimental Immunology*, 2003, 159: 338-343; Tanaka et al., *Diabetes* 58: 2285-2291 (2009); Sarkar et al., *Diabetes*. 2012 February; 61 (2):436-46).

CXCR3 is expressed in a variety of organisms, including, for example, human, mouse, rat, cow, chimp, macaque, dog, frog, platypus, pig, and zebrafish. Table 1 lists the U.S. National Center for Biotechnology Information (NCBI) GeneID and protein reference sequence for CXCR3 from a variety of organisms. SEQ ID NO:1 is the full length human CXCR3 sequence (splice variant A). The peptide sequence of splice variant B is provided by reference sequence NP_001136269.1. Predicted extracellular domains of human CXCR3 splice variant A are described in Colvin et al *Mol. Cell. Bio.*, 26: 5838-49 (2006) and include residues 1-58, 1-16, 111-126, 190-223, 278-301 of SEQ ID NO:1, as shown below.

```
NP_001495 Human CXCR3 isoform A
                                            SEQ ID NO: 1
   1  mvlevsdhqv  lndaevaall  enfsssydyg  enesdsccts
      ppcpqdfsln  fdraflpaly 61  sllfllgllg  ngavaavlls  rrtalsstdt  fllhlavadt
      llvltlplwa  vdaavqwvfg 121  sglckvagal  fninfyagal  llacisfdry  lnivhatqly
      rrgpparvtl  tclavwglcl 181  lfalpdfifl  sahhderina  thcqynfpqv  grtalrylql
      vagfflpllv  maycyahila 241  vllvsrgqrr  lramrlvvvy  vvafalcwtp  yhlvvivdil
      mdlgalarnc  gresrvdvak 301  svtsglgymh  cclnpllyaf  vgvkfrermw  mlllrlgcpn
      qrglqrqpss  srrdsswset 361  seasysgl
```

TABLE 1

| Species | GeneID | Protein Sequence |
|---|---|---|
| *Homo sapiens* | 2833 | NP_001495.1 (A) |
|  |  | NP_001136269.1 (B) |
| *Mus musculus* | 12766 | NP_034040.1 |
| *Rattus norvegicus* | 84475 | NP_445867.1 |
| *Bos taurus* | 497018 | NP_001011673.1 |
| *Macaca mulatta* | 699438 | NP_001138512.1 |
| *Xenopus tropicalis* | 496477 | NP_001011067.1 |
| *Xenopus laevis* | 443669 | AAH73571.1 |
| *Canis lupus familiaris* | 491952 | NP_001011887.1 |
| *Pan troglodytes* | 465704 | XP_521125.2 |
|  |  | XP_001137964.1 |
|  |  | XP_001137867.1 |
| *Sus scrofa* | 492278 | CAH64842.1 |
| *Danio rerio* | 791973 | NP_001007315.1, |
|  |  | XP_001330996.1 |
|  | 654692 | NP_001082899.2 |
|  |  | XP_001923160.1 |
| *Salmo salar* | 100195464 | NP_001133965.1 |
| *Ornithorhynchus anatinus* | 100085584 | XP_001515888.1 |

CXCR3 and CXCL10 are expressed in human T1D patients. Uno et al., *Endocrine J.* 57: 991-996 (2010); Roep et al. *Clin. and Exp. Immun.* 159: 338-343 (2009); Tanaka et al., *Diabetes* 58: 2285-2291 (2009). In these patients, CXCL10 is expressed in the remaining insulin-producing beta cells in the islets. CXCR3 is expressed in invading T cells surrounding the islets. Similar expression patterns have been reproduced in non-obese diabetic (NOD) mice, a mouse models of diabetes. Morimoto et at, *J. Immun.* 173: 7017-7024 (2004); Li et al *World J Gastroenterol.* 11(30): 4750-4752 (2005); Sarkar et al. *Diabetes*. 2012 February; 61(2):436-46).

CXCR3 is also expressed in T cells present in certain types of inflamed tissues, while CXCL9, CXCL10 and CXCL11 are often produced by local cells in inflammatory lesions. Accordingly, in some embodiments, therapies are disclosed for disrupting CXCR3 to treat T1D.

Antibodies

The term "antibody," as used herein, refers to any polypeptide comprising an antigen-binding site regardless of the source, species of origin, method of production, and/or characteristics, and encompasses immunoglobulins or antigen-binding parts or fragments thereof. As a non-limiting example, the term "antibody" includes human, orangutan, mouse, rat, goat, sheep, and chicken antibodies. The term includes but is not limited to polyclonal, monoclonal, monospecific, polyspecific, non-specific, humanized, fully human, camelized, single-chain, chimeric, synthetic, recombinant, hybrid, mutated, back-mutated, and CDR-grafted antibodies. For the purposes of the present invention, it also includes, unless otherwise stated, antibody fragments such as Fab, F(ab')2, Fv, scFv, Fd, dAb, VHH (also referred to as nanobodies), and other antibody fragments that retain antigen-binding function, including bi-specific or multi-specific antibodies. The term "antibody" also refers to antigen-binding molecules that are not based on immunoglobulins. For example, non-immunoglobulin scaffolds known in the art include small modular immunopharmaceuticals (see, e.g., U.S. Patent Application Publication Nos. 20080181892 and 20080227958 published Jul. 31, 2008 and Sep. 18, 2008, respectively), tetranectins, fibronectin domains (e.g., AdNectins, see U.S. Patent Application Publication No. 2007/0082365, published Apr. 12, 2007), protein A, lipocalins (see, e.g., U.S. Pat. No. 7,118,915), ankyrin repeats, and thioredoxin.

The term "antigen-binding domain" refers to the part of an antibody molecule that comprises the area specifically binding to or complementary to a part or all of an antigen. Where an antigen is large, an antibody may only bind to a particular part of the antigen. In certain embodiments, a CXCR3 antibody or antigen-binding fragment comprises at least one antigen-binding domain. In some embodiments, the antibody or fragment is multi-specific and comprises two or more (e.g., 2, 3, 4, 5, or more) antigen-binding domains, such that the antibody or fragment is capable of binding two or more CXCR3 molecules at the same or different epitopes, or capable of binding to CXCR3 and at least one other antigen with high affinity. The antigen-binding portion of an antibody can comprise one or more fragments of an antibody that retains the ability to specifically bind to an antigen. These fragments may comprise the heavy and/or light chain variable region from a parent antibody or from a variant of a parent antibody.

The "epitope" or "antigenic determinant" is a portion of an antigen molecule that is responsible for specific interactions with the antigen-binding domain of an antibody. An antigen-binding domain may be provided by one or more antibody variable domains. An antigen-binding domain can comprise at least one antibody light chain variable region (VL) and at least one antibody heavy chain variable region (VH). An antigen-binding domain can also comprise only VH or only VL regions. For example, antibodies from camels and llamas (Camelidae, camelids) include a unique kind of antibody, which is formed by heavy chains only and is devoid of light chains. The antigen-binding site of such antibodies is one single domain, referred to as VHH. These have been termed "camelized antibodies" or "nanobodies". See, e.g., U.S. Pat. Nos. 5,800,988 and 6,005,079 and International Application Publication Nos. WO 94/04678 and WO 94/25591, which are incorporated by reference.

The anti-CXCR3 antibodies disclosed herein can be generated by any suitable method known in the art. For example, the antibodies may comprise polyclonal antibodies or monoclonal antibodies. Methods of preparing polyclonal antibodies are known to the skilled artisan (Harlow et al., Antibodies: a Laboratory Manual, Cold Spring Harbor Laboratory Press, 2nd ed. (1988)). Immunogens comprising polypeptides of CXCR3, fragments thereof (e.g., one or more extracellular domains, or the N-terminal 58 amino acids, or the N-terminal 37 amino acids, or the N-terminal 20 amino acids, or the N-terminal 16 amino acids, etc.), fusion proteins, or variants thereof can be used in generating the anti-CXCR3 antibodies.

The immunogen may be produced by a cell that produces or overproduces CXCR3, which may be a naturally occurring cell, a naturally occurring mutant cell or a genetically engineered cell. Depending on the nature of the polypeptides (e.g., percent hydrophobicity, percent hydrophilicity, stability, net charge, isoelectric point etc.), the immunogen may be modified or conjugated to alter its immunogenicity. For example, CXCR3 or a portion thereof can be conjugated to a carrier. The conjugation can include either chemical conjugation by derivatizing with active chemical functional groups, or through fusion-protein based methodology, or other methods known to the skilled artisan. Examples of carriers and/or other immunogenicity altering proteins include, but are not limited to, KLH, ovalbumin, serum albumin, bovine thyroglobulin, soybean trypsin inhibitor, and promiscuous T helper peptides.

Various adjuvants may also be used with the CXCR3 immunogen to increase the immunological response. Examples of adjuvants include, but are not limited to, Freund's adjuvant (complete and incomplete), mineral oils, gels, alum (aluminum hydroxide), surface active substances such as lysolecithin, pluronic polyols, polyanions, peptides, oil emulsions, keyhole limpet hemocyanins (KLH), dinitrophenol, and human adjuvants, such as BCG (Bacille Calmette-Guerin) and *Corynebacterium parvum*. Additional examples of adjuvants which may be employed include the MPL-TDM adjuvant (monophosphoryl lipid A, synthetic trehalose dicorynomycolate). Immunization protocols are well known in the art and may be performed by any method that elicit an immune response in the animal host chosen. Thus, various administration routes can be used over various time periods as a design choice.

For example, an immunogen, as exemplified herein, can be administered to various host animals including, but not limited to, rabbits, mice, camelids, rats etc., to induce the production of serum containing polyclonal antibodies specific for CXCR3. The administration of the immunogen may involve one or more injections of an immunizing agent and, optionally, an adjuvant. In some embodiments, the immunogen (with or without adjuvant) is injected into the mammal by multiple subcutaneous or intraperitoneal injections, or intramuscularly or intravenously. In some embodiments, once a suitable polyclonal preparation is obtained, particular antibodies can be isolated by known separation techniques, such as affinity chromatography, panning, absorption, etc., such that an individual antibody species can be obtained. In some embodiments, the individual antibody species is subjected to further study, for example, sequencing to obtain the amino acid sequences of one or more CDRs.

In some embodiments, the CXCR3 antibodies are monoclonal. A monoclonal antibody includes any antibody derived from a single eukaryotic, phage or prokaryotic clone that expresses the antibody. Monoclonal antibodies can be made, for example, via traditional hybridoma techniques (Kohler and Milstein, *Nature* 256: 495-499 (1975) and U.S. Pat. No. 4,376,110, incorporated herein by reference), recombinant DNA methods (U.S. Pat. No. 4,816,567, incorporated herein by reference), or phage display techniques using antibody libraries (Clackson et al., Nature 352: 624-628 (1991); Marks et al., *J. Mol. Biol.* 222: 581-597 (1991)). For various other antibody production techniques, see *Antibodies: A Laboratory Manual*, eds. Harlow et al., Cold Spring Harbor Laboratory, 1988. Other examples of methods which may be employed to produce monoclonal antibodies include, but are not limited to, the human β-cell hybridoma technique (Kosbor et al., *Immunology Today* 4:72 (1983); and Cole et al., *Proc Natl Acad Sci USA* 80:2026 (1983)), and the EBV-hybridoma technique (Cole et al., *Monoclonal Antibodies and Cancer Therapy*, pp. 77-96, Alan R. Liss (1985)). Such antibodies may be of any immunoglobulin class, including IgG, IgM, IgE, IgA and IgD, and any subclass or variant thereof. The hybridoma producing the mAb of the invention may be cultivated in vitro or in vivo.

In some embodiments, an immunogen comprising polypeptides of CXCR3, fragments thereof (e.g., one or more extracellular domains, or the N-terminal 58 amino acids, or the N-terminal 37 amino acids, or the N-terminal 20 amino acids, or the N-terminal 16 amino acids, etc.), fusion proteins, or variants thereof can be used to immunize a host animal (e.g. rabbits, mice, camelids, rats etc.) to generate the hybridomas that produce the monoclonal antibodies. Lymphocytes that produce or are capable of producing antibodies that specifically bind to CXCR3 can be collected from the immunized host and fused with myeloma cells using a suitable fusing agent, such as polyethylene glycol, to form hybridoma cells (Goding, *Monoclonal Antibodies: Principles and Practice*, Academic Press, pp. 59-103 (1986)).

Multiple hybridomas producing monoclonal antibodies can be generated and those that exhibit beneficial properties or suggest therapeutic potential, for example, by preventing binding of CXCR3 ligand to its receptor, can be selected. The selected antibodies can be further modified to obtain or enhance beneficial properties, such as having enhanced stability in vivo. For example, after hybridoma cells are identified that produce antibodies of the desired specificity, affinity, and/or activity, the clones may be subcloned using dilution procedures and grown by standard culture methods (Goding, *Monoclonal Antibodies: Principles and Practice*, Academic Press, pp. 59-103 (1986)). Suitable culture media include, for example, Dulbecco's Modified Eagle's Medium (D-MEM) or RPMI-1640 medium. In addition, the hybridoma cells may be grown in vivo as tumors in an animal. The subclones can be assayed for specificity, affinity, and/or activity, and the subclones exhibiting the most beneficial properties can be selected for further characterization.

A variety of alternative methods exist in the art for the production of monoclonal antibodies, any of which may be used to produce the anti-CXCR3 antibodies disclosed herein. For example, the monoclonal antibodies may be made by recombinant DNA methods, such as those described in U.S. Pat. No. 4,816,567, which is incorporated by reference in its entirety.

DNA encoding monoclonal antibodies can be isolated and sequenced using conventional procedures (e.g., by using oligonucleotide probes that are capable of binding to genes encoding the heavy and light chains of murine antibodies, or the chains from human, humanized or other antibodies) (Innis et al. *PCR Protocols, A Guide to Methods and Applications*, Academic (1990), and Sanger et al., *Proc Natl Acad Sci USA* 74:5463 (1977)). Hybridoma cells can serve as a source of such DNA. Once isolated, the DNA can be placed into expression vectors, which can be transfected into host cells such as *E. coli* cells, NSO cells, COS cells, Chinese hamster ovary (CHO) cells, or myeloma cells that do not otherwise produce immunoglobulin protein, to obtain the synthesis of monoclonal antibodies in the recombinant host cells. The DNA can also be modified, for example, by substituting the coding sequence for human heavy and light chain constant domains in place of the homologous murine sequences (U.S. Pat. No. 4,816,567; and Morrison et al., *Proc Natl Acad Sci USA* 81:6851 (1984)) or by covalently joining to the immunoglobulin coding sequence all or part of the coding sequence from a non-immunoglobulin polypeptide. In some embodiments, a non-immunoglobulin polypeptide can be substituted for the constant domains of an antibody, or can be substituted for the variable domains of one CXCR3-combining site of an antibody to create a chimeric bivalent antibody.

In some embodiments, the antibodies described herein can be modified to generate CDR grafted and/or otherwise humanized antibodies. CDR grafting is a form of humanization, but other humanizing techniques known in the art can also be used. CDR grafting procedures are known to the skilled artisan and may be based on CDR numbering designations including IMGT (the international ImMunoGeneTics information System®, Montpellier, France), Kabat, Chothia and modified-Chothia numbering schemes. See, e.g., imgt.org (summarizing the use of the IMGT continuous numbering system, which takes into account and combines the definition of the framework and complementarity determining regions, structural data from X-ray diffraction studies, and the characterization of the hypervariable loops, to provide unique numbering for all IG and TR V-regions from all species); Abhinandan and Martin, *Mol Immunol.*, 45:3832-9 (2008); see also Abhinandan and Martin, *J. Mol. Biol.*, 369(3):852-62 (2007) (describing methods to assess the "humanness" of a chimeric antibody); Retter et al *Nucleic Acids Res.* 33 (Database issue):D671-4 (2005) (describing the VBASE2 database of variable domain genes); and Johnson and Wu, *Int. Immunol.* 10(12); 1801-5 1998) (describing the distribution of lengths of CDRH3s).

For example, using the IMGT numbering system, conserved amino acids always have the same position. The hydrophobic amino acids of the framework regions are also numbered in conserved positions, allowing for framework amino acids (and codons) located at the same positions in different sequences to be compared without requiring sequence alignments. In another example, the Kabat numbering system is as follows, CDR-HI begins at approximately amino acid 31 (i.e., approximately 9 residues after the first cysteine residue), includes approximately 5-7 amino acids, and ends at the next tyrosine residue. CDR-H2 begins at the fifteenth residue after the end of CDR-HI, includes approximately 16-19 amino acids, and ends at the next arginine or lysine residue. CDR-H3 begins at approximately the thirty third amino acid residue after the end of CDR-H2; includes 3-25 amino acids; and ends at the sequence W-G-X-G, where X is any amino acid. CDR-LI begins at approximately residue 24 (i.e., following a cysteine residue); includes approximately 10-17 residues; and ends at the next tyrosine residue. CDR-L2 begins at approximately the sixteenth residue after the end of CDR-Li and includes approximately 7 residues. CDR-L3 begins at approximately the thirty third residue after the end of CDR-L2; includes approximately 7-11 residues and ends at the sequence F-G-X-G, where X is any amino acid. Antibodies containing at least one of these CDRs can be used in the methods of the present disclosure.

CDR-grafted antibodies can comprise heavy and light chain variable region sequences from a human antibody, wherein one or more of the CDR regions of VH and/or VL are replaced with CDR sequences from the donor antibodies e.g., from the murine antibodies described below that bind CXCR3. A framework sequence from any human antibody may serve as the template for CDR grafting. However, straight CDR chain replacement onto such a framework may lead to some loss of binding affinity to the antigen. The more homologous a human antibody is to the original, e.g. murine antibody, the less likely the possibility that combining the donor CDRs with the human framework will introduce distortions in the CDRs that could reduce affinity. Therefore, in some embodiments, the CDR-grafted CXCR3 antibodies of the present disclosure comprise a human variable framework that has at least a 65% sequence identity with the variable region framework of the donor murine CXCR3 neutralizing antibody. Methods for producing such antibodies are known in the art (see EP 239,400; PCT Publication No. WO 91/09967: and U.S. Pat. Nos. 5,225,539; 5,530,101; and 5,585,089), and include veneering or resurfacing (EP 592,106; EP 519,596; Padlan (1991) Mol. Immunol. 28(4/5): 489-498; Studnicka et al. (1994) Prot. Engineer. 7 (6): 805-814; and Roguska et al. (1994) Proc. Acad. Sci. USA 91: 969-973), chain shuffling (U.S. Pat. No. 5,565,352), and anti-idiotypic antibodies.

In some embodiments, the antibodies described herein can be humanized. "Humanized antibodies" are antibody molecules that bind the desired antigen, have one or more CDRs from a non-human species, and have framework regions and/or constant domains from a human immunoglobulin molecule. Known human Ig sequences are disclosed in, e.g., www.ncbi.nlm.nih.gov/entrez-/query.fcgi; www.atcc.org/phage/hdb.html; www.sciquest.com/; www.abcam.com/; www.antibodyresource.com/onlinecomp.html; and Kabat et al., Sequences of Proteins of Immunological Interest, U.S. Dept. Health (1983). Imported human sequences can be used to reduce immunogenicity or reduce, enhance or modify binding, affinity, on-rate, off-rate, avidity, specificity, half-life, or any other suitable characteristic, as known in the art. Antibodies can be humanized using a variety of techniques known in the art, such as, but not limited to those described in Jones et al. (1986) Nature 321: 522; Verhoeyen et al. (1988) Science 239: 1534; Sims et al, (1993) J. Immunol. 151: 2296; Chothia and Lesk (1987) J. Mol. Biol. 196: 901; Carter et al. (1992) Proc. Natl. Acad. Sci. USA 89: 4285; Presta et al. (1993) J. Immunol. 151: 2623; U.S. Pat. Nos. 5,589,205; 565,332; 6,180,37 6,632, 927; 7,241,877; 7,244,615; 7,244,832; 7,262,0505; and U.S. Patent Publication No. 2004/0236078 (filed Apr. 30, 2004), which are hereby incorporated by reference in their entirety.

In certain embodiments, framework residues in humanized or CDR-grafted antibodies may be substituted with the corresponding residue from the CDR donor antibody, e.g. substituted with framework residues from an anti-mouse CXCR3 neutralizing antibody, in order to alter, e.g., improve, antigen binding. See Queen et al., *Proc. Nat'l. Acad. Sci. USA* 86:10029-33 (December 1989). These framework substitutions are identified by methods well known in the art, e.g., by modeling of the interactions of the CDR and framework residues to identify framework residues important for antigen binding and sequence comparison to identify unusual framework residues at particular positions. See, e.g., U.S. Pat. No. 5,585,089; and Riechmann et al. (1988) *Nature* 332:323, which are hereby incorporated by reference in their entirety. Three-dimensional immunoglobulin models are commonly available and are familiar to those skilled in the art. Computer programs are available which illustrate and display probable three-dimensional conformational structures of selected candidate immunoglobulin sequences. Inspection of these displays permits analysis of the likely role of the residues in the functioning of the candidate immunoglobulin sequence, i.e., the analysis of residues that influence the ability of the candidate immunoglobulin to bind its antigen. In this way, framework residues can be selected and combined from the consensus and import sequences so that the desired antibody characteristic, such as increased affinity for CXCR3, is achieved.

Antibodies can be humanized or CDR-grafted, and framework residues from CDR-donors that are useful for improving antigen binding can be identified, using a variety of techniques known in the art, such as but not limited to those described in Jones et al. (1986) *Nature* 321: 522; Verhoeyen et al. (1988) *Science* 239: 1534; Sims et al. (1993) *J. Immunol.* 151: 2296; Chothia and Lesk (1987) *J. Mol. Biol.* 196: 901; Carter et al. (1992) *Proc. Natl. Acad. Sci. USA* 89: 4285; Presta et al. (1993) *J. Immunol.* 151: 2623; and U.S. Pat. Nos. 5,565,332; 5,723,323; 5,976,862; 5,824,514; 5,817,483; 5,814,476; 5,763,192; 5,723,323; 5,766,886; 5,714,352; 6,204,023; 6,180,370; 5,693,762; 5,530,101; 5,585,089; 5,225,539; and 4,816,567. In some embodiments, 4D humanization is used to prepare antibody variants of the present disclosure (e.g., to prepare the 4D humanized variants of clone 4, comprising any one of heavy chains 4.4-4.6 and any one of light chains 4.4-4.7). See WO 2009/032661 (which is incorporated herein by reference in its entirety), e.g., at paragraphs [0037]-[0044] for methods used in 4D humanization. Briefly, 4D humanization can comprise: a) building a 3-D model of the variable domain that is to be humanized; b) identifying the flexible residues in the variable domain using a molecular dynamics simulation of the 3-D model of the domain; c) identifying the closest human germline by comparing the molecular dynamics trajectory of the 3-D model to the molecular dynamics trajectories of 49 human germlines; and d) mutating the flexible residues, which are not part of the CDR, into their human germline counterpart (as identified in step c).

In some embodiments, the CDR grafted and/or otherwise humanized antibodies can comprise CDR grafted and/or humanized variants of clones 4, 12, 53, 82, and 135. For instance, corresponding heavy and light chain regions from any one of clones 4, 12, 53, 82, and 135 (e.g., clone 4 heavy chain and clone 4 light chain) can be joined to human constant domains to form chimeric antibodies. Chimeric antibodies can be further humanized by changing one or more framework or CDR amino acid to the corresponding human residue. Likewise, in some embodiments the six heavy and light chain CDR regions from any one of clones 4, 12, 53, 82, and 135 (e.g., clone 4 heavy chain CDR1, CDR2, and CDR3, and clone 4 light chain CDR1, CDR2, and CDR3) or from any of the variants of clones 4, 12, 53, 82, and 135 can be subcloned into human framework and/or constant domains to form humanized antibodies. Humanization can include using human variable domains, excluding the amino acids of the CDRs and/or any Vernier position residues. The humanized antibodies can also include further backmutated changes at residues positioned within four amino acids of the CDRs and/or at positions identified as "very dissimilar" between the original antibody sequence and human sequences, e.g., using IMGT-based modeling. Further mutations in the framework or CDR regions can be introduced to enhance stability or therapeutic effectiveness of the antibody, for example by introducing mutations to remove a deamidation site at positions 58 and 59 (IMGT numbering) of clone 4 VH CDR2.

For instance, the antibodies, chimeric antibodies, and humanized antibodies disclosed herein can comprise the six CDRs and/or the heavy and light chain variable domains from any of clones 4, 12, 53, 82, and 135 and their chimeric or humanized variants. For example, the antibody or fragment capable of binding CXCR3 can comprise the three CDRs from any one of heavy chains 4.0-4.11, heavy chains 12.0-12.3, heavy chains 53.0-53.10, heavy chains 82.0-82.3, and heavy chains 135.0-135.3. Similarly, the antibody or fragment can comprise the three CDRs from any one of light chains 4.0-4.7, light chains 12.0-12.3, light chains 53.0-53.13, light chains 82.0-82.3, and light chains 135.0-135.3. In some embodiments, the heavy and light chain CDRs are from the same clone, but can be from different variants of that clone (e.g., the three CDRs from heavy chain 4.1 paired with the three CDRs from light chain 4.2). Heavy and light chains 4.0, 12.0, 82.0, and 135.0 refer to the variable domain in the mouse antibody clones and the chimeric antibodies (where the antibodies comprise mouse variable domains and human framework regions). The remaining heavy and light chains refer to the humanized chains as shown in Table 11.

In some embodiments, the antibody or fragment capable of binding CXCR3 can comprise any one of heavy chains 4.0-4.11, heavy chains 12.0-12.3, heavy chains 53.0-53.10, heavy chains 82.0-82.3, and heavy chains 135.0-135.3. Similarly, the antibody or fragment can comprise any one of light chains 4.0-4.7, light chains 12.0-12.3, light chains 53.0-53.13, light chains 82.0-82.3, and light chains 135.0-135.3.

In some embodiments, the heavy and light chains are selected such that the three CDRs from a heavy chain of a particular clone (e.g., the CDRs from a clone 4 heavy chain) are paired with the three CDRs from any of the light chains for that clone (e.g., the CDRs from a clone 4 light chain). In some embodiments, the heavy and light chains are selected such that a heavy chain from a particular clone (e.g., a clone 4 heavy chain) is paired with any of the light chains for that clone (e.g., a clone 4 light chain).

In some embodiments, the three CDRs from any one of heavy chain variable domains 4.0-4.11 can be paired with the three CDRs from any one of light chain variable domains 4.0-4.7; the three CDRs from any one of heavy chain variable domains 12.0-12.3 can be paired with the three CDRs from any one of light chain variable domains 12.0-12.3; the three CDRs from any one of heavy chain variable domains 53.0-53.10 can be paired with the three CDRs from any one of light chain variable domains 53.0-53.13; the three CDRs from any one of heavy chain variable domains 82.0-82.3 can be paired with the three CDRs from any one of light chain variable domains 82.0-82.3; or the three CDRs from any one of heavy chain variable domains 135.0-135.3 can be paired with the three CDRs from any one of light chain variable domains 135.0-135.3.

In some embodiments, any one of heavy chain variable domains 4.0-4.11 can be paired with any one of light chain variable domains 4.0-4.7, any one of heavy chain variable domains 12.0-12.3 can be paired with any one of light chain variable domains 12.0-12.3, any one of heavy chain variable domains 53.0-53.10 can be paired with any one of light chain variable domains 53.0-53.13, any one of heavy chain variable domains 82.0-82.3 can be paired with any one of light chain variable domains 82.0-82.3, or any one of heavy chain variable domains 135.0-135.3 can be paired with any one of light chain variable domains 135.0-135.3.

An alignment of certain heavy and light chain variable domains is shown in FIG. 17. In some embodiments, an antibody as disclosed herein can comprise the paired heavy and light chain variable domains as shown in Table 2 (Ch=chimeric, Hu=humanized, VH=heavy chain, VK=light chain). For example, the first entry in Table 2 indicates a clone 4 variant comprising heavy chain 4.0 and light chain 4.0. The second entry indicates a clone 4 variant comprising heavy chain 4.1 and light chain 4.1. Each antibody, comprising the indicated heavy chain and light chain sequence, was also assigned an antibody identifier in the second column of Table 2. For instance, the first entry in the table (comprising heavy chain 4.0 and light chain 4.0) was assigned the antibody identifier 4Ch, while the second antibody in the table (comprising heavy chain 4.1 and light chain 4.1) was assigned the identifier 4Hu1.

TABLE 2

| Clone | Antibody | Heavy Chain | VH SEQ ID NO | Light Chain | VK SEQ ID NO |
|---|---|---|---|---|---|
| Clone 4 | 4Ch | VH | 18 | VK | 19 |
| Clone 4 | 4Hu1 | VH1 | 20 | VK1 | 21 |
| Clone 4 | 4Hu2 | VH2 | 22 | VK2 | 23 |
| Clone 4 | 4Hu3 | VH3 | 24 | VK3 | 25 |
| Clone 4 | 4Hu4 | VH2 | 22 | VK3 | 25 |
| Clone 4 | 4Hu5 | VH3 | 24 | VK2 | 23 |
| Clone 4 | 4Hu6 | VH4 | 26 | VK4 | 34 |
| Clone 4 | 4Hu7 | VH4 | 26 | VK7 | 37 |
| Clone 4 | 4Hu8 | VH5 | 27 | VK5 | 35 |
| Clone 4 | 4Hu9 | VH5 | 27 | VK6 | 36 |
| Clone 4 | 4Hu10 | VH6 | 28 | VK4 | 34 |
| Clone 4 | 4Hu11 | VH2 | 22 | VK1 | 21 |
| Clone 4 | 4Hu12 | VH1 | 20 | VK2 | 23 |
| Clone 4 | 4Hu13 | VH3 | 24 | VK1 | 21 |
| Clone 4 | 4Hu14 | VH1 | 20 | VK3 | 25 |
| Clone 4 | 4Hu15 | VH7 | 29 | VK2 | 23 |
| Clone 4 | 4Hu16 | VH8 | 30 | VK2 | 23 |
| Clone 4 | 4Hu17 | VH9 | 31 | VK2 | 23 |
| Clone 4 | 4Hu18 | VH10 | 32 | VK2 | 23 |
| Clone 4 | 4Hu19 | VH11 | 33 | VK2 | 23 |
| Clone 12 | 12Ch | VH | 2 | VK | 3 |
| Clone 12 | 12Hu1 | VH1 | 4 | VK1 | 5 |
| Clone 12 | 12Hu2 | VH2 | 6 | VK2 | 7 |
| Clone 12 | 12Hu3 | VH3 | 8 | VK3 | 9 |
| Clone 82 | 82Ch | VH | 55 | VK | 56 |
| Clone 82 | 82Hu1 | VH1 | 57 | VK1 | 58 |
| Clone 82 | 82Hu2 | VH2 | 59 | VK2 | 60 |
| Clone 82 | 82Hu3 | VH3 | 61 | VK3 | 62 |
| Clone 135 | 135Ch | VH | 10 | VK | 11 |
| Clone 135 | 135Hu1 | VH1 | 12 | VK1 | 13 |
| Clone 135 | 135Hu2 | VH2 | 14 | VK2 | 15 |
| Clone 135 | 135Hu3 | VH3 | 16 | VK3 | 17 |
| Clone 53 | 53Ch | VH | 38 | VK | 39 |
| Clone 53 | 53Hu1 | VH1 | 40 | VK1 | 41 |
| Clone 53 | 53Hu2 | VH2 | 42 | VK2 | 43 |
| Clone 53 | 53Hu3 | VH3 | 44 | VK3 | 45 |
| Clone 53 | 53Hu4 | VH1 | 40 | VK2 | 43 |
| Clone 53 | 53Hu5 | VH2 | 42 | VK1 | 41 |
| Clone 53 | 53Hu6 | VH2 | 42 | VK4 | 49 |
| Clone 53 | 53Hu7 | VH2 | 42 | VK5 | 50 |
| Clone 53 | 53Hu8 | VH2 | 42 | VK6 | 51 |
| Clone 53 | 53Hu9 | VH2 | 42 | VK7 | 52 |
| Clone 53 | 53Hu10 | VH2 | 42 | VK8 | 53 |
| Clone 53 | 53Hu11 | VH2 | 42 | VK9 | 54 |
| Clone 53 | 53Hu12 | VH4 | 46 | VK2 | 43 |
| Clone 53 | 53Hu13 | VH5 | 47 | VK2 | 43 |
| Clone 53 | 53Hu14 | VH6 | 48 | VK2 | 43 |
| Clone 53 | 53Hu15 | VH1 | 40 | VK4 | 49 |
| Clone 53 | 53Hu16 | VH1 | 40 | VK6 | 51 |
| Clone 53 | 53Hu17 | VH6 | 48 | VK4 | 49 |
| Clone 53 | 53Hu18 | VH6 | 48 | VK6 | 51 |

TABLE 2-continued

| Clone | Antibody | Heavy Chain | VH SEQ ID NO | Light Chain | VK SEQ ID NO |
|---|---|---|---|---|---|
| Clone 53 | 53Hu19 | VH7 | 63 | VK10 | 67 |
| Clone 53 | 53Hu20 | VH7 | 63 | VK11 | 68 |

The term "specific interaction," or "specifically binds," or the like, means that two molecules form a complex that is relatively stable under physiologic conditions. Specific binding is characterized by a high affinity and a low to moderate capacity. Nonspecific binding usually has a low affinity with a moderate to high capacity. Typically, the binding is considered specific when the affinity constant Ka is higher than $10^6$ $M^{-1}$, or preferably higher than $10^8$ $M^{-1}$. In some embodiments, antibodies, variants, and fragments thereof bind their antigen(s) with association constants of at least $10^6$, $10^7$, $10^8$, $10^9$ $M^{-1}$, or higher. In some embodiments, the antibodies, variants, and fragments thereof bind CXCR3 with at least the binding kinetics shown in any one of Tables 7A-B, 8-10, and/or 12. If necessary, non-specific binding can be reduced without substantially affecting specific binding by varying the binding conditions. Such conditions are known in the art, and a skilled artisan using routine techniques can select appropriate conditions. The conditions are usually defined in terms of concentration of antibodies, ionic strength of the solution, temperature, time allowed for binding, concentration of blocking molecules, such as serum albumin and milk casein.

Disclosed herein are anti-CXCR3 antibodies that can, in some embodiments, neutralize CXCR3. A "CXCR3 neutralizing antibody," binds to CXCR3 and blocks the activity of the receptor, such as the typical physiological and genetic responses resulting from CXCR3 ligands binding to CXCR3. Neutralizing activity may be complete (100% neutralization) or partial, e.g., approximately 10, 20, 30, 40, 50, 60, 70, 80, 90, 95 (or any percentage in between) or more neutralizing and will depend on various factors known to the skilled artisan, such as antibody concentration, affinity, and epitope as well as the particular assay used to evaluate neutralizing activity. The neutralizing activity of a CXCR3 neutralizing antibody may be shown by assays to measure inhibition of, e.g., ligand binding, GTP binding, calcium mobilization, cell chemotaxis, and/or receptor internalization. Numerous assays for determining the activity of neutralizing antibodies, and particularly CXCR3 neutralizing antibody, are known to the skilled artisan and may be readily adapted to verify that a particular antibody is neutralizing.

For example, in some embodiments, the neutralizing activity of an antibody for use in the methods of the invention may be assessed by a chemotaxis assay, substantially as set forth in the package insert for the antibody produced by clone 49801 and sold by R&D Systems® (Cat. no. MAB160). The Neutralization Dose-50 ($ND_{50}$) is defined as the concentration of antibody required to yield one-half maximal inhibition of the cell surface CXCR3 mediated rhI-TAC response in a responsive cell line, at a specific rhI-TAC concentration. To measure the ability of the antibody to block rhI-TAC induced chemotaxis of hCXCR3 transfected BaF/3 cells, rhI-TAC at 7 ng/mL is added to the lower compartment of a 96-well chemotaxis chamber (NeuroProbe, Cabin John, Md.). The chemotaxis chamber is then assembled using a PVP-free polycarbonate filter (5μ pore size). Serial dilutions of the antibody (e.g., from 0.001 to 10000 μg/mL) and $0.25 \times 10^6$ cells/well are added to the top wells of the chamber. After incubation for 3 hours at 37° C.

in a 5% $CO_2$, humidified incubator, the chamber is disassembled, and the cells that migrate through to the lower chamber are transferred to a working plate and quantitated using, for example, Resazurin Fluorescence.

Colvin et al., *Mol. Cell. Bio.*, 26: 5838-49 (2006) describe additional assays that can be used, in certain embodiments, to determine the neutralizing activity of neutralizing CXCR3 antibodies for use in the invention. Briefly, 300-19 cells, a murine pre-B-cell leukemia cell line that functionally expresses CXCR4 may be used. Following transfection, this line can functionally express other chemokine receptors, e.g., human CXCR3 (see, e.g., paragraphs 201-209 of U.S. Patent Application Publication No. 2010/0061983, which are incorporated by reference). 300-19 cells expressing human CXCR3 may be grown in complete RPMI medium containing 10% fetal bovine serum (FBS). To assess binding of CXCR3 ligands to CXCR3 in the presence of candidate neutralizing CXCR3 antibodies, 400,000 CXCR3/300-19 cells are placed into 96-well tissue culture plates in a total volume of 150 µL of binding buffer (0.5% BSA, 5 mM $MgCl_2$, 1 mM $CaCl_2$, 50 mM HEPES, pH 7.4). A total of 0.04 nM of $^{125}$I-labeled CXCL10 (New England Nuclear, Boston, Mass.) or CXCL11 (Amersham Biosciences, Piscataway, N.J.) and $5\times10^6$ nM to 500 nM of unlabeled CXCL10 or CXCL11 (Peprotech, Rocky Hill, N.J.) may be added to the cells and incubated for 90 min at room temperature with shaking. The cells are transferred onto 96-well filter plates (Millipore, Billerica, Mass.) that are presoaked in 0.3% polyethyleneimine and washed three times with 200 µl binding buffer supplemented with 0.5 M NaCl. The plates are dried, and the radioactivity is measured after the addition of scintillation fluid in a Wallac Microbeta scintillation counter (Perkin-Elmer Life Sciences, Boston, Mass.). Binding of CXCL9 may be assessed analogously to CXCL10 and 11.

In certain embodiments, the antibodies disclosed herein can prevent or reduce calcium flux into CXCR3-expressing cells. In some embodiments, calcium flux may be detected in cells such as CXCR3/300-19 cells. Approximately $5\times10^6$ cells are suspended in 2 ml of RPMI medium with 1% BSA. Fifteen micrograms of Fura-2 (Molecular Probes, Eugene, Oreg.) are added and the cells are incubated at 37° C. for 20 min. The cells are washed twice in PBS and resuspended in 2 ml of calcium flux buffer (145 mM NaCl, 4 mM KCl, 1 mM $NaHPO_4$, 1.8 mM $CaCl_2$, 25 mM HEPES, 0.8 mM $MgCl_2$, and 22 mM glucose). Fluorescence readings are measured at 37° C. in a DeltaRAM fluorimeter (Photon Technology International, Lawrenceville, N.J.). Before and after the addition of chemokines (e.g., CXCL9, 10, or 11), intracellular calcium concentrations are recorded as the excitation fluorescence intensity emitted at 510 nm in response to sequential excitation at 340 nm and 380 nm and presented as the relative ratio of fluorescence at 340 nm to that at 380 nm.

In certain embodiments, CXCR3 neutralization can be evaluated by measuring a reduction in receptor internalization. In some embodiments, receptor internalization assays may be performed by incubating about $2.5\times10^5$ cells, such as CXCR3/300-19 cells in RPMI medium with 1% BSA with various concentrations of CXCL10, CXCL11, or CXCL9 for 30 min at 37° C. The cells may then be washed with ice-cold fluorescence-activated cell sorter buffer and subsequently analyzed for surface expression of CXCR3 using a PE-conjugated CXCR3 antibody.

Additional assays for assessing neutralizing activity are disclosed in, for example, Examples 2-4 of U.S. Pat. No. 7,405,275, which are incorporated by reference.

As assessed by any of the above assays, a neutralizing CXCR3 antibody may have, in certain embodiments, an $ND_{50}$ of approximately 0.01, 0.02, 0.05, 0.1, 0.2, 0.5, 1, 2, 3, 4, 5, 6, 7, 8, 9, 10, 15, 20, 40, 50, or 100 µg/mL. In particular embodiments, the ND50 may be 0.5-12 µg/mL, and in more particular embodiments, 1-6 µg/mL.

Isolated CXCR3 antibodies disclosed herein may include those that bind specific epitopes of CXCR3. For example, antibodies for use in the invention may bind a peptide comprising all or part (e.g., a fragment of at least 5, 6, 8, 10, 12, 14, 15, 16, 18, or 20 residues) of a sequence selected from residues 1-58, 1-16, or 1-37 of SEQ ID NO:1. In some embodiments, the antibodies disclosed herein include those that bind one or more of the epitopes identified in FIG. 18. In some embodiments, an anti-CXCR3 antibody can comprise an antibody that binds to a CXCR3 epitope comprising SDHQVLNDAE (SEQ ID NO: 71). In some embodiments, the epitope comprises SDHQVLND (SEQ ID NO: 72), DHQVLND (SEQ ID NO: 73), and/or VLNDAE (SEQ ID NO: 74). In certain embodiments, the epitope comprises the sequence VLND (SEQ ID NO: 75). In some embodiments, the epitope comprises XDXXVXNDXX (SEQ ID NO: 76), where X indicates any amino acid. In some embodiments, the epitope comprises XDXXVXND (SEQ ID NO: 77), DXXVXND (SEQ ID NO: 78), and/or VXNDXX (SEQ ID NO: 79), where X indicates any amino acid. In certain embodiments, the epitope comprises the sequence VXND (SEQ ID NO: 80), where X indicates any amino acid.

Anti-CXCR3 antibodies may be pan-specific for CXCR3 sequences from different species or selective for CXCR3 sequences from a particular species or a particular isotype of CXCR3. In particular embodiments, the CXCR3 antibody is specific for the subject species to which it is administered. Accordingly, in some embodiments, a CXCR3 antibody may be specific for a human CXCR3 sequence (e.g., capable of binding a peptide comprising a sequence homologous to any of the subsequences of SEQ ID NO:1 listed above). Homologous sequence will be readily identified by a person having ordinary skill in the art by means such as protein sequence alignments (e.g., BLASTp, ClustalW, et cetera). In particular embodiments, an antibody for use in the invention binds to a peptide comprising a sequence at least 90, 95, or 99% (or any percentage in between) similar or identical to SEQ ID NO:1 over the entire length of the sequence or a window of at least 10, 15, 20, 25, 30, 35, 40, 45, 50, 55, 60, 65, or 70 residues (or any value in between). In some embodiments, the antibody is able to bind to an epitope at least 80, 85, 90, 95, or 99% (or any percentage in between) similar or identical to one of the epitopes described above (see also FIG. 18).

Particular antibodies disclosed herein include, for example, antibody clones (Cl) 12, Cl 135, Cl 82, Cl 53, and Cl 4, as well as their chimeric and humanized variants.

In some embodiments, the antibodies disclosed herein exhibit certain improved properties over antibodies known in the art, including antibodies 5H7 and 7H5 (disclosed in, e.g., U.S. Pat. No. 7,405,275; CDRs for the antibodies are disclosed in Tables 1 and 2 and in the referenced sequence listings, which are incorporated by reference); V44D7 (described in International Publication WO 2008/094942), 1C6 (described in U.S. Pat. No. 7,407,655; with epitope mapping described in Examples 8 and 9, which are incorporated by reference), and 49801, sold by R&D Systems as catalog no. MAB160.

In some embodiments, the antibody clones disclosed herein (clones 4, 12, 53, 82, and 135 and their chimeric and humanized counterparts) exhibit certain surprising benefits over the known antibodies 5H7, 7H5, V44D7, 1C6, and 49801. For example, the clones disclosed herein exhibit increased binding affinity as compared to the anti-hCXCR3 clones 5H7, 7H5, V44D7, 1C6, and 49801. The humanized clones disclosed herein may also have reduced immunogenicity as compared to the mouse anti-hCXCR3 clones 5H7, 7H5, V44D7, 1C6, and 49801. In addition, the antibodies disclosed herein, such as those comprising heavy chain clones 4.7-4.11 have been optimized by modification at positions 58 and 59 (using IMGT numbering) to remove a deamidation site to enhance stability. In some embodiments, the antibodies disclosed herein retain CXCR3 neutralizing activity.

In certain embodiments, the antibodies or fragments disclosed herein can comprise VH and/or VL CDR sequences that are about 80% to about 100% (e.g., about 80%, 85%, 90%, 95%, 96%, 97%, 98%, 99%, or 100%) identical to the VH and/or VL CDR sequences in any one of antibodies Cl 12, Cl 135, Cl 82, Cl 53, and Cl 4 or in the chimeric or humanized variants of those clones (e.g., 80-100% identical to the six CDRs in Cl 12, or to the six CDRs in Cl 12.1, etc). In some embodiments, the antibodies or fragments can comprise VH and VL CDR sequences that contain 1, 2, 3, 4, 5, 6, 7, 8, 9, or 10 amino acid substitutions (including additions, deletions, and substitutions, such as conservative substitutions) relative to the VH and/or VL CDR sequences in any one of antibodies Cl 12, Cl 135, Cl 82, Cl 53, and Cl 4.

As used herein, the terms "percent (%) sequence identity" or "homology" are defined as the percentage of amino acid residues or nucleotides in a candidate sequence that are identical with the amino acid residues or nucleotides in the reference sequences after aligning the sequences and introducing gaps, if necessary, to achieve the maximum percent sequence identity, and excluding conservative nucleic acid substitutions. Optimal alignment of the sequences for comparison may be produced, besides manually, by means of local homology algorithms known in the art or by means of computer programs which use these algorithms (e.g., BLAST P).

In some embodiments, an isolated CXCR3 antibody or antigen-binding fragment as disclosed herein comprises a VH amino acid sequence comprising at least 80%, 85%, 90%, 95%, 96%, 97%, 98%, 99% or 100% (or any percentage in between) identity to the amino acid sequence of any one of heavy chains 4.0-4.11, heavy chains 12.0-12.3, heavy chains 53.0-53.10, heavy chains 82.0-82.3, and heavy chains 135.0-135.3. In certain embodiments the antibody or fragment comprises a VH amino acid sequence having 1, 2, 3, 4, 5, 6, 7, 8, 9, or 10 mutations (including additions, deletions, and substitutions, such as conservative substitutions) in the amino acid sequence of SEQ any one of heavy chains 4.0-4.11, heavy chains 12.0-12.3, heavy chains 53.0-53.10, heavy chains 82.0-82.3, and heavy chains 135.0-135.3. As used herein, a "conservative substitution" refers to the replacement of a first amino acid by a second amino acid that does not substantially alter the chemical, physical and/or functional properties of the antibody or fragment (e.g., the antibody or fragment retains the same charge, structure, polarity, hydrophobicity/hydrophilicity, and/or preserves functions such as the ability to recognize, bind to, and/or neutralize CXCR3 activity).

In certain embodiments, an isolated CXCR3 antibody or antigen-binding fragment as disclosed herein comprises a VL amino acid sequence comprising at least 80%, 85%, 90%, 95%, 96%, 97%, 98%, 99%, or 100% (or any percentage in between) identity to the amino acid sequence of any one of light chains 4.0-4.7, light chains 12.0-12.3, light chains 53.0-53.13, light chains 82.0-82.3, and light chains 135.0-135.3. In various embodiments the antibody or fragment comprises a VL amino acid sequence having 1, 2, 3, 4, 5, 6, 7, 8, 9, or 10 mutations (including additions, deletions, and substitutions, such as conservative substitutions) in the amino acid sequence of any one of light chains 4.0-4.7, light chains 12.0-12.3, light chains 53.0-53.13, light chains 82.0-82.3, and light chains 135.0-135.3.

In certain embodiments, an isolated CXCR3 antibody or antigen-binding fragment as disclosed herein comprises a heavy chain variable domain comprising at least 80% identity to the amino acid sequence of any one of heavy chains 4.0-4.11 heavy chains 12.0-12.3, heavy chains 53.0-53.10, heavy chains 82.0-82.3, and heavy chains 135.0-135.3, and comprises a light chain variable domain comprising at least 80% identity to the amino acid sequence of any one of light chains 4.0-4.7, light chains 12.0-12.3, light chains 53.0-53.13, light chains 82.0-82.3, and light chains 135.0-135.3. In some embodiments, the heavy and light chains are selected such that a heavy chain from a particular clone (e.g., a clone 4 heavy chain) is paired with any of the light chains for that clone (e.g., a clone 4 light chain). In some embodiments, the heavy and light chains are paired as shown in Table 2. In further embodiments, the antibody or fragment comprising the disclosed VH and/or VL sequences retains the ability to neutralize CXCR3 activity.

In some embodiments, the antibody disclosed herein is a humanized variant of Cl 12, 135, 82, 53, and/or 4. In other embodiments, the antibody is fully human. In certain embodiments, the antibody is a humanized or fully human derivative of an antibody selected from clones 12, 135, 82, 53, and 4. In some embodiments, the antibody has an affinity constant of at least $10^8$ M$^{-1}$ (e.g., at least $10^8$ M$^{-1}$, at least $10^9$ M$^{-1}$, at least $10^{10}$ M$^{-1}$ or at least $10^{11}$ M$^{-1}$, or any value in between). In some embodiments, the antibody is capable of binding to all CXCR3 isoforms. In certain embodiments, the antibody is capable of binding to both the A and B isoforms of CXCR3. In some embodiments, the antibody does not bind the B-isoform of CXCR3

In some embodiments, an isolated CXCR3 antibody or antigen-binding fragment comprises VH CDR1, VH CDR2, VH CDR3, VL CDR1, VL CDR2 and/or VL CDR3 comprising amino acid sequences about 90% to about 100% (e.g., about 90%, 91%, 92%, 93%, 94%, 95%, 96%, 97%, 98%, 99%, or 100%) identical to the VH and VL CDR sequences from any one of clones 12, 135, 82, 53, and 4 and their chimeric and humanized variants. In some embodiments, an isolated CXCR3 antibody or antigen-binding fragment comprises VH CDR1, VH CDR2, VH CDR3, VL CDR1, VL CDR2 and/or VL CDR3 comprising amino acid sequences identical to, or comprising 1, 2, 3, 4, or 5 amino acid residue mutations (including additions, deletions, and substitutions, such as conservative substitutions) relative to the VH and VL CDR sequences from any one of clones 12, 135, 82, 53, and 4 and their chimeric and humanized variants.

In some embodiments, the anti-CXCR3 antibody or fragment comprises a heavy chain having three CDRs (heavy chain CDR1, CDR2, and CDR3) and a light chain having three CDRs (light chain CDR1, CDR2, and CDR3). In some embodiments, the VH CDR1 has 1, 2, or 3 amino acid mutations relative to the VH CDR1 sequence of any one of clones 12, 135, 82, 53, and 4 and their chimeric and humanized variants. In some embodiments, the VH CDR2 has 1, 2, or 3 amino acid mutations relative to the VH CDR2 sequence of any one of clones 12, 135, 82, 53, and 4 and their chimeric and humanized variants. In some embodiments, the VH CDR3 has 1, 2, or 3 amino acid mutations relative to the VH CDR3 sequence of any one of clones 12, 135, 82, 53, and 4 and their chimeric and humanized variants. In some embodiments, the VL CDR1 has 1, 2, or 3 amino acid mutations relative to the VL CDR1 sequence of any one of clones 12, 135, 82, 53, and 4 and their chimeric and humanized variants. In some embodiments, the VL CDR2 has 1 or 2 amino acid mutations relative to the VL CDR2 sequence of any one of clones 12, 135, 82, 53, and 4 and their chimeric and humanized variants. In some embodiments, the VL CDR3 has 1, 2, or 3 amino acid mutations relative to the VL CDR3 sequence of any one of clones 12, 135, 82, 53 and 4 and their chimeric and humanized variants. In certain embodiments, the heavy and light chain CDR 1, CD2, and CDR3 are the CDRs from any one of clones 12, 135, 82, 53, and 4 and their chimeric and humanized variants, or comprise 1-3 amino acid mutations relative to the CDR set in the selected from any one of the antibody clones or their chimeric/humanized variants. In some embodiments, the mutations are at the highlighted positions shown in the alignments in FIG. 17A-H. In some embodiments, the mutation is at one or more of positions 58 and 59 in VH CDR2 from any one of clones 4.0-4.11.

In some embodiments, the anti-CXCR3 antibody or fragment comprises a heavy chain and a light chain. In some embodiments, the heavy chain is at least about 90% identical (e.g., at least about 90, 91, 92, 93, 94, 95, 96, 97, 98, or 99% identical, or any percentage in between), or has 1, 2, 3, 4, 5, 6, 7, 8, 9, or 10 amino acid mutations relative to, any one of heavy chains 4.0-4.11, heavy chains 12.0-12.3, heavy chains 53.0-53.10, heavy chains 82.0-82.3, and heavy chains 135.0-135.3. In some embodiments, the light chain is at least about 90% identical (e.g., at least about 90, 91, 92, 93, 94, 95, 96, 97, 98, or 99% identical, or any percentage in between), or has 1, 2, 3, 4, 5, 6, 7, 8, 9, or 10 amino acid mutations relative to, any one of light chains 4.0-4.7, light chains 12.0-12.3, light chains 53.0-53.13, light chains 82.0-82.3, and light chains 135.0-135.3. In some embodiments, the heavy chain is at least about 90% identical (e.g., at least about 90, 91, 92, 93, 94, 95, 96, 97, 98, or 99% identical, or any percentage in between), or has 1, 2, 3, 4, 5, 6, 7, 8, 9, or 10 amino acid mutations relative to, any one of heavy chains 4.0-4.11, heavy chains 12.0-12.3, heavy chains 53.0-53.10, heavy chains 82.0-82.3, and heavy chains 135.0-135.3 and/or the light chain is at least about 90% identical (e.g., at least about 90, 91, 92, 93, 94, 95, 96, 97, 98, or 99% identical, or any percentage in between), or has 1, 2, 3, 4, 5, 6, 7, 8, 9, or 10 amino acid mutations relative to, any one of light chains 4.0-4.7, light chains 12.0-12.3, light chains 53.0-53.13, light chains 82.0-82.3, and light chains 135.0-135.3. In some embodiments, the mutations are at the positions shown in the alignments in FIG. 17A-H.

In certain embodiments, an isolated CXCR3 antibody or antigen-binding fragment comprising the VH and/or VL CDR sequences disclosed above retains CXCR3 neutralizing activity.

In various embodiments, the heavy and light chain variable domains of a CXCR3 antibody or fragment can comprise at least one framework region (e.g., at least one of FR1, FR2, FR3, and FR4). The framework regions of the heavy chain are designated VH FR, while the framework regions of the light chain are here designated VL FR. In certain embodiments the framework regions can contain substitutions, insertions, or other alterations. In certain embodiments, these alterations result in an improvement or optimization in the binding affinity of the antibody. Non-limiting examples of framework region residues that can be modified include those that non-covalently bind CXCR3 directly, interact with or effect the conformation of a CDR, and/or participate in the VL-VH interface.

In certain embodiments, the heavy chain (VH) of a CXCR3 antibody or fragment may comprise FR1, FR2, FR3 and/or FR4 having amino acid sequences that are about 80% to about 100% identical (e.g., 80%, 85%, 90%, 91%, 92%, 93%, 94%, 95%, 96%, 97%, 98%, 99%, or 100%, or any percentage in between) to the corresponding VH framework regions within any one of clones 12, 135, 82, 53, and 4 and their chimeric and humanized variants. In certain embodiments, a CXCR3 antibody or fragment may comprise at least one VH FR (FR1, FR2, FR3 and/or FR4) having an amino acid sequence identical to, or having 1, 2, 3, 4, or 5 amino acid mutations (including additions, deletions, and substitutions, such as conservative substitutions) relative to, the corresponding VH FR regions within any one of clones 12, 135, 82, 53, and 4 and their chimeric and humanized variants.

In certain embodiments, the light chain (VL) of a CXCR3 antibody or fragment may comprise FR1, FR2, FR3 and/or FR4 having amino acid sequences that are about 80% to about 100% identical (e.g., 80%, 85%, 90%, 91%, 92%, 93%, 94%, 95%, 96%, 97%, 98%, 99%, or 100%, or any percentage in between) to the corresponding VL framework regions within any one of clones 12, 135, 82, 53, and 4 and their chimeric and humanized variants. In certain embodiments, a CXCR3 antibody or fragment may comprise at least one VL FR (FR1, FR2, FR3 and/or FR4) having an amino acid sequence identical to, or having 1, 2, 3, 4, or 5 amino acid mutations (including additions, deletions, and substitutions, such as conservative substitutions) relative to, the corresponding VL FR regions within any one of clones 12, 135, 82, 53, and 4 and their chimeric and humanized variants.

In certain embodiments, a CXCR3 antibody or fragment comprises VH FR regions (FR1, FR2, FR3 and/or FR4) having amino acid sequences identical to, or comprising 1, 2, 3, 4, or 5 amino acid mutations relative to, the corresponding VH FR regions within any one of clones 12, 135, 82, 53, and 4 and their chimeric and humanized variants, and comprises VL FR regions (FR1, FR2, FR3 and/or FR4) having an amino acid sequence identical to, or comprising 1, 2, 3, 4, or 5 amino acid mutations relative to, the corresponding VL FR of within any one of clones 12, 135, 82, 53, and 4 and their chimeric and humanized variants. In certain embodiments, a CXCR3 antibody or fragment comprises VH FR regions (FR1, FR2, FR3 and/or FR4) having amino acid sequences about 80-100% identical to the corresponding VH FR regions within any one of clones 12, 135, 82, 53, and 4 and their chimeric and humanized variants, and comprises VL FR regions (FR1, FR2, FR3 and/or FR4) having an amino acid sequence about 80-100% identical to the corresponding VL FR of within any one of clones 12, 135, 82, 53, and 4 and their chimeric and humanized variants.

The CDR and FR regions disclosed herein can be combined in a variety of combinations, as each of the CDRs and FR regions can be independently selected and combined with any other CDR or FR region for a given antibody. In certain embodiments, the VH and/or VL CDR and FR sequences can be present in any combination in an antibody or fragment that retains the ability to neutralize CXCR3 activity.

Antibodies and fragments, as disclosed herein, can comprise one or more amino acid sequences that do not substantially alter the amino acid sequences described herein. Amino acid sequences that are substantially the same include sequences comprising conservative amino acid substitutions, as well as amino acid deletions and/or insertions that do not impair the ability of the antibody or fragment to neutralize CXCR3 activity.

Antibodies and fragments disclosed herein can be further conjugated to one or more additional molecules. For example, a conjugate can comprise an antibody joined directly or through a linker to one or more therapeutic agents, solubalizing agents, stabilizing agents, immunosuppressants, receptors and fragments thereof, antigen binding peptides and/or other ligand targeting moieties. In some embodiments, the therapeutic agent is an agent useful for treating T1D and/or other disorders associated with CXCR3. In some embodiments, the antibody or fragment is conjugated to a β-cell stimulating agent or insulin.

Nucleotide Sequences

In addition to the amino acid sequences described above, disclosed herein, in certain embodiments, are nucleotide sequences corresponding to those amino acid sequences. In some embodiments, a nucleotide sequence encodes an antibody or fragment capable of neutralizing CXCR3 activity. In certain embodiments, the nucleotide sequences can be used to prepare expression vectors for the expression of anti-CXCR3 antibodies in cells (e.g., expression in mammalian cells).

Also disclosed herein, in certain embodiments, are polynucleotides substantially identical to those coding for the amino acid sequences disclosed herein. Substantially identical sequences may be polymorphic sequences, i.e., alternative sequences or alleles in a population. Substantially identical sequences may also comprise mutagenized sequences, including sequences comprising silent mutations. A mutation may comprise one or more nucleotide residue changes, a deletion of one or more nucleotide residues, or an insertion of one or more additional nucleotide residues. Substantially identical sequences may also comprise various nucleotide sequences that encode for the same amino acid at any given amino acid position in an amino acid sequence disclosed herein, due to the degeneracy of the nucleic acid code. Also included within substantially identical sequences are sequences that encode a chain or chains of an antibody that retains the ability to neutralize CXCR3.

Also disclosed herein, in certain embodiments, are polynucleotides that hybridize under highly stringent or lower stringency hybridization conditions to polynucleotides that encode a CXCR3 neutralizing antibody or fragment. The term "stringency" as used herein refers to the experimental conditions (e.g., temperature and salt concentration) of a hybridization experiment conducted to evaluate the degree of homology between two nucleic acids; the higher the stringency, the higher percent homology between the two nucleic acids. As used herein, the phrase "hybridizing," or grammatical variations thereof, refers to the binding of a first nucleic acid molecule to a second nucleic acid molecule under low, medium or high stringency conditions, or under nucleic acid synthesis conditions. Hybridization can include instances where a first nucleic acid molecule binds to a second nucleic acid molecule, and where the first and second nucleic acid molecules are complementary.

Stringent hybridization conditions include, but are not limited to, hybridization to filter-bound DNA in 6× sodium chloride/sodium citrate (SSC) at about 45 degrees Celsius, followed by one or more washes in 0.2×SSC/0.1% SDS at about 50-65 degrees Celsius. Other stringent conditions include hybridization to filter-bound DNA in 6×SSC at about 45 degrees Celsius, followed by one or more washes in 0.1×SSC/0.2% SDS at about 65 degrees Celsius. Other hybridization conditions of known stringency are familiar to one of skill and are included herein.

In certain embodiments, a nucleic acid disclosed herein may encode the amino acid sequence of a chain or chains in an antibody or fragment capable of neutralizing CXCR3 activity, or the nucleic acid may hybridize under stringent conditions to a nucleic acid that encodes the amino acid sequence of a chain or chains in the antibody or fragment.

In certain embodiments, a polynucleotide sequence is disclosed herein, comprising a nucleotide sequence encoding an amino acid sequence of a VH domain of a CXCR3 neutralizing antibody or fragment, and which is at least about 80-100%, (e.g., about 80%, 85%, 90%, 91%, 92%, 93%, 94%, 95%, 96%, 97%, 98%, 99%, or 100%) identical (or any percentage in between) to the nucleotide sequence encoding the heavy chain of any one of clones 12, 135, 82, 53, and 4 and their chimeric and humanized variants. In certain embodiments, the polynucleotide sequence may comprise a nucleotide sequence having 0, 1, 2, 3, 4, 5, 6, 7, 8, 9, or 10 mutations (including additions, deletions, and substitutions, such as conservative substitutions) relative to the nucleotide sequence encoding the heavy chain of any one of clones 12, 135, 82, 53, and 4 and their chimeric and humanized variants.

In certain embodiments, a polynucleotide sequence is disclosed herein, comprising a nucleotide sequence encoding an amino acid sequence of a VL domain of a CXCR3 neutralizing antibody or fragment, and which is at least about 80-100%, (e.g., about 80%, 85%, 90%, 91%, 92%, 93%, 94%, 95%, 96%, 97%, 98%, 99%, or 100%) identical (or any percentage in between) to the nucleotide sequence encoding the light chain of any one of clones 12, 135, 82, 53, and 4 and their chimeric and humanized variants. In certain embodiments, the polynucleotide sequence may comprise a nucleotide sequence having 0, 1, 2, 3, 4, 5, 6, 7, 8, 9, or 10 mutations (including additions, deletions, and substitutions, such as conservative substitutions) relative to the nucleotide sequence encoding the light chain of any one of clones 12, 135, 82, 53, and 4 and their chimeric and humanized variants.

In particular embodiments, a polynucleotide sequence is disclosed herein, comprising a nucleotide sequence that is at least about 80%, 85%, 90%, 91%, 92%, 93%, 94%, 95%, 96%, 97%, 98%, 99%, or 100% identical (or any percentage in between) to a VH amino acid sequence and at least about 80%, 85%, 90%, 91%, 92%, 93%, 94%, 95%, 96%, 97%, 98%, 99%, or 100% identical (or any percentage in between) to a VL amino acid sequence, where the nucleotide sequences encode the heavy and light chain amino acid sequences from any one of clones 12, 135, 82, 53, and 4 and their chimeric and humanized variants.

The disclosed polynucleotides may be obtained by any method known in the art. For example, if the nucleotide sequence of an antibody is known, a polynucleotide encoding the antibody may be assembled from chemically synthesized oligonucleotides. This would involve, for example, the synthesis of overlapping oligonucleotides containing portions of the sequence encoding the antibody, annealing and ligating those oligonucleotides, and then amplifying the ligated oligonucleotides by PCR. The disclosed polynucleotides can also be generated from any other suitable source of nucleic acids, such as an antibody cDNA library, or a cDNA library isolated from any tissue or cells expressing the antibody (e.g., from hybridoma cells selected to express an antibody).

In some embodiments, any of the disclosed polynucleotides may be incorporated into an expression vector. Suitable vectors for expression in various human and animal cell types are known in the art. In some embodiments, host cells are provided comprising the vectors. Suitable host cells include, e.g., CHO, COS, SF9, and/or other human or nonhuman cell lines. In some embodiments, the host cells transiently or stably express the nucleic acid on the vector when cultured in culture medium, thereby providing a method for producing the antibodies or fragments disclosed herein.

Pharmaceutical Compositions

A pharmaceutical composition can comprise any of the antibodies disclosed herein, or fragments thereof. Also disclosed are pharmaceutical compositions comprising nucleic acids encoding the antibodies or fragments thereof, e.g., for use in gene therapy applications and/or for transient or stable expression in host cells (e.g., CHO, COS, SF9, and/or other human or nonhuman cell lines) to produce the proteins or fragments thereof.

The pharmaceutical compositions disclosed herein can comprise a pharmaceutically acceptable carrier and/or at least one additive such as a solvent, filler, bulking agent, disintegrant, buffer, or stabilizer. Standard pharmaceutical formulation techniques are well known to persons skilled in the art (see, e.g., 2005 Physicians' Desk Reference®, Thomson Healthcare: Montvale, N.J., 2004; *Remington: The Science and Practice of Pharmacy*, 20th ed., Gennado et al., Eds. Lippincott Williams & Wilkins: Philadelphia, Pa., 2000). Suitable pharmaceutical additives include, e.g., mannitol, starch, glucose, lactose, sucrose, gelatin, malt, rice, flour, chalk, silica gel, sodium stearate, glycerol monostearate, talc, sodium chloride, dried skim milk, glycerol, propylene, glycol, water, ethanol, and the like. In certain embodiments, the pharmaceutical compositions may also contain pH buffering reagents and wetting or emulsifying agents (e.g., phosphate buffered saline, sterile saline for injection, etc.). In further embodiments, the compositions may contain preservatives or other stabilizers.

In some embodiments, the pharmaceutical compositions comprising any of the antibodies disclosed herein, or fragments thereof, or nucleic acids encoding the antibodies or fragments, may further comprise one or more of the following: mannitol, polysorbate 80, sodium phosphate dibasic heptahydrate, and sodium phosphate monobasic monohydrate. In another embodiment, pharmaceutical compositions may contain 10 mM Histidine pH 6.5 with up to 2% glycine, up to 2% mannitol, and up to 0.01% polysorbate 80.

The formulation of pharmaceutical compositions may vary depending on the intended route of administrations and other parameters (see, e.g., Rowe et al., *Handbook of Pharmaceutical Excipients*, 4th ed., APhA Publications, 2003.) In some embodiments, the pharmaceutical composition may be a lyophilized cake or powder. The lyophilized composition may be reconstituted for administration by intravenous injection, for example with Sterile Water for Injection, USP. In other embodiments, the composition may be a sterile, non-pyrogenic solution.

The pharmaceutical compositions described herein may comprise an antibody as disclosed herein, or a fragment thereof, or nucleic acids encoding the antibodies or fragments, as the sole active compound, or the pharmaceutical composition may comprise a combination with another compound, composition, or biological material. For example, the pharmaceutical composition may also comprise one or more small molecules or other agents useful for the treatment of a disease or disorder associated with CXCR3, such as T1D. In some embodiments, the pharmaceutical composition can comprise a β-cell stimulating agent, insulin, and/or an insulin-producing cell. In some embodiments, the pharmaceutical composition may also comprise one or more immunosuppressants, mTOR inhibitors or autophagy inhibitors. Examples of immunosuppressants include rapamycin and velcade. Rapamycin is also an mTOR inhibitor.

Administration and Dosing

In some embodiments, a method is provided for treating a patient suffering from a disease or disorder associated with CXCR3 comprising administering to the patient one or more of the anti-CXCR3 antibodies disclosed herein, and/or a fragment thereof. In some embodiments, the antibody or fragment is capable of neutralizing CXCR3. In some embodiments, the disease or disorder is an inflammatory disorder. In some embodiments, the disorder is T1D. In some embodiments, administering a composition (e.g., a pharmaceutical composition) comprising the antibody or fragment prevents, treats, reduces the severity, and/or otherwise ameliorates the symptoms of a disease or disorder associated with CXCR3. In some embodiments, the antibody or fragment is administered at a dose and frequency sufficient to prevent, treat, reduce the severity, and/or otherwise ameliorate the symptoms of a disease or disorder associated with CXCR3.

In certain embodiments, a composition is provided for use in the manufacture of a medicament for treating a disease or disorder, wherein the medicament comprises any of the antibodies disclosed herein, or fragments thereof. For example, the antibody or fragment can comprise the three CDRs from any one of heavy chain variable domains 4.0-4.11 paired with the three CDRs from any one of light chain variable domains 4.0-4.7; the three CDRs from any one of heavy chain variable domains 12.0-12.3 paired with the three CDRs from any one of light chain variable domains 12.0-12.3; the three CDRs from any one of heavy chain variable domains 53.0-53.10 paired with the three CDRs from any one of light chain variable domains 53.0-53.13; the three CDRs from any one of heavy chain variable domains 82.0-82.3 paired with the three CDRs from any one of light chain variable domains 82.0-82.3; or the three CDRs from any one of heavy chain variable domains 135.0-135.3 paired with the three CDRs from any one of light chain variable domains 135.0-135.3.

In some embodiments, the antibody or fragment in the medicament can comprise any one of heavy chain variable domains 4.0-4.11 paired with any one of light chain variable domains 4.0-4.7, any one of heavy chain variable domains 12.0-12.3 paired with any one of light chain variable domains 12.0-12.3, any one of heavy chain variable domains 53.0-53.10 paired with any one of light chain variable domains 53.0-53.13, any one of heavy chain variable domains 82.0-82.3 paired with any one of light chain variable domains 82.0-82.3, or any one of heavy chain variable domains 135.0-135.3 paired with any one of light chain variable domains 135.0-135.3.

Doses of CXCR3 antibody for use in the methods disclosed herein will vary based on numerous parameters familiar to the skilled artisan, such as patient physiology (size or surface area, weight, age, and metabolism) and disease state, as well as pharmacological parameters, such as the mechanism of delivery, formulation, and any concurrent or sequential therapies. An "effective amount" of CXCR3 antibody can produce a desired in vivo effect such as one or more of maintenance or decreased HA1bc (haemoglobin A1c) levels (less than about 7%, e.g., less than 7.5, 7.4, 7.3, 7.2, 7.1, 7.0, 6.9, 6.8, 6.7, 6.6, or 6.5%, or any percentage in between), increased endogenous insulin production and/or circulating insulin levels, maintenance or increased fasting C-peptide levels, improved glucose tolerance, reduced fasting blood glucose levels in the absence of exogenous insulin, reduction in exogenous insulin usage, reduction in β-cell inflammation, and/or increased β-cell population and/or growth. Direct cellular assays for CXCR3 inhibition can also be used, such as a reduction in the blood of CXCR3+ cells (including but not limited to T cells), inhibition of CXCR3 ligand binding, GTP binding, calcium influx and/or mobilization, cell chemotaxis, and/or receptor internalization.

In certain embodiments, an effective amount of CXCR3 antibody results in about 10%, 20%, 30%, 40%, 50%, 60%, 70%, 80%, 90%, or 100% (or any percentage in between) or 1, 2, 4, 5, 10, 15, 20, 30, 40, 50, or 100 fold (or any fold in between), or more, improvements in any of the above parameters in vivo, relative to controls. In certain embodiments, an improvement can be characterized by a fasting blood glucose level in the absence of exogenous insulin that is reduced to below 100, 110, 120, 130, 140, 150, 160, 180, 200, 220, 240, 250, 300, or 350 mg/dL (or any value in between). In certain embodiments, an improvement can be characterized by an increase in basal serum C-peptide levels to more than 0.2, 0.3, 0.4, 0.5, 0.6, 0.8, or 1.0 nmol/L (or any value in between). In some embodiments, an improvement can be characterized by an increase in fasting integrated serum C-peptide levels during C-peptide challenge (post-oral glucose tolerance test) to greater than about 0.03, 0.033, 0.04, 0.05, 0.06, 0.07, 0.08, 0.09, 0.1, 0.2, 0.4, 0.5, 0.6, 0.8, or 1.0 nmol/L×min (or any value in between). In certain embodiments, the effective dose of CXCR3 antibody may be further characterized by reducing the concentration of CD4+ and/or CD8+ cells in the pancreas by at least 10%, 20%, 30%, 40%, 50%, 60%, 70%, 80%, or 90% (or any percentage in between) or at least 1, 2, 3, 4, or 5 fold (or any value in between), relative to control subjects.

In various embodiments, an effective dose of antibody is also selected to be a safe dose for administration to a human subject. In certain embodiments, a safe dose of anti-CXCR3 antibody may be characterized as one that results in no substantial gross depletion of T cells or T cell activity (other than CXCR3 activity) in the subject (e.g., as measured by T cell concentration or activity in the blood of the subject). In particular embodiments, "no substantial gross depletion of T cells or T cell activity" means a 40%, 30%, 25%, 20%, 15%, 10%, 5% (or any percentage in between) or less reduction in the concentration and/or activity (other than CXCR3 activity) of CD4+ and/or CD8+ cells in the subject treated with CXCR3 neutralizing antibody, relative to control subjects treated with placebo and/or relative to treatment subjects prior to treatment. In some embodiments, the safe dose is further characterized by a 40%, 30%, 25%, 20%, 15%, 10%, 5% (or any percentage in between) or less reduction in the concentration of one or more cell types selected from T regs, B cells, myeloid cells, dendritic cells, and/or granulocytes, relative to control subjects.

Exemplary, non-limiting doses for a subject, such as a human, include about 0.03, 0.06, 0.12, 0.24, 0.5, 1.0, 1.5, 2.0, 2.5. 3.0, 3.5, or 3.7 mg/kg/dose (or any value in between) for an antibody with an $ND_{50}$ of about 1-6 μg/mL in an in vitro chemotaxis assay. In certain embodiments, the antibody may be administered in a range of about 0.03-3.7 mg/kg/dose, 0.15-0.7 mg/kg/dose, or 0.25-0.5 mg/kg/dose.

Anti-CXCR3 antibody may be administered in a single administration or in repeat administrations over different periods of time, such as daily, weekly, biweekly, monthly, bimonthly, quarterly, or yearly. Accordingly, in a non-limiting example based on the dosage ranges discussed above, a patient may receive an approximate total dose of 0.16-18 mg/kg of CXCR3 antibody over the course of a treatment regimen.

Anti-CXCR3 antibodies may be administered by any suitable means known to the skilled artisan, including, for example, intravenously, intraperitoneally, nasally, occularly, orally, parenterally, subcutaneously, or transdermally. In particular embodiments, the antibody may be administered directly to the pancreas of the subject or proximate to the pancreas or to specific regions of the pancreas, such as the islet cells of the pancreas.

Effective dosages achieved in one animal may be converted for use in another animal, including humans, using conversion factors known in the art. See, e.g., Reagan-Shaw et al., *FASEB J.* 22:659-61 (2008); Schein et al., *Clin. Pharmacol. Ther.* 11: 3-40 (1970); and Freireich et al., *Cancer Chemother. Reports* 50(4):219-244 (1966). For example, human equivalent dosing (HED) in mg/kg based on animal dosing may be given by the following equation: HED (mg/kg)=animal dose (mg/kg)×($Km^{animal}/Km^{human}$) where Km=weight/surface area (kg/m²).

Exemplary conversion factors based on the above equation are shown in the following table. The exemplary doses provided above for human may be adjusted for other species or other human patients based on these coefficients or other means known to the skilled artisan.

TABLE 3

| | From: | | | | |
|---|---|---|---|---|---|
| To: | Mouse (20 g) | Rat (150 g) | Monkey (3.5 kg) | Dog (8 kg) | Human (60 kg) |
| Mouse | 1 | 0.5 | 0.25 | 0.17 | 0.08 |
| Rat | 2 | 1 | 0.5 | 0.25 | 0.14 |
| Monkey | 4 | 2 | 1 | 0.6 | 0.33 |
| Dog | 6 | 4 | 1.7 | 1 | 0.5 |
| Human | 12 | 7 | 3 | 2 | 1 |

Subjects

Subjects to be treated by the methods provided by the invention can include humans or animals, such as livestock, domestic, and wild animals. In some embodiments, animals are avian, bovine, canine, cetacean, equine, feline, ovine, pisces/fish, porcine, primate, rodent, or ungulate. Subjects may be at any stage of development, including adult, youth, fetal, or embryo. In particular embodiments, the patient is a mammal, and in more particular embodiments, a human.

In various embodiments, a subject can be treated prophylactically or after onset of any condition associated with aberrant CXCR3 activity or any condition in which the disruption of CXCR3 signaling could be therapeutically beneficial. In some embodiments, a subject can be treated prophylactically or after onset of T1D. In some embodiments, a subject can be treated prophylactically prior to onset of T1D using the methods provided herein, or a subject having new onset T1D can be treated using the methods provided herein.

"A subject having new onset T1D" is any subject who has diminished, but still detectable, insulin-producing capacity from the β-cells of the pancreas, regardless of the age of the subject when diabetes is clinically diagnosed (e.g., including adult, youth, fetal, or embryo subjects). In certain embodiments, a subject having new onset T1D will receive treatment preferably within about six months (e.g., within about 1 day, 1 week, 2 weeks, 3 weeks, 4 weeks, 5 weeks, 1 month, 2 months, 3 months, 4 months, 5 months, 6 months, or any time in between) of the earliest clinical diagnosis of T1D. In other embodiments, the subject may receive treatment more than six months after the earliest clinical diagnosis of T1D, wherein the subject retains minimal but measurable basal serum C-peptide levels of greater than or equal to about 0.2 nmol/L (e.g., at least about 0.2, 0.3, 0.4, 0.5, 0.6, 0.8, or 1.0 nmol/L). In some embodiments, treatment comprises administration of one or more doses comprising one or more of the antibodies disclosed herein. In some embodiments, the antibody is a CXCR3 neutralizing antibody.

In some embodiments, a subject having new onset T1D retains a fasting integrated serum C-peptide level of at least about 0.03, 0.033, 0.04, 0.05, 0.06, 0.07, 0.08, 0.09, 0.1, 0.2. 0.4, 0.5, 0.6, 0.8. or 1.0 nmol/L×min, e.g., about 0.03 to 1.0 or 0.033 to 1.0 nmol/L×min during C-peptide stimulation. In particular embodiments, the subject has a fasting integrated serum C-peptide level of 0.033 to 1.0 nmol/L×min during C-peptide stimulation. In certain embodiments, the C-peptide stimulation is a post-oral glucose test and may comprise measuring integrated serum C-peptide levels for 60-150 minutes following administration of 10.0-13.9 mmol/L glucose. See Keymeulen et al., *Diabetologia* 53: 614-623 (2010). In more particular embodiments, the subject's measurable post-oral glucose tolerance test integrated serum C-peptide level increase is less than 0.8, 0.7, 0.6, 0.54, 0.5, 0.4, 0.3, 0.2, or 0.1 nmol/L×min. In still more particular embodiments, the subject has an increase of 0.54 nmol/L× min, or less, in post-oral glucose tolerance test integrated serum C-peptide level. C-peptide corresponds to residues 57-87 of the insulin precursor peptide (human reference sequence NP_000198), with residues 90-110 and 25-54 corresponding to the A and B chains of insulin, respectively.

In some embodiments, a subject having new onset T1D has an elevated fasting blood glucose level in the absence of exogenous insulin of greater than about 100, 110, 120, 130, 140, 150, 160, 180, 200, 220, 240, 250, 300, 350 mg/dL (or any value in between), or more. In certain embodiments, the subject may have both an elevated fasting blood glucose level as described above, as well as a reduced fasting integrated serum C-peptide level, as described above.

In certain embodiments, a subject is treated by the methods disclosed herein shortly after being diagnosed with new onset T1D. In more particular embodiments, the subject is first treated by the methods of the invention within 1, 2, 3, 4, 5, 6, 7, 8, 9, or 10 days, or 1, 2, 3, 4, 5, 6, 7, 8, 9, or 10 weeks, or 1, 2, 3, 4, 5, 6, 7, 8, 9, 10, 11, or 12 months of clinical diagnosis of new onset T1D (or at any time in between). In more specific embodiments, a subject is first treated by the methods of the invention within 6 months of clinical diagnosis of new onset T1D. In other embodiments, a subject having T1D is treated by the methods disclosed herein at any point, regardless of time since clinical diagnosis, wherein the subject retains residual serum C-peptide levels of at least about 0.2 nmol/L.

Additional Methods

The methods provided herein may, in certain embodiments, comprise additional treatments that may be administered concurrently or sequentially (before or after) with the administration of an anti-CXCR3 antibody disclosed herein. For example, in some embodiments, methods are disclosed comprising the further step of administering an immunosuppressant to the subject in addition to an anti-CXCR3 antibody. The immunosuppressants can include, but are not limited to, one or more of Azathioprine (Imuran), β interferon 1a, β interferon 1b, basiliximab, corticosteroids, Cyclosporine (Sandimmune), cyclophosphamide, chlorambucil, daclizumab, deoxyspergualin, Etanercept, glatiramer acetate, infliximab, leflunomide, Mercaptopurine (6-MP), methotrexate, mitoxantrone, Muromonab-CD3, Mycophenolate (MFM or CellCept), natalizumab, anakinra, canakinumab, rituximab, belimumab, abatacept, aldesleukin, prednisone, rapamycin, sirolimus, tacrolimus, and Ustekinumab.

In some embodiments, the methods disclosed herein may comprise, in addition to administering an anti-CXCR3 antibody, the step of administering a β-cell stimulating agent to the subject. The step of administering a β-cell stimulating agent may be concurrent or sequential (before or after) with administering an anti-CXCR3 antibody. Exemplary β-cell stimulating agents include, but are not limited to, one or more of transplanted β-cells (autologous, allogenic, or syngenic), transplanted insulin-producing cells (allogeneic or syngenic), DDP4 (human protein reference sequence NP_001926.2) inhibitors, TM4SF20 peptides (human protein reference sequence NP_079071), TMEM27 peptides (human protein reference sequence NP_065716), exendin 1 or GLP-1 (human protein reference sequence NP_002045) analogs, gp130 and EGF receptor ligands, and those disclosed in paragraphs 8-11 of U.S. Patent Application Publication No. 20100130476. A β-cell stimulating agent may be administered along with an immunosuppressant in the methods of the invention, either concurrently or sequentially (before or after). In certain embodiments, a β-cell stimulating agent, insulin-producing cell, and/or immunosuppressant may be administered by implanting a device capable of delivering the β-cell stimulating agent, insulin-producing cell, and/or immunosuppressant to the targeted tissue or organ.

Also disclosed herein are methods for detecting and/or quantifying CXCR3 and/or cells expressing CXCR3 (e.g., CXCR3+ T cells). In some embodiments, the methods comprise using one or more of the anti-CXCR3 antibodies disclosed herein to detect and/or quantify CXCR3 and/or cells expressing CXCR3. For example, one or more antibody can be added to a patient sample (e.g., a blood sample) and detected using detectable label such as a secondary antibody conjugated to a detectable signal (e.g., a fluorescent secondary detection antibody). For example, FACS sorting can be used to quantify the level of CXCR3-expressing cells in a sample following primary and fluorescent secondary antibody binding.

In some embodiments, the diagnostic methods can be used to diagnose a CXCR3 disorder or a CXCR3-associated disorder (e.g., diabetes, T1D). For example, a disorder can be diagnosed by detecting the presence or absence of CXCR3 in a patient sample, or by comparing the concentration of CXCR3 in a sample to the level in one or more reference standards, wherein a deviation from the level in the standard indicates the presence of a disorder.

In various embodiments, kits comprising at least one anti-CXCR3 antibody or fragment are also provided. The kits are useful for various research, diagnostic, and therapeutic purposes. For example, the kits can be used to detect CXCR3+ T cells, or to treat type I diabetes by administering the anti-CXCR3 antibody or fragment contained within the kit to a subject. For isolation and purification purposes, the kit may contain an antibody or fragment coupled to a bead (e.g., sepharose beads). In certain embodiments, the kit also comprises instructions for using the anti-CXCR3 antibody or fragment for the desired research, diagnostic, and/or therapeutic purpose.

In this application, the use of the singular includes the plural unless specifically stated otherwise. Also in this application, the use of "or" means "and/or" unless stated otherwise. Furthermore, the use of the term "including," as well as other forms, such as "includes" and "included," are not limiting. Any range described herein will be understood to include the endpoints and all values between the endpoints.

The section headings used herein are for organizational purposes only and are not to be construed as limiting the subject matter described. All documents, or portions of documents, cited in this application, including but not limited to patents, patent applications, articles, books, and treatises, are hereby expressly incorporated by reference in their entirety for any purpose. To the extent publications and patents or patent applications incorporated by reference contradict the invention contained in the specification, the specification will supersede any contradictory material.

All information associated with reference gene sequences disclosed in this application, such as GeneIDs or accession numbers, including, for example, genomic loci, genomic sequences, functional annotations, allelic variants, and reference mRNA (including, e.g., exon boundaries) and protein sequences (such as conserved domain structures) are hereby incorporated by reference in their entirety.

EXAMPLES

The following examples serve to illustrate, and in no way limit, the present disclosure.

Example 1

Materials and Methods

Generation of immunogen. CHO cells were transformed with DNA encoding full-length human CXCR3 and CXCR3 was expressed on the cell surface ("r-CXCR3-CHO cells"). The CXCR3 sequence used to transform the cells was obtained and the CXCR3 open reading frame was placed into an expression vector pcDNA3.1neo_DEST, and then transfected into 300-19 cells (Immunogen). An N-terminal peptide fragment of the CXCR3 extracellular domain (EC domain), with the amino acid sequence, MVLEVSDHQV-LNDAEVAALLENFSSSYDYGENESDSC (SEQ ID NO: 81), was conjugated to KLH by the C terminal cysteine, and used as an immunogen. The cells expressing CXCR3 were maintained at 37° C. under 5% CO2 in RPMI (Invitrogen, Carlsbad, Calif.) supplemented with 10% dialyzed fetal bovine serum (FBS) (Invitrogen). Cells were prepared for injection by substituting the above culture medium with phosphate-buffered (Ca/Mg-free) saline (CMF-PBS) supplemented with 5 mM EDTA, and harvesting the cells in that buffer. The harvested cells were pelleted by centrifugation at 500×g for about 5 minutes, washed once by re-suspending the pellet in CMF-PBS and centrifuging as before, counted, and adjusted to the appropriate volume (such as 5×10$^6$ cells in 0.2 ml) for injection by resuspending the cell pellet in CMF-PBS.

Antibody preparation. The N-terminal 37 amino acids of human CXCR3 were used to generate mouse monoclonal hybridomas for anti-human CXCR3, and five antibody clones (4, 12, 53, 82, and 135) were selected for further characterization. The 37 amino acid N-terminus of human CXCR3 is 65% homologous to the aligned region in mouse CXCR3 and contains residues important for CXCL9, CXCL10, and CXCL11 binding. BALB/c mice, about 6-8 weeks old (Charles River Laboratories, Wilmington, Mass.) were immunized with the cells expressing CXCR3 or an extracellular peptide of CXCR3. A group of mice were primed subcutaneously (SC) on day 0 with a 1:1 emulsion of KLH-conjugated peptide mixed with adjuvant (TiterMax Gold, Sigma Aldrich, #T2685-1ML), boosted SC 3-5 times at 2-3 week intervals with a 1:1 emulsion of peptide to adjuvant or intraperitoneal (IP) with cells in PBS without adjuvant, and boosted two consecutive days prior to sacrifice via IP with either peptide and/or cells in PBS all without adjuvant. Another group of mice were primed IP 3-5 times at 2-3 week intervals and boosted via IP with cells in PBS two consecutive days prior to sacrifice. For both groups of mice, each injection contained approximately 2×10^6 cells in a volume of approximately 100 µl.

The day after the last injection, mice were sacrificed and the spleen was removed and placed in approximately 10 ml of serum-free DMEM (Gibco) in a Petri dish. Sp2\O mouse myeloma cells (ATCC CRL-1581) were fused with spleen cells from the immunized mouse using 50% (w/w) PEG based on the method of Kohler and Milstein (*Nature*, 256: 495-7, (1975)). At the end of the procedure the cells were resuspended in 50 ml of ClonaCell-Hy Hybridoma Recovery medium (StemCell Technologies), transferred to a T75 cm$^2$ flask and incubated for 16-24 hrs at 37° C. Following this incubation the cells were harvested and added to 100 ml of ClonaCell-HY methylcellulose selection media (StemCell Technologies). This mixture was then aliquoted into ten 100 mm$^2$ tissue culture dishes and incubated for 10-14 days. Clonal hybridomas were transferred from the methylcellulose to liquid medium and grown in 96 multi-well plates for assays to identify monoclonal antibodies specific for CXCR3.

Unless indicated otherwise, reference in these examples to an antibody variant, such as Hu4.1, refers to an antibody containing a heavy chain variant and light chain variant of the same number (e.g., Hu4.1 would contain heavy chain 4.1 and light chain 4.1). All references to antibodies are consistent with the antibody numbering and VHNK chain pairing shown in Table 2.

Animals. Female NOD/LtJ mice were purchased from the Jackson Laboratory (Bar Harbor, Me.) and were maintained under pathogen-free conditions. Mice were screened for glycosuria using an ACCU-CHEK® Compact Plus Blood Glucose Meter (Roche, Indianapolis, Ind.) by tail vein puncture two times a week starting at 10 weeks of age. Mice were deemed diabetic when blood glucose measured above 250 mg/dL for three consecutive days. Mice were observed for a minimum of 100 days post treatment start. All animal experiments were approved by in-house IACUC.

Antibody injections. For prevention studies, pre-diabetic NOD mice were injected with 100 µg antibody intraperitoneally (i.p.) once a week for 6 weeks starting at 10 weeks of age. For reversal studies, animals were randomly enrolled in treatment groups within 1 week after mice were deemed diabetic, blood glucose was measured twice a day, at least six hours between readings, and insulin was administered by i.p. injection to those mice with a blood glucose above 250 mg/dL for the duration of the study. Mice in the treatment groups that maintained insulin independence for 30 consecutive days were considered reversed. Five mice from each group were harvested between the fifth and sixth treatments and lymphoid organs, blood, bone marrow, and pancreas were harvested for cellular analysis. At the end of the study, the pancreas was harvested and processed for histological and immunohistochemical analysis. The anti-mouse CXCR3 antibody, clone CXCR3-173 (Uppaluri et al.

2008), and the hamster IgG control antibody were purchased from BioLegend San Diego, Calif.).

FACS analysis. Single cell suspensions of the spleen, inguinal lymph nodes, pancreatic lymph nodes, and bone marrow were made. The pancreas was snipped into small pieces and incubated in 2 mg/ml collagenase D (Roche Diagnostics, Indianapolis, Ind.) for 30 minutes at 37° C., filtered through a 70 micron cell strainer (BD Biosciences, San Jose, Calif.), and lymphocytes were separated from pancreas tissue using density gradient centrifugation. Cells were stained with APC labeled anti-mouse CD25, FITC labeled anti-mouse CD4 and PE labeled anti-mouse Foxp3 (eBiosciences, San Diego. CA) for regulatory cells (T regs), PerCP labeled anti-mouse CD8α, PE labeled anti-mouse CD44, APC labeled anti-mouse CD62L, and PeCy7 labeled anti-mouse CXCR3 for activated/memory T cells, and FITC labeled anti-mouse CD94, PerCP labeled anti-mouse CD4, APC-labeled anti-mouse B220, PeCy7 labeled anti-mouse CD11c, Pacific blue labeled anti-mouse CD11b, and PE labeled anti-mouse NKp46 for B cells, myeloid cells, dendritic cells, NK cells and NKT cells. The cells were incubated for 30 min at 4° C. after blocking with anti-mouse CD16/32 for 20 min on ice. For the T reg stain, surface staining was performed, the cells were washed, fixed and permeabilized in Cytofix/Perm buffer (eBiosciences) then stained with the anti-mouse Foxp3 antibody for 30 min on ice. After staining, cells were washed twice, fixed in paraformaldehyde and acquired on the LSRII cytometer, and data was analyzed using Flow Jo software (Treestar, Ashland, Oreg.). All antibodies were purchased from BD Biosciences unless stated otherwise.

Chemotaxis assay. The assay for chemotaxis was performed in 24-well plates (Costar) carrying transwell permeable supports with a 5 μm membrane. CXCR3-transfected 300.19 cells were placed in the transwell inserts at $1 \times 10^6$ cells in 2.5% heat-inactivated fetal bovine serum in RPM1640 (0.2 ml total volume). Media alone or supplemented with recombinant chemokine 300 ng/ml CXCL9 (MIG), 100 ng/ml CXCL10 (IP-10) or 100 ng/ml CXCL11 (I-TAC) was placed in the lower compartment (0.6 mls) and the transwell inserts containing the cells were loaded into the lower compartment. The plates were incubated between 4-5 hours in a 5% $CO_2$ humidified incubator at 37° C. Following the incubation period, transwell inserts were removed and the total media in the lower compartment was pooled and the cells pelleted by centrifugation for 5 min at 1200 RPM. The media was aspirated and the cells were stained with Calcein AM (10 μg/ml final) for 30 minutes at 37° C. The cells were pelleted and washed, media was added (0.1 ml), and the suspension transferred to 96 well black-walled clear bottom plates. The plates were pulsed at 1200 RPM to settle the cells and the fluorescence was measured at 490/520 nm on a Flexstation. All conditions were tested in triplicate. The resulting data is expressed as mean relative fluorescence units (RFUs) of the migrated cells. See FIG. 14 A-C and FIG. 15A-C.

For chemotaxis with CXCR3 blockade, the CXCR3 transfected 300.19 cells were pre-treated with various amounts of blocking antibody or control IgG for 20-30 minutes at 37° C. prior to being used in the chemotaxis assay. The antibody was not washed out but was present during the assay incubation.

Calcium mobilization assay using FLIPR. Human Embryonic Kidney 293 (HEK) cells expressing hCXCR3 were harvested at 80% confluency by treating with PBS+2 mM EDTA. The cells were suspended in serum free HEK-SFM media at a density of $1 \times 10^6$ cells/mL. 15 μL (15,000 cells) of the suspension was dispensed into each well of a 384 well plate. Cells were dye loaded for 30 minutes at room temperature by adding 15 μL of reconstituted FLIPR Calcium 4 Dye. Anti-human CXCR3 antibody clones and isotype controls were serially diluted (3 fold) in HBSS+20 mM HEPES+1% BSA to generate 10 test concentrations per clone. Each test concentration was tested in duplicate (n=2) on the same plate. 15 μL of the test concentration was added to the cells in each well and the plate was incubated at room temperature for 1 hour. A fixed concentration of CXCL11 (R & D Systems) representing EC80 for eliciting intracellular calcium mobilization was added on the FLIPR into each well and the change in fluorescence was monitored over time. The maximum response of each well was normalized to the baseline and the data were fit after averaging to a four parameter equation using Graph Pad Prism and the IC50 for each clone was determined. See FIG. 14D and FIG. 21.

Biacore analysis for affinity. Biacore surface preparation. Binding affinities of mouse a-human CXCR3 hybridoma antibody clones 4, 12, 53, 82 and 135 to human CXCR3 peptide were calculated using a Biacore T100 Kinetics/ Affinity assay. A Biacore CM5 Series S sensor chip (GE #BR-1006-68) was immobilized with rabbit-anti-mouse-Fc (RAM-Fc) capture antibody (GE# BR-1008-38) using the standard amine coupling program. The chip's carboxymethyl dextran surface was activated using a 1:1 mixture of 0.1M N-hydroxysuccinimide (NHS) and 0.4M N-ethyl-N'-(3-dimethylaminopropyl)carbodiimide hydrochloride (EDC), allowing the surface to bind reactive amine groups on the capture antibody. Following antibody immobilization, the reactive sensor chip surface was quenched using 1M ethanolamine hydrochloride/NaOH pH 8.5. Immobilization resulted in 8,000 RU of the RAM-Fc capture antibody on one flow cell. Another blank flow cell was used as a surface for reference subtraction during data analysis.

Biacore Assay Conditions. The Biacore T100 instrument sample chamber and assay temperatures were set to 4° C. and 25° C. respectively. Mouse anti-hCXCR3 antibodies were diluted to 500 nM in HBS-EP+ running buffer (10 mM HEPES, 150 mM NaCl, 0.05% P20 surfactant, 3 mM EDTA, pH 7.4), and were captured using a thirty second injection at 10 μl/min. These conditions resulted in ~1,200 RU stable capture of each mouse anti-hCXCR3 clone tested. hCXCR3 peptides were diluted to 200, 100, 50, 25, 12.5 and 0 nM concentrations in HBS-EP+. Each assay cycle, peptide was injected for five minutes at a 50 μl/min flow rate to measure association, then washed in HBS-EP+ for ten minutes at 50 μl/min flow rate to measure dissociation. The capture surface (RAM-Fc) was regenerated between assay cycles using 10 mM glycine-HCl pH 1.7 at 50 μl/min for three minutes. Analysis was performed in Biacore T100 Kinetics Evaluation software v2.0 (GE Healthcare). Sensorgrams fit to a 1:1 binding model with reference flow cell and 0 nM concentration subtraction (double-reference subtraction).

Biacore whole receptor assay. Full-length human CXCR3 receptor protein with C-terminal 6×His (SEQ ID NO: 82) and HPC4 tag was expressed in insect Sf9 cells with a baculovirus vector. The receptor protein was then purified via Ni-NTA and HPC4 affinity purifications. The final product was buffer exchanged into 10 mM HEPES, 300 mM NaCl, 0.5% n-Dodecyl β-D-Maltopyranoside and 5% glycerol. The receptor protein was captured on NTA chips via Ni-chelating and further stabilized by amine coupling using 1:10 diluted mixture of the 1:1 mixture of 0.1M N-hydroxysuccinimide (NHS) and 0.4M N-ethyl-N'-(3-dimethylaminopropyl) carbodiimide hydrochloride (EDC). The stabilized receptor surface was tested for ligand binding activity by injecting 20 nM of hCXCL10 and hCXCL11 ligands. For kinetics analysis, human CXCR3 ligands (hCXCL9, hCXCL10 and hCXCL11) were diluted to 20, 10, 5, 2.5, 1.25, 0.6125, 0.3125 and 0 nM concentrations in HBS-EP+. Anti-CXCR3 antibodies were diluted to 80, 40, 20, 10, 5, 2.5, 1.25 and 0 nM concentrations in HBS-EP+. Analyte was injected for five minutes at a 50 µl/min flow rate to measure association, and then washed in HBS-EP+ for ten minutes at 50 µl/min flow rate to measure dissociation. The receptor surface was regenerated between assay cycles using 10 mM glycine-HCl pH 1.7 at 50 µl/min for 1 minute. Analysis was performed in Biacore T100 Kinetics Evaluation software v2.0 (GE Healthcare). Sensorgrams fit to a 1:1 binding model with reference flow cell and 0 nM concentration subtraction (double-reference subtraction).

Glucose tolerance testing. The evening before glucose challenge, non-fasting blood glucose was monitored and insulin treatment of diabetic animals was withheld. Mice were fasted for 12 hours before D-glucose (20%; Sigma) at 2 mg/g body weight was injected i.p. Blood glucose was measured before and 15, 30, 60, and 120 minutes after the injection.

Example 2

Characterization of NOD Mice

Representative sections of pancreas from 6 to 10 week old pre-diabetic female NOD mice and new-onset diabetes female NOD mice embedded in paraffin were stained for insulin, CXCL10, and the T cell marker CD3. FIG. 1. CXCL10 expression was detected in the pancreas of NOD mice within islets surrounded by infiltrating cells (arrows in central column of FIG. 1). Older pre-diabetic and new-onset diabetic mice had a marked increase in T cell infiltration of the islets (FIG. 1, right column) and a decrease in insulin production within the islets (FIG. 1, left column).

Figure 2:
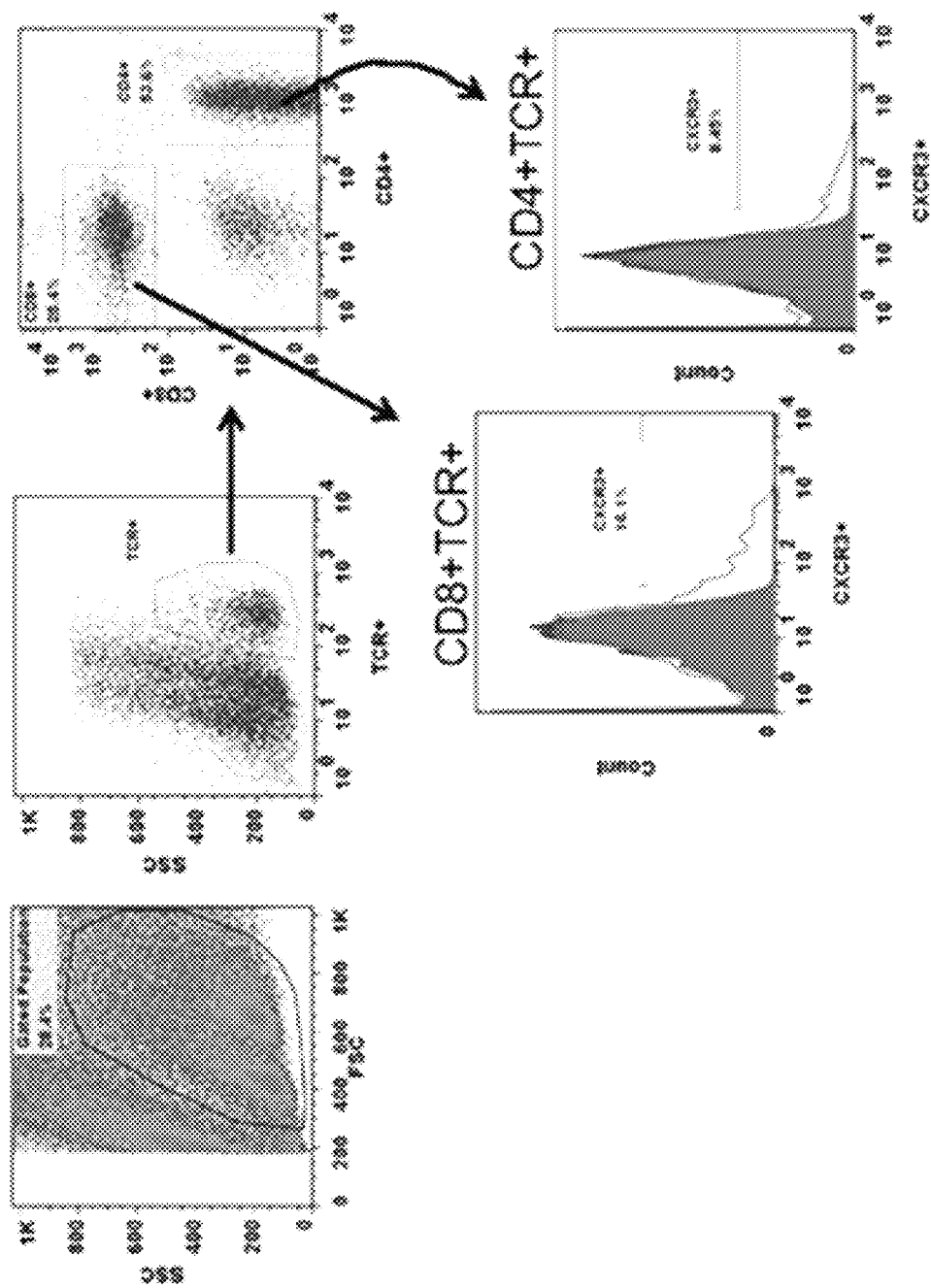
FIG. 2 is a flow cytometry analysis of CXCR3 expression on T cells from the pancreas of female NOD mice with new-onset diabetes. CD4+ and CD8+ T cells were identified and stained for CXCR3 expression, as shown by the solid line in the bottom two graphs. Isotype control staining is shown by the shaded curve in the same two graphs.

To further evaluate whether CXCR3+ T cells were present in the pancreas of NOD mice, flow cytometry analysis was conducted on pancreas tissue harvested from female NOD mice with new-onset diabetes. FIG. 2. CXCR3 expression was evaluated on CD4+/TCR+ and CD8+/TCR+ T cells. Staining with isotype control antibody is represented by the shaded curve. Flow cytometry was performed on single cell suspensions of pooled pancreas tissue harvested from several mice. The data indicate that CXCR3+ cytotoxic and helper T cells were present in the pancreas of NOD mice.

Example 3

Prophylactic Treatment of NOD Mice with Anti-CXCR3 Antibody

Figure 3:
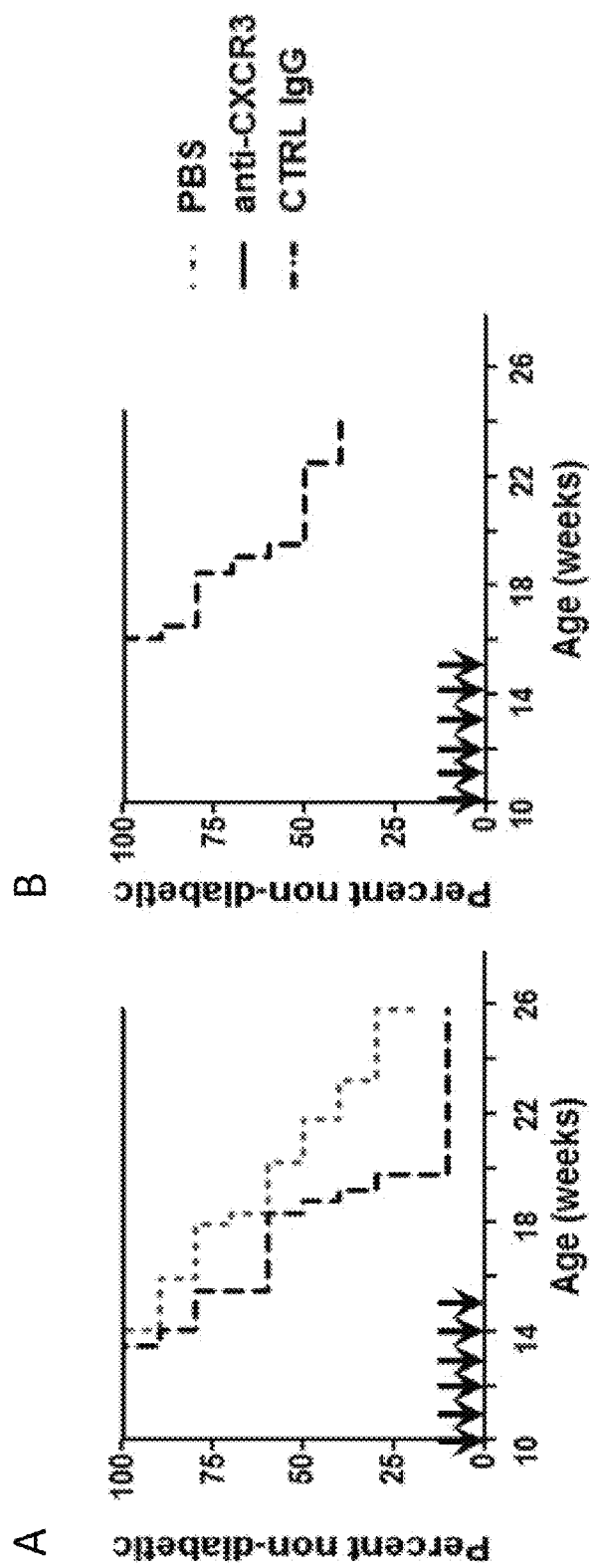
FIGS. 3A-3B show the percentage of non-diabetic female NOD mice over time for animals treated with PBS, anti-CXCR3, and control IgG starting at 10 weeks of age, before diabetes onset. Results from two independent studies are shown in FIGS. 3A and 3B.

Pre-diabetic female NOD mice were treated once a week for six weeks with 100 µg of a hamster anti-mouse CXCR3 antibody (clone CXCR3-173, purchased from BioLegend, San Diego, Calif.), or with a control hamster IgG or PBS, starting at 10 weeks of age. Blood glucose was monitored twice a week and an animal was considered diabetic and euthanized after exhibiting three consecutive blood glucose readings above 250 mg/dL. FIG. 3 shows the percentage of mice that developed diabetes over time for each treatment group. Each line represents the combined results from ten mice per group. Results from two independent studies are shown (FIGS. 3A and 3B). The plots illustrate that prophylactic treatment with an anti-CXCR3 antibody prevented development of diabetes in pre-diabetic female NOD mice.

Figure 4:
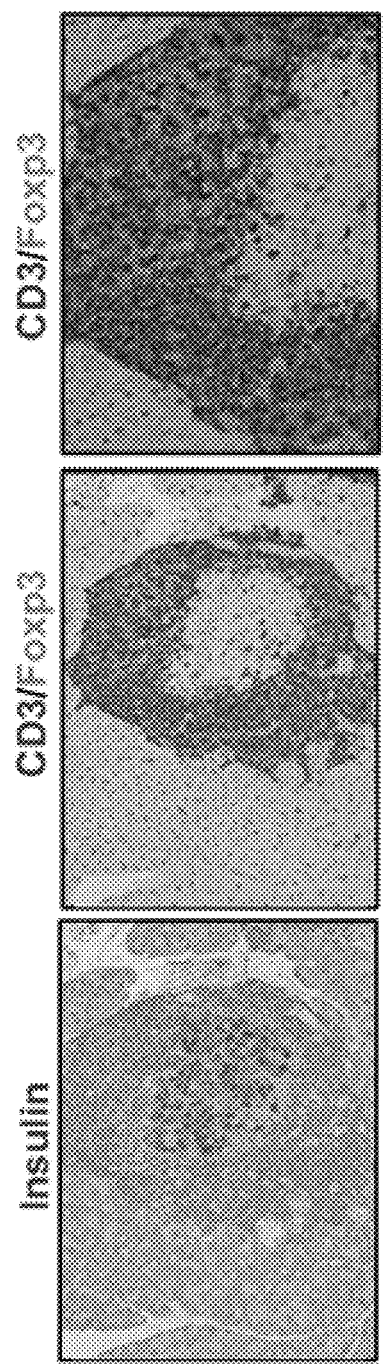
FIG. 4 shows pancreas sections from 26 week old non-diabetic female NOD mice treated with anti-CXCR3 antibody prophylactically starting at 10 weeks of age and stained for insulin (left panel) or CD3/Foxp3 (center and right panels). The right panel is an increased magnification image of the section shown in the center panel.

To further evaluate the effects of prophylactic anti-CXCR3 antibody administration, representative pancreas sections from female NOD mice treated with anti-CXCR3 antibody were stained for insulin (FIG. 4, left panel), CD3 and Foxp3 (FIG. 4, center and right panels). The right hand panel in FIG. 4 is an increased magnification image of the section shown in the center panel. The pancreas tissue was harvested from mice at the end of the study period (26 weeks of age). FIG. 4 demonstrates that insulin-positive islets were present in NOD mice treated with an anti-CXCR3 antibody, while the majority of T cells surrounded and had not invaded the islets.

Example 4

Reversal of New Onset Diabetes in NOD Mice

Figure 5:
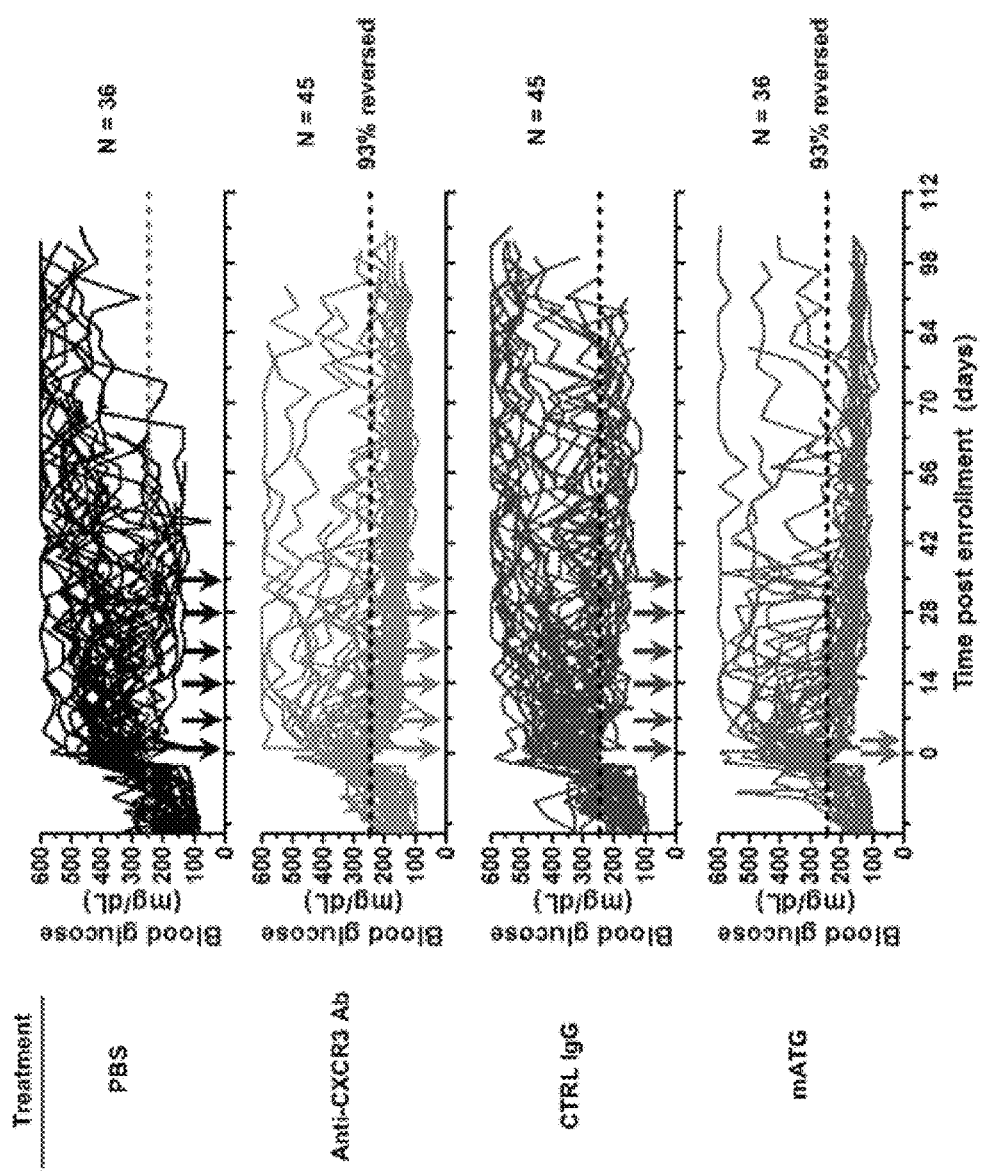
FIG. 5 shows daily morning blood glucose values for female NOD mice treated with PBS, anti-CXCR3 antibody, control IgG, and murine anti-thymocyte globulin (murine thymoglobulin, mATG) antibody starting within 3-4 days after mouse was deemed diabetic. Each line represents an individual mouse. Arrows indicate days when treatment was provided.

Female mice with three consecutive blood glucose readings above 250 mg/dL were deemed diabetic and randomly enrolled in treatment groups. Treatment was started within one week of enrollment. Mice were treated with PBS, anti-mouse CXCR3 antibody (100 µg administered intraperitoneally, clone CXCR3-173) or control IgG (100 µg administered i.p.) once a week for six weeks, or murine anti-thymocyte globulin (mATG; 500 µg administered i.p.) on days 0 and 4. Once enrolled, blood glucose was measured in the morning and afternoon (at least six hours in between), and insulin was administered by i.p. injection only to those mice whose blood glucose was above 250 mg/dL. Daily morning blood glucose values for individual mice are shown (FIG. 5). Data is pooled from four independent reversal studies with 8-10 mice per group per study. The data demonstrates reversal of new-onset diabetes in NOD mice after treatment with anti-CXCR3 antibody.

Figure 6:
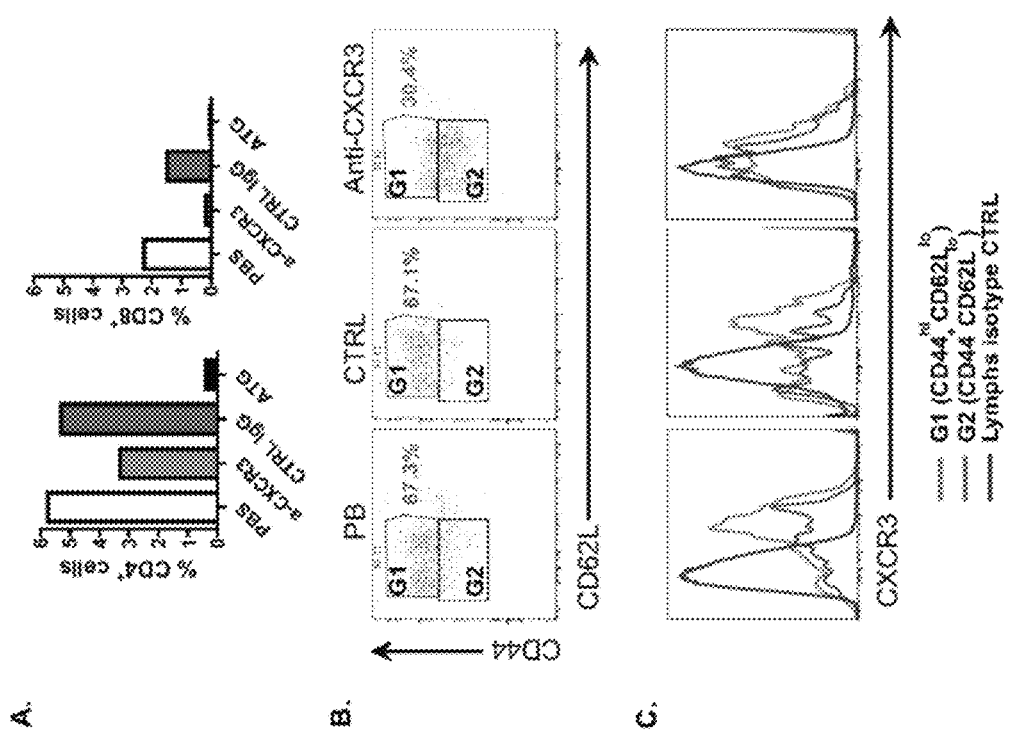
FIG. 6A is a bar graph showing the percentage of T cells from female NOD mice treated with PBS, anti-CXCR3 antibody, control IgG, and mATG antibody that were CD4+ (left graph) and CD8+ (right graph). The pancreas was harvested from mice during the treatment course after the fifth injection of test article and from age-matched mATG treated mice.
FIG. 6B is a plot of CD44 expression (vertical axis) against CD62L expression (horizontal axis) on CD4+ T cells from the pancreas of mice treated with PBS, control antibody, or anti-CXCR3 antibody. G1 and G2 refer to gated high CD44/low CD62L and low CD44/low CD62L T cells, respectively.
FIG. 6C shows the expression of CXCR3 on CD4+ T cells in G1 and G2, as compared to CXCR3 expression on cells stained with isotype control antibody and gated on lymphocytes.

To evaluate changes in T cell subsets in the pancreas of mice treated with anti-CXCR3 antibody, single cell suspensions of pancreas from four mice per treatment group (PBS, anti-mouse CXCR3, control IgG or mATG treated mice) were pooled, stained for T cells and analyzed by flow cytometry. Pancreas tissue was harvested a few days after the fifth treatment dose of PBS, anti-mouse CXCR3, or control IgG, and from age-matched mATG-treated mice. The percentage of CD4+ and CD8+ T cells in the suspensions are shown in FIG. 6A. FIG. 6B shows the expression of CD44 and CD62L on CD4+ T cells in the pancreas from mice treated with PBS (left), control IgG (middle), and anti-mouse CXCR3 antibody (right). The percentage of cells in gate 1 (G1; CD44$^{hi}$CD62L$^{lo}$) is indicated for each treatment group (67.3% for PBS, 67.1% for control IgG, and 30.4% for anti-CXCR3 treatment). FIG. 6C is a plot of CXCR3 expression on CD4+ T cells in gate 1 (G1) or gate 2 (G2) as defined in FIG. 6B, compared to cells stained with isotype control antibody and gated on lymphocytes.

Figure 7:
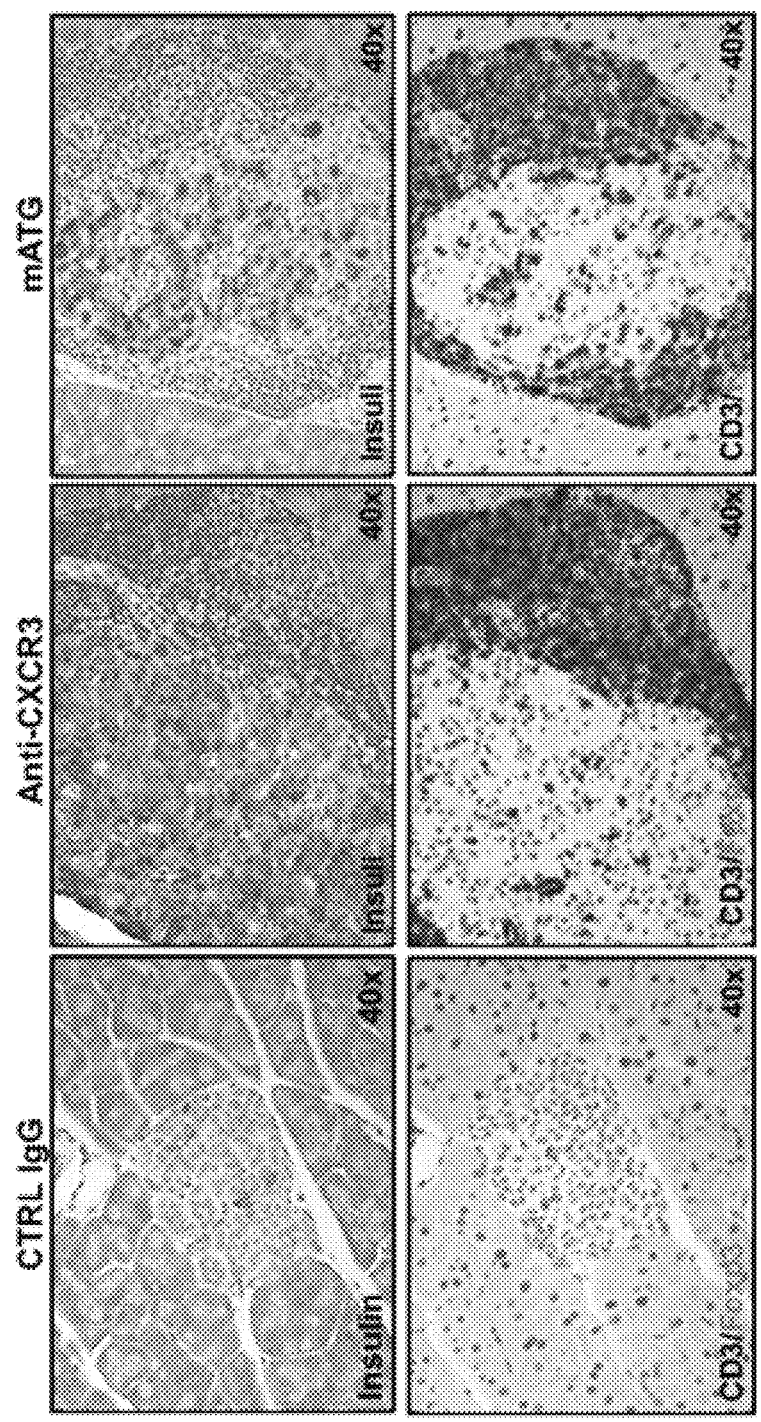
FIG. 7 shows pancreas sections from female NOD mice treated with control IgG (left panels), anti-CXCR3 antibody (center panels), and mATG (right panels) and stained for insulin (top row) or CD3/Foxp3 (bottom row).

To evaluate whether insulin-positive islets are present in NOD mice reversed with anti-CXCR3 treatment, paraffin-embedded pancreas sections were prepared from female NOD mice treated with control IgG (left panels), anti-mouse CXCR3 antibody (middle panels) or murine ATG (right panels) and stained for insulin (top row) or co-stained for CD3 and Foxp3 (bottom row). See FIG. 7. The pancreas tissue was harvested from mice at the end of the study (around 100 days post enrollment). The stained sections demonstrated that insulin-positive islets were present in NOD mice reversed with anti-CXCR3 treatment, and that T cells surrounded the islets but few invaded the islets.

Figure 8:
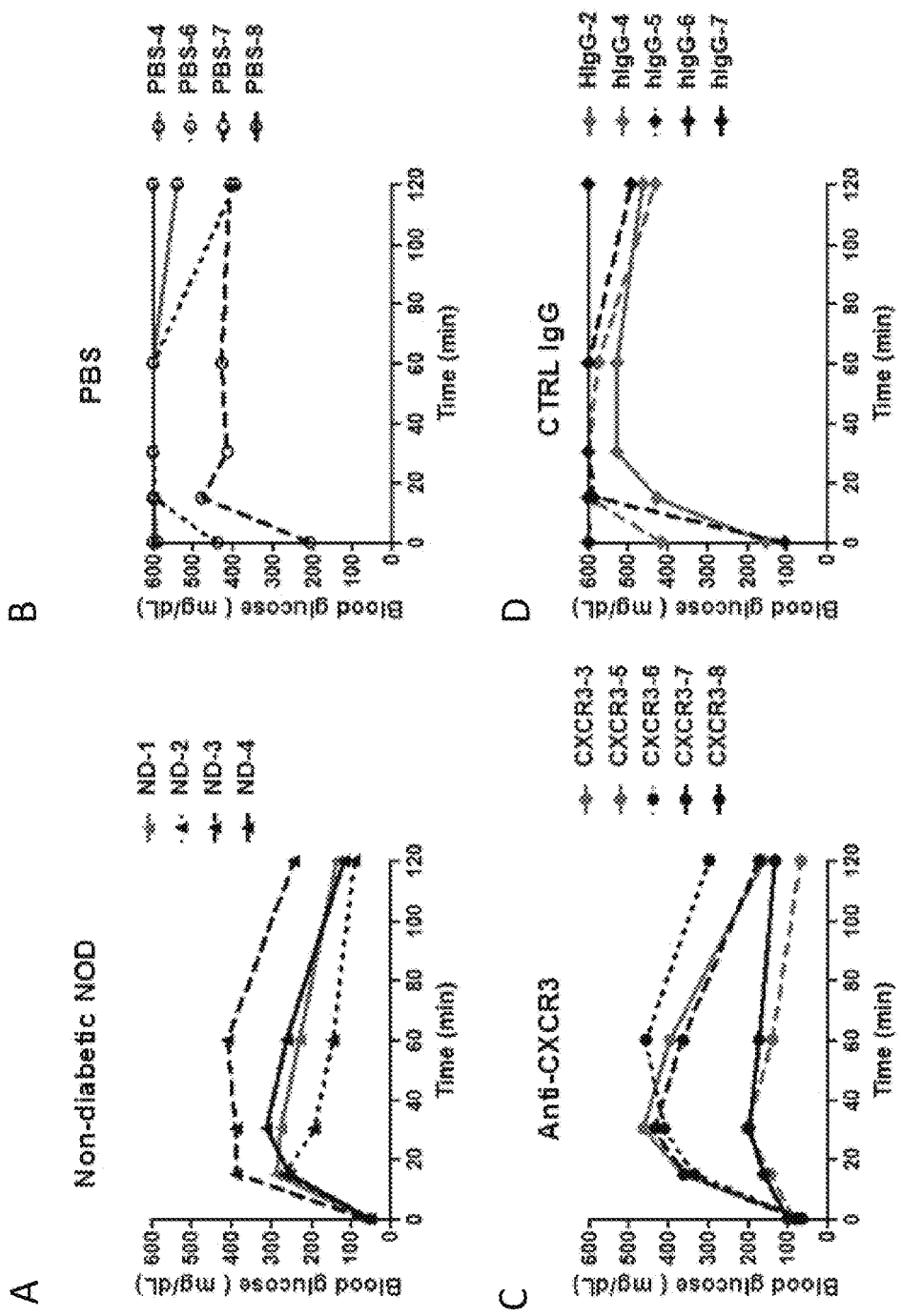
FIG. 8A-D is a plot of blood glucose levels following glucose challenge in age-matched non-diabetic female NOD mice (FIG. 8A), diabetic NOD mice treated with PBS (FIG. 8B), NOD mice in disease remission following anti-CXCR3 antibody treatment (FIG. 8C), and diabetic NOD mice treated with control IgG antibody (FIG. 8D). Glucose challenge was performed on mice 100 days after initial diabetes diagnosis and study enrollment. Each line represents data from an individual animal.

To evaluate the response to glucose challenge, a glucose tolerance test was performed. FIG. 8. Age-matched female non-diabetic NOD mice (FIG. 8A), diabetic NOD mice that had been treated with PBS (FIG. 8B), diabetic NOD mice reversed with anti-mouse CXCR3 treatment (FIG. 8C), and diabetic NOD mice that had been treated with IgG (FIG. 8D) were fasted overnight and challenged with glucose by i.p. injection. Blood glucose was measured before (time 0) and after challenge at the indicated times. Representative data from 4-5 mice per treatment group are shown. The data illustrate that anti-CXCR3 antibody treatment improved fasting glucose tolerance 100 days post-enrollment.

Example 5

Adoptive Transfer of T Cells

Figure 9:
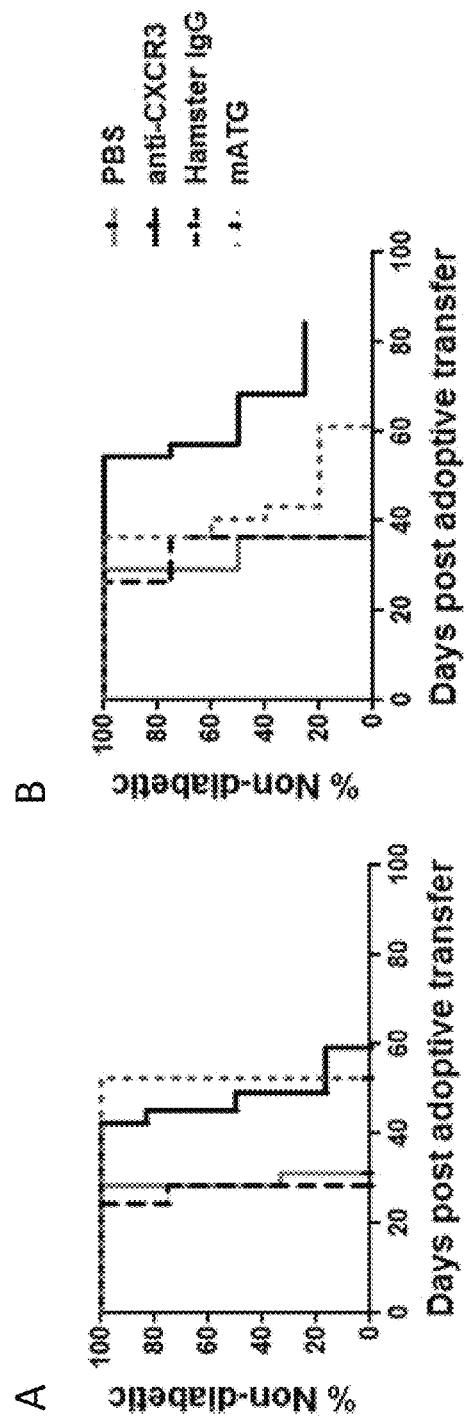
FIG. 9A-B shows the percentage of non-diabetic mice over time for NOD.Scid recipients receiving pooled donor CD4+ and CD8+ T cells isolated from female NOD mice treated with PBS, anti-CXCR3, control IgG, or mATG antibodies. T cells were isolated from diabetic female NOD mice around 80-90 days following treatment with PBS or control IgG, or from female NOD mice in disease remission around 80-90 days following treatment with anti-CXCR3 or mATG antibodies. Results from two independent studies are shown in FIGS. 9A and 9B.

To evaluate the ability of T cells from NOD mice treated with anti-CXCR3 antibody (clone CXCR3-173) and exhibiting disease remission to induce diabetes in recipient animals, isolated CD4+ and CD8+ T cells were adoptively transferred to recipient NOD.scid (non-obese diabetic-severe combined immunodeficiency) mice by intravenous injection. FIG. 9 shows the percentage of non-diabetic mice over time after adoptive transfer of isolated CD4+ and CD8+ T cells from diabetic mice treated with PBS or control IgG, or mice in disease remission after treatment with murine ATG or anti-mouse CXCR3 antibody. CD4+ and CD8+ T cells were isolated from spleen, pancreatic lymph nodes, and inguinal lymph nodes harvested 80-90 days post-enrollment from female NOD mice in the different treatment groups. CD4+ and CD8+ T cells were pooled and 8 million total cells were adoptively transferred to NOD.Scid recipients, and the development of diabetes was monitored by bi-weekly blood glucose measurements. Each line in FIG. 9 represents the combined data from five mice per group. Two representative studies are shown (FIGS. 9A and 9B). Isolated T cells from anti-CXCR3 antibody-treated mice exhibit a delay in disease transfer.

Figure 10:
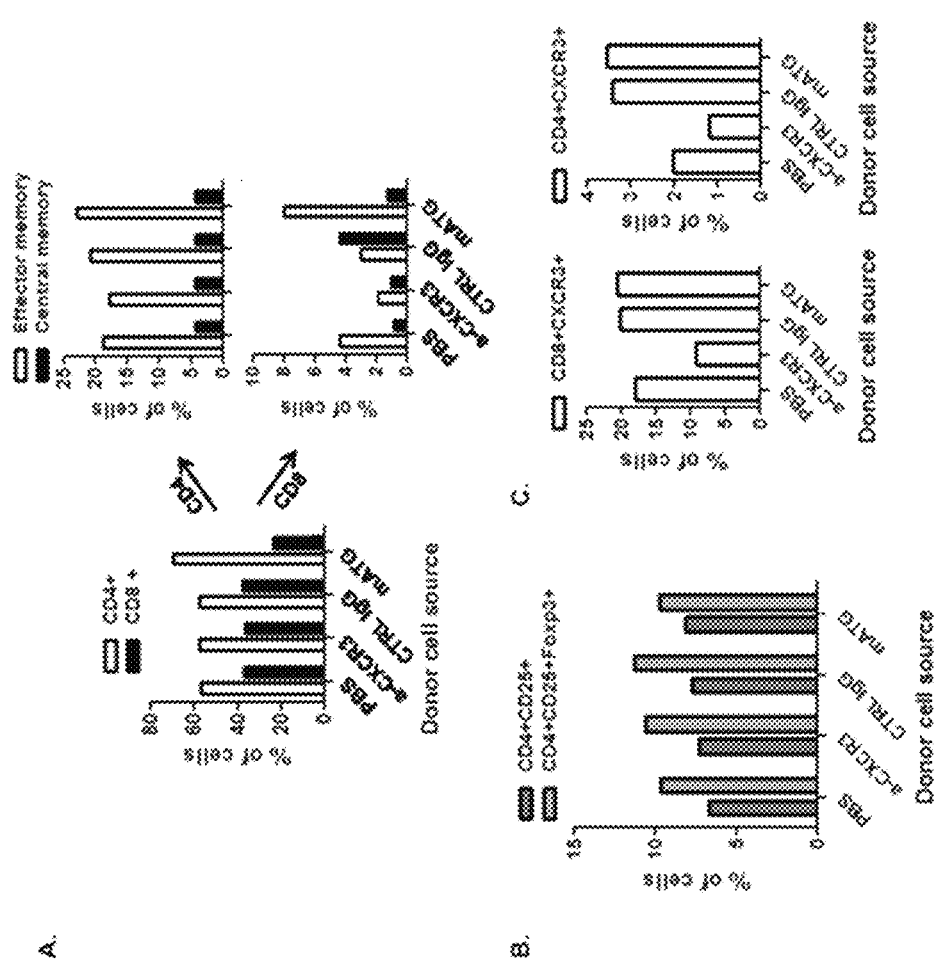
FIG. 10A shows the percentage of CD4+ and CD8+ donor T cells isolated from female NOD mice treated with PBS, anti-CXCR3, control IgG, or mATG antibodies (left panel) as described in FIG. 9. The percentage of effector and central memory cells in the CD4+ and CD8+ T cell donor pools for each treatment group are shown in the right panels of FIG. 10A.
FIG. 10B shows the percentage of regulatory T cells in the donor I cell pools, identified by the expression of CD4 and CD25 or by the expression of CD4, CD25, and Foxp3.
FIG. 10C shows the percentage of CD8+ (left panel) and CD4+ (right panel) in the donor T cell pools that also express CXCR3.

The isolated donor T cells were further characterized. FIG. 10A shows the percentage of total CD4+ and CD8+ T cells (left panel) in the donor T cells isolated from mice treated with PBS, anti-mouse CXCR3 antibody, control IgG, or murine ATG as described in the previous paragraph. The right panels of FIG. 10A show the percentage of effector and central memory T cells in the subset of T cells that were CD4+ (upper panel) and CD8+ (lower panel) for each donor cell suspension, as defined by expression of CD44 and CD62L. Isolated pooled CD4+ and CD8+ T cells were stained for CD44 and CD62L expression before transfer, acquired on a flow cytometer and analyzed. The percentage of regulatory T cells in the pools of isolated donor T cells was also evaluated. FIG. 10B shows the percentage of regulatory T cells for each treatment group, as defined by CD4 and CD25 expression or by CD4, CD25 and intracellular Foxp3 expression. FIG. 10C shows the percentage of CD8+ (left panel) and CD4+ (right panel) T cells in the donor cells that also express CXCR3. The data demonstrate that there was a reduced percentage of CXCR3+ T cells in donor cells from mice reversed with anti-CXCR3 antibody treatment The effectiveness of CXCR3 treatment following adoptive transfer of OT-1 CD8+ donor T cells was evaluated using the RIP-OVA model of type 1 diabetes. RIP-OVA mice are transgenic mice where a transgene encoding ovalbumin protein (OVA) driven by the rat insulin promoter (RIP) has been introduced into the mouse genome and results in the expression of a membrane form of ovalbumin in islet β cells. The background strain of mice is C57BL/6 and the RIP-OVA mice do not spontaneously develop diabetes. RIP-OVA mice, also called C57BL/6-Tg(Ins2-TFRC/OVA)296Wehi/WehiJ, were purchased from the Jackson Laboratory. Diabetes develops in these mice after adoptive transfer of ovalbumin-specific CD8+ T cells from OT-1 TCR (T cell receptor) transgenic mice (Kurts et al. *J Exp Med* 184: 923-930) purchased from the Jackson Laboratory. OT-1 mice contain transgenic inserts for mouse TCRa-V2 and TCRb-V5 genes (Hogquist et al. *Cell* 76:17-27). The transgenic TCR recognizes ovalbumin residues in the context of MHCl H2K$^b$ proteins. Greater than 95% of CD8+ T cells in OT-1 mice express the transgenic TCR and recognize and are activated by ovalbumin peptide.

Figure 11:
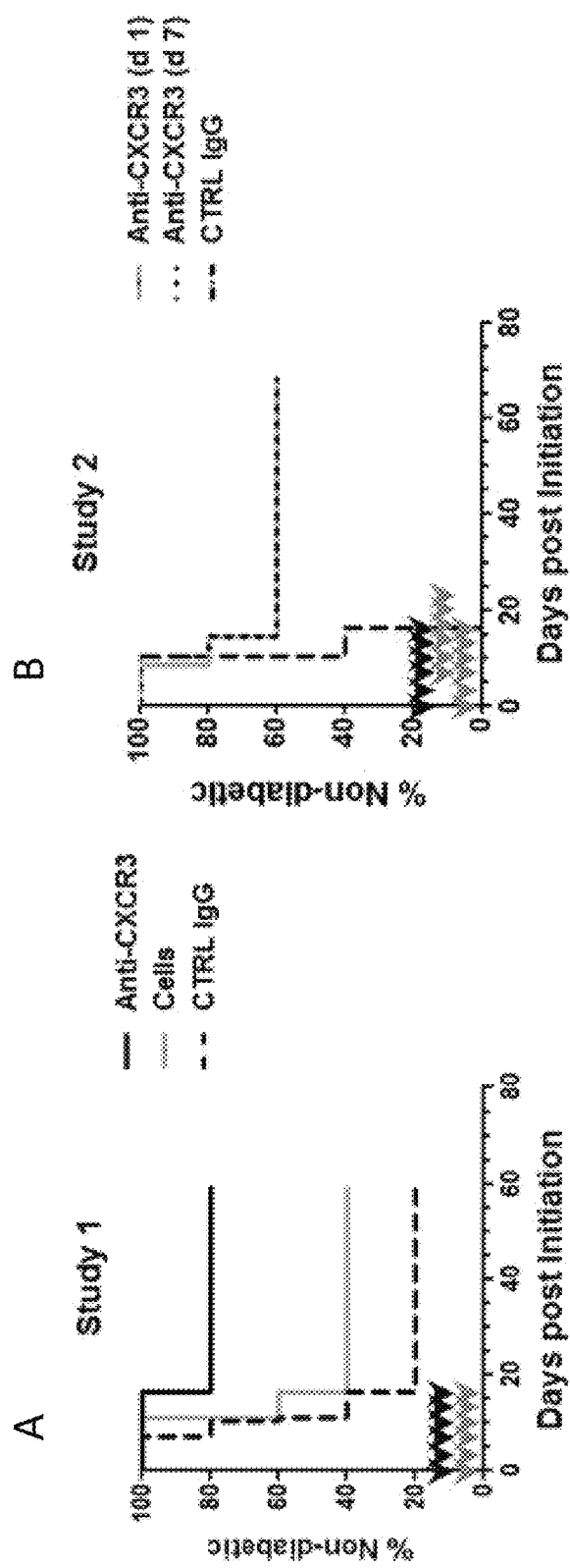
FIG. 11A-B shows the percentage of non-diabetic mice over time following adoptive transfer of T cells from donor OVA-specific TCR transgenic mice into RIP-OVA recipient mice that were left untreated or treated with anti-CXCR3 antibody or control IgG. Results from two studies are shown in FIGS. 11A and 11B.

FIG. 11 shows the percentage of non-diabetic mice over time following adoptive transfer of OT-1 CD8+ T cells into RIP-OVA recipient mice that were then left untreated, treated with anti-mouse CXCR3 antibody, or treated with control IgG. Treatment (100 μg i.p.) was started 1 day (study 1 and study 2) or 7 days (study 2) after adoptive transfer and was given twice a week for 3 weeks. Each line represents the combined data from five mice per group. Results from two studies are shown in FIGS. 11A and 11B. The data demonstrate that anti-CXCR3 antibody treatment protected mice from developing diabetes in the RIP-OVA model.

Figure 12:
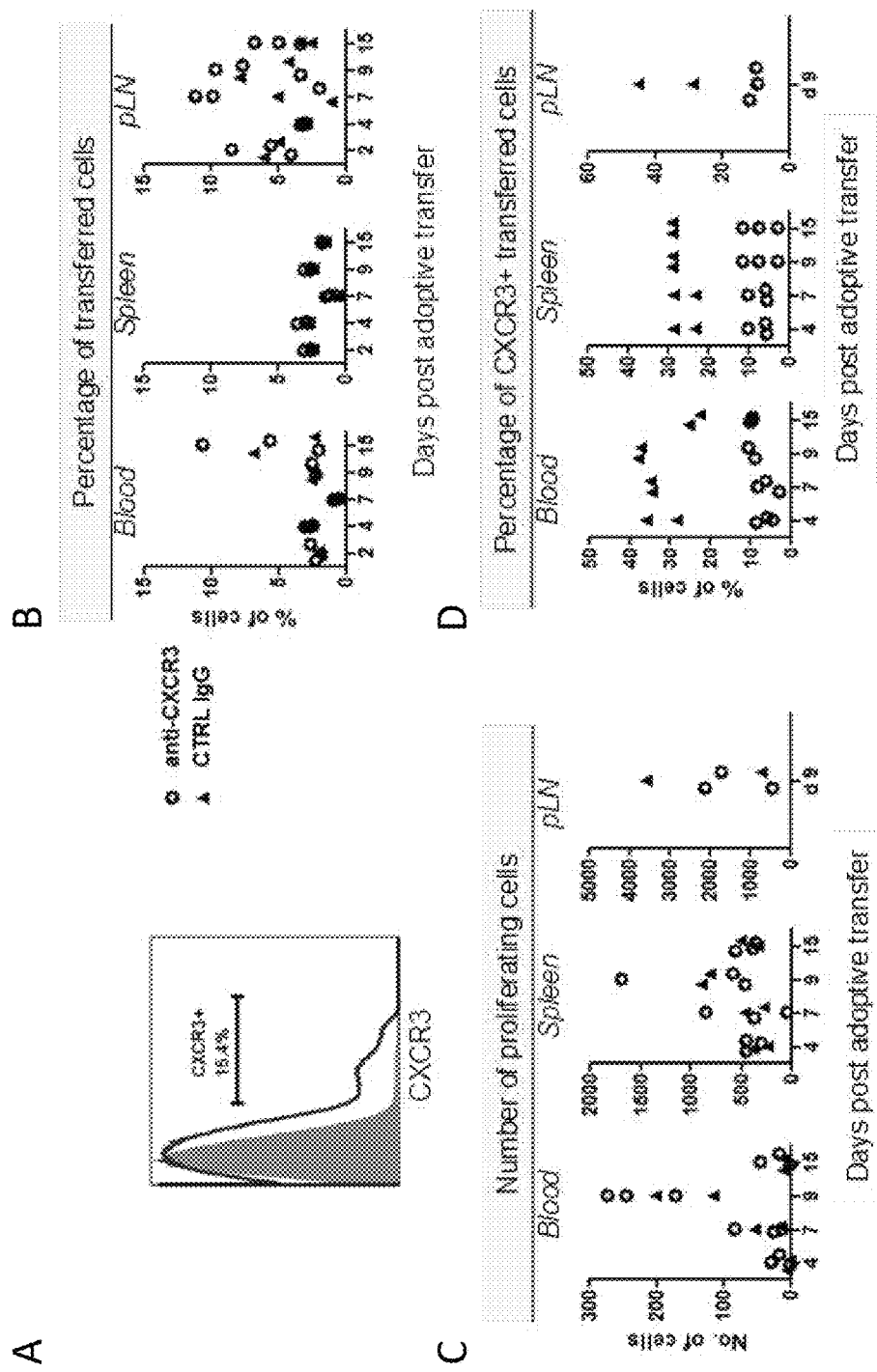
FIG. 12A shows CXCR3 expression on donor T cells analyzed by flow cytometry before adoptive transfer into RIP-OVA recipient mice (solid curve). Staining with isotype control antibody is shown in the shaded curve.
FIG. 12B shows the percentage of donor cells in the blood, spleen and pancreatic lymph nodes of recipient mice treated with anti-CXCR3 or control IgG antibody on days 2, 4, 7, 9, and 15 post adoptive transfer.
FIG. 12C shows the percentage of proliferating donor cells in the blood, spleen and pancreatic lymph nodes of recipient mice treated with anti-CXCR3 or control IgG antibody following adoptive transfer.
FIG. 12D shows the percentage of CXCR3+ donor cells in the blood, spleen, and pancreatic lymph nodes of recipient mice treated with anti-CXCR3 or control IgG antibody following adoptive transfer.

FIG. 12 provides further data characterizing the effectiveness of different treatments following adoptive transfer of OT-1 T cells into RIP-OVA recipient mice. FIG. 12A shows CXCR3 expression on donor T cells analyzed by flow cytometry before adoptive transfer into RIP-OVA recipients. Staining with isotype control antibody is represented by the shaded curve. FIG. 12B shows the percentage of donor cells in the blood, spleen, and pancreatic lymph nodes (pLN) at the indicated times following adoptive transfer of OT-1 T cells to RIP-OVA recipient mice treated with anti-mouse CXCR3 antibody or control IgG. Antibody treatment (100 μg i.p.) was started one day after T cell transfer and was given twice a week for two weeks. Each dot represents data from one individual mouse. FIG. 12C indicates the number of donor cells in the blood, spleen and pancreatic lymph nodes (pLN) that were proliferating in response to autoantigen (OVA) stimulation in RIP-OVA recipient mice treated with anti-mouse CXCR3 antibody or control IgG at the indicated times following adoptive transfer. Antibody treatment (100 μg i.p.) was started one day after OT-1 T cell transfer and was given twice a week for two weeks. Each dot represents data from one individual mouse. FIG. 12D shows the percentage of CXCR3-expressing donor cells in the blood, spleen, and pancreatic lymph nodes (pLN) at the indicated times following adoptive transfer of OT-1 T cells to RIP-OVA recipient mice treated with anti-mouse CXCR3 antibody or control IgG. Antibody treatment (100 μg i.p.) was started one day after OT-1 T cell transfer and was given twice a week for two weeks. Each dot represents data from one individual mouse. Treatment with anti-CXCR3 antibody led to a reduced percentage of CXCR3+ T cells in RIP-OVA mice.

Figure 13:
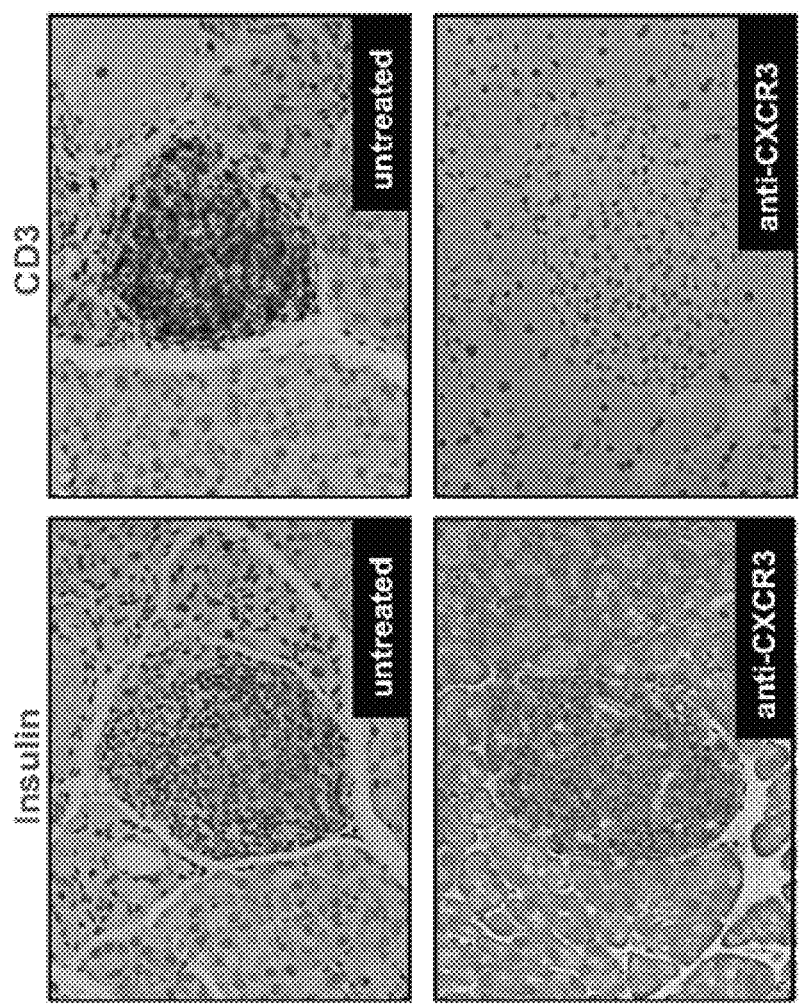
FIG. 13 shows sections of pancreas from RIP-OVA recipient mice left untreated and stained for insulin (upper left) or CD3 (upper right), or treated with anti-CXCR3 antibody and stained for insulin (bottom left) or CD3 (bottom right). The pancreas was harvested 60 days after adoptive transfer of donor T cells.

FIG. 13 shows representative paraffin-embedded pancreas sections from RIP-OVA recipient mice left untreated and stained for insulin (FIG. 13A) or CD3 (FIG. 13B), or treated with anti-mouse CXCR3 antibody and stained for insulin (FIG. 13C) or CD3 (FIG. 13D). Anti-CXCR3 treatment (100 μg i.p.) was started one day after OT-1 T cell transfer and given twice a week for 3 weeks. The pancreas tissue was harvested at the end of the study (around 60 days post T cell transfer). The sections show a lack of T cell infiltration in RIP-OVA mice treated with anti-mouse CXCR3 antibody.

Example 6

Evaluation of Anti-human CXCR3 Antibody Clones

Figure 14:
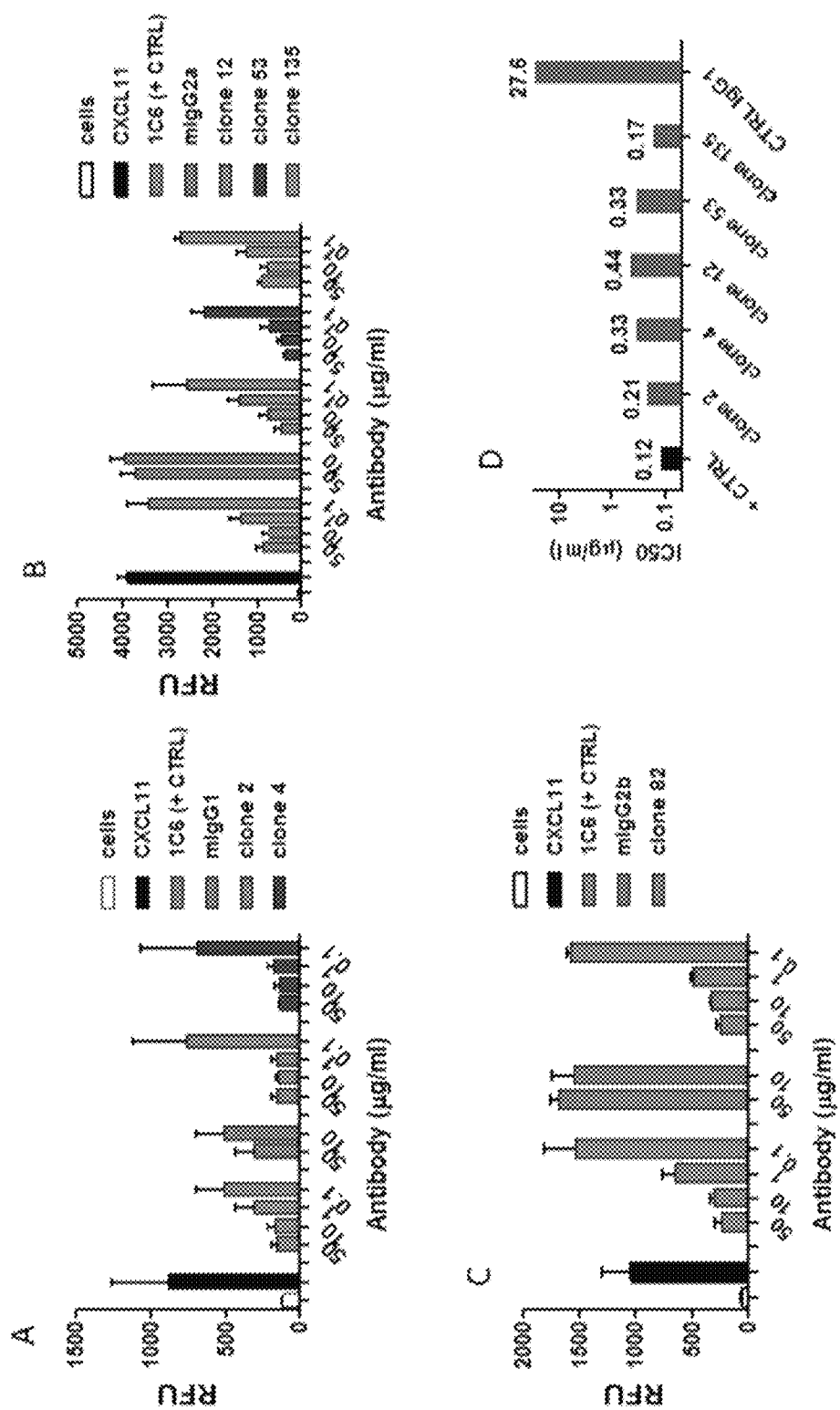
FIGS. 14A-C show the level of inhibition of CXCR3-mediated chemotaxis to CXCL11 mediated by clones Cl 4, 12, 53, 82, and 135. The data is shown as mean relative fluorescence units (RFUs) of the cells that migrate in the chemotaxis assay.
FIG. 14D shows the concentration of antibody needed to inhibit calcium mobilization by 50% for antibody clones Cl 4, 12, 53, and 135.

Anti-human CXCR3 antibody clones Cl 4, 12, 53, 82, and 135 were evaluated for their effect on CXCR3 chemotaxis and calcium mobilization, using the methods described above in the Materials and Methods section (Example 1). For the chemotaxis assay, human CXCR3 transfected 300.19 cells were pre-incubated in media alone or with various concentration of antibody, as indication in FIGS. 14 A-C, prior to being added to the chemotaxis assay. FIG. 14A-C shows that CXCR3-mediated chemotaxis to CXCL 11 is inhibited by clones Cl 4, 12, 53. 82, and 135. Clone 2 in FIG. 14 is identical to clone 4.

For the calcium flux assay, human CXCR3-transfected HEK cells were pre-incubated in various concentrations of antibody prior to being added to the FLIPR according to the methods described above in the Materials and Methods section (Example 1). The concentration of antibody needed to inhibit calcium mobilization by 50% for each antibody is shown in FIG. 14D. FIG. 14D shows that CXCR3-mediated calcium mobilization to CXCL11 is inhibited by clones Cl 4, 12, 53, and 135.

Figure 15:
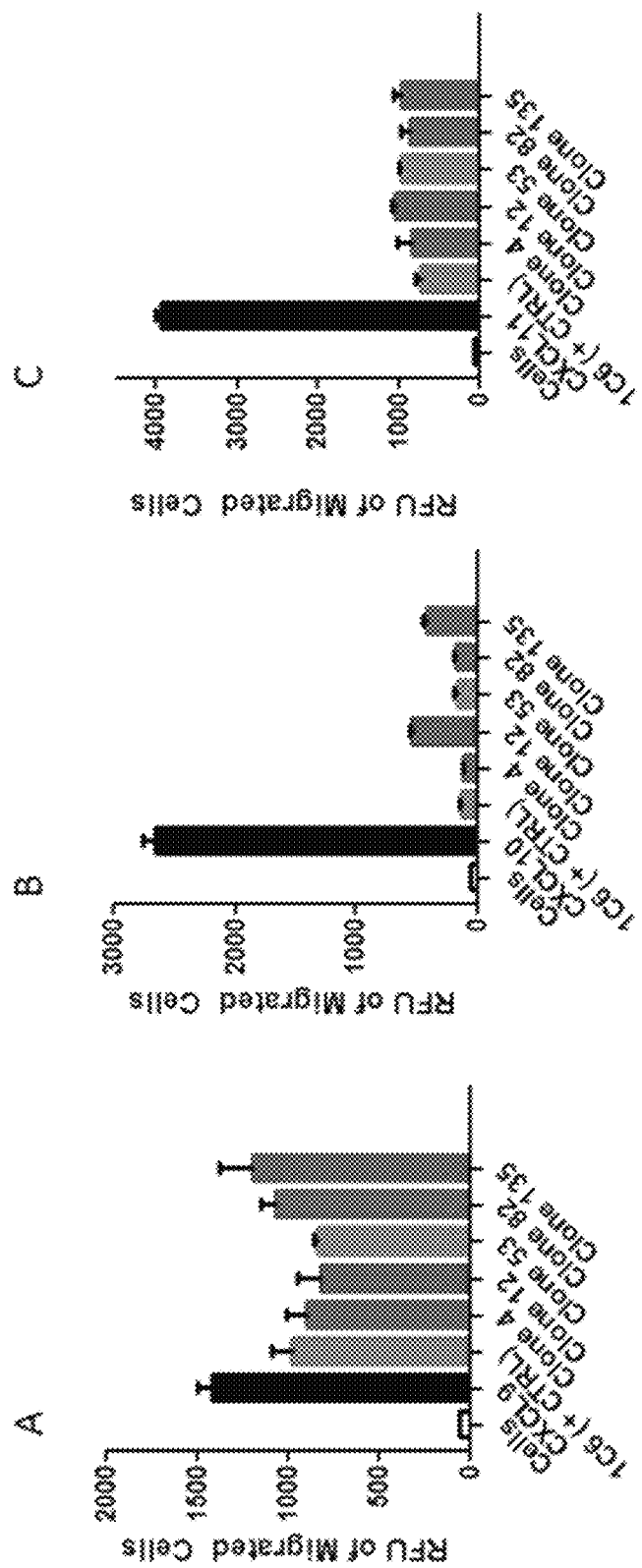
FIG. 15A-C show the level of inhibition of CXCR3-mediated chemotaxis to CXCL9 (FIG. 15A), CXCL10 (FIG. 15B), and CXCL11 (FIG. 15C) mediated by clones Cl 4, 12, 53, 82, and 135. The data is shown as mean relative fluorescence units (RFUs) of the cells that migrate in the chemotaxis assay.

To further assess the effect of clones 4, 12, 53, 82, and 135 on chemotaxis, hCXCR3-transfected 300.19 cells were pre-incubated in media alone or with 50 µg/ml antibody prior to being added to the chemotaxis assay and assessed for migration to CXCL9 (FIG. 15A), CXCL10 (FIG. 15B), and CXCL11 (FIG. 15C). The data demonstrate that clones 4, 12, 53, 82, and 135 inhibit migration to CXCL10 and CXCL11 and partially inhibit migration to CXCL9.

Figure 16:
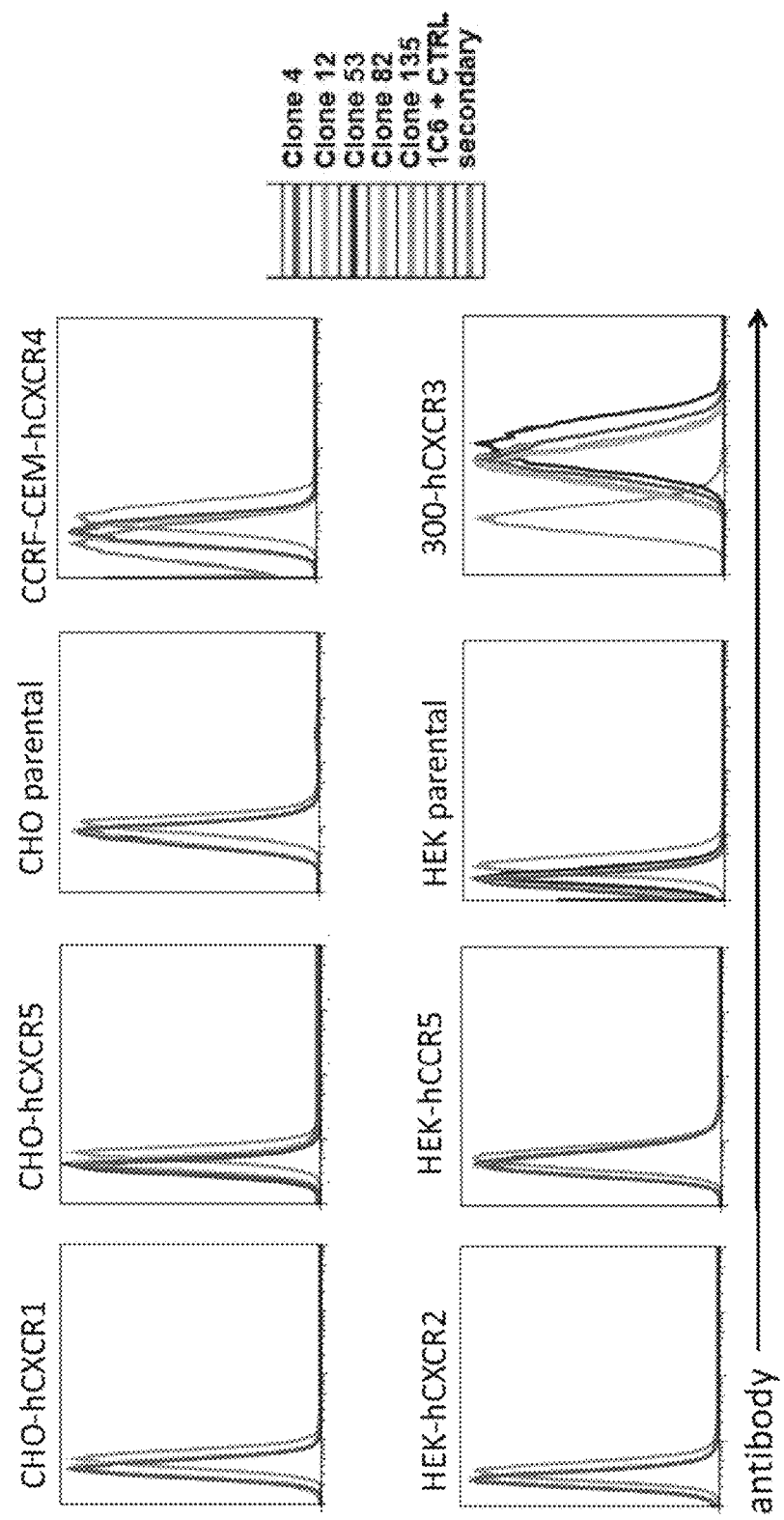
FIG. 16 shows histogram plots of antibody binding to cells expressing various different chemokine receptors. The concentration of bound antibody increases along the horizontal axis for each histogram plot.
Figure 17A:
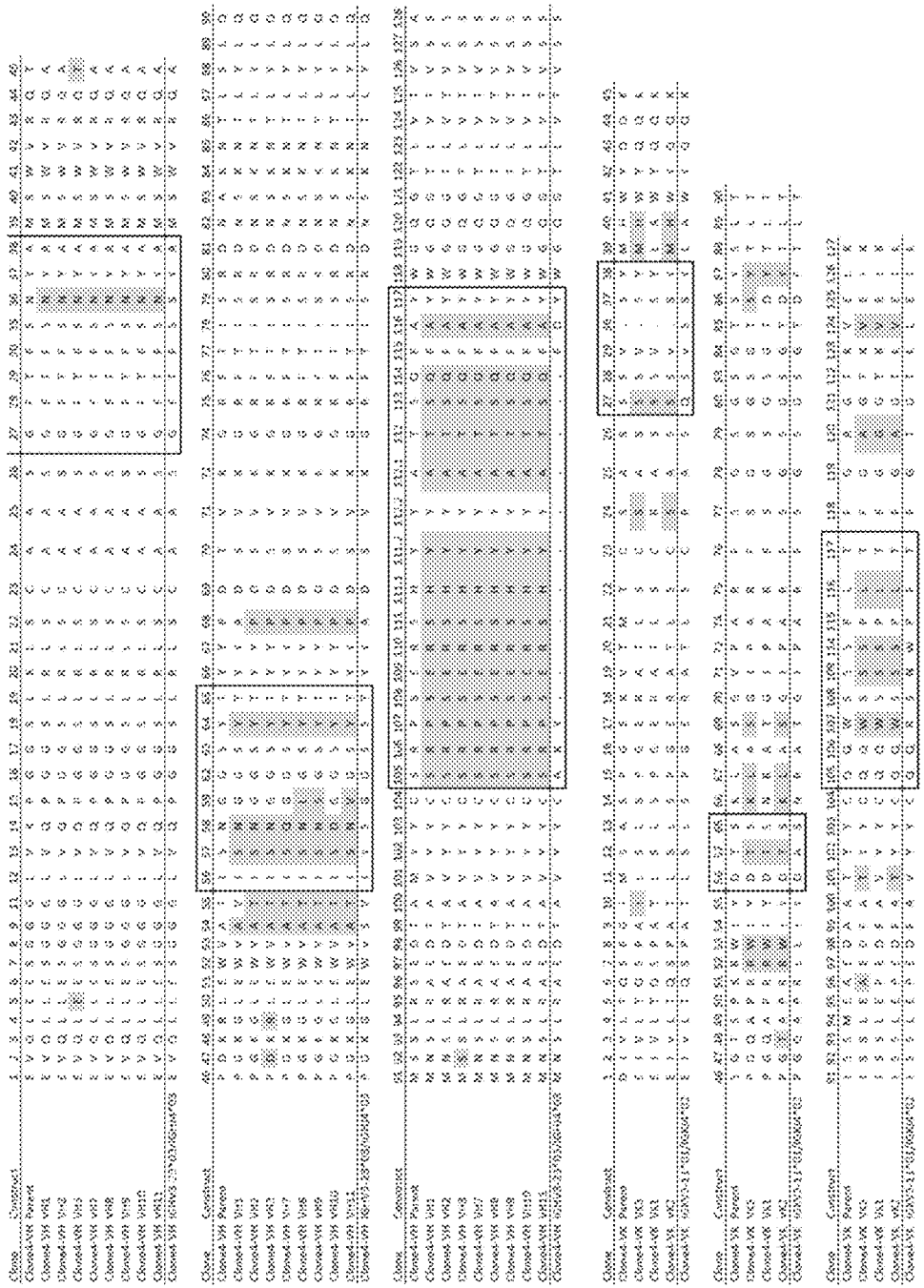
FIG. 17A shows an alignment of the heavy (VH) and light (VK) chain variable domains for clone 4.0 (labeled "parent") and certain humanized variants (labeled VH1-3 and 7-11 and VK 1-3).
Figure 17C:
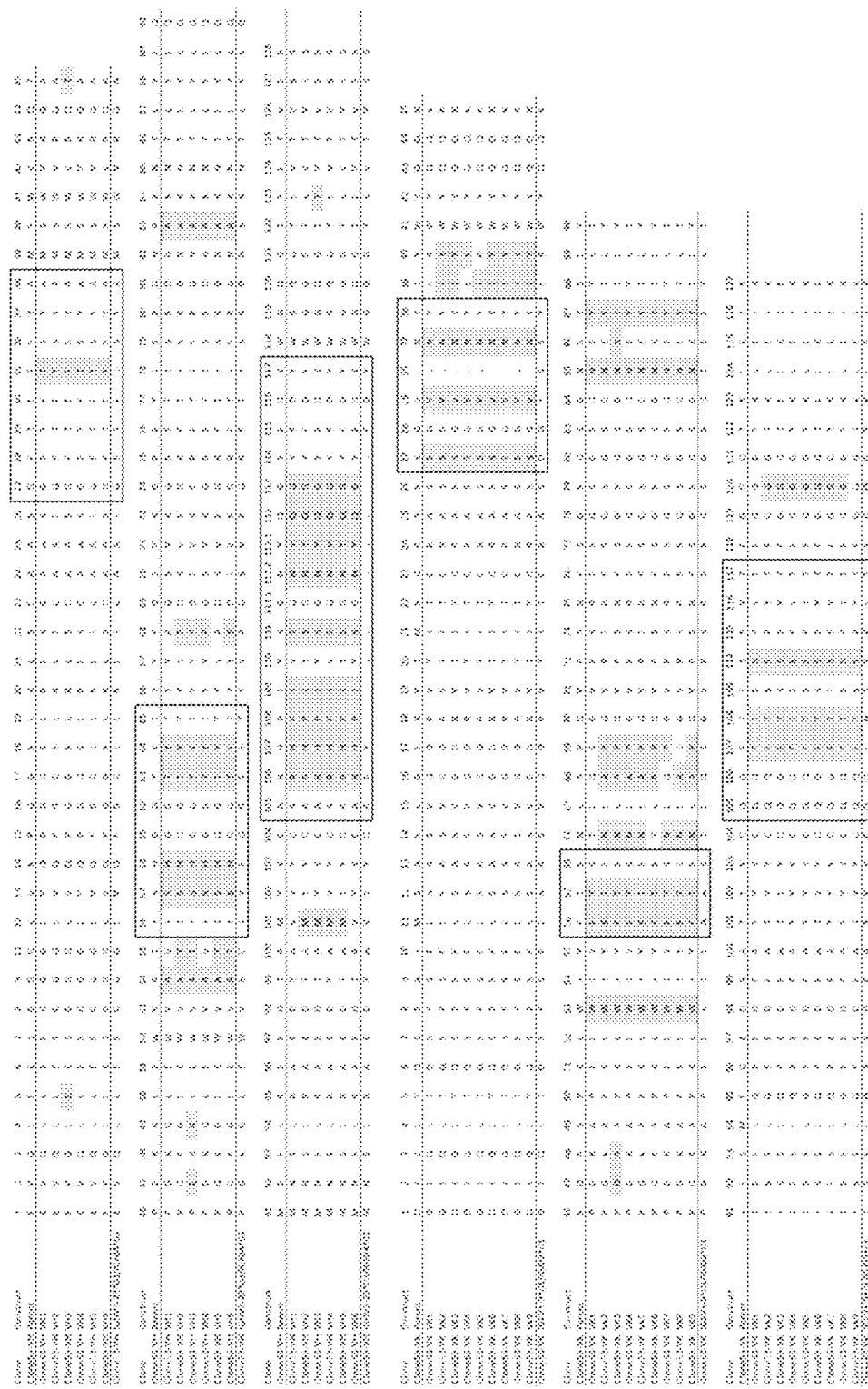
FIG. 17C shows an alignment of the heavy (VH) and light (VK) chain variable domains for clone 53.0 (labeled "parent") and certain humanized variants (labeled VH1-6 and VK 1-9).
Figure 17F:
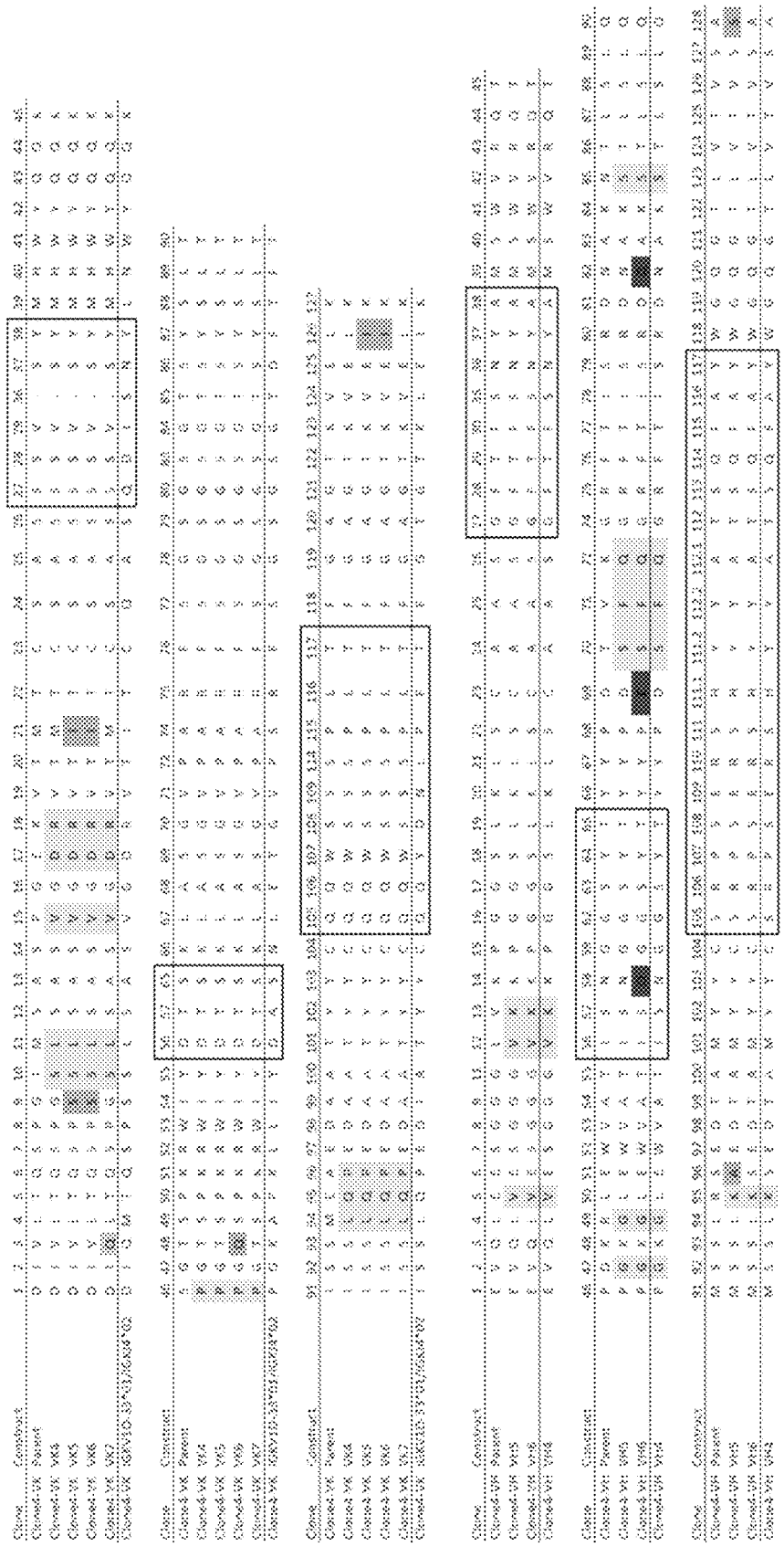
FIG. 17F shows an alignment of the heavy (VH) and light (VK) chain variable domains for clone 4.0 (labeled "parent") and certain 4D humanized variants (labeled VH4-6 and VK4-7).
Figure 17G:
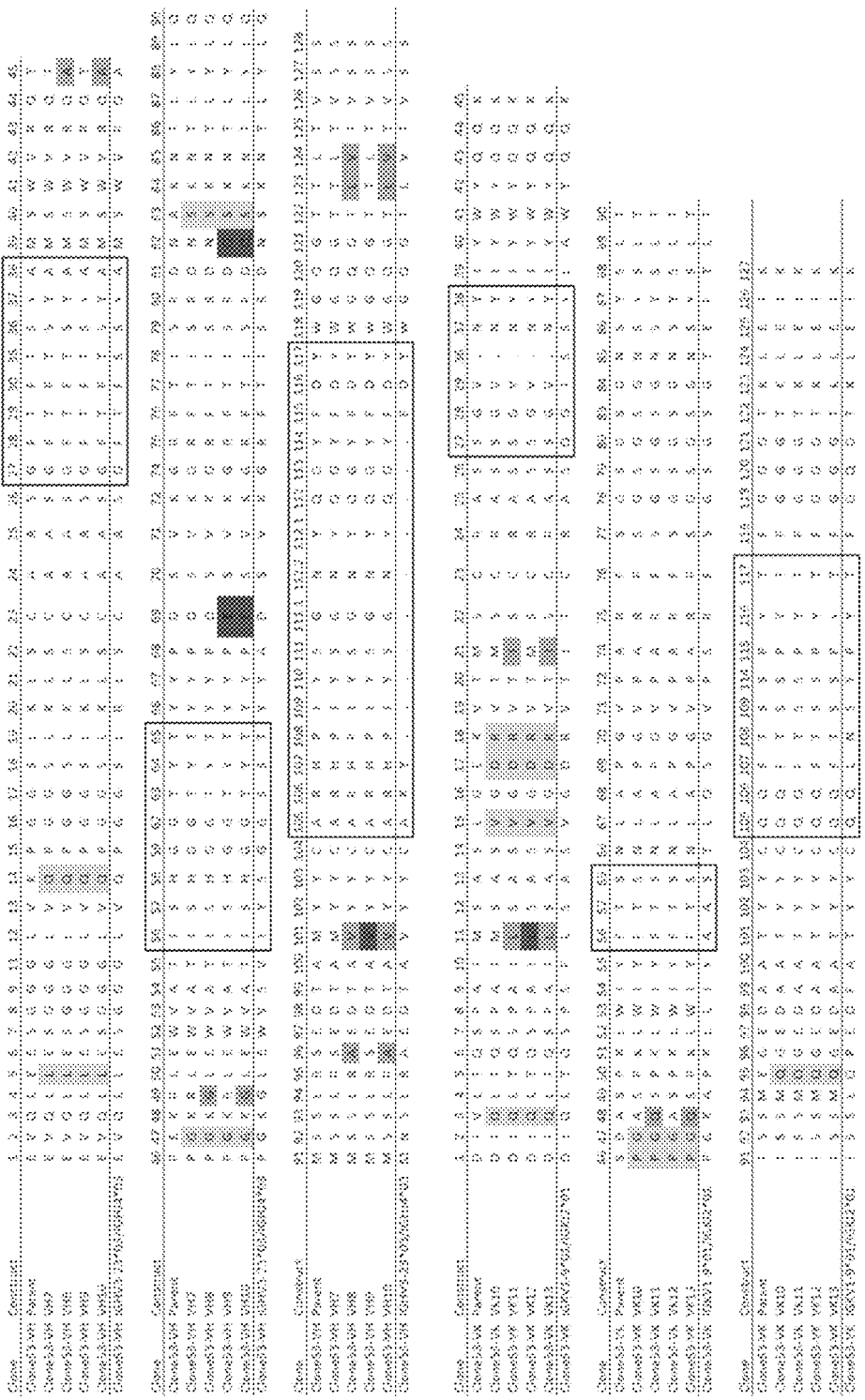
FIG. 17G shows an alignment of the heavy (VH) and light (VK) chain variable domains for clone 53.0 (labeled "parent") and certain 4D humanized variants (labeled VH7-10 and VK10-13).
Figure 17H:
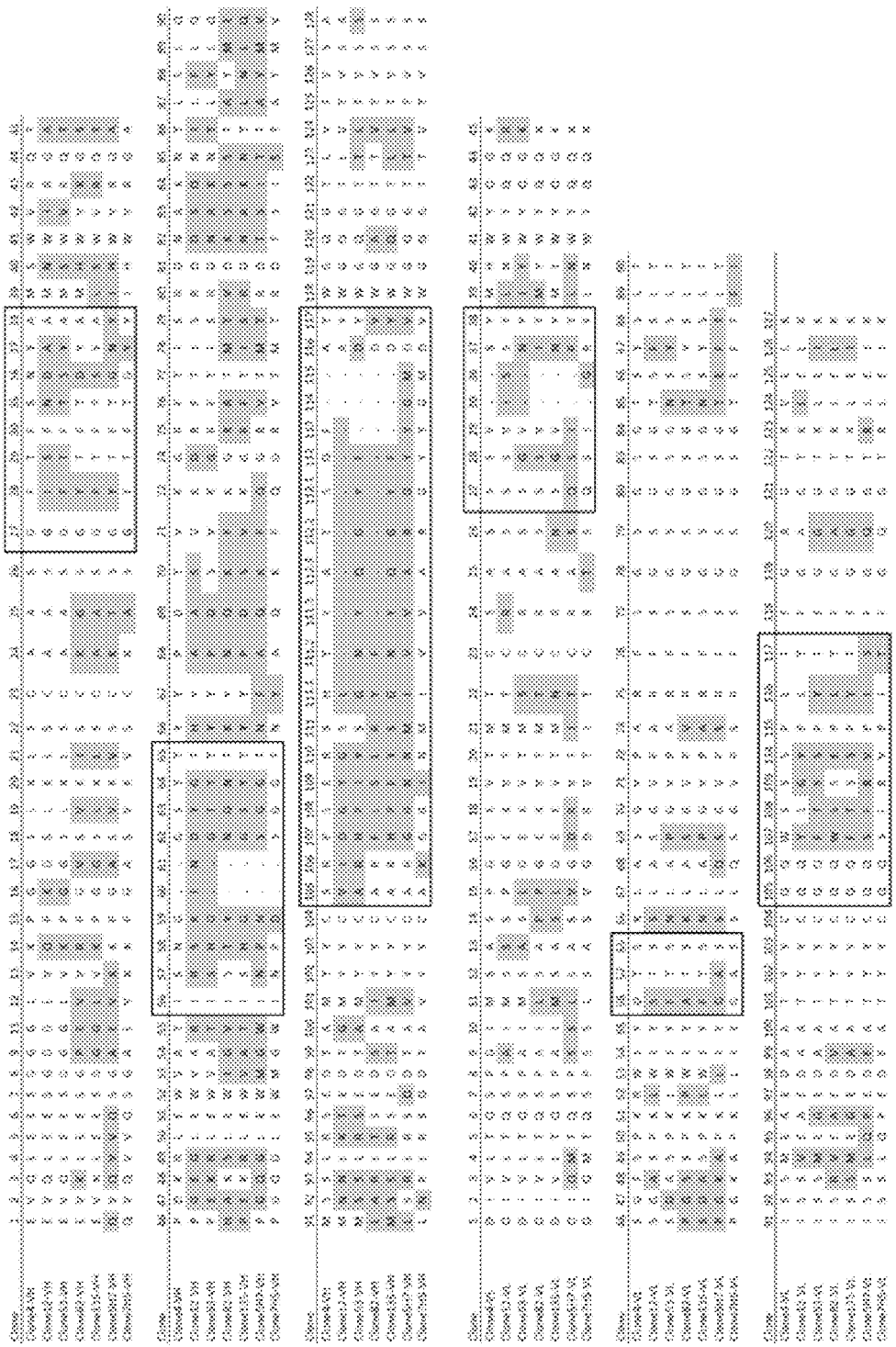
FIG. 17H shows an alignment of the heavy (VH) and light (VK) chain variable domains for clones 4.0, 12.0, 82.0, and 135, as well as the antibody clones 5H7 and 7H5.

To evaluate the specificity of clones 4, 12, 53, 82, and 135, the antibodies were assayed for binding to other chemokine receptors. 300.19 cells were transfected with human CXCR1, CXCR5, CXCR2, CXCR4 or CCR5 and antibody binding was analyzed by incubation with the anti-human CXCR3 antibody clones, followed by secondary antibody staining and flow cytometry. Administration of the secondary antibody alone served as the negative control. 300.19 cells transfected with human CXCR3 served as a positive control for staining by the clones. FIG. 16 shows histogram plots of antibody binding to cells expressing the different chemokine receptors, demonstrating that clones 4, 12, 53, 82, and 135 do not bind the other chemokine receptors and are specific for CXCR3.

Standard flow cytometry procedures were employed in the chemokine receptor binding assay. Briefly, cell lines were harvested by Versene treatment and each cell line was divided into seven samples. Each sample was incubated on ice with one primary antibody (5 µg/ml) followed by staining with a FITC-conjugated secondary antibody to detect the bound primary antibody. As a negative control, cells were stained with secondary antibody alone (no primary antibody incubation). The primary antibody was an anti-human CXCR3 antibody clone or the anti-human CXCR3 control antibody clone 1C6. After staining, the cells were acquired on a flow cytometer and the data analyzed using FlowJo software. Each line in FIG. 16 represents an individual sample of cells stained with one primary antibody and the secondary antibody, or with the secondary antibody alone.

Affinity (Ka) and off-rate (Kd) for clones 4, 12, 53, 82, and 135 were analyzed using a Biacore assay according to the methods described above (Example 1). The results are summarized below in Table 4.

TABLE 4

| Clone # | ka (1/Ms) | kd (1/s) | KD (M) |
| --- | --- | --- | --- |
| 4 | 108539.245 | 0.000348 | 3.2076E−09 |
| 53 | 79557.574 | 0.000581 | 7.3085E−09 |
| 12 | 183854.704 | 0.001473 | 8.01056E−09 |
| 82 | 195114.396 | 0.001828 | 9.36793E−09 |
| 135 | 88939.340 | 0.001214 | 1.36548E−08 |

Example 7

Epitope Mapping

Truncated, biotinylated human CXCR3 peptides (16 amino acid N-terminal fragments) from the CXCR3 N-terminal extracellular domain were used to determine epitopes for clones 4, 12, 53, 82, and 135. A series of alanine substituted fragments were generated (see table 5 below, alanine substitution in bold) and biotinylated. Epitope mapping was evaluated by Octet® (ForteBio, Menlo Park, Calif.) and Biacore™ (GE Healthcare) analyses.

For Octet analysis, peptides were re-suspended in 80% DMSO and diluted to 10 µg/ml in PBS. Antibody clones 4, 12, 53, 82, 135 and commercial clone 1C6 (BD Biosciences) were diluted to 120 nM in PBS. The kinetics assay was performed in 96-well plate format with 300 µl/well on an Octet QK system (ForteBio). Each assay plate included N-terminally biotinylated full-length WT hCXCR3 ECD peptide (Abgent) as a positive control, as well as PBS buffer blank for reference subtraction. Octet Streptavidin biosensors (ForteBio) were pre-soaked in PBS for at least five minutes prior to running the assay. Biosensors were first immersed in PBS for five minutes with no shaking for a baseline. For all remaining steps, the shake speed was 1000 rpm. The biosensors were dipped in peptide solutions for five minutes to load peptides. Another baseline step in PBS for five minutes was performed. Biosensors were then dipped into antibody solutions for ten minutes to measure association. Finally, the biosensors were transferred into PBS for fifteen minutes for dissociation. Sensorgrams were analyzed using Octet Data Analysis v7.0. Binding activity was expressed as a percentage of each antibody's maximum response level compared to WT full-length hCXCR3 peptide.

Relative response levels were recorded in an epitope heat map. Maximal sensorgram responses to wild type hCXCR3 ECD peptide ranged between 4-8 nm. Each clone screened had a unique epitope. None of the mutants tested completely abolished binding of clone 1C6. The Valine residue in position 10 and Aspartate in position 13 played a role in binding of all antibodies screened. Antibodies 12 and 1C6 had the most N-terminal epitopes, with position 5 Valine mutations influencing activity of both. Antibody 82 had the most C-terminal epitope, and a reduction in binding activity started with position 9 Glutamine. Based on these data, amino acid epitope boundaries on the CXCR3 sequence were as follows for each antibody; Cl 4: amino acids 7-13; Cl 12: amino acids 5-13; Cl 53: amino acids 7-13; Cl 82: amino acids 9-15; Cl 135: amino acids 7-13; and clone 106: amino acids 5-13

For Biacore analysis, peptides were diluted to 10 ng/ml in HBS-EP+ running buffer (10 mM HEPES, 150 mM NaCl, 3 mM EDTA, 0.005% Polysorbate 20). Using a Biacore T100™, peptides were injected over CM5-SA (GE #BR-1005-31) chips at a rate of 5 μl/min until 20 response unit (RU) stable capture was obtained per flow cell. Flow cell 1 remained blank for reference subtraction on each chip. Wild-type 37AA hCXCR3 peptide was included on one flow cell of each chip as a positive control. Mouse anti-hCXCR3 antibodies 4, 12, 53, 82, and 135 were diluted to 50, 25, 12.5, 6.25, and 3.125 nM in HBS-EP+. Each cycle, antibodies were injected for three minutes at a flow rate of 50 μl/min to measure association, followed by three minutes of buffer at 50 μl/min to measure dissociation. The peptide surface was regenerated between cycles using 10 mM glycine-HCl pH 2.0 at 50 μl/min for sixty seconds. Sensorgrams were fit to a 1:1 binding model and analyzed using double-reference subtraction in BiaEvaluation v2.0.1 and captured on streptavidin biosensors. Typical response levels ranged between 0-500RU, and cutoffs for 'Strong', 'Moderate', and 'Weak' binding responses were determined. Relative response levels were recorded to generate an epitope map. Off-rates were ranked, and peptides which resulted in fast Kd values (greater than $0.001s^{-1}$) were also recorded.

TABLE 5

| Seq Id No. | Sequence | Seq Id No. | Sequence |
|---|---|---|---|
| 83 | AVLEVSDHQVLNDAEV | 91 | MVLEVSDHAVLNDAEV |
| 84 | MALEVSDHQVLNDAEV | 92 | MVLEVSDHQALNDAEV |
| 85 | MVAEVSDHQVLNDAEV | 93 | MVLEVSDHQVANDAEV |
| 86 | MVLAVSDHQVLNDAEV | 94 | MVLEVSDHQVLADAEV |
| 87 | MVLEASDHQVLNDAEV | 95 | MVLEVSDHQVLNAAEV |
| 88 | MVLEVADHQVLNDAEV | 96 | MVLEVSDHQVLNDAEV (wild type) |
| 89 | MVLEVSAHQVLNDAEV | 97 | MVLEVSDHQVLNDAAV |
| 90 | MVLEVSDAQVLNDAEV | 98 | MVLEVSDHQVLNDAEA |

Figure 18:
FIG. 18 shows the boundaries of the minimum epitope residues for antibody clones 4, 12, 53, 82, and 135. Residues important for binding activity are indicated by an X.

All antibodies bound to wild-type hCXCR3 and within the first 16AAs of the hCXCR3 sequence. The binding data is shown in Table 6 for clones 4, 12, 53, 82, and 135, and the corresponding map showing the boundaries of the minimum epitope required for binding activity for each antibody clone is shown in FIG. 18, with important residues marked with an X. All antibody epitopes mapped within human CXCR3 sequence residues 6-15, the region involved in CXCL10 and CXCL11 binding. Amino acids within the epitope were determined by detecting a reduction in binding response after an alanine substitution at a given position in the CXCR3 peptide fragment. Clones 53 and 135 had the most similar epitopes. Clones 4 and 12 had the most N-terminal epitope (binding strength affected starting with the valine at position five). Clone 82 had the most C-terminal epitope, with a reduction in binding activity starting with position 9 glutamine. The aspartate at position 7 in CXCR3 is required for every clone except 82. The valine at position ten and the aspartate at position thirteen in CXCR3 both play a role in binding of all clones. There identified as "very dissimilar" between mouse and human using IMGT-based modeling. The twenty total variants were transiently expressed in CHO-NRC cells and purified for in vitro assays.

Additional humanization was performed for clones 4 and 53. Heavy chains 4.7-4.11 included further humanized backmutations outside the CDRs, as well as modifications to remove a deamidation site at positions 58 and 59 (IMGT numbering) in VH CDR2 in an effort to improve clone stability. In particular, the deamidation site in VH 4.2 was replaced with a number of alternative residues. Clones VH 53.4-53.6 and VL 53.4-53.9 included further humanized backmutations outside the CDRs, particularly in an effort to make the chains more similar to VH 4.1 and VL 4.1.

Example 9

Whole Receptor Binding Kinetics

The binding kinetics of the twenty anti-CXCR3 variants was evaluated using Octet® and Biacore™ with intact CXCR3 peptides. Octet analysis was conducted as described previously. For Biacore analysis, three column step purified human wild type CXCR3 peptides were C-terminal His and HPC4 tagged and captured on NTA chips via nickel chelating and amine coupling. Medium RU (approximately 1200RU) chips were used for better data quality and to minimize bivalent binding effect. 0-80 nM of the antibody samples were injected over the receptor. Standard Biacore™ evaluation analysis was conducted using sensorgram plots with local Rmax fit for better curve fitting. The binding curves for the four variants (chimeric (Ch) and humanized (Hu) 1-3) for the five clones (4, 12, 53, 82, and 135) were evaluated. For comparison purposes, the binding kinetics of the human CXCR3 ligands CXCL9, CXCL10, and CXCL11, and mouse CXCL11 (mCXCL11) were also evaluated. The results are shown below in Tables 7A (ranked by KD) and 7B (ranked by Kd). The top four variants by KD and Kd are highlighted in the tables. When the humanized anti-hCXCR3 mAb variants were ranked by off rates (Kd), most of the variants showed at least 1 digit slower off rates than the most potent human CXCR3 ligand hCXCL11.

TABLE 7A

| Sample | ka (1/Ms) | kd (1/s) | KD (M) |
| --- | --- | --- | --- |
| 4Hu2 | 1.59E+05 | 8.18E-05 | 5.16E-10 |
| 4Ch | 2.09E+05 | 1.15E-04 | 5.46E-10 |
| 4Hu3 | 1.54E+05 | 8.62E-05 | 5.80E-10 |
| 4Hu1(low RU) | 2.24E+05 | 1.40E-04 | 6.34E-10 |
| mCXCL11 | 3.69E+06 | 4.26E-03 | 1.17E-09 |
| 82Hu3 | 3.40E+05 | 4.82E-04 | 1.42E-09 |
| 53Ch | 4.44E+04 | 7.07E-05 | 1.60E-09 |
| CXCL11 | 2.58E+06 | 4.41E-03 | 1.72E-09 |
| 53Hu3 | 6.88E+04 | 1.13E-04 | 1.72E-09 |
| 82Hu2 | 8.67E+04 | 2.62E-04 | 3.02E-09 |
| 12Ch | 9.66E+04 | 4.52E-04 | 5.00E-09 |
| 135Hu3 | 6.68E+04 | 3.35E-04 | 5.01E-09 |
| 82Ch | 1.61E+05 | 8.92E-04 | 5.84E-09 |
| 53Hu2 | 3.05E+04 | 2.04E-04 | 6.70E-09 |
| 135Ch | 5.52E+04 | 3.82E-04 | 6.93E-09 |
| CXCL10 | 1.36E+05 | 1.27E-03 | 9.76E-09 |
| 12Hu3 | 6.60E+04 | 1.02E-03 | 1.66E-08 |
| 12Hu2 | 6.39E+04 | 1.02E-03 | 1.60E-08 |
| CXCL9 | | poor data quality | |
| 135Hu2 | | No binding | |
| 12Hu1 | | | |
| 53Hu1 | | | |
| 82Hu1 | | | |
| 135Hu1 | | | |

TABLE 7B

| Sample | ka (1/Ms) | kd (1/s) | KD (M) |
| --- | --- | --- | --- |
| 53Ch | 4.44E+04 | 7.07E-05 | 1.60E-09 |
| 4Hu2 | 1.59E+05 | 8.18E-05 | 5.15E-10 |
| 4Hu3 | 1.54E+05 | 8.62E-05 | 5.60E-10 |
| 53Hu3 | 6.88E+04 | 1.13E-04 | 1.72E-09 |
| 4Ch | 2.09E+05 | 1.15E-04 | 5.48E-10 |
| 4Hu1(low RU) | 2.24E+05 | 1.40E-04 | 6.34E-10 |
| 53Hu2 | 3.05E+04 | 2.04E-04 | 6.70E-09 |
| 82Hu2 | 8.67E+04 | 2.62E-04 | 3.02E-09 |
| 135Hu3 | 6.68E+04 | 3.35E-04 | 5.01E-09 |
| 135Ch | 5.52E+04 | 3.82E-04 | 6.93E-09 |
| 12Ch | 9.66E+04 | 4.52E-04 | 5.00E-09 |
| 82Hu3 | 3.40E+05 | 4.82E-04 | 1.42E-09 |
| 82Ch | 1.61E+05 | 8.92E-04 | 5.54E-09 |
| 12Hu2 | 6.39E+04 | 1.02E-03 | 1.60E-08 |
| 12Hu3 | 6.60E+04 | 1.02E-03 | 1.56E-08 |
| CXCL10 | 1.36E+05 | 1.27E-03 | 9.76E-09 |
| mCXCL11 | 3.69E+06 | 4.26E-03 | 1.17E-09 |
| CSCL11 | 2.58E+06 | 4.41E-03 | 1.72E-09 |
| CXCL9 | | poor data quality | |
| 135Hu2 | | No binding | |
| 12Hu1 | | | |
| 53Hu1 | | | |
| 82Hu1 | | | |
| 135Hu1 | | | |

As indicated in Table 7A, the top four variants by KD are chimeric clone 4 (fast on rate, slow off rate), Hu 3 clone 4 (fast on rate, slow off rate), Hu3 clone 82 (fast on rate, average off rate), and chimeric clone 53 (average on rate, slow off rate).

Figure 19:
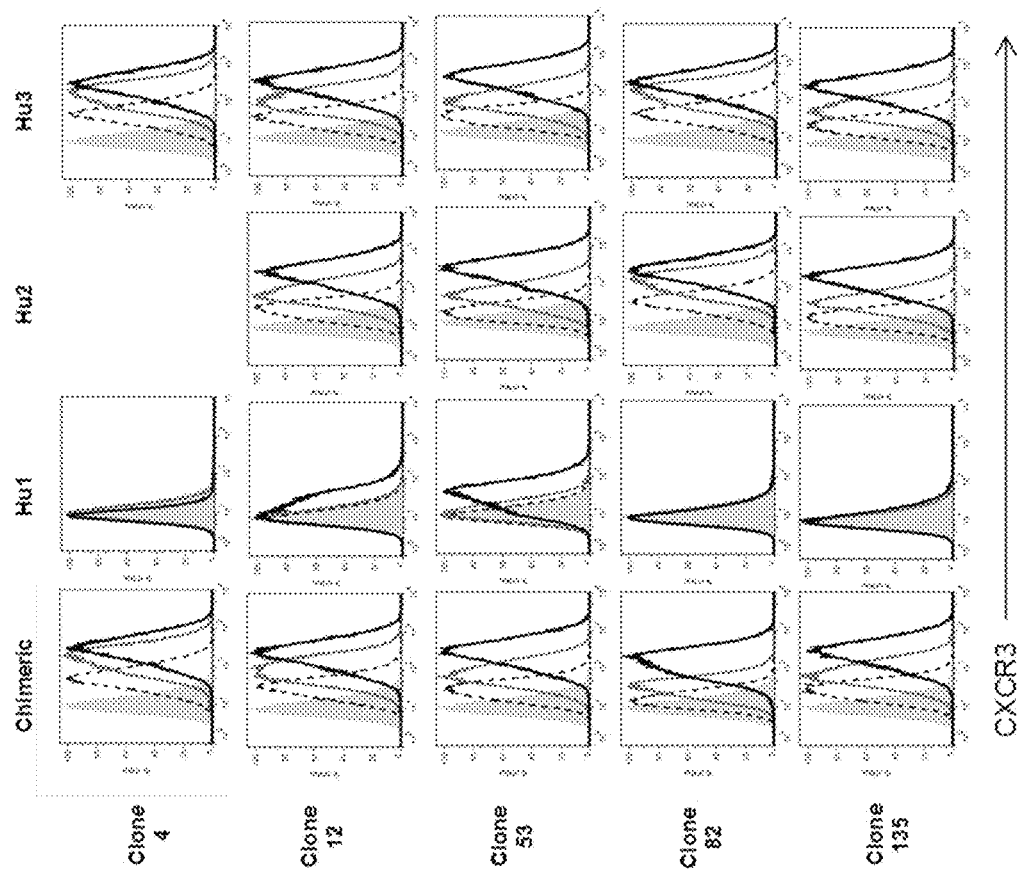
FIG. 19 is a histogram plot showing antibody binding in human CXCR3 transfected 300.19 cells for chimeric clones 4, 12, 53, 82, and 135, as well as the humanized variants Hu1, Hu2, Hu3. Antibody was administered at 5 µg/ml (black line), 0.5 µg/ml (dark gray line), or 0.1 µg/ml (black dashed line) or 5 µg/ml secondary antibody alone (filled gray histogram), and data is plotted as number of cells (horizontal axis) against percentage of maximum fluorescence.

Antibody binding was further evaluated in CXCR3-expressing cells. Human CXCR3 transfected 300.19 cells were contacted with purified humanized anti-hCXCR3 antibody variants Hu1, Hu2, Hu3, and the chimeric antibody. As shown in FIG. 19 for each of clones 4, 12, 53, 82, and 135 at 5 µg/ml (black line), 0.5 µg/ml (dark gray line), or 0.1 µg/ml (black dashed line) or 5 µg/ml secondary antibody alone (filled gray histogram). The cells were stained with the unlabeled antibody clones for 30 min on ice followed by two washes with PBS-1% FBS and bound antibody was detected using a FITC-conjugated anti-human IgG1 specific secondary antibody by incubating on ice for 30 min in the dark. The samples were washed twice, fixed in a 2% paraformaldehyde PBS solution, stored in the dark at 4° C. and acquired on a flow cytometer. Histograms of CXCR3 positivity gated on viable cells are shown in FIG. 19.

Example 10

Comparison to Antibody 1C6

Anti-hCXCR3 mAb clone 1C6 (Becton, Dickinson catalog #557183, same clone reported U.S. Pat. No. 6,184,358) was compared to mouse anti-hCXCR3 mAb clone 4 and its humanized variants Hu2 and Hu3 using the Biacore whole receptor assay method. Clone 4 exhibited about 2-fold better affinity (KD). The humanized variants exhibited further improved affinity (approximately 4-fold better affinity for both the Hu2 and Hu3 variants). Table 8 lists binding kinetics and affinity for clone 1C6 and for clone 4 and its humanized variants Hu2 and Hu3.

TABLE 8

| Sample | ka (1/Ms) | kd (1/s) | KD (M) |
|---|---|---|---|
| 1C6-Hybridoma | 4.11E+04 | 1.42E−04 | 3.51E−09 |
| 4-Hybridoma | 1.18E+05 | 2.22E−04 | 1.88E−09 |
| 4Hu3 | 1.54E+05 | 8.62E−05 | 5.60E−10 |
| 4Hu2 | 1.59E+05 | 8.18E−05 | 5.15E−10 |

Example 11

Functional Assays

The functional effects of the twenty variant antibodies were evaluated. The antibodies were evaluated for their effect on cell chemotaxis in response to CXCL9, CXCL10, and CXCL11, and inhibition of calcium mobilization by FLIPR® calcium assay.

Figure 20:
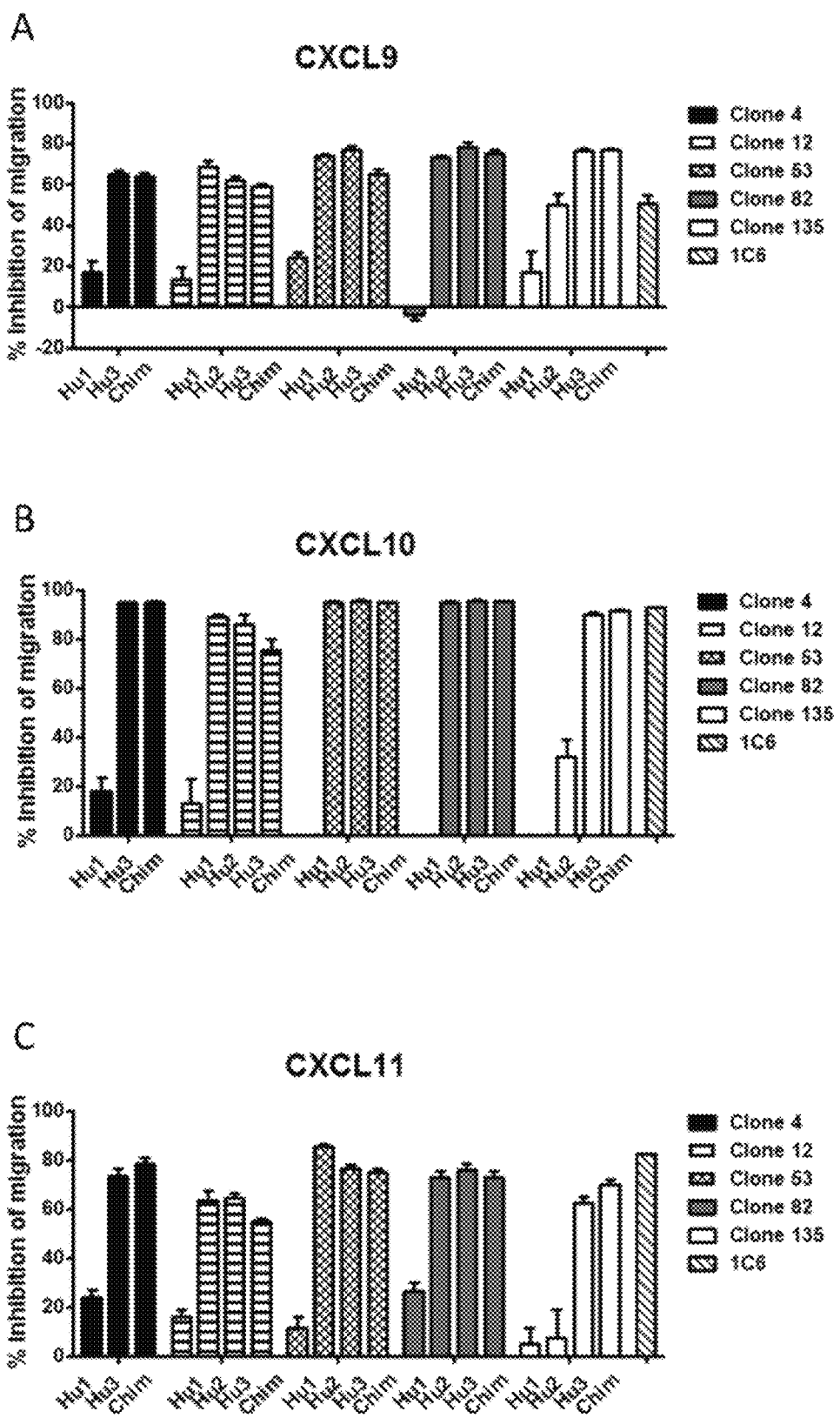
FIG. 20A-C shows percentage inhibition of migration (vertical axis) of human CXCR3-transfected cells to CXCL9 (FIG. 20A), CXCL10 (FIG. 20B), and CXCL11 (FIG. 20C) in the presence or absence of 10 µg/ml of chimeric (Chim) or humanized (Hu1, Hu2 or Hu3) antibody variants of clones 4, 12, 53, 82, and 135, or the commercial clone 1C6.

Chemotaxis of human CXCR3-transfected 300.19 cells to the CXCR3 ligands CXCL9, CXCL10, and CXCL11 was evaluated in the presence or absence of 10 μg/ml humanized anti-human CXCR3 antibody variants of clones 4, 12, 53, 82, and 135. Transfected cells were pre-treated for 20 min at 37° C. with 10 μg/ml humanized anti-human CXCR3 antibody variants or the commercial antibody 1C6. Cells with antibody were transferred to 5 micron transwells and inserts were placed in the receiver well containing 100 or 300 ng/ml of recombinant mouse CXCL10 and CXCL11 or CXCL9, respectively. The chemotaxis plates were incubated at 37° C., 5% CO$_2$ for 4 hr. The transwell inserts were removed and the cells that migrated into the receiver wells were transferred to U-bottom 96 well plates, pelleted and resuspended in calcein AM dye. The cells were incubated for 30 min at 37° C., 5% CO$_2$, washed once, transferred to a black clear plate and immediately read on the FlexStation at 490/520 nm. Data is presented as percent inhibition of chemotaxis. FIG. 20 provides representative data showing the ability of the different variants for each of the five clones to inhibit chemotaxis to CXCL9, CXCL10, and CXCL11.

Figure 21:
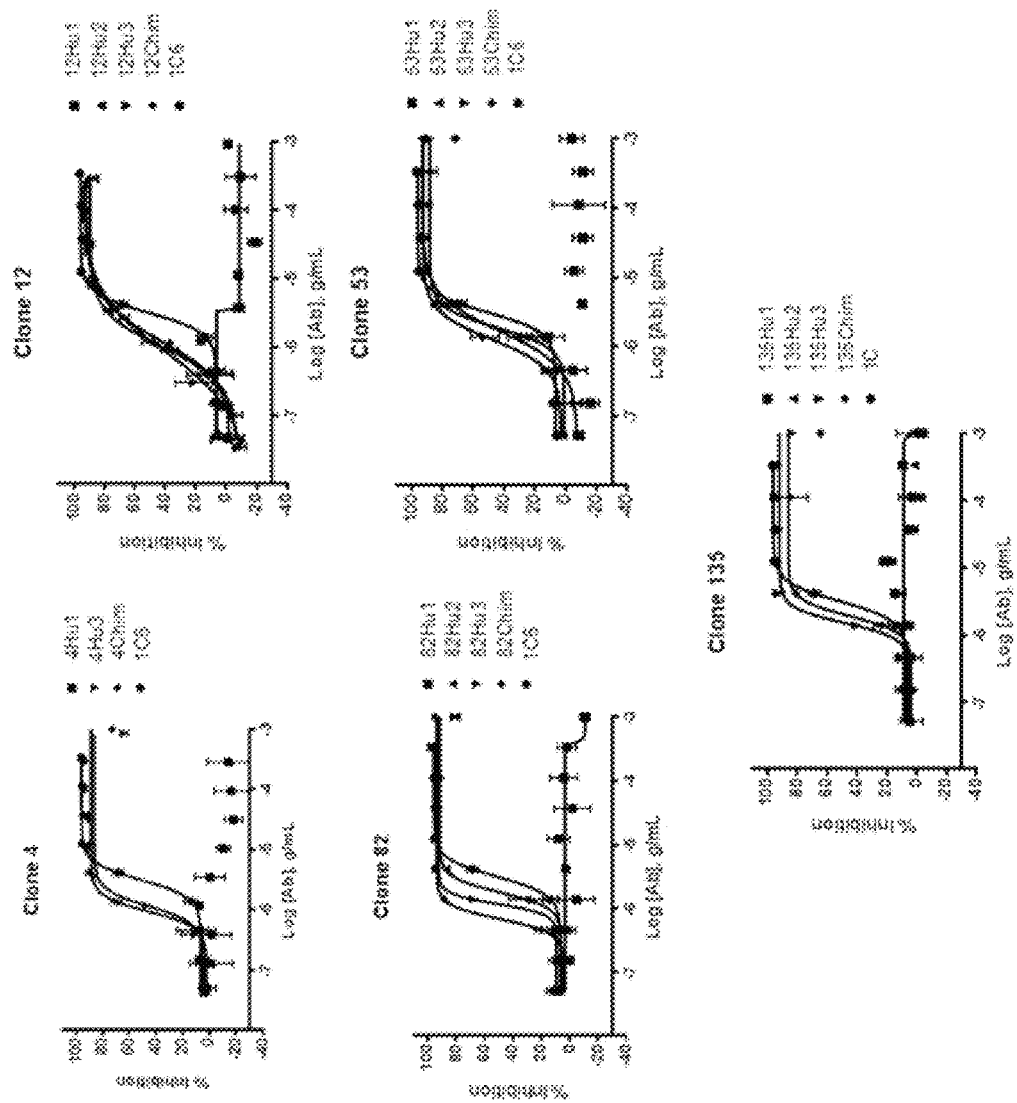
FIG. 21 is a plot showing the ability of chimeric (Chim) and humanized (Hu1, Hu2 or Hu3) antibody variants of clones 4, 12, 53, 82, and 135 and the commercial clone 1C6 to inhibit calcium mobilization in human CXCR3-Gqi4qi4 transfected CHO cells. Antibody concentration (horizontal axis) is plotted against percent maximal inhibition (vertical axis).

To evaluate the inhibition of intracellular calcium mobilization, calcium flow in human CXCR3-Gqi4qi4 transfected CHO cells was measured in response to CXCL10 in the presence or absence of various concentrations of anti-CXCR3 antibody variants or the positive control antibody 1C6. Cells were seeded (12,000/well) in 384-black plates and allowed to attach overnight. The next day, cells were loaded with calcium sensitive dye, Fluo-4NW dye, for 40 min prior to the addition of antibody and incubated at 37° C. Antibody was added and allowed to incubate for 20 min prior to addition of the CXCR3 ligand, recombinant human CXCL10, at the pre-determined EC$_{80}$ concentration of CXCL10. Addition of dye was performed manually using an electronic multichannel pipet but antibody and agonist addition was automated on the FLIPR Tetra® and the plate immediately read at 470-495 nm after the addition of CXCL10. Samples were run in duplicate and the average percent inhibition (±Standard Deviation) at each antibody concentration was graphed. Clone 4 Hu1 did not inhibit calcium mobilization and was used as a negative control in these experiments. FIG. 21 shows the ability of the different variants for each of the five clones to inhibit calcium mobilization and compares them to the commercial clone 1C6. Representative IC50 values (M) of antibodies against CXCL10 in the calcium mobilization assay are shown in Table 9 below.

TABLE 9

| | Clone 4 | Clone 12 | Clone 53 | Clone 82 | Clone 135 | 1C6 |
|---|---|---|---|---|---|---|
| Hu1 | N/A | N/A | N/A | N/A | N/A | — |
| Hu2 | N/A | 1.038E−06 | 1.675E−06 | 1.772E−06 | N/A | — |
| Hu3 | 1.146E−06 | 8.636E−07 | 1.261E−06 | 1.169E−06 | 1.499E−06 | — |
| Chimeric | 9.352E−07 | 1.204E−06 | 1.87E−06 | 6.778E−07 | 1.891E−06 | 3.135E−06* |

*in Table 9 indicates that the 1C6 antibody is not a chimeric antibody but a fully mouse IgG1 antibody against human CXCR3.

As shown in Table 10, the binding kinetic data (see Example 9), correlated well with the functional assay results. Based on the binding kinetic data and the functional assay results, clones 4 and 53 were selected for further evaluation and 4D humanization,

TABLE 10

| Shading Code Clone | Best Epitope Group | Average Octet Peptide Binding Response | Poor Octet Peptide Binding Kd (M) | Biacore Whole Receptor Binding ka (1/Ms) | Biacore Whole Receptor Binding kd (1/s) | Biacore Whole Receptor Binding KD (M) | In Vitro Assays Flow | In Vitro Assays Chemotaxis CXCL11 | In Vitro Assays Chemotaxis CXCL9 | In Vitro Assays Primary CXCL10 | In Vitro Assays FLIPR |
|---|---|---|---|---|---|---|---|---|---|---|---|
| 4 chimeric | 2 | 7.1859 | 6.57E−11 | 2.09E+05 | 1.15E−04 | 5.48E−10 | | | | | |
| 4 Hu1 | 2 | 3.5399 | 1.52E−08 | 2.24E+05 | 1.40E−04 | 6.34E−10 | | | | | |
| 4 Hu2 | 2 | 6.7746 | 3.78E−11 | 1.59E+05 | 1.70E−03 | 1.07E−08 | | | | | |
| 4 Hu3 | 2 | 6.8723 | 4.06E−11 | 2.26E+05 | 1.47E−04 | 6.49E−10 | | | | | |
| 12 chimeric | 1 | 6.4469 | <1.0E−12 | 9.66E+04 | 4.52E−04 | 5.00E−09 | | | | <50% inhibition for all variants | |
| 12 Hu1 | 1 | 4.6044 | 9.54E−09 | | no binding | | | | | | |
| 12 Hu2 | 1 | 6.9715 | 3.44E−10 | 6.39E+04 | 1.02E−03 | 1.60E−08 | | | | | |
| 12 Hu3 | 1 | 7.0274 | <1.0E−12 | 6.60E+04 | 1.02E−03 | 1.56E−08 | | | | | |
| 53 chimeric | 3 | 6.1886 | <1.0E−12 | 4.44E+04 | 7.07E−05 | 1.60E−09 | | | | | |
| 53 Hu1 | 3 | 2.0452 | 5.27E−08 | | no binding | | | | | | |
| 53 Hu2 | 3 | 6.0166 | 2.96E−11 | 3.09E+04 | 2.04E−04 | 6.70E−09 | | | | | |
| 53 Hu3 | 3 | 6.929 | 1.43E−11 | 6.88E+04 | 1.13E−04 | 1.72E−09 | | | | | |
| 82 chimeric | 4 | 0.6554 | <1.0E−12 | 1.61E+05 | 8.92E−04 | 5.54E−09 | | | | | |

TABLE 10-continued

| Shading Code Clone | Best Epitope Group | Average Octet Peptid Binding Response | Poor Kd (M) | Biacore Whole Receptor Binding ka (1/Ms) | kd (1/s) | KD (M) | In Vitro Assays Flow | Chemotaxis CXCL11 | Chemotaxis CXCL9 | Primary CXCL10 | FLIPR |
|---|---|---|---|---|---|---|---|---|---|---|---|
| 82 Hu1 | 4 | 2.2913 | 3.81E−09 | | no binding | | | | | | |
| 82 Hu2 | 4 | 6.225 | 4.89E−12 | 8.67E+04 | 2.62E−04 | 3.02E−09 | | | | | |
| 82 Hu3 | 4 | 8.1277 | 5.07E−12 | 3.40E+05 | 4.82E−04 | 1.42E−09 | | | | | |
| 135 chimeric | 3 | 7.0143 | <1.0E−12 | 5.52E+04 | 3.82E−04 | 6.93E−09 | | | | <50% inhibition for all variants | |
| 135 Hu1 | 3 | 0.0289 | 5.74E−05 | | no binding | | | | | | |
| 135 Hu2 | 3 | 0.9256 | 4.00E−08 | | no binding | | | | | | |
| 135 Hu3 | 3 | 7.1572 | 2.42E−11 | 6.68E+04 | 3.35E−04 | 5.01E−09 | | | | | |

Example 12

4D Humanization 4D humanization of anti-hCXCR3 antibody clones is done as described in WO 2009/032661 (e.g., at paragraphs [0037]-[0044]). Briefly, 4D humanization comprises: a) building a 3-D model of the variable domain that is to be humanized; b) identifying the flexible residues in the variable domain using a molecular dynamics simulation of the 3-D model of the domain; c) identifying the closest human germline by comparing the molecular dynamics trajectory of the 3-D model to the molecular dynamics trajectories of 49 human germlines (rather than a comparison of antibody sequences, as is done in traditional humanization); and d) mutating the flexible residues, which are not part of the CDR, into their human germline counterpart (identified in step c). Heavy chains 4.4-4.6 and light chains 4.4-4.7 were designed using this method. In particular, an initial 4D humanized construct (VH 4.4 and VL 4.4) was designed and then further modifications to the heavy and light chain were designed (VH 4.5-4.6 and VL 4.5-4.7) to introduce stabilizing and anti-aggregating mutations and to eliminate other unwanted motifs. Similar methods were also used to design 4D humanized constructs VH 53.7-53.10 and VL 53.10-53.13.

Table 11 indicates the humanizing strategy (and the additional modifications, where applicable) used to prepare the heavy and light chain variants for clones 4 12, 53, 82, and 135, including the humanized and 4D humanized chains (VH=heavy chain; VK=light chain).

Several 4D variants of clone 4 (4Hu6, 4Hu7, 4Hu8, 4Hu9, 4Hu10) were evaluated by Biacore whole receptor assay to evaluate binding kinetics and CXCR3 affinity and compared to the clone 4 chimeric antibody. As shown in Table 2, Clone 4Hu6 contained heavy chain 4.4 and light chain 4.4. Clone 4Hu7 contained heavy chain 4.4 and light chain 4.7. Clone 4Hu8 contained heavy chain 4.5 and light chain 4.5. Clone 4Hu9 contained heavy chain 4.5 and light chain 4.6. And clone 4Hu10 contained heavy chain 4.6 and light chain 4.4.

As shown in Table 12, when the 4D modeling variants of clone 4 were compared to the chimeric variant (4Ch), four out of five variants showed improved affinity (KD). The 4D variant 4Hu10, however, showed nearly 1 order of magnitude decreased affinity.

TABLE 11

| Clone | heavy/ light chain variant | strategy |
|---|---|---|
| 4 | VH1 | CDR grafting |
| 4 | VH2 | CDR grafting |
| 4 | VH3 | CDR grafting |
| 4 | VH4 | 4D modeling |
| 4 | VH5 | 4D modeling, includes stabilizing mutations |
| 4 | VH6 | 4D modeling, includes mutations to remove unwanted motifs |
| 4 | VH7 | CDR grafting, modification of VH 4.2 at residues NG >QG to remove CDR2 deamidation site |
| 4 | VH8 | CDR grafting, modification of VH 4.2 at residues NG >NL to remove CDR2 deamidation site |
| 4 | VH9 | modification of VH 4.2 at residues NG >NS to remove CDR2 deamidation site |
| 4 | VH10 | modification of VH 4.2 at residues NG >DG to remove CDR2 deamidation site |
| 4 | VH11 | modification of VH 4.2 at residues NG >NV to remove CDR2 deamidation site |
| 4 | VK1 | CDR grafting |
| 4 | VK2 | CDR grafting |
| 4 | VK3 | CDR grafting |
| 4 | VK4 | 4D modeling |
| 4 | VK5 | 4D modeling, includes stabilizing mutations |
| 4 | VK6 | 4D modeling, includes other stabilizing mutations |
| 4 | VK7 | 4D modeling, includes anti-aggregation mutations |
| 53 | VH1 | CDR grafting |
| 53 | VH2 | CDR grafting |
| 53 | VH3 | CDR grafting |
| 53 | VH4 | modification of VH 4.2 at residue T50 >V-back mutation to incorporate VH 4.1 residue |
| 53 | VH5 | modification of VH 4.2 at residue P61 >A-back mutation to incorporate VH 4.1 residue |
| 53 | VH6 | modification of VH 4.2 at residue M93 <V-back mutation to incorporate VH 4.1 residue |
| 53 | VH7 | 4D modeling |
| 53 | VH8 | 4D modeling |
| 53 | VH9 | 4D modeling |
| 53 | VH10 | 4D modeling |
| 53 | VK1 | CDR grafting |
| 53 | VK2 | CDR grafting |
| 53 | VK3 | CDR grafting |
| 53 | VK4 | modification of VK 4.2 at residue 132 >L-back mutation to incorporate VK1 residue |
| 53 | VK5 | modification of VK 4.2 at residue Y33 >A-back mutation to incorporate VK1 residue |
| 53 | VK6 | modification of VK 4.2 at residue N52 >T-back mutation to incorporate VK1 residue |
| 53 | VK7 | modification of VK 4.2 at residue A54 >Q-back mutation to incorporate VK1 residue |
| 53 | VK8 | modification of VK 4.2 at residue P55 >S-back mutation to incorporate VK1 residue |
| 53 | VK9 | modification of VK 4.2 at residue G99 >Q-back mutation to incorporate VK1 residue |
| 53 | VK10 | 4D modeling |
| 53 | VK11 | 4D modeling |
| 53 | VK12 | 4D modeling |
| 53 | VK13 | 4D modeling |

TABLE 11-continued

| Clone | heavy/light chain variant | strategy |
|---|---|---|
| 12 | VH1 | CDR grafting |
| 12 | VH2 | CDR grafting |
| 12 | VH3 | CDR grafting |
| 12 | VK1 | CDR grafting |
| 12 | VK2 | CDR grafting |
| 12 | VK3 | CDR grafting |
| 82 | VH1 | CDR grafting |
| 82 | VH2 | CDR grafting |
| 82 | VH3 | CDR grafting |
| 82 | VK1 | CDR grafting |
| 82 | VK2 | CDR grafting |
| 82 | VK3 | CDR grafting |
| 135 | VH1 | CDR grafting |
| 135 | VH2 | CDR grafting |
| 135 | VH3 | CDR grafting |
| 135 | VK1 | CDR grafting |
| 135 | VK2 | CDR grafting |
| 135 | VK3 | CDR grafting |

TABLE 12

| Curve | ka (1/Ms) | kd (1/s) | KD (M) |
|---|---|---|---|
| 4Ch | 1.71E+05 | 8.57E−05 | 5.09E−10 |
| 4Hu6 | 4.76E+05 | 1.55E−04 | 3.27E−10 |
| 4Hu7 | 4.12E+05 | 1.33E−04 | 3.26E−10 |
| 4Hu8 | 3.27E+05 | 1.13E−04 | 3.49E−10 |
| 4Hu8 | 3.48E+05 | 1.34E−04 | 3.87E−10 |
| 4Hu10 | 3.55E+05 | 1.05E−03 | 2.96E−09 |

Example 13

NSG-PBL Mouse Model

Figure 22:
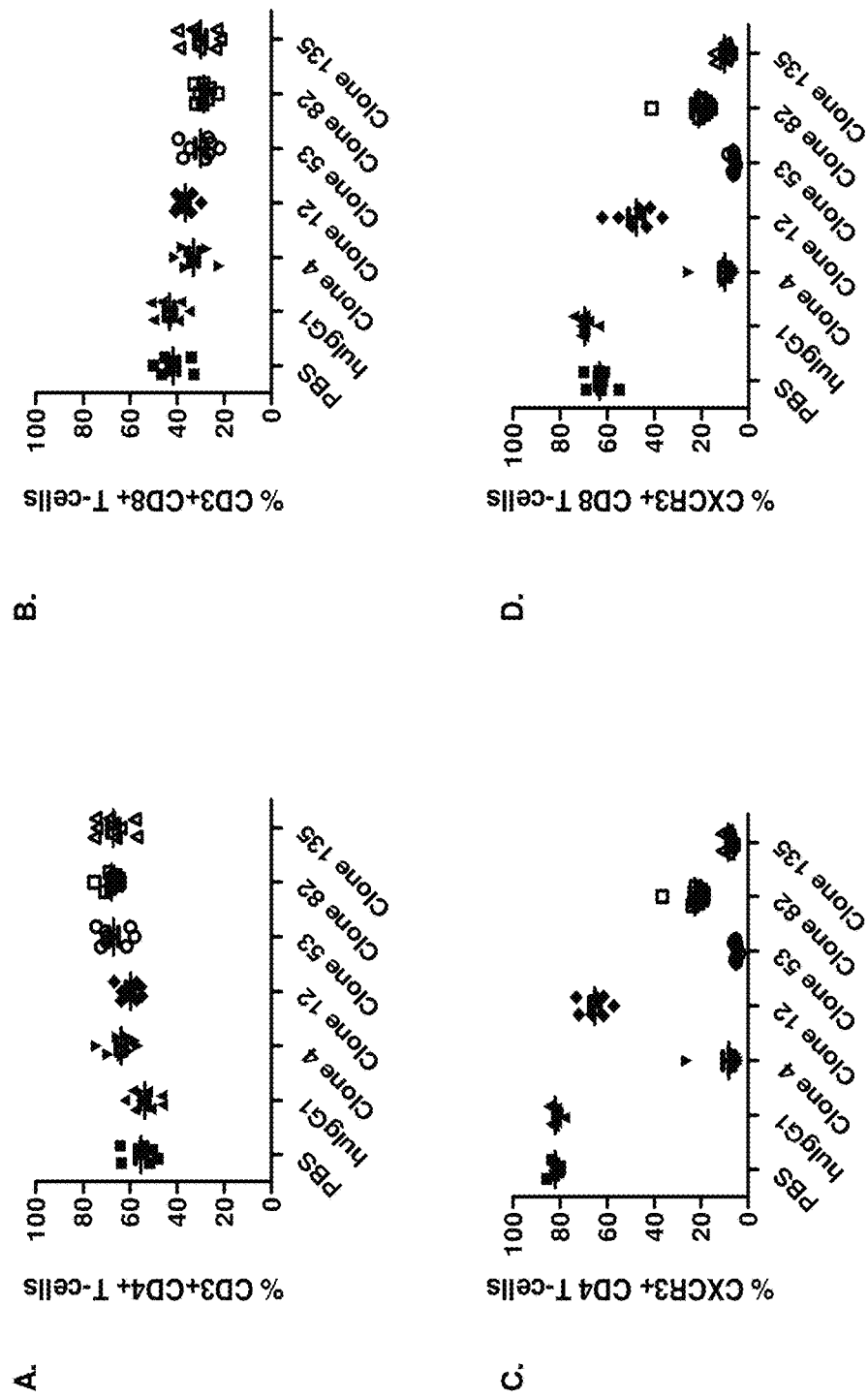
FIG. 22A-D show the effects of anti-CXCR3 antibody treatment on the percentage of CD3+/CD4+ T cells (FIG. 22A), CD3+/CD8+ T cells (FIG. 22B), CXCR3+/CD3+/CD4+ T cells (FIG. 22C), and CXCR3+/CD3+/CD8+ T cells (FIG. 22D) in NOD-scid IL2rγ$^{null}$ (NSG) mice. HuIgG1 indicates human IgG1 (Herceptin), clones 4, 12, 53, 82, and 135 refer to the chimeric antibody clones.

NOD-scid IL2ry$^{null}$ (NSG) mice were injected with 2E7 fresh primary human ficoll isolated peripheral blood mononuclear cells (PBMCs) on day 0. Animals (n=8/group) were treated with 5 mg/kg anti-human CXCR3 chimeric antibodies or control human IgG1 (Herceptin) twice a week for the entire study starting on day 3 post cell transfer. Blood taken on day 14 post initiation was processed for flow cytometry and stained using standard procedures with antibodies to human CD45 (hCD45), human CD3 (hCD3), human CD4 (hCD4), human CD8 (hCD8), and human CXCR3. Cells in the lymphocyte gate were gated on hCD45+ cells followed by gating on hCD3+ cells. hCD4 and hCD8 expression on hCD45+ hCD3+ T cells were evaluated and the percentage of human CD4+CD45+CD3+ T cells and human CD8+C45+CD3+ T cells was determined. The percentage of CXCR3 expressing human CD4+ T cells and CD8+ T cells was determined. Each dot in FIG. 22 represents a single mouse, with representative data are shown from three experiments. The data show that anti-CXCR3 antibody treatment in the NSG-PBL mouse model of xenogeneic GvHD (graft vs. host disease) resulted in modulation of CXCR3-expressing T cells, but reveals functional differences between the five clones.

Table 12 shows the median survival of NSG-PBL mice with xenogeneic GvHD after treatment with chimeric anti-human CXCR3 candidate antibodies.

TABLE 13

| Treatment | Median survival (days) |
|---|---|
| PBS | 31 |
| huIgG1 | 33.5 |
| Clone 4 chimeric | 43** |
| Clone 12 chimeric | 41 |
| Clone 53 chimeric | 44* |
| Clone 82 chimeric | 36.5 |
| Clone 135 chimeric | 45*** |

*p = 0.043;
**p = 0.016;
***p = 0.010 anti-CXCR3 antibody treatment versus huIgG1 treatment using Log Rank test.

The preceding examples are intended to illustrate and in no way limit the present disclosure. Other embodiments of the disclosed devices and methods will be apparent to those skilled in the art from consideration of the specification and practice of the devices and methods disclosed herein.

What is claimed is:

1. An isolated nucleic acid encoding the amino acid sequence of an antibody or antigen binding fragment capable of binding to Chemokine (C-X-C motif) receptor 3 (CXCR3), said antibody or antigen binding fragment comprising six complementarity determining regions (CDRs): heavy chain variable domain (VH) CDR1, VH CDR2, VH CDR3, light chain variable domain (VL) CDR1, VL CDR2, and VL CDR3,
wherein:
a) VH CDR1 is selected from the group consisting of: SEQ ID NO: 116, SEQ ID NO: 228, SEQ ID NO: 368, and SEQ ID NO: 543;
b) VH CDR2 is selected from the group consisting of: SEQ ID NO: 118, SEQ ID NO: 174, SEQ ID NO: 230, SEQ ID NO: 370, and SEQ ID NO: 545;
c) VH CDR3 is selected from the group consisting of: SEQ ID NO: 120, SEQ ID NO: 176, SEQ ID NO: 232, SEQ ID NO: 372, and SEQ ID NO: 547;
d) VL CDR1 is selected from the group consisting of: SEQ ID NO: 123, SEQ ID NO: 179, SEQ ID NO: 235, SEQ ID NO: 375, and SEQ ID NO: 550;
e) VL CDR2 is selected from the group consisting of: SEQ ID NO: 125, SEQ ID NO: 181, SEQ ID NO: 237, SEQ ID NO: 377, and SEQ ID NO: 552; and
f) VL CDR3 is selected from the group consisting of: SEQ ID NO: 127, SEQ ID NO:239, SEQ ID NO: 379, and SEQ ID NO: 554.

2. The isolated nucleic acid of claim 1, wherein the antibody or fragment is chimeric, CDR grafted, mutated, mutated to remove one or more deamidation site, human, humanized, humanized and back-mutated, synthetic, or recombinant.

3. The isolated nucleic acid of claim 1, wherein the antibody or fragment is capable of binding to a polypeptide comprising a peptide selected from the group consisting of:
a) a peptide comprising the amino acid sequence SEQ ID NO:71;
b) a peptide comprising the amino acid sequence SEQ ID NO:72;
c) a peptide comprising the amino acid sequence SEQ ID NO:73;
d) a peptide comprising the amino acid sequence SEQ ID NO:74;
e) a peptide comprising the amino acid sequence SEQ ID NO:75;
f) a peptide comprising the amino acid sequence SEQ ID NO:76;
g) a peptide comprising the amino acid sequence SEQ ID NO:77;
h) a peptide comprising the amino acid sequence SEQ ID NO:78;
i) a peptide comprising the amino acid sequence SEQ ID NO:79;
j) a peptide comprising the amino acid sequence SEQ ID NO:80;
k) a peptide comprising residues 1-58 of SEQ ID NO:1;
l) a peptide comprising residues 1-16 of SEQ ID NO:1; and
m) a peptide comprising residues 1-37 of SEQ ID NO:1, wherein X indicates any amino acid.

4. The isolated nucleic acid of claim 1, wherein the antibody or fragment comprises a heavy chain variable region and a light chain variable region, wherein the heavy chain variable region comprises an amino acid sequence at least 90% identical to a sequence selected from the group consisting of SEQ ID NO: 2, 4, 6, 8, 10, 12, 14, 16, 18, 20, 22, 24, 26-33, 38, 40, 42, 44, 46-48, 55, 57, 59, 61 and 63-66;
and
wherein the light chain variable region comprises a sequence at least 90% identical to an amino acid sequence selected from the group consisting of SEQ ID NO: 3, 5, 7, 9, 11, 13, 15, 17, 19, 21, 23, 25, 34-37, 39, 41, 43, 45, 49-54, 56, 58, 60, 61 and 67-70.

5. The isolated nucleic acid of claim 4, wherein the heavy chain variable region comprises an amino acid sequence selected from the group consisting of SEQ ID NO: 2, 4, 6, 8, 10, 12, 14, 16, 18, 20, 22, 24, 26-33, 38, 40, 42, 44, 46-48, 55, 57, 59, 61 and 63-66;
and
wherein the light chain variable region comprises an amino acid sequence selected from the group consisting of SEQ ID NO: 3, 5, 7, 9, 11, 13, 15, 17, 19, 21, 23, 25, 34-37, 39, 41, 43, 45, 49-54, 56, 58, 60, 61 and 67-70.

6. The isolated nucleic acid of claim 1, wherein said antibody or fragment comprises 3 CDRs selected from the group of variable domain CDR sets consisting of:
Clone 12 VH CDR set: SEQ ID NO: 116, SEQ ID NO: 118, and SEQ ID NO: 120;
Clone 12VL CDR set: SEQ ID NO: 123, SEQ ID NO: 125, and SEQ ID NO: 127;
Clone 135 VH CDR set: SEQ ID NO: 368, SEQ ID NO: 174, and SEQ ID NO: 176;
Clone 135 VL CDR set: SEQ ID NO: 179, SEQ ID NO: 181, and SEQ ID NO: 379;
Clone 4 VH CDR set: SEQ ID NO: 228, SEQ ID NO: 230, and SEQ ID NO: 232;
Clone 4 VL CDR set: SEQ ID NO: 235, SEQ ID NO: 237, and SEQ ID NO: 239;
Clone 53 VH CDR set: SEQ ID NO: 368, SEQ ID NO: 370, and SEQ ID NO: 372;
Clone 53 VL CDR set: SEQ ID NO: 375, SEQ ID NO: 377, and SEQ ID NO: 379;
Clone 82 VH CDR set: SEQ ID NO: 543, SEQ ID NO: 545, and SEQ ID NO: 547;
and
Clone 82 VL CDR set: SEQ ID NO: 550, SEQ ID NO: 552, and SEQ ID NO: 554.

7. The isolated nucleic acid of claim 1, wherein said antibody or fragment comprises two variable domain CDR sets selected from a group consisting of:

Clone 12 VH CDR set and Clone 12 VL CDR set;
Clone 135 VH CDR set and Clone 135 VL CDR set;
Clone 4 VH CDR set and Clone 4 VL CDR set;
Clone 53 VH CDR set and Clone 53 VL CDR set; and
Clone 82 VH CDR set and Clone 82 VL CDR set.

8. The isolated nucleic acid of claim 1, wherein the antibody or fragment comprises a combination of heavy chain and light chain variable regions selected from the group consisting of:
  SEQ ID NOs: 18 and 19; SEQ ID NOs: 20 and 21; SEQ ID NOs: 22 and 23;
  SEQ ID NOs: 24 and 25; SEQ ID NOs: 22 and 25; SEQ ID NOs: 24 and 23;
  SEQ ID NOs: 26 and 34; SEQ ID NOs: 26 and 37; SEQ ID NOs: 27 and 35;
  SEQ ID NOs: 27 and 36; SEQ ID NOs: 28 and 34; SEQ ID NOs: 22 and 21;
  SEQ ID NOs: 20 and 23; SEQ ID NOs: 24 and 21; SEQ ID NOs: 20 and 25;
  SEQ ID NOs: 29 and 23; SEQ ID NOs: 30 and 23; SEQ ID NOs: 31 and 23;
  SEQ ID NOs: 32 and 23; SEQ ID NOs: 33 and 23; SEQ ID NOs: 2 and 3;
  SEQ ID NOs: 4 and 5; SEQ ID NOs: 6 and 7; SEQ ID NOs: 8 and 9;
  SEQ ID NOs: 55 and 56; SEQ ID NOs: 57 and 58; SEQ ID NOs: 59 and 60;
  SEQ ID NOs: 61 and 62; SEQ ID NOs: 10 and 11; SEQ ID NOs: 12 and 13;
  SEQ ID NOs: 14 and 15; SEQ ID NOs: 16 and 17; SEQ ID NOs: 38 and 39;
  SEQ ID NOs: 40 and 41; SEQ ID NOs: 42 and 43 SEQ ID NOs: 44 and -45;
  SEQ ID NOs: 40 and 43; SEQ ID NOs: 42 and 41; SEQ ID NOs: 42 and 49;
  SEQ ID NOs: 42 and 50; SEQ ID NOs: 42 and 51; SEQ ID NOs: 42 and 52;
  SEQ ID NOs: 42 and 53; SEQ ID NOs: 42 and 54; SEQ ID NOs: 46 and 43;
  SEQ ID NOs: 47 and 43; SEQ ID NOs: 48 and 43; SEQ ID NOs: 40 and 49;
  SEQ ID NOs: 40 and 51; SEQ ID NOs: 48 and 49; SEQ ID NOs: 48 and 51;
  SEQ ID NOs: 63 and 67; and SEQ ID NOs: 63 and 68.

9. The isolated nucleic acid of claim 1, wherein the antibody or fragment is capable of preferentially binding to A-isoform of CXCR3.

10. A vector comprising the isolated nucleic acid of claim 1.

11. A vector comprising the isolated nucleic acid of claim 7.

12. A vector comprising the isolated nucleic acid of claim 8.

13. An isolated host cell comprising the vector of claim 10.

14. An isolated host cell comprising the vector of claim 11.

15. The host cell according to claim 13, wherein said host cell is a cell selected from the group consisting of an *E. coli* cell, a COS cell, and a Chinese hamster ovary (CHO) cell.

16. The host cell according to claim 14, wherein said host cell is a cell selected from the group consisting of an *E. coli* cell, a COS cell, and a Chinese hamster ovary (CHO) cell.

17. A method of producing the antibody or fragment encoded by the isolated nucleic acid of claim 1, comprising culturing a host cell comprising a vector comprising the isolated nucleic acid of claim 1 in a culture medium under conditions suitable to produce said antibody or fragment.

18. A method of producing the antibody or fragment encoded by the isolated nucleic acid of claim 7, comprising culturing a host cell comprising a vector comprising the isolated nucleic acid of claim 7 in a culture medium under conditions suitable to produce said antibody or fragment.

19. The method of claim 17, wherein said antibody or fragment is capable of preferentially binding to A-isoform of CXCR3.

20. An isolated nucleic acid encoding the heavy chain variable region of an antibody or antigen binding fragment capable of binding to Chemokine (C-X-C motif) receptor 3 (CXCR3), said antibody or antigen binding fragment comprising six complementarity determining regions (CDRs): heavy chain variable domain (VH) CDR1, VH CDR2, VH CDR3, light chain variable domain (VL) CDR1, VL CDR2, and VL CDR3, wherein:
  a) VH CDR1 is selected from the group consisting of: SEQ ID NO: 116, SEQ ID NO: 228, SEQ ID NO: 368, and SEQ ID NO: 543;
  b) VH CDR2 is selected from the group consisting of: SEQ ID NO: 118, SEQ ID NO: 174, SEQ ID NO: 230, SEQ ID NO: 370, and SEQ ID NO: 545;
  c) VH CDR3 is selected from the group consisting of: SEQ ID NO: 120, SEQ ID NO: 176, SEQ ID NO: 232, SEQ ID NO: 372, and SEQ ID NO: 547;
  d) VL CDR1 is selected from the group consisting of: SEQ ID NO: 123, SEQ ID NO: 179, SEQ ID NO: 235, SEQ ID NO: 375, and SEQ ID NO: 550;
  e) VL CDR2 is selected from the group consisting of: SEQ ID NO: 125, SEQ ID NO: 181, SEQ ID NO: 237, SEQ ID NO: 377, and SEQ ID NO: 552; and
  g) VL CDR3 is selected from the group consisting of: SEQ ID NO: 127, SEQ ID NO: 239, SEQ ID NO: 379, and SEQ ID NO: 554, and
  wherein said heavy chain variable region comprises an amino acid sequence at least 90% identical to a sequence selected from the group consisting of SEQ ID NO: 2, 4, 6, 8, 10, 12, 14, 16, 18, 20, 22, 24, 26-33, 38, 40, 42, 44, 46-48, 55, 57, 59, 61 and 63-66.

21. The isolated nucleic acid of claim 20, wherein the heavy chain variable region comprises a sequence at least 95% identical to an amino acid sequence selected from the group consisting of SEQ ID NO: 2, 4, 6, 8, 10, 12, 14, 16, 18, 20, 22, 24, 26-33, 38, 40, 42, 44, 46-48, 55, 57, 59, 61 and 63-66.

22. The isolated nucleic acid of claim 20, wherein the heavy chain variable region comprises a sequence at least 99% identical to an amino acid sequence selected from the group consisting of SEQ ID NO: 2, 4, 6, 8, 10, 12, 14, 16, 18, 20, 22, 24, 26-33, 38, 40, 42, 44, 46-48, 55, 57, 59, 61 and 63-66.

23. The isolated nucleic acid of claim 20, wherein the heavy chain variable region comprises an amino acid sequence selected from the group consisting of SEQ ID NO: 2, 4, 6, 8, 10, 12, 14, 16, 18, 20, 22, 24, 26-33, 38, 40, 42, 44, 46-48, 55, 57, 59, 61 and 63-66.

24. A vector comprising the isolated nucleic acid of claim 20.

25. An isolated host cell comprising the vector of claim 24.

26. The host cell according to claim 25, wherein said host cell is a cell selected from the group consisting of an *E. coli* cell, a COS cell, and a Chinese hamster ovary (CHO) cell.

27. A method of producing the antibody or fragment encoded by the isolated nucleic acid of claim 20, comprising culturing a host cell comprising a vector comprising the isolated nucleic acid of claim 20 in a culture medium under conditions suitable to produce said antibody or fragment.

28. An isolated nucleic acid encoding the light chain variable region of an antibody or antigen binding fragment capable of binding to Chemokine (C-X-C motif) receptor 3 (CXCR3), said antibody or antigen binding fragment comprising six complementarity determining regions (CDRs): heavy chain variable domain (VH) CDR1, VH CDR2, VH CDR3, light chain variable domain (VL) CDR1, VL CDR2, and VL CDR3, wherein:
a) VH CDR1 is selected from the group consisting of: SEQ ID NO: 116, SEQ ID NO: 228, SEQ ID NO: 368, and SEQ ID NO: 543;
b) VH CDR2 is selected from the group consisting of: SEQ ID NO: 118, SEQ ID NO: 174, SEQ ID NO: 230, SEQ ID NO: 370, and SEQ ID NO: 545;
c) VH CDR3 is selected from the group consisting of: SEQ ID NO: 120, SEQ ID NO: 176, SEQ ID NO: 232, SEQ ID NO: 372, and SEQ ID NO: 547;
d) VL CDR1 is selected from the group consisting of: SEQ ID NO: 123, SEQ ID NO: 179, SEQ ID NO: 235, SEQ ID NO: 375, and SEQ ID NO: 550;
e) VL CDR2 is selected from the group consisting of: SEQ ID NO: 125, SEQ ID NO: 181, SEQ ID NO: 237, SEQ ID NO: 377, and SEQ ID NO: 552; and f) VL CDR3 is selected from the group consisting of: SEQ ID NO: 127, SEQ ID NO: 239, SEQ ID NO: 379, and SEQ ID NO: 554, and wherein said light chain variable region comprises an amino acid sequence at least 90% identical to a sequence selected from the group consisting of SEQ ID NO: 3, 5, 7, 9, 11, 13, 15, 17, 19, 21, 23, 25, 34-37, 39, 41, 43, 45, 49-54, 56, 58, 60, 62 and 67-70.

29. The isolated nucleic acid of claim 28, wherein said light chain variable region comprises an amino acid sequence at least 95% identical to a sequence selected from the group consisting of SEQ ID NO: 3, 5, 7, 9, 11, 13, 15, 17, 19, 21, 23, 25, 34-37, 39, 41, 43, 45, 49-54, 56, 58, 60, 62 and 67-70.

30. The isolated nucleic acid of claim 28, wherein said light chain variable region comprises an amino acid sequence at least 95% identical to a sequence selected from the group consisting of SEQ ID NO: 41, 43, 45, and 49-54.

31. The isolated nucleic acid of claim 28, wherein said light chain variable region comprises an amino acid sequence selected from the group consisting of SEQ ID NO: 41, 43, 45, and 49-54.

32. The isolated nucleic acid of claim 20, wherein said heavy chain variable region comprises 3 CDRs selected from the group of variable domain CDR sets consisting of:
Clone 12 VH CDR set: SEQ ID NO: 116, SEQ ID NO: 118, and SEQ ID NO: 120;
Clone 135 VH CDR set: SEQ ID NO: 368, SEQ ID NO: 174, and SEQ ID NO: 176;
Clone 4 VH CDR set: SEQ ID NO: 228, SEQ ID NO: 230, and SEQ ID NO: 232;
Clone 53 VH CDR set: SEQ ID NO: 368, SEQ ID NO: 370, and SEQ ID NO: 372; and
Clone 82 VH CDR set: SEQ ID NO: 543, SEQ ID NO: 545, and SEQ ID NO: 547.

33. The isolated nucleic acid of claim 28, wherein said light chain variable region comprises 3 CDRs selected from the group of variable domain CDR sets consisting of:
Clone 12 VL CDR set: SEQ ID NO: 123, SEQ ID NO: 125, and SEQ ID NO: 127;
Clone 135 VL CDR set: SEQ ID NO: 179, SEQ ID NO: 181, and SEQ ID NO: 379;
Clone 4 VL CDR set: SEQ ID NO: 235, SEQ ID NO: 237, and SEQ ID NO: 239;
Clone 53 VL CDR set: SEQ ID NO: 375, SEQ ID NO: 377, and SEQ ID NO: 379; and
Clone 82 VL CDR set: SEQ ID NO:550, SEQ ID NO: 552, and SEQ ID NO: 554.

34. A vector comprising the isolated nucleic acid of claim 28.

35. An isolated host cell comprising the vector of claim 34.

36. The host cell according to claim 35, wherein said host cell is a cell selected from the group consisting of an *E. coli* cell, a COS cell, and a Chinese hamster ovary (CHO) cell.

37. A method of producing the antibody or fragment encoded by the isolated nucleic acid of claim 28, comprising culturing a host cell comprising a vector comprising the isolated nucleic acid of claim 28 in a culture medium under conditions suitable to produce said antibody or fragment.

* * * * *

```
                       SEQUENCE LISTING

<160> NUMBER OF SEQ ID NOS: 673

<210> SEQ ID NO 1
<211> LENGTH: 368
<212> TYPE: PRT
<213> ORGANISM: Homo sapiens

<400> SEQUENCE: 1

Met Val Leu Glu Val Ser Asp His Gln Val Leu Asn Asp Ala Glu Val
1               5                   10                  15

Ala Ala Leu Leu Glu Asn Phe Ser Ser Ser Tyr Asp Tyr Gly Glu Asn
                20                  25                  30

Glu Ser Asp Ser Cys Cys Thr Ser Pro Pro Cys Pro Gln Asp Phe Ser
            35                  40                  45

Leu Asn Phe Asp Arg Ala Phe Leu Pro Ala Leu Tyr Ser Leu Leu Phe
        50                  55                  60

Leu Leu Gly Leu Leu Gly Asn Gly Ala Val Ala Ala Val Leu Leu Ser
65                  70                  75                  80
```

```
Arg Arg Thr Ala Leu Ser Ser Thr Asp Thr Phe Leu Leu His Leu Ala
                85                  90                  95

Val Ala Asp Thr Leu Leu Val Leu Thr Leu Pro Leu Trp Ala Val Asp
            100                 105                 110

Ala Ala Val Gln Trp Val Phe Gly Ser Gly Leu Cys Lys Val Ala Gly
        115                 120                 125

Ala Leu Phe Asn Ile Asn Phe Tyr Ala Gly Ala Leu Leu Leu Ala Cys
    130                 135                 140

Ile Ser Phe Asp Arg Tyr Leu Asn Ile Val His Ala Thr Gln Leu Tyr
145                 150                 155                 160

Arg Arg Gly Pro Pro Ala Arg Val Thr Leu Thr Cys Leu Ala Val Trp
                165                 170                 175

Gly Leu Cys Leu Leu Phe Ala Leu Pro Asp Phe Ile Phe Leu Ser Ala
            180                 185                 190

His His Asp Glu Arg Leu Asn Ala Thr His Cys Gln Tyr Asn Phe Pro
        195                 200                 205

Gln Val Gly Arg Thr Ala Leu Arg Val Leu Gln Leu Val Ala Gly Phe
    210                 215                 220

Leu Leu Pro Leu Leu Val Met Ala Tyr Cys Tyr Ala His Ile Leu Ala
225                 230                 235                 240

Val Leu Leu Val Ser Arg Gly Gln Arg Arg Leu Arg Ala Met Arg Leu
                245                 250                 255

Val Val Val Val Val Val Ala Phe Ala Leu Cys Trp Thr Pro Tyr His
            260                 265                 270

Leu Val Val Leu Val Asp Ile Leu Met Asp Leu Gly Ala Leu Ala Arg
        275                 280                 285

Asn Cys Gly Arg Glu Ser Arg Val Asp Val Ala Lys Ser Val Thr Ser
    290                 295                 300

Gly Leu Gly Tyr Met His Cys Cys Leu Asn Pro Leu Leu Tyr Ala Phe
305                 310                 315                 320

Val Gly Val Lys Phe Arg Glu Arg Met Trp Met Leu Leu Leu Arg Leu
                325                 330                 335

Gly Cys Pro Asn Gln Arg Gly Leu Gln Arg Gln Pro Ser Ser Ser Arg
            340                 345                 350

Arg Asp Ser Ser Trp Ser Glu Thr Ser Glu Ala Ser Tyr Ser Gly Leu
        355                 360                 365

<210> SEQ ID NO 2
<211> LENGTH: 119
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 2

Glu Val Gln Leu Glu Glu Ser Gly Gly Gly Leu Val Gln Pro Lys Gly
1               5                   10                  15

Ser Leu Lys Leu Ser Cys Ala Ala Ser Gly Ile Ser Phe Asn Asp Ala
            20                  25                  30

Ala Met Asn Trp Ile Arg Gln Ala Pro Gly Glu Gly Leu Glu Trp Val
        35                  40                  45

Ala Arg Ile Arg Ser Lys Ile Asn Asp Tyr Gly Thr His Tyr Ala Ala
    50                  55                  60

Ser Val Lys Asp Arg Phe Thr Ile Ser Arg Asp Asp Ser Gln Asn Ile
```

```
                65                  70                  75                  80
Leu Phe Leu Gln Met Asn Asn Leu Lys Thr Glu Asp Thr Gly Met Tyr
                    85                  90                  95

Tyr Cys Val Ile Asp Gly Tyr Gly Ser Leu Ala Tyr Trp Gly Gln Gly
                100                 105                 110

Thr Leu Val Thr Val Ser Ala
        115

<210> SEQ ID NO 3
<211> LENGTH: 108
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 3

Asp Ile Val Leu Thr Gln Ser Pro Ala Ile Met Ser Ser Ser Pro Gly
1               5                   10                  15

Glu Lys Val Thr Met Thr Cys Arg Ala Ser Ser Ser Val Ile Ser Ser
                20                  25                  30

Tyr Leu His Trp Tyr Gln Gln Arg Ser Gly Ala Ser Pro Lys Leu Trp
            35                  40                  45

Ile Tyr Ser Thr Ser Ser Leu Ala Ser Gly Val Pro Ala Arg Phe Ser
        50                  55                  60

Gly Ser Gly Ser Gly Thr Ser Phe Ser Leu Thr Ile Ser Ser Val Glu
65                  70                  75                  80

Ala Glu Asp Ala Ala Thr Tyr Tyr Cys Gln Gln Tyr Ser Gly Tyr Pro
                85                  90                  95

Leu Thr Phe Gly Ala Gly Thr Lys Leu Glu Leu Lys
                100                 105

<210> SEQ ID NO 4
<211> LENGTH: 119
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 4

Glu Val Gln Leu Val Glu Ser Gly Gly Gly Leu Val Gln Pro Gly Gly
1               5                   10                  15

Ser Leu Lys Leu Ser Cys Ala Ala Ser Gly Ile Ser Phe Asn Asp Ala
                20                  25                  30

Ala Met His Trp Val Arg Gln Ala Ser Gly Lys Gly Leu Glu Trp Val
            35                  40                  45

Ala Arg Ile Arg Ser Lys Ile Asn Asp Tyr Gly Thr Ala Tyr Ala Ala
        50                  55                  60

Ser Val Lys Gly Arg Phe Thr Ile Ser Arg Asp Asp Ser Gln Asn Thr
65                  70                  75                  80

Leu Tyr Leu Gln Met Asn Ser Leu Lys Thr Glu Asp Thr Ala Val Tyr
                85                  90                  95

Tyr Cys Val Ile Asp Gly Tyr Gly Ser Leu Ala Tyr Trp Gly Gln Gly
                100                 105                 110

Thr Leu Val Thr Val Ser Ser
        115
```

-continued

<210> SEQ ID NO 5
<211> LENGTH: 108
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 5

Glu Ile Val Leu Thr Gln Ser Pro Ala Thr Leu Ser Leu Ser Pro Gly
1               5                   10                  15

Glu Arg Ala Thr Leu Ser Cys Arg Ala Ser Ser Ser Val Ile Ser Ser
            20                  25                  30

Tyr Leu Ala Trp Tyr Gln Gln Lys Pro Gly Gln Ala Pro Arg Leu Trp
        35                  40                  45

Ile Tyr Ser Thr Ser Asn Arg Ala Thr Gly Ile Pro Ala Arg Phe Ser
    50                  55                  60

Gly Ser Gly Ser Gly Thr Asp Phe Thr Leu Thr Ile Ser Ser Leu Glu
65                  70                  75                  80

Pro Glu Asp Phe Ala Thr Tyr Tyr Cys Gln Gln Tyr Ser Gly Tyr Pro
                85                  90                  95

Leu Thr Phe Gly Gly Gly Thr Lys Val Glu Ile Lys
            100                 105

<210> SEQ ID NO 6
<211> LENGTH: 119
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 6

Glu Val Gln Leu Val Glu Ser Gly Gly Gly Leu Val Gln Pro Gly Gly
1               5                   10                  15

Ser Leu Lys Leu Ser Cys Ala Ala Ser Gly Ile Ser Phe Asn Asp Ala
            20                  25                  30

Ala Met Asn Trp Ile Arg Gln Ala Ser Gly Lys Gly Leu Glu Trp Val
        35                  40                  45

Ala Arg Ile Arg Ser Lys Ile Asn Asp Tyr Gly Thr His Tyr Ala Ala
    50                  55                  60

Ser Val Lys Gly Arg Phe Thr Ile Ser Arg Asp Asp Ser Gln Asn Thr
65                  70                  75                  80

Leu Tyr Leu Gln Met Asn Ser Leu Lys Thr Glu Asp Thr Ala Met Tyr
                85                  90                  95

Tyr Cys Val Ile Asp Gly Tyr Gly Ser Leu Ala Tyr Trp Gly Gln Gly
            100                 105                 110

Thr Leu Val Thr Val Ser Ser
        115

<210> SEQ ID NO 7
<211> LENGTH: 108
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 7

Glu Ile Val Leu Thr Gln Ser Pro Ala Thr Leu Ser Leu Ser Pro Gly
1               5                   10                  15

Glu Arg Ala Thr Leu Ser Cys Arg Ala Ser Ser Val Ile Ser Ser
            20                  25                  30

Tyr Leu His Trp Tyr Gln Gln Lys Pro Gly Gln Ala Pro Arg Leu Trp
            35                  40                  45

Ile Tyr Ser Thr Ser Ser Leu Ala Ser Gly Ile Pro Ala Arg Phe Ser
50                      55                  60

Gly Ser Gly Ser Gly Thr Asp Phe Thr Leu Thr Ile Ser Ser Leu Glu
65                  70                  75                  80

Pro Glu Asp Phe Ala Thr Tyr Tyr Cys Gln Gln Tyr Ser Gly Tyr Pro
                    85                  90                  95

Leu Thr Phe Gly Ala Gly Thr Lys Val Glu Ile Lys
                100                 105

<210> SEQ ID NO 8
<211> LENGTH: 119
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 8

Glu Val Gln Leu Val Glu Ser Gly Gly Gly Leu Val Gln Pro Lys Gly
1               5                   10                  15

Ser Leu Lys Leu Ser Cys Ala Ala Ser Gly Ile Ser Phe Asn Asp Ala
            20                  25                  30

Ala Met Asn Trp Ile Arg Gln Ala Ser Gly Lys Gly Leu Glu Trp Val
            35                  40                  45

Ala Arg Ile Arg Ser Lys Ile Asn Asp Tyr Gly Thr His Tyr Ala Ala
50                      55                  60

Ser Val Lys Asp Arg Phe Thr Ile Ser Arg Asp Asp Ser Gln Asn Ile
65                  70                  75                  80

Leu Tyr Leu Gln Met Asn Asn Leu Lys Thr Glu Asp Thr Ala Met Tyr
                85                  90                  95

Tyr Cys Val Ile Asp Gly Tyr Gly Ser Leu Ala Tyr Trp Gly Gln Gly
                100                 105                 110

Thr Leu Val Thr Val Ser Ser
        115

<210> SEQ ID NO 9
<211> LENGTH: 108
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 9

Glu Ile Val Leu Thr Gln Ser Pro Ala Ile Leu Ser Ser Ser Pro Gly
1               5                   10                  15

Glu Arg Ala Thr Leu Ser Cys Arg Ala Ser Ser Val Ile Ser Ser
            20                  25                  30

Tyr Leu His Trp Tyr Gln Gln Lys Pro Gly Ala Ala Pro Arg Leu Trp
            35                  40                  45

Ile Tyr Ser Thr Ser Ser Leu Ala Ser Gly Ile Pro Ala Arg Phe Ser
50                      55                  60

Gly Ser Gly Ser Gly Thr Ser Phe Thr Leu Thr Ile Ser Ser Leu Glu
65                  70                  75                  80

```
Ala Glu Asp Phe Ala Thr Tyr Tyr Cys Gln Gln Tyr Ser Gly Tyr Pro
                85                  90                  95

Leu Thr Phe Gly Ala Gly Thr Lys Val Glu Ile Lys
            100                 105

<210> SEQ ID NO 10
<211> LENGTH: 123
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 10

Glu Val Lys Leu Glu Glu Ser Gly Gly Gly Leu Val Lys Pro Gly Gly
1               5                   10                  15

Ser Leu Lys Leu Ser Cys Ala Ala Ser Gly Phe Thr Phe Thr Ser Tyr
            20                  25                  30

Ala Leu Ser Trp Val Arg Gln Thr Pro Glu Lys Arg Leu Glu Trp Val
        35                  40                  45

Ala Thr Ile Ser His Gly Gly Ser Tyr Thr Tyr Tyr Pro Asp Ser Val
    50                  55                  60

Lys Gly Arg Phe Thr Ile Ser Arg Asp Asn Ala Lys Asn Thr Leu Asn
65                  70                  75                  80

Leu Gln Met Ser Ser Leu Arg Ser Glu Asp Thr Ala Met Tyr Tyr Cys
                85                  90                  95

Ala Arg His Pro Phe Tyr Ser Gly Asn Tyr Gln Gly Tyr Phe Asp Tyr
            100                 105                 110

Trp Gly Gln Gly Thr Leu Leu Thr Val Ser Ser
        115                 120

<210> SEQ ID NO 11
<211> LENGTH: 106
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 11

Asp Ile Val Leu Thr Gln Ser Pro Ala Ile Met Ser Ala Ser Leu Gly
1               5                   10                  15

Glu Lys Val Thr Met Asn Cys Arg Ala Asn Ser Gly Val Asn Tyr Met
            20                  25                  30

Tyr Trp Tyr Gln Gln Lys Ser Asp Ala Ser Pro Lys Leu Trp Ile Tyr
        35                  40                  45

Phe Thr Ser Asn Leu Ala Pro Gly Val Pro Ala Arg Phe Ser Gly Ser
    50                  55                  60

Gly Ser Gly Asn Ser Tyr Ser Leu Thr Ile Ser Ser Met Glu Gly Glu
65                  70                  75                  80

Asp Ala Ala Thr Tyr Tyr Cys Gln Gln Phe Thr Ser Ser Pro Tyr Thr
                85                  90                  95

Phe Gly Gly Gly Thr Lys Leu Glu Ile Lys
            100                 105

<210> SEQ ID NO 12
<211> LENGTH: 123
<212> TYPE: PRT
<213> ORGANISM: Artificial Sequence
```

```
<220> FEATURE:
<223> OTHER INFORMATION: Description of Artificial Sequence: Synthetic
      polypeptide

<400> SEQUENCE: 12

Glu Val Gln Leu Glu Glu Ser Gly Gly Gly Leu Val Gln Pro Gly Gly
1               5                   10                  15

Ser Leu Arg Leu Ser Cys Ala Ala Ser Gly Phe Thr Phe Thr Ser Tyr
            20                  25                  30

Ala Met Ser Trp Val Arg Gln Ala Pro Gly Lys Gly Leu Glu Trp Val
        35                  40                  45

Ala Val Ile Ser His Gly Gly Ser Tyr Thr Tyr Tyr Ala Asp Ser Val
    50                  55                  60

Lys Gly Arg Phe Thr Ile Ser Arg Asp Asn Ser Lys Asn Thr Leu Tyr
65                  70                  75                  80

Leu Gln Met Asn Ser Leu Arg Ala Glu Asp Thr Ala Val Tyr Tyr Cys
                85                  90                  95

Ala Arg His Pro Phe Tyr Ser Gly Asn Tyr Gln Gly Tyr Phe Asp Tyr
            100                 105                 110

Trp Gly Gln Gly Thr Leu Val Thr Val Ser Ser
        115                 120

<210> SEQ ID NO 13
<211> LENGTH: 106
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 13

Asp Ile Gln Leu Thr Gln Ser Pro Ser Phe Leu Ser Ala Ser Val Gly
1               5                   10                  15

Asp Arg Val Thr Ile Thr Cys Arg Ala Ser Ser Gly Val Asn Tyr Leu
            20                  25                  30

Ala Trp Tyr Gln Gln Lys Pro Gly Lys Ala Pro Lys Leu Trp Ile Tyr
        35                  40                  45

Phe Thr Ser Thr Leu Gln Ser Gly Val Pro Ser Arg Phe Ser Gly Ser
    50                  55                  60

Gly Ser Gly Asn Glu Tyr Thr Leu Thr Ile Ser Ser Leu Gln Phe Glu
65                  70                  75                  80

Asp Phe Ala Thr Tyr Tyr Cys Gln Gln Phe Thr Ser Ser Pro Tyr Thr
                85                  90                  95

Phe Gly Gln Gly Thr Lys Leu Glu Ile Lys
            100                 105

<210> SEQ ID NO 14
<211> LENGTH: 123
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 14

Glu Val Gln Leu Glu Glu Ser Gly Gly Gly Leu Val Gln Pro Gly Gly
1               5                   10                  15

Ser Leu Arg Leu Ser Cys Ala Ala Ser Gly Phe Thr Phe Thr Ser Tyr
            20                  25                  30
```

```
Ala Leu Ser Trp Val Arg Gln Ala Pro Gly Lys Gly Leu Glu Trp Val
        35                  40                  45

Ala Thr Ile Ser His Gly Gly Ser Tyr Thr Tyr Tyr Pro Asp Ser Val
 50                  55                  60

Lys Gly Arg Phe Thr Ile Ser Arg Asp Asn Ser Lys Asn Thr Leu Tyr
 65                  70                  75                  80

Leu Gln Met Asn Ser Leu Arg Ala Glu Asp Thr Ala Val Tyr Tyr Cys
                 85                  90                  95

Ala Arg His Pro Phe Tyr Ser Gly Asn Tyr Gln Gly Tyr Phe Asp Tyr
             100                 105                 110

Trp Gly Gln Gly Thr Leu Val Thr Val Ser Ser
        115                 120
```

<210> SEQ ID NO 15
<211> LENGTH: 106
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 15

```
Asp Ile Gln Leu Thr Gln Ser Pro Ser Phe Leu Ser Ala Ser Val Gly
 1               5                  10                  15

Asp Arg Val Thr Ile Thr Cys Arg Ala Asn Ser Gly Val Asn Tyr Met
             20                  25                  30

Tyr Trp Tyr Gln Gln Lys Pro Gly Lys Ala Pro Lys Leu Trp Ile Tyr
         35                  40                  45

Phe Thr Ser Asn Leu Ala Pro Gly Val Pro Ser Arg Phe Ser Gly Ser
 50                  55                  60

Gly Ser Gly Asn Glu Tyr Thr Leu Thr Ile Ser Ser Leu Gln Phe Glu
 65                  70                  75                  80

Asp Phe Ala Thr Tyr Tyr Cys Gln Gln Phe Thr Ser Ser Pro Tyr Thr
                 85                  90                  95

Phe Gly Gly Gly Thr Lys Leu Glu Ile Lys
             100                 105
```

<210> SEQ ID NO 16
<211> LENGTH: 123
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 16

```
Glu Val Gln Leu Leu Glu Ser Gly Gly Gly Leu Val Gln Pro Gly Gly
 1               5                  10                  15

Ser Leu Arg Leu Ser Cys Ala Ala Ser Gly Phe Thr Phe Thr Ser Tyr
             20                  25                  30

Ala Leu Ser Trp Val Arg Gln Thr Pro Glu Lys Arg Leu Glu Trp Val
         35                  40                  45

Ala Thr Ile Ser His Gly Gly Ser Tyr Thr Tyr Tyr Pro Asp Ser Val
 50                  55                  60

Lys Gly Arg Phe Thr Ile Ser Arg Asp Asn Ser Lys Asn Thr Leu Asn
 65                  70                  75                  80

Leu Gln Met Ser Ser Leu Arg Ala Glu Asp Thr Ala Val Tyr Tyr Cys
                 85                  90                  95
```

-continued

```
Ala Arg His Pro Phe Tyr Ser Gly Asn Tyr Gln Gly Tyr Phe Asp Tyr
            100                 105                 110

Trp Gly Gln Gly Thr Leu Val Thr Val Ser Ser
        115                 120
```

<210> SEQ ID NO 17
<211> LENGTH: 106
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 17

```
Asp Ile Gln Leu Thr Gln Ser Pro Ser Phe Leu Ser Ala Ser Val Gly
1               5                   10                  15

Asp Arg Val Thr Ile Thr Cys Arg Ala Asn Ser Gly Val Asn Tyr Met
            20                  25                  30

Tyr Trp Tyr Gln Gln Lys Pro Asp Ala Ala Pro Lys Leu Trp Ile Tyr
        35                  40                  45

Phe Thr Ser Asn Leu Ala Pro Gly Val Pro Ser Arg Phe Ser Gly Ser
    50                  55                  60

Gly Ser Gly Asn Ser Tyr Thr Leu Thr Ile Ser Ser Leu Gln Phe Glu
65                  70                  75                  80

Asp Phe Ala Thr Tyr Tyr Cys Gln Gln Phe Thr Ser Ser Pro Tyr Thr
                85                  90                  95

Phe Gly Gly Gly Thr Lys Leu Glu Ile Lys
            100                 105
```

<210> SEQ ID NO 18
<211> LENGTH: 124
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 18

```
Glu Val Gln Leu Glu Glu Ser Gly Gly Gly Leu Val Lys Pro Gly Gly
1               5                   10                  15

Ser Leu Lys Leu Ser Cys Ala Ala Ser Gly Phe Thr Phe Ser Asn Tyr
            20                  25                  30

Ala Met Ser Trp Val Arg Gln Thr Pro Asp Lys Arg Leu Glu Trp Val
        35                  40                  45

Ala Thr Ile Ser Asn Gly Gly Ser Tyr Thr Tyr Tyr Pro Asp Thr Val
    50                  55                  60

Lys Gly Arg Phe Thr Ile Ser Arg Asp Asn Ala Lys Asn Thr Leu Ser
65                  70                  75                  80

Leu Gln Met Ser Ser Leu Arg Ser Glu Asp Thr Ala Met Tyr Tyr Cys
                85                  90                  95

Ser Arg Pro Ser Glu Arg Ser His Tyr Tyr Ala Thr Ser Gln Phe Ala
            100                 105                 110

Tyr Trp Gly Gln Gly Thr Leu Val Thr Val Ser Ala
        115                 120
```

<210> SEQ ID NO 19
<211> LENGTH: 106
<212> TYPE: PRT
<213> ORGANISM: Artificial Sequence
<220> FEATURE:

<223> OTHER INFORMATION: Description of Artificial Sequence: Synthetic
    polypeptide

<400> SEQUENCE: 19

Asp Ile Val Leu Thr Gln Ser Pro Gly Ile Met Ser Ala Ser Pro Gly
1               5                   10                  15

Glu Lys Val Thr Met Thr Cys Ser Ala Ser Ser Ser Val Ser Tyr Met
            20                  25                  30

His Trp Tyr Gln Gln Lys Ser Gly Thr Ser Pro Lys Arg Trp Ile Tyr
        35                  40                  45

Asp Thr Ser Lys Leu Ala Ser Gly Val Pro Ala Arg Phe Ser Gly Ser
    50                  55                  60

Gly Ser Gly Thr Ser Tyr Ser Leu Thr Ile Ser Ser Met Glu Ala Glu
65                  70                  75                  80

Asp Ala Ala Thr Tyr Tyr Cys Gln Gln Trp Ser Ser Ser Pro Leu Thr
                85                  90                  95

Phe Gly Ala Gly Thr Lys Val Glu Leu Lys
            100                 105

<210> SEQ ID NO 20
<211> LENGTH: 124
<212> TYPE: PRT
<213> ORGANISM: Artificial Sequence
<220> FEATURE:
<223> OTHER INFORMATION: Description of Artificial Sequence: Synthetic
    polypeptide

<400> SEQUENCE: 20

Glu Val Gln Leu Leu Glu Ser Gly Gly Gly Leu Val Gln Pro Gly Gly
1               5                   10                  15

Ser Leu Arg Leu Ser Cys Ala Ala Ser Gly Phe Thr Phe Ser Asn Tyr
            20                  25                  30

Ala Met Ser Trp Val Arg Gln Ala Pro Gly Lys Gly Leu Glu Trp Val
        35                  40                  45

Ala Val Ile Ser Asn Gly Gly Ser Tyr Thr Tyr Tyr Ala Asp Ser Val
    50                  55                  60

Lys Gly Arg Phe Thr Ile Ser Arg Asp Asn Ser Lys Asn Thr Leu Tyr
65                  70                  75                  80

Leu Gln Met Asn Ser Leu Arg Ala Glu Asp Thr Ala Val Tyr Tyr Cys
                85                  90                  95

Ser Arg Pro Ser Glu Arg Ser His Tyr Tyr Ala Thr Ser Gln Phe Ala
            100                 105                 110

Tyr Trp Gly Gln Gly Thr Leu Val Thr Val Ser Ser
        115                 120

<210> SEQ ID NO 21
<211> LENGTH: 106
<212> TYPE: PRT
<213> ORGANISM: Artificial Sequence
<220> FEATURE:
<223> OTHER INFORMATION: Description of Artificial Sequence: Synthetic
    polypeptide

<400> SEQUENCE: 21

Glu Ile Val Leu Thr Gln Ser Pro Ala Thr Leu Ser Leu Ser Pro Gly
1               5                   10                  15

Glu Arg Ala Thr Leu Ser Cys Arg Ala Ser Ser Ser Val Ser Tyr Leu
            20                  25                  30

Ala Trp Tyr Gln Gln Lys Pro Gly Gln Ala Pro Arg Arg Trp Ile Tyr

```
                35                  40                  45
Asp Thr Ser Asn Arg Ala Thr Gly Ile Pro Ala Arg Phe Ser Gly Ser
             50                  55                  60
Gly Ser Gly Thr Asp Tyr Thr Leu Thr Ile Ser Ser Leu Glu Pro Glu
 65                  70                  75                  80
Asp Phe Ala Val Tyr Tyr Cys Gln Gln Trp Ser Ser Pro Leu Thr
                 85                  90                  95
Phe Gly Gly Gly Thr Lys Val Glu Ile Lys
            100                 105

<210> SEQ ID NO 22
<211> LENGTH: 124
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 22

Glu Val Gln Leu Leu Glu Ser Gly Gly Gly Leu Val Gln Pro Gly Gly
 1               5                  10                  15
Ser Leu Arg Leu Ser Cys Ala Ala Ser Gly Phe Thr Phe Ser Asn Tyr
             20                  25                  30
Ala Met Ser Trp Val Arg Gln Ala Pro Gly Lys Gly Leu Glu Trp Val
         35                  40                  45
Ala Thr Ile Ser Asn Gly Gly Ser Tyr Thr Tyr Tyr Pro Asp Ser Val
     50                  55                  60
Lys Gly Arg Phe Thr Ile Ser Arg Asp Asn Ser Lys Asn Thr Leu Tyr
 65                  70                  75                  80
Leu Gln Met Asn Ser Leu Arg Ala Glu Asp Thr Ala Val Tyr Tyr Cys
                 85                  90                  95
Ser Arg Pro Ser Glu Arg Ser His Tyr Tyr Ala Thr Ser Gln Phe Ala
            100                 105                 110
Tyr Trp Gly Gln Gly Thr Leu Val Thr Val Ser Ser
        115                 120

<210> SEQ ID NO 23
<211> LENGTH: 106
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 23

Glu Ile Val Leu Thr Gln Ser Pro Ala Thr Leu Ser Leu Ser Pro Gly
 1               5                  10                  15
Glu Arg Ala Thr Leu Ser Cys Ser Ala Ser Ser Ser Val Ser Tyr Met
             20                  25                  30
His Trp Tyr Gln Gln Lys Pro Gly Thr Ala Pro Arg Arg Trp Ile Tyr
         35                  40                  45
Asp Thr Ser Lys Leu Ala Ser Gly Ile Pro Ala Arg Phe Ser Gly Ser
     50                  55                  60
Gly Ser Gly Thr Asp Tyr Thr Leu Thr Ile Ser Ser Leu Glu Pro Glu
 65                  70                  75                  80
Asp Phe Ala Thr Tyr Tyr Cys Gln Gln Trp Ser Ser Ser Pro Leu Thr
                 85                  90                  95
Phe Gly Ala Gly Thr Lys Val Glu Ile Lys
```

<210> SEQ ID NO 24
<211> LENGTH: 124
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 24

```
Glu Val Gln Leu Glu Glu Ser Gly Gly Gly Leu Val Gln Pro Gly Gly
1               5                   10                  15

Ser Leu Arg Leu Ser Cys Ala Ala Ser Gly Phe Thr Phe Ser Asn Tyr
            20                  25                  30

Ala Met Ser Trp Val Arg Gln Thr Pro Asp Lys Arg Leu Glu Trp Val
        35                  40                  45

Ala Thr Ile Ser Asn Gly Gly Ser Tyr Thr Tyr Tyr Pro Asp Ser Val
    50                  55                  60

Lys Gly Arg Phe Thr Ile Ser Arg Asp Asn Ser Lys Asn Thr Leu Tyr
65                  70                  75                  80

Leu Gln Met Ser Ser Leu Arg Ala Glu Asp Thr Ala Val Tyr Tyr Cys
                85                  90                  95

Ser Arg Pro Ser Glu Arg Ser His Tyr Tyr Ala Thr Ser Gln Phe Ala
            100                 105                 110

Tyr Trp Gly Gln Gly Thr Leu Val Thr Val Ser Ser
        115                 120
```

<210> SEQ ID NO 25
<211> LENGTH: 106
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 25

```
Glu Ile Val Leu Thr Gln Ser Pro Ala Ile Leu Ser Leu Ser Pro Gly
1               5                   10                  15

Glu Arg Ala Thr Leu Ser Cys Ser Ala Ser Ser Ser Val Ser Tyr Met
            20                  25                  30

His Trp Tyr Gln Gln Lys Pro Gly Gln Ala Pro Arg Arg Trp Ile Tyr
        35                  40                  45

Asp Thr Ser Lys Leu Ala Ser Gly Ile Pro Ala Arg Phe Ser Gly Ser
    50                  55                  60

Gly Ser Gly Thr Ser Tyr Thr Leu Thr Ile Ser Ser Leu Glu Ala Glu
65                  70                  75                  80

Asp Phe Ala Thr Tyr Tyr Cys Gln Gln Trp Ser Ser Ser Pro Leu Thr
                85                  90                  95

Phe Gly Ala Gly Thr Lys Val Glu Ile Lys
            100                 105
```

<210> SEQ ID NO 26
<211> LENGTH: 124
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 26

Glu Val Gln Leu Val Glu Ser Gly Gly Gly Val Lys Lys Pro Gly Gly
1               5                   10                  15

Ser Leu Lys Leu Ser Cys Ala Ala Ser Gly Phe Thr Phe Ser Asn Tyr
            20                  25                  30

Ala Met Ser Trp Val Arg Gln Thr Pro Gly Lys Gly Leu Glu Trp Val
        35                  40                  45

Ala Thr Ile Ser Asn Gly Gly Ser Tyr Thr Tyr Tyr Pro Asp Ser Phe
    50                  55                  60

Gln Gly Arg Phe Thr Ile Ser Arg Asp Asn Ala Lys Ser Thr Leu Ser
65                  70                  75                  80

Leu Gln Met Ser Ser Leu Lys Ser Glu Asp Thr Ala Met Tyr Tyr Cys
            85                  90                  95

Ser Arg Pro Ser Glu Arg Ser His Tyr Tyr Ala Thr Ser Gln Phe Ala
            100                 105                 110

Tyr Trp Gly Gln Gly Thr Leu Val Thr Val Ser Ala
        115                 120

<210> SEQ ID NO 27
<211> LENGTH: 124
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 27

Glu Val Gln Leu Val Glu Ser Gly Gly Gly Val Lys Lys Pro Gly Gly
1               5                   10                  15

Ser Leu Lys Leu Ser Cys Ala Ala Ser Gly Phe Thr Phe Ser Asn Tyr
            20                  25                  30

Ala Met Ser Trp Val Arg Gln Thr Pro Gly Lys Gly Leu Glu Trp Val
        35                  40                  45

Ala Thr Ile Ser Asn Gly Gly Ser Tyr Thr Tyr Tyr Pro Asp Ser Phe
    50                  55                  60

Gln Gly Arg Phe Thr Ile Ser Arg Asp Asn Ala Lys Ser Thr Leu Ser
65                  70                  75                  80

Leu Gln Met Ser Ser Leu Lys Ala Glu Asp Thr Ala Met Tyr Tyr Cys
            85                  90                  95

Ser Arg Pro Ser Glu Arg Ser His Tyr Tyr Ala Thr Ser Gln Phe Ala
            100                 105                 110

Tyr Trp Gly Gln Gly Thr Leu Val Thr Val Ser Ser
        115                 120

<210> SEQ ID NO 28
<211> LENGTH: 124
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 28

Glu Val Gln Leu Val Glu Ser Gly Gly Gly Val Lys Lys Pro Gly Gly
1               5                   10                  15

Ser Leu Lys Leu Ser Cys Ala Ala Ser Gly Phe Thr Phe Ser Asn Tyr
            20                  25                  30

Ala Met Ser Trp Val Arg Gln Thr Pro Gly Lys Gly Leu Glu Trp Val
        35                  40                  45

Ala Thr Ile Ser Gln Gly Gly Ser Tyr Thr Tyr Tyr Pro Glu Ser Phe
            50                  55                  60

Gln Gly Arg Phe Thr Ile Ser Arg Asp Gln Ala Lys Ser Thr Leu Ser
65                  70                  75                  80

Leu Gln Met Ser Ser Leu Lys Ser Glu Asp Thr Ala Met Tyr Tyr Cys
                85                  90                  95

Ser Arg Pro Ser Glu Arg Ser His Tyr Tyr Ala Thr Ser Gln Phe Ala
            100                 105                 110

Tyr Trp Gly Gln Gly Thr Leu Val Thr Val Ser Ala
            115                 120

<210> SEQ ID NO 29
<211> LENGTH: 124
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 29

Glu Val Gln Leu Leu Glu Ser Gly Gly Gly Leu Val Gln Pro Gly Gly
1               5                   10                  15

Ser Leu Arg Leu Ser Cys Ala Ala Ser Gly Phe Thr Phe Ser Asn Tyr
            20                  25                  30

Ala Met Ser Trp Val Arg Gln Ala Pro Gly Lys Gly Leu Glu Trp Val
        35                  40                  45

Ala Thr Ile Ser Gln Gly Gly Ser Tyr Thr Tyr Tyr Pro Asp Ser Val
    50                  55                  60

Lys Gly Arg Phe Thr Ile Ser Arg Asp Asn Ser Lys Asn Thr Leu Tyr
65                  70                  75                  80

Leu Gln Met Asn Ser Leu Arg Ala Glu Asp Thr Ala Val Tyr Tyr Cys
                85                  90                  95

Ser Arg Pro Ser Glu Arg Ser His Tyr Tyr Ala Thr Ser Gln Phe Ala
            100                 105                 110

Tyr Trp Gly Gln Gly Thr Leu Val Thr Val Ser Ser
            115                 120

<210> SEQ ID NO 30
<211> LENGTH: 124
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 30

Glu Val Gln Leu Leu Glu Ser Gly Gly Gly Leu Val Gln Pro Gly Gly
1               5                   10                  15

Ser Leu Arg Leu Ser Cys Ala Ser Gly Phe Thr Phe Ser Asn Tyr
            20                  25                  30

Ala Met Ser Trp Val Arg Gln Ala Pro Gly Lys Gly Leu Glu Trp Val
        35                  40                  45

Ala Thr Ile Ser Asn Leu Gly Ser Tyr Thr Tyr Tyr Pro Asp Ser Val
    50                  55                  60

Lys Gly Arg Phe Thr Ile Ser Arg Asp Asn Ser Lys Asn Thr Leu Tyr
65                  70                  75                  80

Leu Gln Met Asn Ser Leu Arg Ala Glu Asp Thr Ala Val Tyr Tyr Cys
                85                  90                  95

```
Ser Arg Pro Ser Glu Arg Ser His Tyr Tyr Ala Thr Ser Gln Phe Ala
            100                 105                 110

Tyr Trp Gly Gln Gly Thr Leu Val Thr Val Ser Ser
        115                 120

<210> SEQ ID NO 31
<211> LENGTH: 124
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 31

Glu Val Gln Leu Leu Glu Ser Gly Gly Gly Leu Val Gln Pro Gly Gly
1               5                   10                  15

Ser Leu Arg Leu Ser Cys Ala Ala Ser Gly Phe Thr Phe Ser Asn Tyr
            20                  25                  30

Ala Met Ser Trp Val Arg Gln Ala Pro Gly Lys Gly Leu Glu Trp Val
        35                  40                  45

Ala Thr Ile Ser Asn Ser Gly Ser Tyr Thr Tyr Tyr Pro Asp Ser Val
    50                  55                  60

Lys Gly Arg Phe Thr Ile Ser Arg Asp Asn Ser Lys Asn Thr Leu Tyr
65                  70                  75                  80

Leu Gln Met Asn Ser Leu Arg Ala Glu Asp Thr Ala Val Tyr Tyr Cys
                85                  90                  95

Ser Arg Pro Ser Glu Arg Ser His Tyr Tyr Ala Thr Ser Gln Phe Ala
            100                 105                 110

Tyr Trp Gly Gln Gly Thr Leu Val Thr Val Ser Ser
        115                 120

<210> SEQ ID NO 32
<211> LENGTH: 124
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 32

Glu Val Gln Leu Leu Glu Ser Gly Gly Gly Leu Val Gln Pro Gly Gly
1               5                   10                  15

Ser Leu Arg Leu Ser Cys Ala Ala Ser Gly Phe Thr Phe Ser Asn Tyr
            20                  25                  30

Ala Met Ser Trp Val Arg Gln Ala Pro Gly Lys Gly Leu Glu Trp Val
        35                  40                  45

Ala Thr Ile Ser Asp Gly Gly Ser Tyr Thr Tyr Tyr Pro Asp Ser Val
    50                  55                  60

Lys Gly Arg Phe Thr Ile Ser Arg Asp Asn Ser Lys Asn Thr Leu Tyr
65                  70                  75                  80

Leu Gln Met Asn Ser Leu Arg Ala Glu Asp Thr Ala Val Tyr Tyr Cys
                85                  90                  95

Ser Arg Pro Ser Glu Arg Ser His Tyr Tyr Ala Thr Ser Gln Phe Ala
            100                 105                 110

Tyr Trp Gly Gln Gly Thr Leu Val Thr Val Ser Ser
        115                 120

<210> SEQ ID NO 33
```

```
<211> LENGTH: 124
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 33

Glu Val Gln Leu Leu Glu Ser Gly Gly Gly Leu Val Gln Pro Gly Gly
1               5                   10                  15

Ser Leu Arg Leu Ser Cys Ala Ala Ser Gly Phe Thr Phe Ser Asn Tyr
            20                  25                  30

Ala Met Ser Trp Val Arg Gln Ala Pro Gly Lys Gly Leu Glu Trp Val
        35                  40                  45

Ala Thr Ile Ser Asn Val Gly Ser Tyr Thr Tyr Tyr Pro Asp Ser Val
    50                  55                  60

Lys Gly Arg Phe Thr Ile Ser Arg Asp Asn Ser Lys Asn Thr Leu Tyr
65                  70                  75                  80

Leu Gln Met Asn Ser Leu Arg Ala Glu Asp Thr Ala Val Tyr Tyr Cys
                85                  90                  95

Ser Arg Pro Ser Glu Arg Ser His Tyr Tyr Ala Thr Ser Gln Phe Ala
            100                 105                 110

Tyr Trp Gly Gln Gly Thr Leu Val Thr Val Ser Ser
        115                 120

<210> SEQ ID NO 34
<211> LENGTH: 106
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 34

Asp Ile Val Leu Thr Gln Ser Pro Gly Ser Leu Ser Ala Ser Val Gly
1               5                   10                  15

Asp Arg Val Thr Met Thr Cys Ser Ala Ser Ser Ser Val Ser Tyr Met
            20                  25                  30

His Trp Tyr Gln Gln Lys Pro Gly Thr Ser Pro Lys Arg Trp Ile Tyr
        35                  40                  45

Asp Thr Ser Lys Leu Ala Ser Gly Val Pro Ala Arg Phe Ser Gly Ser
    50                  55                  60

Gly Ser Gly Thr Ser Tyr Ser Leu Thr Ile Ser Ser Leu Gln Pro Glu
65                  70                  75                  80

Asp Ala Ala Thr Tyr Tyr Cys Gln Gln Trp Ser Ser Ser Pro Leu Thr
                85                  90                  95

Phe Gly Ala Gly Thr Lys Val Glu Leu Lys
            100                 105

<210> SEQ ID NO 35
<211> LENGTH: 106
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 35

Asp Ile Val Leu Thr Gln Ser Pro Ser Ser Leu Ser Ala Ser Val Gly
1               5                   10                  15
```

Asp Arg Val Thr Ile Thr Cys Ser Ala Ser Ser Val Ser Tyr Met
                20                  25                  30

His Trp Tyr Gln Gln Lys Pro Gly Thr Ser Pro Lys Arg Trp Ile Tyr
            35                  40                  45

Asp Thr Ser Lys Leu Ala Ser Gly Val Pro Ala Arg Phe Ser Gly Ser
        50                  55                  60

Gly Ser Gly Thr Ser Tyr Ser Leu Thr Ile Ser Ser Leu Gln Pro Glu
65                  70                  75                  80

Asp Ala Ala Thr Tyr Tyr Cys Gln Gln Trp Ser Ser Ser Pro Leu Thr
                85                  90                  95

Phe Gly Ala Gly Thr Lys Val Glu Ile Lys
            100                 105

<210> SEQ ID NO 36
<211> LENGTH: 106
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 36

Asp Ile Val Leu Thr Gln Ser Pro Ser Ser Leu Ser Ala Ser Val Gly
1               5                   10                  15

Asp Arg Val Thr Ile Thr Cys Ser Ala Ser Ser Val Ser Tyr Met
                20                  25                  30

His Trp Tyr Gln Gln Lys Pro Gly Gln Ser Pro Lys Arg Trp Ile Tyr
            35                  40                  45

Asp Thr Ser Lys Leu Ala Ser Gly Val Pro Ala Arg Phe Ser Gly Ser
        50                  55                  60

Gly Ser Gly Thr Ser Tyr Ser Leu Thr Ile Ser Ser Leu Gln Pro Glu
65                  70                  75                  80

Asp Ala Ala Thr Tyr Tyr Cys Gln Gln Trp Ser Ser Ser Pro Leu Thr
                85                  90                  95

Phe Gly Ala Gly Thr Lys Val Glu Ile Lys
            100                 105

<210> SEQ ID NO 37
<211> LENGTH: 106
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 37

Asp Ile Gln Leu Thr Gln Ser Pro Gly Ser Leu Ser Ala Ser Val Gly
1               5                   10                  15

Asp Arg Val Thr Met Thr Cys Ser Ala Ser Ser Val Ser Tyr Met
                20                  25                  30

His Trp Tyr Gln Gln Lys Pro Gly Thr Ser Pro Lys Arg Trp Ile Tyr
            35                  40                  45

Asp Thr Ser Lys Leu Ala Ser Gly Val Pro Ala Arg Phe Ser Gly Ser
        50                  55                  60

Gly Ser Gly Thr Ser Tyr Ser Leu Thr Ile Ser Ser Leu Gln Pro Glu
65                  70                  75                  80

Asp Ala Ala Thr Tyr Tyr Cys Gln Gln Trp Ser Ser Ser Pro Leu Thr
                85                  90                  95

```
Phe Gly Ala Gly Thr Lys Val Glu Leu Lys
        100                 105
```

<210> SEQ ID NO 38
<211> LENGTH: 123
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 38

```
Glu Val Gln Leu Glu Glu Ser Gly Gly Gly Leu Val Lys Pro Gly Gly
1               5                   10                  15

Ser Leu Lys Leu Ser Cys Ala Ala Ser Gly Phe Thr Phe Thr Ser Tyr
            20                  25                  30

Ala Met Ser Trp Val Arg Gln Thr Pro Glu Lys Arg Leu Glu Trp Val
        35                  40                  45

Ala Thr Ile Ser His Gly Gly Thr Tyr Thr Tyr Pro Asp Ser Val
    50                  55                  60

Lys Gly Arg Phe Thr Ile Ser Arg Asp Asn Ala Lys Asn Thr Leu Tyr
65                  70                  75                  80

Leu Gln Met Ser Ser Leu Arg Ser Glu Asp Thr Ala Met Tyr Tyr Cys
                85                  90                  95

Ala Arg His Pro Ile Tyr Ser Gly Asn Tyr Gln Gly Tyr Phe Asp Tyr
            100                 105                 110

Trp Gly Gln Gly Thr Thr Leu Thr Val Ser Ser
        115                 120
```

<210> SEQ ID NO 39
<211> LENGTH: 106
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 39

```
Asp Ile Val Leu Thr Gln Ser Pro Ala Ile Met Ser Ala Ser Leu Gly
1               5                   10                  15

Glu Lys Val Thr Met Ser Cys Arg Ala Ser Ser Gly Val Asn Tyr Ile
            20                  25                  30

Tyr Trp Tyr Gln Gln Lys Ser Asp Ala Ser Pro Lys Leu Trp Ile Tyr
        35                  40                  45

Phe Thr Ser Asn Leu Ala Pro Gly Val Pro Ala Arg Phe Ser Gly Ser
    50                  55                  60

Gly Ser Gly Asn Ser Tyr Ser Leu Thr Ile Ser Ser Met Glu Gly Glu
65                  70                  75                  80

Asp Ala Ala Thr Tyr Tyr Cys Gln Gln Phe Thr Ser Ser Pro Tyr Thr
                85                  90                  95

Phe Gly Gly Gly Thr Lys Leu Glu Ile Lys
        100                 105
```

<210> SEQ ID NO 40
<211> LENGTH: 123
<212> TYPE: PRT
<213> ORGANISM: Artificial Sequence
<220> FEATURE:
<223> OTHER INFORMATION: Description of Artificial Sequence: Synthetic
      polypeptide

```
<400> SEQUENCE: 40

Glu Val Gln Leu Leu Glu Ser Gly Gly Gly Leu Val Gln Pro Gly Gly
1               5                   10                  15

Ser Leu Arg Leu Ser Cys Ala Ala Ser Gly Phe Thr Phe Thr Ser Tyr
            20                  25                  30

Ala Met Ser Trp Val Arg Gln Ala Pro Gly Lys Gly Leu Glu Trp Val
        35                  40                  45

Ala Val Ile Ser His Gly Gly Thr Tyr Thr Tyr Ala Asp Ser Val
    50                  55                  60

Lys Gly Arg Phe Thr Ile Ser Arg Asp Asn Ala Lys Asn Thr Leu Tyr
65                  70                  75                  80

Leu Gln Met Asn Ser Leu Arg Ala Glu Asp Thr Ala Val Tyr Tyr Cys
                85                  90                  95

Ala Arg His Pro Ile Tyr Ser Gly Asn Tyr Gln Gly Tyr Phe Asp Tyr
            100                 105                 110

Trp Gly Gln Gly Thr Leu Val Thr Val Ser Ser
        115                 120

<210> SEQ ID NO 41
<211> LENGTH: 106
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 41

Asp Ile Gln Leu Thr Gln Ser Pro Ser Phe Leu Ser Ala Ser Val Gly
1               5                   10                  15

Asp Arg Val Thr Ile Thr Cys Arg Ala Ser Ser Gly Val Asn Tyr Leu
            20                  25                  30

Ala Trp Tyr Gln Gln Lys Pro Gly Lys Ala Pro Lys Leu Trp Ile Tyr
        35                  40                  45

Phe Thr Ser Thr Leu Gln Ser Gly Val Pro Ser Arg Phe Ser Gly Ser
    50                  55                  60

Gly Ser Gly Asn Glu Tyr Thr Leu Thr Ile Ser Ser Leu Gln Pro Glu
65                  70                  75                  80

Asp Phe Ala Thr Tyr Tyr Cys Gln Gln Phe Thr Ser Ser Pro Tyr Thr
                85                  90                  95

Phe Gly Gln Gly Thr Lys Leu Glu Ile Lys
            100                 105

<210> SEQ ID NO 42
<211> LENGTH: 123
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 42

Glu Val Gln Leu Leu Glu Ser Gly Gly Gly Leu Val Gln Pro Gly Gly
1               5                   10                  15

Ser Leu Arg Leu Ser Cys Ala Ala Ser Gly Phe Thr Phe Thr Ser Tyr
            20                  25                  30

Ala Met Ser Trp Val Arg Gln Ala Pro Gly Lys Gly Leu Glu Trp Val
        35                  40                  45

Ala Thr Ile Ser His Gly Gly Thr Tyr Thr Tyr Tyr Pro Asp Ser Val
```

```
            50                  55                  60
Lys Gly Arg Phe Thr Ile Ser Arg Asp Asn Ala Lys Asn Thr Leu Tyr
 65                  70                  75                  80

Leu Gln Met Asn Ser Leu Arg Ala Glu Asp Thr Ala Met Tyr Tyr Cys
                 85                  90                  95

Ala Arg His Pro Ile Tyr Ser Gly Asn Tyr Gln Gly Tyr Phe Asp Tyr
                100                 105                 110

Trp Gly Gln Gly Thr Leu Val Thr Val Ser Ser
                115                 120

<210> SEQ ID NO 43
<211> LENGTH: 106
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 43

Asp Ile Gln Leu Thr Gln Ser Pro Ser Phe Leu Ser Ala Ser Val Gly
  1               5                  10                  15

Asp Arg Val Thr Ile Thr Cys Arg Ala Ser Ser Gly Val Asn Tyr Ile
                 20                  25                  30

Tyr Trp Tyr Gln Gln Lys Pro Gly Lys Ala Pro Lys Leu Trp Ile Tyr
                 35                  40                  45

Phe Thr Ser Asn Leu Ala Pro Gly Val Pro Ser Arg Phe Ser Gly Ser
             50                  55                  60

Gly Ser Gly Asn Glu Tyr Thr Leu Thr Ile Ser Ser Leu Gln Pro Glu
 65                  70                  75                  80

Asp Phe Ala Thr Tyr Tyr Cys Gln Gln Phe Thr Ser Ser Pro Tyr Thr
                 85                  90                  95

Phe Gly Gly Gly Thr Lys Leu Glu Ile Lys
                100                 105

<210> SEQ ID NO 44
<211> LENGTH: 123
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 44

Glu Val Gln Leu Glu Glu Ser Gly Gly Gly Leu Val Gln Pro Gly Gly
  1               5                  10                  15

Ser Leu Arg Leu Ser Cys Ala Ala Ser Gly Phe Thr Phe Thr Ser Tyr
                 20                  25                  30

Ala Met Ser Trp Val Arg Gln Thr Pro Glu Lys Arg Leu Glu Trp Val
                 35                  40                  45

Ala Thr Ile Ser His Gly Gly Thr Tyr Thr Tyr Tyr Pro Asp Ser Val
             50                  55                  60

Lys Gly Arg Phe Thr Ile Ser Arg Asp Asn Ala Lys Asn Thr Leu Tyr
 65                  70                  75                  80

Leu Gln Met Asn Ser Leu Arg Ala Glu Asp Thr Ala Met Tyr Tyr Cys
                 85                  90                  95

Ala Arg His Pro Ile Tyr Ser Gly Asn Tyr Gln Gly Tyr Phe Asp Tyr
                100                 105                 110

Trp Gly Gln Gly Thr Thr Val Thr Val Ser Ser
```

<210> SEQ ID NO 45
<211> LENGTH: 106
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 45

Asp Ile Gln Leu Thr Gln Ser Pro Ser Phe Leu Ser Ala Ser Val Gly
1               5                   10                  15

Asp Arg Val Thr Ile Thr Cys Arg Ala Ser Ser Gly Val Asn Tyr Ile
            20                  25                  30

Tyr Trp Tyr Gln Gln Lys Pro Asp Ala Ala Pro Lys Leu Trp Ile Tyr
        35                  40                  45

Phe Thr Ser Asn Leu Ala Pro Gly Val Pro Ser Arg Phe Ser Gly Ser
    50                  55                  60

Gly Ser Gly Asn Ser Tyr Thr Leu Thr Ile Ser Ser Leu Gln Pro Glu
65                  70                  75                  80

Asp Phe Ala Thr Tyr Tyr Cys Gln Gln Phe Thr Ser Ser Pro Tyr Thr
                85                  90                  95

Phe Gly Gly Gly Thr Lys Leu Glu Ile Lys
            100                 105

<210> SEQ ID NO 46
<211> LENGTH: 123
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 46

Glu Val Gln Leu Leu Glu Ser Gly Gly Gly Leu Val Gln Pro Gly Gly
1               5                   10                  15

Ser Leu Arg Leu Ser Cys Ala Ala Ser Gly Phe Thr Phe Thr Ser Tyr
            20                  25                  30

Ala Met Ser Trp Val Arg Gln Ala Pro Gly Lys Gly Leu Glu Trp Val
        35                  40                  45

Ala Val Ile Ser His Gly Gly Thr Tyr Thr Tyr Tyr Pro Asp Ser Val
    50                  55                  60

Lys Gly Arg Phe Thr Ile Ser Arg Asp Asn Ala Lys Asn Thr Leu Tyr
65                  70                  75                  80

Leu Gln Met Asn Ser Leu Arg Ala Glu Asp Thr Ala Met Tyr Tyr Cys
                85                  90                  95

Ala Arg His Pro Ile Tyr Ser Gly Asn Tyr Gln Gly Tyr Phe Asp Tyr
            100                 105                 110

Trp Gly Gln Gly Thr Leu Val Thr Val Ser Ser
        115                 120

<210> SEQ ID NO 47
<211> LENGTH: 123
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 47

```
Glu Val Gln Leu Leu Glu Ser Gly Gly Gly Leu Val Gln Pro Gly Gly
1               5                   10                  15

Ser Leu Arg Leu Ser Cys Ala Ala Ser Gly Phe Thr Phe Thr Ser Tyr
            20                  25                  30

Ala Met Ser Trp Val Arg Gln Ala Pro Gly Lys Gly Leu Glu Trp Val
        35                  40                  45

Ala Thr Ile Ser His Gly Gly Thr Tyr Thr Tyr Tyr Ala Asp Ser Val
    50                  55                  60

Lys Gly Arg Phe Thr Ile Ser Arg Asp Asn Ala Lys Asn Thr Leu Tyr
65                  70                  75                  80

Leu Gln Met Asn Ser Leu Arg Ala Glu Asp Thr Ala Met Tyr Tyr Cys
                85                  90                  95

Ala Arg His Pro Ile Tyr Ser Gly Asn Tyr Gln Gly Tyr Phe Asp Tyr
            100                 105                 110

Trp Gly Gln Gly Thr Leu Val Thr Val Ser Ser
        115                 120
```

<210> SEQ ID NO 48
<211> LENGTH: 123
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 48

```
Glu Val Gln Leu Leu Glu Ser Gly Gly Gly Leu Val Gln Pro Gly Gly
1               5                   10                  15

Ser Leu Arg Leu Ser Cys Ala Ala Ser Gly Phe Thr Phe Thr Ser Tyr
            20                  25                  30

Ala Met Ser Trp Val Arg Gln Ala Pro Gly Lys Gly Leu Glu Trp Val
        35                  40                  45

Ala Thr Ile Ser His Gly Gly Thr Tyr Thr Tyr Tyr Pro Asp Ser Val
    50                  55                  60

Lys Gly Arg Phe Thr Ile Ser Arg Asp Asn Ala Lys Asn Thr Leu Tyr
65                  70                  75                  80

Leu Gln Met Asn Ser Leu Arg Ala Glu Asp Thr Ala Val Tyr Tyr Cys
                85                  90                  95

Ala Arg His Pro Ile Tyr Ser Gly Asn Tyr Gln Gly Tyr Phe Asp Tyr
            100                 105                 110

Trp Gly Gln Gly Thr Leu Val Thr Val Ser Ser
        115                 120
```

<210> SEQ ID NO 49
<211> LENGTH: 106
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 49

```
Asp Ile Gln Leu Thr Gln Ser Pro Ser Phe Leu Ser Ala Ser Val Gly
1               5                   10                  15

Asp Arg Val Thr Ile Thr Cys Arg Ala Ser Ser Gly Val Asn Tyr Leu
            20                  25                  30

Tyr Trp Tyr Gln Gln Lys Pro Gly Lys Ala Pro Lys Leu Trp Ile Tyr
        35                  40                  45
```

```
Phe Thr Ser Asn Leu Ala Pro Gly Val Pro Ser Arg Phe Ser Gly Ser
            50                  55                  60

Gly Ser Gly Asn Glu Tyr Thr Leu Thr Ile Ser Ser Leu Gln Pro Glu
 65                  70                  75                  80

Asp Phe Ala Thr Tyr Tyr Cys Gln Gln Phe Thr Ser Ser Pro Tyr Thr
                 85                  90                  95

Phe Gly Gly Gly Thr Lys Leu Glu Ile Lys
            100                 105

<210> SEQ ID NO 50
<211> LENGTH: 106
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 50

Asp Ile Gln Leu Thr Gln Ser Pro Ser Phe Leu Ser Ala Ser Val Gly
  1               5                  10                  15

Asp Arg Val Thr Ile Thr Cys Arg Ala Ser Ser Gly Val Asn Tyr Ile
                 20                  25                  30

Ala Trp Tyr Gln Gln Lys Pro Gly Lys Ala Pro Lys Leu Trp Ile Tyr
             35                  40                  45

Phe Thr Ser Asn Leu Ala Pro Gly Val Pro Ser Arg Phe Ser Gly Ser
 50                  55                  60

Gly Ser Gly Asn Glu Tyr Thr Leu Thr Ile Ser Ser Leu Gln Pro Glu
 65                  70                  75                  80

Asp Phe Ala Thr Tyr Tyr Cys Gln Gln Phe Thr Ser Ser Pro Tyr Thr
                 85                  90                  95

Phe Gly Gly Gly Thr Lys Leu Glu Ile Lys
            100                 105

<210> SEQ ID NO 51
<211> LENGTH: 106
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 51

Asp Ile Gln Leu Thr Gln Ser Pro Ser Phe Leu Ser Ala Ser Val Gly
  1               5                  10                  15

Asp Arg Val Thr Ile Thr Cys Arg Ala Ser Ser Gly Val Asn Tyr Ile
                 20                  25                  30

Tyr Trp Tyr Gln Gln Lys Pro Gly Lys Ala Pro Lys Leu Trp Ile Tyr
             35                  40                  45

Phe Thr Ser Thr Leu Ala Pro Gly Val Pro Ser Arg Phe Ser Gly Ser
 50                  55                  60

Gly Ser Gly Asn Glu Tyr Thr Leu Thr Ile Ser Ser Leu Gln Pro Glu
 65                  70                  75                  80

Asp Phe Ala Thr Tyr Tyr Cys Gln Gln Phe Thr Ser Ser Pro Tyr Thr
                 85                  90                  95

Phe Gly Gly Gly Thr Lys Leu Glu Ile Lys
            100                 105

<210> SEQ ID NO 52
```

```
<211> LENGTH: 106
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 52

Asp Ile Gln Leu Thr Gln Ser Pro Ser Phe Leu Ser Ala Ser Val Gly
1               5                   10                  15

Asp Arg Val Thr Ile Thr Cys Arg Ala Ser Ser Gly Val Asn Tyr Ile
            20                  25                  30

Tyr Trp Tyr Gln Gln Lys Pro Gly Lys Ala Pro Lys Leu Trp Ile Tyr
        35                  40                  45

Phe Thr Ser Asn Leu Gln Pro Gly Val Pro Ser Arg Phe Ser Gly Ser
    50                  55                  60

Gly Ser Gly Asn Glu Tyr Thr Leu Thr Ile Ser Ser Leu Gln Pro Glu
65                  70                  75                  80

Asp Phe Ala Thr Tyr Tyr Cys Gln Gln Phe Thr Ser Ser Pro Tyr Thr
                85                  90                  95

Phe Gly Gly Gly Thr Lys Leu Glu Ile Lys
                100                 105

<210> SEQ ID NO 53
<211> LENGTH: 106
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 53

Asp Ile Gln Leu Thr Gln Ser Pro Ser Phe Leu Ser Ala Ser Val Gly
1               5                   10                  15

Asp Arg Val Thr Ile Thr Cys Arg Ala Ser Ser Gly Val Asn Tyr Ile
            20                  25                  30

Tyr Trp Tyr Gln Gln Lys Pro Gly Lys Ala Pro Lys Leu Trp Ile Tyr
        35                  40                  45

Phe Thr Ser Asn Leu Ala Ser Gly Val Pro Ser Arg Phe Ser Gly Ser
    50                  55                  60

Gly Ser Gly Asn Glu Tyr Thr Leu Thr Ile Ser Ser Leu Gln Pro Glu
65                  70                  75                  80

Asp Phe Ala Thr Tyr Tyr Cys Gln Gln Phe Thr Ser Ser Pro Tyr Thr
                85                  90                  95

Phe Gly Gly Gly Thr Lys Leu Glu Ile Lys
                100                 105

<210> SEQ ID NO 54
<211> LENGTH: 106
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 54

Asp Ile Gln Leu Thr Gln Ser Pro Ser Phe Leu Ser Ala Ser Val Gly
1               5                   10                  15

Asp Arg Val Thr Ile Thr Cys Arg Ala Ser Ser Gly Val Asn Tyr Ile
            20                  25                  30
```

```
Tyr Trp Tyr Gln Gln Lys Pro Gly Lys Ala Pro Lys Leu Trp Ile Tyr
            35                  40                  45

Phe Thr Ser Asn Leu Ala Pro Gly Val Pro Ser Arg Phe Ser Gly Ser
 50                  55                  60

Gly Ser Gly Asn Glu Tyr Thr Leu Thr Ile Ser Ser Leu Gln Pro Glu
 65                  70                  75                  80

Asp Phe Ala Thr Tyr Tyr Cys Gln Gln Phe Thr Ser Ser Pro Tyr Thr
                 85                  90                  95

Phe Gly Gln Gly Thr Lys Leu Glu Ile Lys
            100                 105

<210> SEQ ID NO 55
<211> LENGTH: 118
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 55

Glu Val Lys Leu Glu Glu Ser Gly Pro Glu Val Val Arg Pro Gly Val
 1               5                  10                  15

Ser Val Lys Ile Ser Cys Lys Gly Ser Gly Tyr Thr Phe Thr Asp Tyr
             20                  25                  30

Ala Met His Trp Val Lys Gln Ser His Ala Lys Ser Leu Glu Trp Ile
         35                  40                  45

Gly Val Ile Ser Thr Tyr Asn Gly Asn Thr Lys Tyr Asn Gln Lys Phe
 50                  55                  60

Lys Gly Lys Ala Thr Met Thr Val Asp Lys Ser Ser Ser Thr Ala Tyr
 65                  70                  75                  80

Met Glu Leu Ala Arg Leu Thr Ser Glu Asp Ser Ala Ile Tyr Tyr Cys
                 85                  90                  95

Ala Arg Phe Leu Ser Leu Arg Tyr Phe Asp Val Trp Gly Ala Gly Thr
            100                 105                 110

Thr Val Thr Val Ser Ser
        115

<210> SEQ ID NO 56
<211> LENGTH: 106
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 56

Asp Ile Val Leu Thr Gln Ser Pro Ala Ile Leu Ser Ala Pro Pro Gly
 1               5                  10                  15

Glu Lys Val Thr Met Thr Cys Arg Ala Ser Ser Ser Val Ile Tyr Met
             20                  25                  30

Tyr Trp Tyr Gln Gln Lys Pro Gly Ser Ser Pro Lys Pro Trp Ile Tyr
            35                  40                  45

Ala Thr Ser Lys Leu Ala Ser Gly Val Pro Val Arg Phe Ser Gly Ser
 50                  55                  60

Gly Ser Gly Thr Ser Tyr Ser Leu Thr Ile Ser Arg Val Glu Ala Glu
 65                  70                  75                  80

Asp Val Ala Thr Tyr Tyr Cys Gln Gln Trp Ser Ser Glu Pro Leu Thr
                 85                  90                  95
```

```
Phe Gly Ala Gly Thr Lys Leu Glu Leu Lys
            100                 105
```

<210> SEQ ID NO 57
<211> LENGTH: 118
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 57

```
Gln Val Lys Leu Val Gln Ser Gly Ala Glu Val Lys Lys Pro Gly Ala
1               5                   10                  15

Ser Val Lys Val Ser Cys Lys Ala Ser Gly Tyr Thr Phe Thr Asp Tyr
            20                  25                  30

Ala Met His Trp Val Arg Gln Ala Pro Gly Gln Arg Leu Glu Trp Ile
        35                  40                  45

Gly Trp Ile Ser Thr Tyr Asn Gly Asn Thr Lys Tyr Ser Gln Lys Phe
    50                  55                  60

Gln Gly Arg Ala Thr Met Thr Val Asp Lys Ser Ala Ser Thr Ala Tyr
65                  70                  75                  80

Met Glu Leu Ser Ser Leu Arg Ser Glu Asp Thr Ala Val Tyr Tyr Cys
                85                  90                  95

Ala Arg Phe Leu Ser Leu Arg Tyr Phe Asp Val Trp Gly Lys Gly Thr
            100                 105                 110

Thr Val Thr Val Ser Ser
        115
```

<210> SEQ ID NO 58
<211> LENGTH: 106
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 58

```
Asp Ile Gln Leu Thr Gln Ser Pro Ser Phe Leu Ser Ala Ser Val Gly
1               5                   10                  15

Asp Arg Val Thr Ile Thr Cys Arg Ala Ser Ser Ser Val Ile Tyr Leu
            20                  25                  30

Ala Trp Tyr Gln Gln Lys Pro Gly Lys Ala Pro Lys Pro Trp Ile Tyr
        35                  40                  45

Ala Thr Ser Thr Leu Gln Ser Gly Val Pro Ser Arg Phe Ser Gly Ser
    50                  55                  60

Gly Ser Gly Thr Glu Tyr Thr Leu Thr Ile Ser Ser Leu Gln Pro Glu
65                  70                  75                  80

Asp Phe Ala Thr Tyr Tyr Cys Gln Gln Trp Ser Ser Glu Pro Leu Thr
                85                  90                  95

Phe Gly Gly Gly Thr Lys Val Glu Ile Lys
            100                 105
```

<210> SEQ ID NO 59
<211> LENGTH: 118
<212> TYPE: PRT
<213> ORGANISM: Artificial Sequence
<220> FEATURE:
<223> OTHER INFORMATION: Description of Artificial Sequence: Synthetic
      polypeptide -continued

<400> SEQUENCE: 59

Gln Val Lys Leu Val Gln Ser Gly Ala Glu Val Lys Pro Gly Ala
1               5                   10                  15

Ser Val Lys Val Ser Cys Lys Gly Ser Gly Tyr Thr Phe Thr Asp Tyr
            20                  25                  30

Ala Met His Trp Val Arg Gln Ala Pro Gly Gln Arg Leu Glu Trp Ile
        35                  40                  45

Gly Val Ile Ser Thr Tyr Asn Gly Asn Thr Lys Tyr Asn Gln Lys Phe
    50                  55                  60

Gln Gly Arg Ala Thr Met Thr Val Asp Lys Ser Ala Ser Thr Ala Tyr
65                  70                  75                  80

Met Glu Leu Ser Ser Leu Arg Ser Glu Asp Thr Ala Ile Tyr Tyr Cys
                85                  90                  95

Ala Arg Phe Leu Ser Leu Arg Tyr Phe Asp Val Trp Gly Ala Gly Thr
            100                 105                 110

Thr Val Thr Val Ser Ser
            115

<210> SEQ ID NO 60
<211> LENGTH: 106
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 60

Asp Ile Gln Leu Thr Gln Ser Pro Ser Phe Leu Ser Ala Ser Val Gly
1               5                   10                  15

Asp Arg Val Thr Ile Thr Cys Arg Ala Ser Ser Ser Val Ile Tyr Met
            20                  25                  30

Tyr Trp Tyr Gln Gln Lys Pro Gly Lys Ala Pro Lys Pro Trp Ile Tyr
        35                  40                  45

Ala Thr Ser Lys Leu Ala Ser Gly Val Pro Ser Arg Phe Ser Gly Ser
    50                  55                  60

Gly Ser Gly Thr Glu Tyr Thr Leu Thr Ile Ser Ser Leu Gln Pro Glu
65                  70                  75                  80

Asp Phe Ala Thr Tyr Tyr Cys Gln Gln Trp Ser Ser Glu Pro Leu Thr
                85                  90                  95

Phe Gly Ala Gly Thr Lys Val Glu Ile Lys
            100                 105

<210> SEQ ID NO 61
<211> LENGTH: 118
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 61

Gln Val Lys Leu Val Gln Ser Gly Pro Glu Val Lys Val Pro Gly Ala
1               5                   10                  15

Ser Val Lys Val Ser Cys Lys Gly Ser Gly Tyr Thr Phe Thr Asp Tyr
            20                  25                  30

Ala Met His Trp Val Arg Gln Ala Pro Gly Gln Ser Leu Glu Trp Ile
        35                  40                  45

Gly Val Ile Ser Thr Tyr Asn Gly Asn Thr Lys Tyr Asn Gln Lys Phe

```
                50                  55                  60
Gln Gly Arg Ala Thr Met Thr Val Asp Lys Ser Ala Ser Thr Ala Tyr
 65                  70                  75                  80

Met Glu Leu Ser Arg Leu Arg Ser Glu Asp Thr Ala Ile Tyr Tyr Cys
                 85                  90                  95

Ala Arg Phe Leu Ser Leu Arg Tyr Phe Asp Val Trp Gly Ala Gly Thr
                100                 105                 110

Thr Val Thr Val Ser Ser
            115

<210> SEQ ID NO 62
<211> LENGTH: 106
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 62

Asp Ile Gln Leu Thr Gln Ser Pro Ser Phe Leu Ser Ala Ser Pro Gly
  1               5                  10                  15

Asp Arg Val Thr Ile Thr Cys Arg Ala Ser Ser Ser Val Ile Tyr Met
                 20                  25                  30

Tyr Trp Tyr Gln Gln Lys Pro Gly Ser Ala Pro Lys Pro Trp Ile Tyr
             35                  40                  45

Ala Thr Ser Lys Leu Ala Ser Gly Val Pro Val Arg Phe Ser Gly Ser
         50                  55                  60

Gly Ser Gly Thr Ser Tyr Thr Leu Thr Ile Ser Arg Leu Gln Ala Glu
 65                  70                  75                  80

Asp Phe Ala Thr Tyr Tyr Cys Gln Gln Trp Ser Ser Glu Pro Leu Thr
                 85                  90                  95

Phe Gly Ala Gly Thr Lys Val Glu Ile Lys
                100                 105

<210> SEQ ID NO 63
<211> LENGTH: 123
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 63

Glu Val Gln Leu Leu Glu Ser Gly Gly Gly Leu Val Gln Pro Gly Gly
  1               5                  10                  15

Ser Leu Lys Leu Ser Cys Ala Ala Ser Gly Phe Thr Phe Thr Ser Tyr
                 20                  25                  30

Ala Met Ser Trp Val Arg Gln Thr Pro Gly Lys Arg Leu Glu Trp Val
             35                  40                  45

Ala Thr Ile Ser His Gly Gly Thr Tyr Thr Tyr Tyr Pro Asp Ser Val
         50                  55                  60

Lys Gly Arg Phe Thr Ile Ser Arg Asp Asn Ser Lys Asn Thr Leu Tyr
 65                  70                  75                  80

Leu Gln Met Ser Ser Leu Arg Ser Glu Asp Thr Ala Met Tyr Tyr Cys
                 85                  90                  95

Ala Arg His Pro Ile Tyr Ser Gly Asn Tyr Gln Gly Tyr Phe Asp Tyr
                100                 105                 110

Trp Gly Gln Gly Thr Thr Leu Thr Val Ser Ser
```

115                 120

<210> SEQ ID NO 64
<211> LENGTH: 123
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 64

Glu Val Gln Leu Leu Glu Ser Gly Gly Gly Leu Val Gln Pro Gly Gly
1               5                   10                  15

Ser Leu Lys Leu Ser Cys Ala Ala Ser Gly Phe Thr Phe Thr Ser Tyr
            20                  25                  30

Ala Met Ser Trp Val Arg Gln Ala Pro Gly Lys Gly Leu Glu Trp Val
        35                  40                  45

Ala Thr Ile Ser His Gly Gly Thr Tyr Thr Tyr Tyr Pro Asp Ser Val
    50                  55                  60

Lys Gly Arg Phe Thr Ile Ser Arg Asp Asn Ser Lys Asn Thr Leu Tyr
65                  70                  75                  80

Leu Gln Met Ser Ser Leu Arg Ala Glu Asp Thr Ala Val Tyr Tyr Cys
                85                  90                  95

Ala Arg His Pro Ile Tyr Ser Gly Asn Tyr Gln Gly Tyr Phe Asp Tyr
            100                 105                 110

Trp Gly Gln Gly Thr Leu Val Thr Val Ser Ser
        115                 120

<210> SEQ ID NO 65
<211> LENGTH: 123
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 65

Glu Val Gln Leu Leu Glu Ser Gly Gly Gly Leu Val Gln Pro Gly Gly
1               5                   10                  15

Ser Leu Lys Leu Ser Cys Ala Ala Ser Gly Phe Thr Phe Thr Ser Tyr
            20                  25                  30

Ala Met Ser Trp Val Arg Gln Thr Pro Gly Lys Arg Leu Glu Trp Val
        35                  40                  45

Ala Thr Ile Ser His Gly Gly Thr Tyr Thr Tyr Tyr Pro Glu Ser Val
    50                  55                  60

Lys Gly Arg Phe Thr Ile Ser Arg Asp Gln Ser Lys Asn Thr Leu Tyr
65                  70                  75                  80

Leu Gln Met Ser Ser Leu Arg Ser Glu Asp Thr Ala Val Tyr Tyr Cys
                85                  90                  95

Ala Arg His Pro Ile Tyr Ser Gly Asn Tyr Gln Gly Tyr Phe Asp Tyr
            100                 105                 110

Trp Gly Gln Gly Thr Thr Leu Thr Val Ser Ser
        115                 120

<210> SEQ ID NO 66
<211> LENGTH: 123
<212> TYPE: PRT
<213> ORGANISM: Artificial Sequence
<220> FEATURE:
<223> OTHER INFORMATION: Description of Artificial Sequence: Synthetic polypeptide

<400> SEQUENCE: 66

Glu Val Gln Leu Leu Glu Ser Gly Gly Gly Leu Val Gln Pro Gly Gly
1               5                   10                  15

Ser Leu Lys Leu Ser Cys Ala Ala Ser Gly Phe Thr Phe Thr Ser Tyr
            20                  25                  30

Ala Met Ser Trp Val Arg Gln Ala Pro Gly Lys Gly Leu Glu Trp Val
        35                  40                  45

Ala Thr Ile Ser His Gly Gly Thr Tyr Thr Tyr Tyr Pro Glu Ser Val
    50                  55                  60

Lys Gly Arg Phe Thr Ile Ser Arg Asp Gln Ser Lys Asn Thr Leu Tyr
65                  70                  75                  80

Leu Gln Met Ser Ser Leu Arg Ala Glu Asp Thr Ala Val Tyr Tyr Cys
                85                  90                  95

Ala Arg His Pro Ile Tyr Ser Gly Asn Tyr Gln Gly Tyr Phe Asp Tyr
            100                 105                 110

Trp Gly Gln Gly Thr Leu Val Thr Val Ser Ser
        115                 120

<210> SEQ ID NO 67
<211> LENGTH: 106
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 67

Asp Ile Gln Leu Thr Gln Ser Pro Ala Ile Met Ser Ala Ser Val Gly
1               5                   10                  15

Asp Arg Val Thr Met Ser Cys Arg Ala Ser Ser Gly Val Asn Tyr Ile
            20                  25                  30

Tyr Trp Tyr Gln Gln Lys Pro Gly Ala Ser Pro Lys Leu Trp Ile Tyr
        35                  40                  45

Phe Thr Ser Asn Leu Ala Pro Gly Val Pro Ala Arg Phe Ser Gly Ser
    50                  55                  60

Gly Ser Gly Asn Ser Tyr Ser Leu Thr Ile Ser Ser Met Gln Gly Glu
65                  70                  75                  80

Asp Ala Ala Thr Tyr Tyr Cys Gln Gln Phe Thr Ser Ser Pro Tyr Thr
                85                  90                  95

Phe Gly Gly Gly Thr Lys Leu Glu Ile Lys
            100                 105

<210> SEQ ID NO 68
<211> LENGTH: 106
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 68

Asp Ile Gln Leu Thr Gln Ser Pro Ala Ile Leu Ser Ala Ser Val Gly
1               5                   10                  15

Asp Arg Val Thr Ile Ser Cys Arg Ala Ser Ser Gly Val Asn Tyr Ile
            20                  25                  30

Tyr Trp Tyr Gln Gln Lys Pro Gly Gln Ser Pro Lys Leu Trp Ile Tyr
        35                  40                  45

```
Phe Thr Ser Asn Leu Ala Pro Gly Val Pro Ala Arg Phe Ser Gly Ser
         50                  55                  60

Gly Ser Gly Asn Ser Tyr Ser Leu Thr Ile Ser Ser Met Gln Gly Glu
 65                  70                  75                  80

Asp Ala Ala Thr Tyr Tyr Cys Gln Gln Phe Thr Ser Ser Pro Tyr Thr
                 85                  90                  95

Phe Gly Gly Gly Thr Lys Leu Glu Ile Lys
             100                 105

<210> SEQ ID NO 69
<211> LENGTH: 106
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 69

Asp Ile Gln Leu Thr Gln Ser Pro Ala Ile Leu Ser Ala Ser Val Gly
 1               5                  10                  15

Asp Arg Val Thr Met Ser Cys Arg Ala Ser Ser Gly Val Asn Tyr Ile
             20                  25                  30

Tyr Trp Tyr Gln Gln Lys Pro Gly Ala Ser Pro Lys Leu Trp Ile Tyr
         35                  40                  45

Phe Thr Ser Asn Leu Ala Pro Gly Val Pro Ala Arg Phe Ser Gly Ser
         50                  55                  60

Gly Ser Gly Asn Ser Tyr Ser Leu Thr Ile Ser Ser Met Gln Gly Glu
 65                  70                  75                  80

Asp Ala Ala Thr Tyr Tyr Cys Gln Gln Phe Thr Ser Ser Pro Tyr Thr
                 85                  90                  95

Phe Gly Gly Gly Thr Lys Leu Glu Ile Lys
             100                 105

<210> SEQ ID NO 70
<211> LENGTH: 106
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 70

Asp Ile Gln Leu Thr Gln Ser Pro Ala Ile Leu Ser Ala Ser Val Gly
 1               5                  10                  15

Asp Arg Val Thr Ile Ser Cys Arg Ala Ser Ser Gly Val Asn Tyr Ile
             20                  25                  30

Tyr Trp Tyr Gln Gln Lys Pro Gly Gln Ser Pro Lys Leu Trp Ile Tyr
         35                  40                  45

Phe Thr Ser Asn Leu Ala Pro Gly Val Pro Ala Arg Phe Ser Gly Ser
         50                  55                  60

Gly Ser Gly Asn Ser Tyr Ser Leu Thr Ile Ser Ser Met Gln Gly Glu
 65                  70                  75                  80

Asp Ala Ala Thr Tyr Tyr Cys Gln Gln Phe Thr Ser Ser Pro Tyr Thr
                 85                  90                  95

Phe Gly Gly Gly Thr Lys Leu Glu Ile Lys
             100                 105

<210> SEQ ID NO 71
```

```
<211> LENGTH: 10
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 71

Ser Asp His Gln Val Leu Asn Asp Ala Glu
1               5                   10

<210> SEQ ID NO 72
<211> LENGTH: 8
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 72

Ser Asp His Gln Val Leu Asn Asp
1               5

<210> SEQ ID NO 73
<211> LENGTH: 7
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 73

Asp His Gln Val Leu Asn Asp
1               5

<210> SEQ ID NO 74
<211> LENGTH: 6
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 74

Val Leu Asn Asp Ala Glu
1               5

<210> SEQ ID NO 75
<211> LENGTH: 4
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 75

Val Leu Asn Asp
1

<210> SEQ ID NO 76
<211> LENGTH: 10
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (1)..(1)
```

<223> OTHER INFORMATION: Any amino acid
<220> FEATURE:
<221> NAME/KEY: MOD_RES
<222> LOCATION: (3)..(4)
<223> OTHER INFORMATION: Any amino acid
<220> FEATURE:
<221> NAME/KEY: MOD_RES
<222> LOCATION: (6)..(6)
<223> OTHER INFORMATION: Any amino acid
<220> FEATURE:
<221> NAME/KEY: MOD_RES
<222> LOCATION: (9)..(10)
<223> OTHER INFORMATION: Any amino acid

<400> SEQUENCE: 76

Xaa Asp Xaa Xaa Val Xaa Asn Asp Xaa Xaa
1               5                   10

<210> SEQ ID NO 77
<211> LENGTH: 8
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (1)..(1)
<223> OTHER INFORMATION: Any amino acid
<220> FEATURE:
<221> NAME/KEY: MOD_RES
<222> LOCATION: (3)..(4)
<223> OTHER INFORMATION: Any amino acid
<220> FEATURE:
<221> NAME/KEY: MOD_RES
<222> LOCATION: (6)..(6)
<223> OTHER INFORMATION: Any amino acid

<400> SEQUENCE: 77

Xaa Asp Xaa Xaa Val Xaa Asn Asp
1               5

<210> SEQ ID NO 78
<211> LENGTH: 7
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (2)..(3)
<223> OTHER INFORMATION: Any amino acid
<220> FEATURE:
<221> NAME/KEY: MOD_RES
<222> LOCATION: (5)..(5)
<223> OTHER INFORMATION: Any amino acid

<400> SEQUENCE: 78

Asp Xaa Xaa Val Xaa Asn Asp
1               5

<210> SEQ ID NO 79
<211> LENGTH: 6
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (2)..(2)
<223> OTHER INFORMATION: Any amino acid

```
<220> FEATURE:
<221> NAME/KEY: MOD_RES
<222> LOCATION: (5)..(6)
<223> OTHER INFORMATION: Any amino acid

<400> SEQUENCE: 79

Val Xaa Asn Asp Xaa Xaa
1               5

<210> SEQ ID NO 80
<211> LENGTH: 4
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (2)..(2)
<223> OTHER INFORMATION: Any amino acid

<400> SEQUENCE: 80

Val Xaa Asn Asp
1

<210> SEQ ID NO 81
<211> LENGTH: 37
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 81

Met Val Leu Glu Val Ser Asp His Gln Val Leu Asn Asp Ala Glu Val
1               5                   10                  15

Ala Ala Leu Leu Glu Asn Phe Ser Ser Ser Tyr Asp Tyr Gly Glu Asn
            20                  25                  30

Glu Ser Asp Ser Cys
        35

<210> SEQ ID NO 82
<211> LENGTH: 6
<212> TYPE: PRT
<213> ORGANISM: Artificial Sequence
<220> FEATURE:
<223> OTHER INFORMATION: Description of Artificial Sequence: Synthetic
      6xHis tag

<400> SEQUENCE: 82

His His His His His His
1               5

<210> SEQ ID NO 83
<211> LENGTH: 16
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 83

Ala Val Leu Glu Val Ser Asp His Gln Val Leu Asn Asp Ala Glu Val
1               5                   10                  15

<210> SEQ ID NO 84
<211> LENGTH: 16
```

```
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 84

Met Ala Leu Glu Val Ser Asp His Gln Val Leu Asn Asp Ala Glu Val
1               5                   10                  15

<210> SEQ ID NO 85
<211> LENGTH: 16
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 85

Met Val Ala Glu Val Ser Asp His Gln Val Leu Asn Asp Ala Glu Val
1               5                   10                  15

<210> SEQ ID NO 86
<211> LENGTH: 16
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 86

Met Val Leu Ala Val Ser Asp His Gln Val Leu Asn Asp Ala Glu Val
1               5                   10                  15

<210> SEQ ID NO 87
<211> LENGTH: 16
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 87

Met Val Leu Glu Ala Ser Asp His Gln Val Leu Asn Asp Ala Glu Val
1               5                   10                  15

<210> SEQ ID NO 88
<211> LENGTH: 16
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 88

Met Val Leu Glu Val Ala Asp His Gln Val Leu Asn Asp Ala Glu Val
1               5                   10                  15

<210> SEQ ID NO 89
<211> LENGTH: 16
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 89

Met Val Leu Glu Val Ser Ala His Gln Val Leu Asn Asp Ala Glu Val
```

```
                1               5                  10                  15
```

<210> SEQ ID NO 90
<211> LENGTH: 16
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 90

Met Val Leu Glu Val Ser Asp Ala Gln Val Leu Asn Asp Ala Glu Val
1               5                  10                  15

<210> SEQ ID NO 91
<211> LENGTH: 16
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 91

Met Val Leu Glu Val Ser Asp His Ala Val Leu Asn Asp Ala Glu Val
1               5                  10                  15

<210> SEQ ID NO 92
<211> LENGTH: 16
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 92

Met Val Leu Glu Val Ser Asp His Gln Ala Leu Asn Asp Ala Glu Val
1               5                  10                  15

<210> SEQ ID NO 93
<211> LENGTH: 16
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 93

Met Val Leu Glu Val Ser Asp His Gln Val Ala Asn Asp Ala Glu Val
1               5                  10                  15

<210> SEQ ID NO 94
<211> LENGTH: 16
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 94

Met Val Leu Glu Val Ser Asp His Gln Val Leu Ala Asp Ala Glu Val
1               5                  10                  15

<210> SEQ ID NO 95
<211> LENGTH: 16
<212> TYPE: PRT
<213> ORGANISM: Artificial Sequence
<220> FEATURE:
<223> OTHER INFORMATION: Description of Artificial Sequence: Synthetic

```
                                peptide

<400> SEQUENCE: 95

Met Val Leu Glu Val Ser Asp His Gln Val Leu Asn Ala Ala Glu Val
1               5                   10                  15

<210> SEQ ID NO 96
<211> LENGTH: 16
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 96

Met Val Leu Glu Val Ser Asp His Gln Val Leu Asn Asp Ala Glu Val
1               5                   10                  15

<210> SEQ ID NO 97
<211> LENGTH: 16
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 97

Met Val Leu Glu Val Ser Asp His Gln Val Leu Asn Asp Ala Ala Val
1               5                   10                  15

<210> SEQ ID NO 98
<211> LENGTH: 16
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 98

Met Val Leu Glu Val Ser Asp His Gln Val Leu Asn Asp Ala Glu Ala
1               5                   10                  15

<210> SEQ ID NO 99
<211> LENGTH: 16
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<223> OTHER INFORMATION: N-term biotin

<400> SEQUENCE: 99

Ala Val Leu Glu Val Ser Asp His Gln Val Leu Asn Asp Ala Glu Val
1               5                   10                  15

<210> SEQ ID NO 100
<211> LENGTH: 16
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<223> OTHER INFORMATION: N-term biotin

<400> SEQUENCE: 100

Met Ala Leu Glu Val Ser Asp His Gln Val Leu Asn Asp Ala Glu Val
```

<210> SEQ ID NO 101
<211> LENGTH: 16
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<223> OTHER INFORMATION: N-term biotin

<400> SEQUENCE: 101

Met Val Ala Glu Val Ser Asp His Gln Val Leu Asn Asp Ala Glu Val
1               5                   10                  15

<210> SEQ ID NO 102
<211> LENGTH: 16
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<223> OTHER INFORMATION: N-term biotin

<400> SEQUENCE: 102

Met Val Leu Ala Val Ser Asp His Gln Val Leu Asn Asp Ala Glu Val
1               5                   10                  15

<210> SEQ ID NO 103
<211> LENGTH: 16
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<223> OTHER INFORMATION: N-term biotin

<400> SEQUENCE: 103

Met Val Leu Glu Ala Ser Asp His Gln Val Leu Asn Asp Ala Glu Val
1               5                   10                  15

<210> SEQ ID NO 104
<211> LENGTH: 16
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<223> OTHER INFORMATION: N-term biotin

<400> SEQUENCE: 104

Met Val Leu Glu Val Ala Asp His Gln Val Leu Asn Asp Ala Glu Val
1               5                   10                  15

<210> SEQ ID NO 105
<211> LENGTH: 16
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<223> OTHER INFORMATION: N-term biotin

<400> SEQUENCE: 105

Met Val Leu Glu Val Ser Ala His Gln Val Leu Asn Asp Ala Glu Val
1               5                   10                  15

<210> SEQ ID NO 106
<211> LENGTH: 16
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<223> OTHER INFORMATION: N-term biotin

<400> SEQUENCE: 106

Met Val Leu Glu Val Ser Asp Ala Gln Val Leu Asn Asp Ala Glu Val
1               5                   10                  15

<210> SEQ ID NO 107
<211> LENGTH: 16
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<223> OTHER INFORMATION: N-term biotin

<400> SEQUENCE: 107

Met Val Leu Glu Val Ser Asp His Ala Val Leu Asn Asp Ala Glu Val
1               5                   10                  15

<210> SEQ ID NO 108
<211> LENGTH: 16
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<223> OTHER INFORMATION: N-term biotin

<400> SEQUENCE: 108

Met Val Leu Glu Val Ser Asp His Gln Ala Leu Asn Asp Ala Glu Val
1               5                   10                  15

<210> SEQ ID NO 109
<211> LENGTH: 16
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<223> OTHER INFORMATION: N-term biotin

<400> SEQUENCE: 109

Met Val Leu Glu Val Ser Asp His Gln Val Ala Asn Asp Ala Glu Val
1               5                   10                  15

<210> SEQ ID NO 110
<211> LENGTH: 16
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<223> OTHER INFORMATION: N-term biotin

<400> SEQUENCE: 110

```
Met Val Leu Glu Val Ser Asp His Gln Val Leu Ala Asp Ala Glu Val
1               5                   10                  15

<210> SEQ ID NO 111
<211> LENGTH: 16
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<223> OTHER INFORMATION: N-term biotin

<400> SEQUENCE: 111

Met Val Leu Glu Val Ser Asp His Gln Val Leu Asn Ala Ala Glu Val
1               5                   10                  15

<210> SEQ ID NO 112
<211> LENGTH: 16
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<223> OTHER INFORMATION: N-term biotin

<400> SEQUENCE: 112

Met Val Leu Glu Val Ser Asp His Gln Val Leu Asn Asp Ala Glu Val
1               5                   10                  15

<210> SEQ ID NO 113
<211> LENGTH: 16
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<223> OTHER INFORMATION: N-term biotin

<400> SEQUENCE: 113

Met Val Leu Glu Val Ser Asp His Gln Val Leu Asn Asp Ala Ala Val
1               5                   10                  15

<210> SEQ ID NO 114
<211> LENGTH: 16
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<223> OTHER INFORMATION: N-term biotin

<400> SEQUENCE: 114

Met Val Leu Glu Val Ser Asp His Gln Val Leu Asn Asp Ala Glu Ala
1               5                   10                  15

<210> SEQ ID NO 115
<211> LENGTH: 25
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 115
```

```
Glu Val Gln Leu Glu Glu Ser Gly Gly Gly Leu Val Gln Pro Lys Gly
1               5                   10                  15

Ser Leu Lys Leu Ser Cys Ala Ala Ser
            20                  25

<210> SEQ ID NO 116
<211> LENGTH: 8
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 116

Gly Ile Ser Phe Asn Asp Ala Ala
1               5

<210> SEQ ID NO 117
<211> LENGTH: 17
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 117

Met Asn Trp Ile Arg Gln Ala Pro Gly Glu Gly Leu Glu Trp Val Ala
1               5                   10                  15

Arg

<210> SEQ ID NO 118
<211> LENGTH: 10
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 118

Ile Arg Ser Lys Ile Asn Asp Tyr Gly Thr
1               5                   10

<210> SEQ ID NO 119
<211> LENGTH: 38
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 119

His Tyr Ala Ala Ser Val Lys Asp Arg Phe Thr Ile Ser Arg Asp Asp
1               5                   10                  15

Ser Gln Asn Ile Leu Phe Leu Gln Met Asn Asn Leu Lys Thr Glu Asp
            20                  25                  30

Thr Gly Met Tyr Tyr Cys
            35

<210> SEQ ID NO 120
<211> LENGTH: 10
<212> TYPE: PRT
<213> ORGANISM: Artificial Sequence
<220> FEATURE:
<223> OTHER INFORMATION: Description of Artificial Sequence: Synthetic
      peptide
```

```
<400> SEQUENCE: 120

Val Ile Asp Gly Tyr Gly Ser Leu Ala Tyr
1               5                   10

<210> SEQ ID NO 121
<211> LENGTH: 11
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 121

Trp Gly Gln Gly Thr Leu Val Thr Val Ser Ala
1               5                   10

<210> SEQ ID NO 122
<211> LENGTH: 26
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 122

Asp Ile Val Leu Thr Gln Ser Pro Ala Ile Met Ser Ser Pro Gly
1               5                   10                  15

Glu Lys Val Thr Met Thr Cys Arg Ala Ser
            20                  25

<210> SEQ ID NO 123
<211> LENGTH: 7
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 123

Ser Ser Val Ile Ser Ser Tyr
1               5

<210> SEQ ID NO 124
<211> LENGTH: 17
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 124

Leu His Trp Tyr Gln Gln Arg Ser Gly Ala Ser Pro Lys Leu Trp Ile
1               5                   10                  15

Tyr

<210> SEQ ID NO 125
<211> LENGTH: 3
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 125

Ser Thr Ser
1
```

```
<210> SEQ ID NO 126
<211> LENGTH: 36
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 126

Ser Leu Ala Ser Gly Val Pro Ala Arg Phe Ser Gly Ser Gly Ser Gly
1               5                   10                  15

Thr Ser Phe Ser Leu Thr Ile Ser Ser Val Glu Ala Glu Asp Ala Ala
            20                  25                  30

Thr Tyr Tyr Cys
        35

<210> SEQ ID NO 127
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 127

Gln Gln Tyr Ser Gly Tyr Pro Leu Thr
1               5

<210> SEQ ID NO 128
<211> LENGTH: 10
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 128

Phe Gly Ala Gly Thr Lys Leu Glu Leu Lys
1               5                   10

<210> SEQ ID NO 129
<211> LENGTH: 25
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 129

Glu Val Gln Leu Val Glu Ser Gly Gly Gly Leu Val Gln Pro Gly Gly
1               5                   10                  15

Ser Leu Lys Leu Ser Cys Ala Ala Ser
            20                  25

<210> SEQ ID NO 130
<211> LENGTH: 8
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 130

Gly Ile Ser Phe Asn Asp Ala Ala
1               5
```

```
<210> SEQ ID NO 131
<211> LENGTH: 17
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 131

Met His Trp Val Arg Gln Ala Ser Gly Lys Gly Leu Glu Trp Val Ala
1               5                   10                  15

Arg

<210> SEQ ID NO 132
<211> LENGTH: 10
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 132

Ile Arg Ser Lys Ile Asn Asp Tyr Gly Thr
1               5                   10

<210> SEQ ID NO 133
<211> LENGTH: 38
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 133

Ala Tyr Ala Ala Ser Val Lys Gly Arg Phe Thr Ile Ser Arg Asp Asp
1               5                   10                  15

Ser Gln Asn Thr Leu Tyr Leu Gln Met Asn Ser Leu Lys Thr Glu Asp
            20                  25                  30

Thr Ala Val Tyr Tyr Cys
        35

<210> SEQ ID NO 134
<211> LENGTH: 10
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 134

Val Ile Asp Gly Tyr Gly Ser Leu Ala Tyr
1               5                   10

<210> SEQ ID NO 135
<211> LENGTH: 11
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 135

Trp Gly Gln Gly Thr Leu Val Thr Val Ser Ser
1               5                   10
```

<210> SEQ ID NO 136
<211> LENGTH: 26
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 136

Glu Ile Val Leu Thr Gln Ser Pro Ala Thr Leu Ser Leu Ser Pro Gly
1               5                   10                  15

Glu Arg Ala Thr Leu Ser Cys Arg Ala Ser
            20                  25

<210> SEQ ID NO 137
<211> LENGTH: 7
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 137

Ser Ser Val Ile Ser Ser Tyr
1               5

<210> SEQ ID NO 138
<211> LENGTH: 17
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 138

Leu Ala Trp Tyr Gln Gln Lys Pro Gly Gln Ala Pro Arg Leu Trp Ile
1               5                   10                  15

Tyr

<210> SEQ ID NO 139
<211> LENGTH: 3
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 139

Ser Thr Ser
1

<210> SEQ ID NO 140
<211> LENGTH: 36
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 140

Asn Arg Ala Thr Gly Ile Pro Ala Arg Phe Ser Gly Ser Gly Ser Gly
1               5                   10                  15

Thr Asp Phe Thr Leu Thr Ile Ser Ser Leu Glu Pro Glu Asp Phe Ala
            20                  25                  30

Thr Tyr Tyr Cys

```
<210> SEQ ID NO 141
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 141

Gln Gln Tyr Ser Gly Tyr Pro Leu Thr
1               5

<210> SEQ ID NO 142
<211> LENGTH: 10
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 142

Phe Gly Gly Gly Thr Lys Val Glu Ile Lys
1               5                   10

<210> SEQ ID NO 143
<211> LENGTH: 25
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 143

Glu Val Gln Leu Val Glu Ser Gly Gly Gly Leu Val Gln Pro Gly Gly
1               5                   10                  15

Ser Leu Lys Leu Ser Cys Ala Ala Ser
            20                  25

<210> SEQ ID NO 144
<211> LENGTH: 8
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 144

Gly Ile Ser Phe Asn Asp Ala Ala
1               5

<210> SEQ ID NO 145
<211> LENGTH: 17
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 145

Met Asn Trp Ile Arg Gln Ala Ser Gly Lys Gly Leu Glu Trp Val Ala
1               5                   10                  15

Arg

<210> SEQ ID NO 146
```

```
<211> LENGTH: 10
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 146

Ile Arg Ser Lys Ile Asn Asp Tyr Gly Thr
1               5                   10

<210> SEQ ID NO 147
<211> LENGTH: 38
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 147

His Tyr Ala Ala Ser Val Lys Gly Arg Phe Thr Ile Ser Arg Asp Asp
1               5                   10                  15

Ser Gln Asn Thr Leu Tyr Leu Gln Met Asn Ser Leu Lys Thr Glu Asp
            20                  25                  30

Thr Ala Met Tyr Tyr Cys
        35

<210> SEQ ID NO 148
<211> LENGTH: 10
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 148

Val Ile Asp Gly Tyr Gly Ser Leu Ala Tyr
1               5                   10

<210> SEQ ID NO 149
<211> LENGTH: 11
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 149

Trp Gly Gln Gly Thr Leu Val Thr Val Ser Ser
1               5                   10

<210> SEQ ID NO 150
<211> LENGTH: 26
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 150

Glu Ile Val Leu Thr Gln Ser Pro Ala Thr Leu Ser Leu Ser Pro Gly
1               5                   10                  15

Glu Arg Ala Thr Leu Ser Cys Arg Ala Ser
            20                  25

<210> SEQ ID NO 151
```

<211> LENGTH: 7
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 151

Ser Ser Val Ile Ser Ser Tyr
1               5

<210> SEQ ID NO 152
<211> LENGTH: 17
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 152

Leu His Trp Tyr Gln Gln Lys Pro Gly Gln Ala Pro Arg Leu Trp Ile
1               5                   10                  15

Tyr

<210> SEQ ID NO 153
<211> LENGTH: 3
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 153

Ser Thr Ser
1

<210> SEQ ID NO 154
<211> LENGTH: 36
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 154

Ser Leu Ala Ser Gly Ile Pro Ala Arg Phe Ser Gly Ser Gly Ser Gly
1               5                   10                  15

Thr Asp Phe Thr Leu Thr Ile Ser Ser Leu Glu Pro Glu Asp Phe Ala
            20                  25                  30

Thr Tyr Tyr Cys
            35

<210> SEQ ID NO 155
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 155

Gln Gln Tyr Ser Gly Tyr Pro Leu Thr
1               5

<210> SEQ ID NO 156
<211> LENGTH: 10

```
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 156

Phe Gly Ala Gly Thr Lys Val Glu Ile Lys
1               5                   10

<210> SEQ ID NO 157
<211> LENGTH: 25
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 157

Glu Val Gln Leu Val Glu Ser Gly Gly Gly Leu Val Gln Pro Lys Gly
1               5                   10                  15

Ser Leu Lys Leu Ser Cys Ala Ala Ser
            20                  25

<210> SEQ ID NO 158
<211> LENGTH: 8
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 158

Gly Ile Ser Phe Asn Asp Ala Ala
1               5

<210> SEQ ID NO 159
<211> LENGTH: 17
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 159

Met Asn Trp Ile Arg Gln Ala Ser Gly Lys Gly Leu Glu Trp Val Ala
1               5                   10                  15

Arg

<210> SEQ ID NO 160
<211> LENGTH: 10
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 160

Ile Arg Ser Lys Ile Asn Asp Tyr Gly Thr
1               5                   10

<210> SEQ ID NO 161
<211> LENGTH: 38
<212> TYPE: PRT
<213> ORGANISM: Artificial Sequence
<220> FEATURE:
<223> OTHER INFORMATION: Description of Artificial Sequence: Synthetic
```

```
                            polypeptide

<400> SEQUENCE: 161

His Tyr Ala Ala Ser Val Lys Asp Arg Phe Thr Ile Ser Arg Asp Asp
1               5                   10                  15

Ser Gln Asn Ile Leu Tyr Leu Gln Met Asn Asn Leu Lys Thr Glu Asp
            20                  25                  30

Thr Ala Met Tyr Tyr Cys
            35

<210> SEQ ID NO 162
<211> LENGTH: 10
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 162

Val Ile Asp Gly Tyr Gly Ser Leu Ala Tyr
1               5                   10

<210> SEQ ID NO 163
<211> LENGTH: 11
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 163

Trp Gly Gln Gly Thr Leu Val Thr Val Ser Ser
1               5                   10

<210> SEQ ID NO 164
<211> LENGTH: 26
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 164

Glu Ile Val Leu Thr Gln Ser Pro Ala Ile Leu Ser Ser Ser Pro Gly
1               5                   10                  15

Glu Arg Ala Thr Leu Ser Cys Arg Ala Ser
            20                  25

<210> SEQ ID NO 165
<211> LENGTH: 7
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 165

Ser Ser Val Ile Ser Ser Tyr
1               5

<210> SEQ ID NO 166
<211> LENGTH: 17
<212> TYPE: PRT
<213> ORGANISM: Artificial Sequence
<220> FEATURE:
<223> OTHER INFORMATION: Description of Artificial Sequence: Synthetic
```

-continued peptide

<400> SEQUENCE: 166

Leu His Trp Tyr Gln Gln Lys Pro Gly Ala Ala Pro Arg Leu Trp Ile
1               5                   10                  15

Tyr

<210> SEQ ID NO 167
<211> LENGTH: 3
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 167

Ser Thr Ser
1

<210> SEQ ID NO 168
<211> LENGTH: 36
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 168

Ser Leu Ala Ser Gly Ile Pro Ala Arg Phe Ser Gly Ser Gly Ser Gly
1               5                   10                  15

Thr Ser Phe Thr Leu Thr Ile Ser Ser Leu Glu Ala Glu Asp Phe Ala
            20                  25                  30

Thr Tyr Tyr Cys
        35

<210> SEQ ID NO 169
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 169

Gln Gln Tyr Ser Gly Tyr Pro Leu Thr
1               5

<210> SEQ ID NO 170
<211> LENGTH: 10
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 170

Phe Gly Ala Gly Thr Lys Val Glu Ile Lys
1               5                   10

<210> SEQ ID NO 171
<211> LENGTH: 25
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 171

Glu Val Lys Leu Glu Glu Ser Gly Gly Gly Leu Val Lys Pro Gly Gly
1               5                   10                  15

Ser Leu Lys Leu Ser Cys Ala Ala Ser
            20                  25

<210> SEQ ID NO 172
<211> LENGTH: 8
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 172

Gly Phe Thr Phe Thr Ser Tyr Ala
1               5

<210> SEQ ID NO 173
<211> LENGTH: 17
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 173

Leu Ser Trp Val Arg Gln Thr Pro Glu Lys Arg Leu Glu Trp Val Ala
1               5                   10                  15

Thr

<210> SEQ ID NO 174
<211> LENGTH: 8
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 174

Ile Ser His Gly Gly Ser Tyr Thr
1               5

<210> SEQ ID NO 175
<211> LENGTH: 38
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 175

Tyr Tyr Pro Asp Ser Val Lys Gly Arg Phe Thr Ile Ser Arg Asp Asn
1               5                   10                  15

Ala Lys Asn Thr Leu Asn Leu Gln Met Ser Ser Leu Arg Ser Glu Asp
            20                  25                  30

Thr Ala Met Tyr Tyr Cys
        35

<210> SEQ ID NO 176
<211> LENGTH: 16
<212> TYPE: PRT
<213> ORGANISM: Artificial Sequence
<220> FEATURE:

```
<223> OTHER INFORMATION: Description of Artificial Sequence: Synthetic
      peptide

<400> SEQUENCE: 176

Ala Arg His Pro Phe Tyr Ser Gly Asn Tyr Gln Gly Tyr Phe Asp Tyr
1               5                   10                  15

<210> SEQ ID NO 177
<211> LENGTH: 11
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 177

Trp Gly Gln Gly Thr Leu Leu Thr Val Ser Ser
1               5                   10

<210> SEQ ID NO 178
<211> LENGTH: 26
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 178

Asp Ile Val Leu Thr Gln Ser Pro Ala Ile Met Ser Ala Ser Leu Gly
1               5                   10                  15

Glu Lys Val Thr Met Asn Cys Arg Ala Asn
            20                  25

<210> SEQ ID NO 179
<211> LENGTH: 5
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 179

Ser Gly Val Asn Tyr
1               5

<210> SEQ ID NO 180
<211> LENGTH: 17
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 180

Met Tyr Trp Tyr Gln Gln Lys Ser Asp Ala Ser Pro Lys Leu Trp Ile
1               5                   10                  15

Tyr

<210> SEQ ID NO 181
<211> LENGTH: 3
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 181
```

```
<210> SEQ ID NO 182
<211> LENGTH: 36
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 182

Asn Leu Ala Pro Gly Val Pro Ala Arg Phe Ser Gly Ser Gly Ser Gly
1               5                   10                  15

Asn Ser Tyr Ser Leu Thr Ile Ser Ser Met Glu Gly Glu Asp Ala Ala
            20                  25                  30

Thr Tyr Tyr Cys
        35

<210> SEQ ID NO 183
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 183

Gln Gln Phe Thr Ser Ser Pro Tyr Thr
1               5

<210> SEQ ID NO 184
<211> LENGTH: 10
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 184

Phe Gly Gly Gly Thr Lys Leu Glu Ile Lys
1               5                   10

<210> SEQ ID NO 185
<211> LENGTH: 25
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 185

Glu Val Gln Leu Glu Glu Ser Gly Gly Gly Leu Val Gln Pro Gly Gly
1               5                   10                  15

Ser Leu Arg Leu Ser Cys Ala Ala Ser
            20                  25

<210> SEQ ID NO 186
<211> LENGTH: 8
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 186
```

Phe Thr Ser
1

```
Gly Phe Thr Phe Thr Ser Tyr Ala
1               5
```

<210> SEQ ID NO 187
<211> LENGTH: 17
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 187

```
Met Ser Trp Val Arg Gln Ala Pro Gly Lys Gly Leu Glu Trp Val Ala
1               5                   10                  15

Val
```

<210> SEQ ID NO 188
<211> LENGTH: 8
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 188

```
Ile Ser His Gly Gly Ser Tyr Thr
1               5
```

<210> SEQ ID NO 189
<211> LENGTH: 38
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 189

```
Tyr Tyr Ala Asp Ser Val Lys Gly Arg Phe Thr Ile Ser Arg Asp Asn
1               5                   10                  15

Ser Lys Asn Thr Leu Tyr Leu Gln Met Asn Ser Leu Arg Ala Glu Asp
            20                  25                  30

Thr Ala Val Tyr Tyr Cys
        35
```

<210> SEQ ID NO 190
<211> LENGTH: 16
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 190

```
Ala Arg His Pro Phe Tyr Ser Gly Asn Tyr Gln Gly Tyr Phe Asp Tyr
1               5                   10                  15
```

<210> SEQ ID NO 191
<211> LENGTH: 11
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 191

Trp Gly Gln Gly Thr Leu Val Thr Val Ser Ser
1               5                   10

<210> SEQ ID NO 192
<211> LENGTH: 26
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 192

Asp Ile Gln Leu Thr Gln Ser Pro Ser Phe Leu Ser Ala Ser Val Gly
1               5                   10                  15

Asp Arg Val Thr Ile Thr Cys Arg Ala Ser
            20                  25

<210> SEQ ID NO 193
<211> LENGTH: 5
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 193

Ser Gly Val Asn Tyr
1               5

<210> SEQ ID NO 194
<211> LENGTH: 17
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 194

Leu Ala Trp Tyr Gln Gln Lys Pro Gly Lys Ala Pro Lys Leu Trp Ile
1               5                   10                  15

Tyr

<210> SEQ ID NO 195
<211> LENGTH: 3
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 195

Phe Thr Ser
1

<210> SEQ ID NO 196
<211> LENGTH: 36
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 196

Thr Leu Gln Ser Gly Val Pro Ser Arg Phe Ser Gly Ser Gly Ser Gly
1               5                   10                  15

Asn Glu Tyr Thr Leu Thr Ile Ser Ser Leu Gln Phe Glu Asp Phe Ala

Thr Tyr Tyr Cys
        35

<210> SEQ ID NO 197
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 197

Gln Gln Phe Thr Ser Ser Pro Tyr Thr
1               5

<210> SEQ ID NO 198
<211> LENGTH: 10
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 198

Phe Gly Gln Gly Thr Lys Leu Glu Ile Lys
1               5                   10

<210> SEQ ID NO 199
<211> LENGTH: 25
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 199

Glu Val Gln Leu Glu Glu Ser Gly Gly Gly Leu Val Gln Pro Gly Gly
1               5                   10                  15

Ser Leu Arg Leu Ser Cys Ala Ala Ser
            20                  25

<210> SEQ ID NO 200
<211> LENGTH: 8
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 200

Gly Phe Thr Phe Thr Ser Tyr Ala
1               5

<210> SEQ ID NO 201
<211> LENGTH: 17
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 201

Leu Ser Trp Val Arg Gln Ala Pro Gly Lys Gly Leu Glu Trp Val Ala
1               5                   10                  15

Thr

```
<210> SEQ ID NO 202
<211> LENGTH: 8
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 202

Ile Ser His Gly Gly Ser Tyr Thr
1               5

<210> SEQ ID NO 203
<211> LENGTH: 38
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 203

Tyr Tyr Pro Asp Ser Val Lys Gly Arg Phe Thr Ile Ser Arg Asp Asn
1               5                   10                  15

Ser Lys Asn Thr Leu Tyr Leu Gln Met Asn Ser Leu Arg Ala Glu Asp
            20                  25                  30

Thr Ala Val Tyr Tyr Cys
        35

<210> SEQ ID NO 204
<211> LENGTH: 16
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 204

Ala Arg His Pro Phe Tyr Ser Gly Asn Tyr Gln Gly Tyr Phe Asp Tyr
1               5                   10                  15

<210> SEQ ID NO 205
<211> LENGTH: 11
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 205

Trp Gly Gln Gly Thr Leu Val Thr Val Ser Ser
1               5                   10

<210> SEQ ID NO 206
<211> LENGTH: 26
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 206

Asp Ile Gln Leu Thr Gln Ser Pro Ser Phe Leu Ser Ala Ser Val Gly
1               5                   10                  15

Asp Arg Val Thr Ile Thr Cys Arg Ala Asn
            20                  25
```

```
<210> SEQ ID NO 207
<211> LENGTH: 5
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 207

Ser Gly Val Asn Tyr
1               5

<210> SEQ ID NO 208
<211> LENGTH: 17
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 208

Met Tyr Trp Tyr Gln Gln Lys Pro Gly Lys Ala Pro Lys Leu Trp Ile
1               5                   10                  15

Tyr

<210> SEQ ID NO 209
<211> LENGTH: 3
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 209

Phe Thr Ser
1

<210> SEQ ID NO 210
<211> LENGTH: 36
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 210

Asn Leu Ala Pro Gly Val Pro Ser Arg Phe Ser Gly Ser Gly Ser Gly
1               5                   10                  15

Asn Glu Tyr Thr Leu Thr Ile Ser Ser Leu Gln Phe Glu Asp Phe Ala
            20                  25                  30

Thr Tyr Tyr Cys
            35

<210> SEQ ID NO 211
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 211

Gln Gln Phe Thr Ser Ser Pro Tyr Thr
1               5
```

```
<210> SEQ ID NO 212
<211> LENGTH: 10
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 212

Phe Gly Gly Gly Thr Lys Leu Glu Ile Lys
1               5                   10

<210> SEQ ID NO 213
<211> LENGTH: 25
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 213

Glu Val Gln Leu Leu Glu Ser Gly Gly Gly Leu Val Gln Pro Gly Gly
1               5                   10                  15

Ser Leu Arg Leu Ser Cys Ala Ala Ser
            20                  25

<210> SEQ ID NO 214
<211> LENGTH: 8
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 214

Gly Phe Thr Phe Thr Ser Tyr Ala
1               5

<210> SEQ ID NO 215
<211> LENGTH: 17
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 215

Leu Ser Trp Val Arg Gln Thr Pro Glu Lys Arg Leu Glu Trp Val Ala
1               5                   10                  15

Thr

<210> SEQ ID NO 216
<211> LENGTH: 8
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 216

Ile Ser His Gly Gly Ser Tyr Thr
1               5

<210> SEQ ID NO 217
<211> LENGTH: 38
<212> TYPE: PRT
```

<213> ORGANISM: Artificial Sequence
<220> FEATURE:
<223> OTHER INFORMATION: Description of Artificial Sequence: Synthetic
      polypeptide

<400> SEQUENCE: 217

Tyr Tyr Pro Asp Ser Val Lys Gly Arg Phe Thr Ile Ser Arg Asp Asn
1               5                   10                  15

Ser Lys Asn Thr Leu Asn Leu Gln Met Ser Ser Leu Arg Ala Glu Asp
            20                  25                  30

Thr Ala Val Tyr Tyr Cys
        35

<210> SEQ ID NO 218
<211> LENGTH: 16
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 218

Ala Arg His Pro Phe Tyr Ser Gly Asn Tyr Gln Gly Tyr Phe Asp Tyr
1               5                   10                  15

<210> SEQ ID NO 219
<211> LENGTH: 11
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 219

Trp Gly Gln Gly Thr Leu Val Thr Val Ser Ser
1               5                   10

<210> SEQ ID NO 220
<211> LENGTH: 26
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 220

Asp Ile Gln Leu Thr Gln Ser Pro Ser Phe Leu Ser Ala Ser Val Gly
1               5                   10                  15

Asp Arg Val Thr Ile Thr Cys Arg Ala Asn
            20                  25

<210> SEQ ID NO 221
<211> LENGTH: 5
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 221

Ser Gly Val Asn Tyr
1               5

<210> SEQ ID NO 222
<211> LENGTH: 17
<212> TYPE: PRT

```
<213> ORGANISM: Artificial Sequence
<220> FEATURE:
<223> OTHER INFORMATION: Description of Artificial Sequence: Synthetic
      peptide

<400> SEQUENCE: 222

Met Tyr Trp Tyr Gln Gln Lys Pro Asp Ala Ala Pro Lys Leu Trp Ile
1               5                   10                  15

Tyr

<210> SEQ ID NO 223
<211> LENGTH: 3
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 223

Phe Thr Ser
1

<210> SEQ ID NO 224
<211> LENGTH: 36
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 224

Asn Leu Ala Pro Gly Val Pro Ser Arg Phe Ser Gly Ser Gly Ser Gly
1               5                   10                  15

Asn Ser Tyr Thr Leu Thr Ile Ser Ser Leu Gln Phe Glu Asp Phe Ala
            20                  25                  30

Thr Tyr Tyr Cys
        35

<210> SEQ ID NO 225
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 225

Gln Gln Phe Thr Ser Ser Pro Tyr Thr
1               5

<210> SEQ ID NO 226
<211> LENGTH: 10
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 226

Phe Gly Gly Gly Thr Lys Leu Glu Ile Lys
1               5                   10

<210> SEQ ID NO 227
<211> LENGTH: 25
<212> TYPE: PRT
<213> ORGANISM: Artificial Sequence
```

```
<220> FEATURE:
<223> OTHER INFORMATION: Description of Artificial Sequence: Synthetic
      peptide

<400> SEQUENCE: 227

Glu Val Gln Leu Glu Glu Ser Gly Gly Gly Leu Val Lys Pro Gly Gly
1               5                   10                  15

Ser Leu Lys Leu Ser Cys Ala Ala Ser
            20                  25

<210> SEQ ID NO 228
<211> LENGTH: 8
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 228

Gly Phe Thr Phe Ser Asn Tyr Ala
1               5

<210> SEQ ID NO 229
<211> LENGTH: 17
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 229

Met Ser Trp Val Arg Gln Thr Pro Asp Lys Arg Leu Glu Trp Val Ala
1               5                   10                  15

Thr

<210> SEQ ID NO 230
<211> LENGTH: 8
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 230

Ile Ser Asn Gly Gly Ser Tyr Thr
1               5

<210> SEQ ID NO 231
<211> LENGTH: 38
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 231

Tyr Tyr Pro Asp Thr Val Lys Gly Arg Phe Thr Ile Ser Arg Asp Asn
1               5                   10                  15

Ala Lys Asn Thr Leu Ser Leu Gln Met Ser Ser Leu Arg Ser Glu Asp
            20                  25                  30

Thr Ala Met Tyr Tyr Cys
                35

<210> SEQ ID NO 232
<211> LENGTH: 17
```

<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 232

Ser Arg Pro Ser Glu Arg Ser His Tyr Tyr Ala Thr Ser Gln Phe Ala
1               5                   10                  15

Tyr

<210> SEQ ID NO 233
<211> LENGTH: 11
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 233

Trp Gly Gln Gly Thr Leu Val Thr Val Ser Ala
1               5                   10

<210> SEQ ID NO 234
<211> LENGTH: 26
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 234

Asp Ile Val Leu Thr Gln Ser Pro Gly Ile Met Ser Ala Ser Pro Gly
1               5                   10                  15

Glu Lys Val Thr Met Thr Cys Ser Ala Ser
            20                  25

<210> SEQ ID NO 235
<211> LENGTH: 5
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 235

Ser Ser Val Ser Tyr
1               5

<210> SEQ ID NO 236
<211> LENGTH: 17
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 236

Met His Trp Tyr Gln Gln Lys Ser Gly Thr Ser Pro Lys Arg Trp Ile
1               5                   10                  15

Tyr

<210> SEQ ID NO 237
<211> LENGTH: 3
<212> TYPE: PRT
<213> ORGANISM: Artificial Sequence

```
<220> FEATURE:
<223> OTHER INFORMATION: Description of Artificial Sequence: Synthetic
      peptide

<400> SEQUENCE: 237

Asp Thr Ser
1

<210> SEQ ID NO 238
<211> LENGTH: 36
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 238

Lys Leu Ala Ser Gly Val Pro Ala Arg Phe Ser Gly Ser Gly Ser Gly
1               5                   10                  15

Thr Ser Tyr Ser Leu Thr Ile Ser Ser Met Glu Ala Glu Asp Ala Ala
            20                  25                  30

Thr Tyr Tyr Cys
        35

<210> SEQ ID NO 239
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 239

Gln Gln Trp Ser Ser Ser Pro Leu Thr
1               5

<210> SEQ ID NO 240
<211> LENGTH: 10
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 240

Phe Gly Ala Gly Thr Lys Val Glu Leu Lys
1               5                   10

<210> SEQ ID NO 241
<211> LENGTH: 25
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 241

Glu Val Gln Leu Leu Glu Ser Gly Gly Gly Leu Val Gln Pro Gly Gly
1               5                   10                  15

Ser Leu Arg Leu Ser Cys Ala Ala Ser
            20                  25

<210> SEQ ID NO 242
<211> LENGTH: 8
<212> TYPE: PRT
<213> ORGANISM: Artificial Sequence
```

```
<220> FEATURE:
<223> OTHER INFORMATION: Description of Artificial Sequence: Synthetic
      peptide

<400> SEQUENCE: 242

Gly Phe Thr Phe Ser Asn Tyr Ala
1               5

<210> SEQ ID NO 243
<211> LENGTH: 17
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 243

Met Ser Trp Val Arg Gln Ala Pro Gly Lys Gly Leu Glu Trp Val Ala
1               5                   10                  15

Val

<210> SEQ ID NO 244
<211> LENGTH: 8
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 244

Ile Ser Asn Gly Gly Ser Tyr Thr
1               5

<210> SEQ ID NO 245
<211> LENGTH: 38
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 245

Tyr Tyr Ala Asp Ser Val Lys Gly Arg Phe Thr Ile Ser Arg Asp Asn
1               5                   10                  15

Ser Lys Asn Thr Leu Tyr Leu Gln Met Asn Ser Leu Arg Ala Glu Asp
            20                  25                  30

Thr Ala Val Tyr Tyr Cys
        35

<210> SEQ ID NO 246
<211> LENGTH: 17
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 246

Ser Arg Pro Ser Glu Arg Ser His Tyr Tyr Ala Thr Ser Gln Phe Ala
1               5                   10                  15

Tyr

<210> SEQ ID NO 247
<211> LENGTH: 11
<212> TYPE: PRT
```

```
<213> ORGANISM: Artificial Sequence
<220> FEATURE:
<223> OTHER INFORMATION: Description of Artificial Sequence: Synthetic
      peptide

<400> SEQUENCE: 247

Trp Gly Gln Gly Thr Leu Val Thr Val Ser Ser
1               5                   10

<210> SEQ ID NO 248
<211> LENGTH: 26
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 248

Glu Ile Val Leu Thr Gln Ser Pro Ala Thr Leu Ser Leu Ser Pro Gly
1               5                   10                  15

Glu Arg Ala Thr Leu Ser Cys Arg Ala Ser
            20                  25

<210> SEQ ID NO 249
<211> LENGTH: 5
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 249

Ser Ser Val Ser Tyr
1               5

<210> SEQ ID NO 250
<211> LENGTH: 17
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 250

Leu Ala Trp Tyr Gln Gln Lys Pro Gly Gln Ala Pro Arg Arg Trp Ile
1               5                   10                  15

Tyr

<210> SEQ ID NO 251
<211> LENGTH: 3
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 251

Asp Thr Ser
1

<210> SEQ ID NO 252
<211> LENGTH: 36
<212> TYPE: PRT
<213> ORGANISM: Artificial Sequence
<220> FEATURE:
<223> OTHER INFORMATION: Description of Artificial Sequence: Synthetic
      polypeptide
```

<400> SEQUENCE: 252

Asn Arg Ala Thr Gly Ile Pro Ala Arg Phe Ser Gly Ser Gly Ser Gly
1               5                   10                  15

Thr Asp Tyr Thr Leu Thr Ile Ser Ser Leu Glu Pro Glu Asp Phe Ala
            20                  25                  30

Val Tyr Tyr Cys
        35

<210> SEQ ID NO 253
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 253

Gln Gln Trp Ser Ser Ser Pro Leu Thr
1               5

<210> SEQ ID NO 254
<211> LENGTH: 10
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 254

Phe Gly Gly Gly Thr Lys Val Glu Ile Lys
1               5                   10

<210> SEQ ID NO 255
<211> LENGTH: 25
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 255

Glu Val Gln Leu Leu Glu Ser Gly Gly Gly Leu Val Gln Pro Gly Gly
1               5                   10                  15

Ser Leu Arg Leu Ser Cys Ala Ala Ser
            20                  25

<210> SEQ ID NO 256
<211> LENGTH: 8
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 256

Gly Phe Thr Phe Ser Asn Tyr Ala
1               5

<210> SEQ ID NO 257
<211> LENGTH: 17
<212> TYPE: PRT
<213> ORGANISM: Artificial Sequence
<220> FEATURE:
<223> OTHER INFORMATION: Description of Artificial Sequence: Synthetic
      peptide -continued

<400> SEQUENCE: 257

Met Ser Trp Val Arg Gln Ala Pro Gly Lys Gly Leu Glu Trp Val Ala
1               5                   10                  15

Thr

<210> SEQ ID NO 258
<211> LENGTH: 8
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 258

Ile Ser Asn Gly Gly Ser Tyr Thr
1               5

<210> SEQ ID NO 259
<211> LENGTH: 38
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 259

Tyr Tyr Pro Asp Ser Val Lys Gly Arg Phe Thr Ile Ser Arg Asp Asn
1               5                   10                  15

Ser Lys Asn Thr Leu Tyr Leu Gln Met Asn Ser Leu Arg Ala Glu Asp
            20                  25                  30

Thr Ala Val Tyr Tyr Cys
        35

<210> SEQ ID NO 260
<211> LENGTH: 17
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 260

Ser Arg Pro Ser Glu Arg Ser His Tyr Tyr Ala Thr Ser Gln Phe Ala
1               5                   10                  15

Tyr

<210> SEQ ID NO 261
<211> LENGTH: 11
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 261

Trp Gly Gln Gly Thr Leu Val Thr Val Ser Ser
1               5                   10

<210> SEQ ID NO 262
<211> LENGTH: 26
<212> TYPE: PRT
<213> ORGANISM: Artificial Sequence
<220> FEATURE:
<223> OTHER INFORMATION: Description of Artificial Sequence: Synthetic

```
                        peptide

<400> SEQUENCE: 262

Glu Ile Val Leu Thr Gln Ser Pro Ala Thr Leu Ser Leu Ser Pro Gly
1               5                   10                  15

Glu Arg Ala Thr Leu Ser Cys Ser Ala Ser
            20                  25

<210> SEQ ID NO 263
<211> LENGTH: 5
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 263

Ser Ser Val Ser Tyr
1               5

<210> SEQ ID NO 264
<211> LENGTH: 17
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 264

Met His Trp Tyr Gln Gln Lys Pro Gly Thr Ala Pro Arg Arg Trp Ile
1               5                   10                  15

Tyr

<210> SEQ ID NO 265
<211> LENGTH: 3
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 265

Asp Thr Ser
1

<210> SEQ ID NO 266
<211> LENGTH: 36
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 266

Lys Leu Ala Ser Gly Ile Pro Ala Arg Phe Ser Gly Ser Gly Ser Gly
1               5                   10                  15

Thr Asp Tyr Thr Leu Thr Ile Ser Ser Leu Glu Pro Glu Asp Phe Ala
            20                  25                  30

Thr Tyr Tyr Cys
        35

<210> SEQ ID NO 267
<211> LENGTH: 9
<212> TYPE: PRT
<213> ORGANISM: Artificial Sequence
```

```
<220> FEATURE:
<223> OTHER INFORMATION: Description of Artificial Sequence: Synthetic
      peptide

<400> SEQUENCE: 267

Gln Gln Trp Ser Ser Ser Pro Leu Thr
1               5

<210> SEQ ID NO 268
<211> LENGTH: 10
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 268

Phe Gly Ala Gly Thr Lys Val Glu Ile Lys
1               5                   10

<210> SEQ ID NO 269
<211> LENGTH: 25
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 269

Glu Val Gln Leu Glu Glu Ser Gly Gly Gly Leu Val Gln Pro Gly Gly
1               5                   10                  15

Ser Leu Arg Leu Ser Cys Ala Ala Ser
            20                  25

<210> SEQ ID NO 270
<211> LENGTH: 8
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 270

Gly Phe Thr Phe Ser Asn Tyr Ala
1               5

<210> SEQ ID NO 271
<211> LENGTH: 17
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 271

Met Ser Trp Val Arg Gln Thr Pro Asp Lys Arg Leu Glu Trp Val Ala
1               5                   10                  15

Thr

<210> SEQ ID NO 272
<211> LENGTH: 8
<212> TYPE: PRT
<213> ORGANISM: Artificial Sequence
<220> FEATURE:
<223> OTHER INFORMATION: Description of Artificial Sequence: Synthetic
      peptide
```

-continued

```
<400> SEQUENCE: 272

Ile Ser Asn Gly Gly Ser Tyr Thr
1               5

<210> SEQ ID NO 273
<211> LENGTH: 38
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 273

Tyr Tyr Pro Asp Ser Val Lys Gly Arg Phe Thr Ile Ser Arg Asp Asn
1               5                   10                  15

Ser Lys Asn Thr Leu Tyr Leu Gln Met Ser Ser Leu Arg Ala Glu Asp
            20                  25                  30

Thr Ala Val Tyr Tyr Cys
        35

<210> SEQ ID NO 274
<211> LENGTH: 17
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 274

Ser Arg Pro Ser Glu Arg Ser His Tyr Tyr Ala Thr Ser Gln Phe Ala
1               5                   10                  15

Tyr

<210> SEQ ID NO 275
<211> LENGTH: 11
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 275

Trp Gly Gln Gly Thr Leu Val Thr Val Ser Ser
1               5                   10

<210> SEQ ID NO 276
<211> LENGTH: 26
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 276

Glu Ile Val Leu Thr Gln Ser Pro Ala Ile Leu Ser Leu Ser Pro Gly
1               5                   10                  15

Glu Arg Ala Thr Leu Ser Cys Ser Ala Ser
            20                  25

<210> SEQ ID NO 277
<211> LENGTH: 5
<212> TYPE: PRT
<213> ORGANISM: Artificial Sequence
<220> FEATURE:
<223> OTHER INFORMATION: Description of Artificial Sequence: Synthetic
```

-continued peptide

<400> SEQUENCE: 277

Ser Ser Val Ser Tyr
1               5

<210> SEQ ID NO 278
<211> LENGTH: 17
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 278

Met His Trp Tyr Gln Gln Lys Pro Gly Gln Ala Pro Arg Arg Trp Ile
1               5                   10                  15

Tyr

<210> SEQ ID NO 279
<211> LENGTH: 3
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 279

Asp Thr Ser
1

<210> SEQ ID NO 280
<211> LENGTH: 36
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 280

Lys Leu Ala Ser Gly Ile Pro Ala Arg Phe Ser Gly Ser Gly Ser Gly
1               5                   10                  15

Thr Ser Tyr Thr Leu Thr Ile Ser Ser Leu Glu Ala Glu Asp Phe Ala
                20                  25                  30

Thr Tyr Tyr Cys
            35

<210> SEQ ID NO 281
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 281

Gln Gln Trp Ser Ser Ser Pro Leu Thr
1               5

<210> SEQ ID NO 282
<211> LENGTH: 10
<212> TYPE: PRT
<213> ORGANISM: Artificial Sequence
<220> FEATURE:
<223> OTHER INFORMATION: Description of Artificial Sequence: Synthetic
      peptide

```
<400> SEQUENCE: 282

Phe Gly Ala Gly Thr Lys Val Glu Ile Lys
1               5                   10

<210> SEQ ID NO 283
<211> LENGTH: 25
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 283

Glu Val Gln Leu Val Glu Ser Gly Gly Gly Val Lys Lys Pro Gly Gly
1               5                   10                  15

Ser Leu Lys Leu Ser Cys Ala Ala Ser
            20                  25

<210> SEQ ID NO 284
<211> LENGTH: 8
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 284

Gly Phe Thr Phe Ser Asn Tyr Ala
1               5

<210> SEQ ID NO 285
<211> LENGTH: 17
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 285

Met Ser Trp Val Arg Gln Thr Pro Gly Lys Gly Leu Glu Trp Val Ala
1               5                   10                  15

Thr

<210> SEQ ID NO 286
<211> LENGTH: 8
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 286

Ile Ser Asn Gly Gly Ser Tyr Thr
1               5

<210> SEQ ID NO 287
<211> LENGTH: 38
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 287

Tyr Tyr Pro Asp Ser Phe Gln Gly Arg Phe Thr Ile Ser Arg Asp Asn
```

```
                1               5                  10                 15
Ala Lys Ser Thr Leu Ser Leu Gln Met Ser Ser Leu Lys Ser Glu Asp
                20                 25                 30

Thr Ala Met Tyr Tyr Cys
            35
```

<210> SEQ ID NO 288
<211> LENGTH: 17
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 288

```
Ser Arg Pro Ser Glu Arg Ser His Tyr Tyr Ala Thr Ser Gln Phe Ala
1               5                  10                 15

Tyr
```

<210> SEQ ID NO 289
<211> LENGTH: 11
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 289

```
Trp Gly Gln Gly Thr Leu Val Thr Val Ser Ala
1               5                  10
```

<210> SEQ ID NO 290
<211> LENGTH: 25
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 290

```
Glu Val Gln Leu Val Glu Ser Gly Gly Gly Val Lys Lys Pro Gly Gly
1               5                  10                 15

Ser Leu Lys Leu Ser Cys Ala Ala Ser
            20                 25
```

<210> SEQ ID NO 291
<211> LENGTH: 8
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 291

```
Gly Phe Thr Phe Ser Asn Tyr Ala
1               5
```

<210> SEQ ID NO 292
<211> LENGTH: 17
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 292

```
Met Ser Trp Val Arg Gln Thr Pro Gly Lys Gly Leu Glu Trp Val Ala
1               5                   10                  15

Thr

<210> SEQ ID NO 293
<211> LENGTH: 8
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 293

Ile Ser Asn Gly Gly Ser Tyr Thr
1               5

<210> SEQ ID NO 294
<211> LENGTH: 38
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 294

Tyr Tyr Pro Asp Ser Phe Gln Gly Arg Phe Thr Ile Ser Arg Asp Asn
1               5                   10                  15

Ala Lys Ser Thr Leu Ser Leu Gln Met Ser Ser Leu Lys Ala Glu Asp
            20                  25                  30

Thr Ala Met Tyr Tyr Cys
        35

<210> SEQ ID NO 295
<211> LENGTH: 17
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 295

Ser Arg Pro Ser Glu Arg Ser His Tyr Tyr Ala Thr Ser Gln Phe Ala
1               5                   10                  15

Tyr

<210> SEQ ID NO 296
<211> LENGTH: 11
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 296

Trp Gly Gln Gly Thr Leu Val Thr Val Ser Ser
1               5                   10

<210> SEQ ID NO 297
<211> LENGTH: 25
<212> TYPE: PRT
<213> ORGANISM: Artificial Sequence
<220> FEATURE:
<223> OTHER INFORMATION: Description of Artificial Sequence: Synthetic
      peptide
```

<400> SEQUENCE: 297

Glu Val Gln Leu Val Glu Ser Gly Gly Gly Val Lys Lys Pro Gly Gly
1               5                   10                  15

Ser Leu Lys Leu Ser Cys Ala Ala Ser
            20                  25

<210> SEQ ID NO 298
<211> LENGTH: 8
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 298

Gly Phe Thr Phe Ser Asn Tyr Ala
1               5

<210> SEQ ID NO 299
<211> LENGTH: 17
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 299

Met Ser Trp Val Arg Gln Thr Pro Gly Lys Gly Leu Glu Trp Val Ala
1               5                   10                  15

Thr

<210> SEQ ID NO 300
<211> LENGTH: 8
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 300

Ile Ser Gln Gly Gly Ser Tyr Thr
1               5

<210> SEQ ID NO 301
<211> LENGTH: 38
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 301

Tyr Tyr Pro Glu Ser Phe Gln Gly Arg Phe Thr Ile Ser Arg Asp Gln
1               5                   10                  15

Ala Lys Ser Thr Leu Ser Leu Gln Met Ser Ser Leu Lys Ser Glu Asp
            20                  25                  30

Thr Ala Met Tyr Tyr Cys
        35

<210> SEQ ID NO 302
<211> LENGTH: 17
<212> TYPE: PRT
<213> ORGANISM: Artificial Sequence
<220> FEATURE:
<223> OTHER INFORMATION: Description of Artificial Sequence: Synthetic -continued

```
      peptide

<400> SEQUENCE: 302

Ser Arg Pro Ser Glu Arg Ser His Tyr Tyr Ala Thr Ser Gln Phe Ala
1               5                   10                  15

Tyr

<210> SEQ ID NO 303
<211> LENGTH: 11
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 303

Trp Gly Gln Gly Thr Leu Val Thr Val Ser Ala
1               5                   10

<210> SEQ ID NO 304
<211> LENGTH: 25
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 304

Glu Val Gln Leu Leu Glu Ser Gly Gly Gly Leu Val Gln Pro Gly Gly
1               5                   10                  15

Ser Leu Arg Leu Ser Cys Ala Ala Ser
            20                  25

<210> SEQ ID NO 305
<211> LENGTH: 8
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 305

Gly Phe Thr Phe Ser Asn Tyr Ala
1               5

<210> SEQ ID NO 306
<211> LENGTH: 17
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 306

Met Ser Trp Val Arg Gln Ala Pro Gly Lys Gly Leu Glu Trp Val Ala
1               5                   10                  15

Thr

<210> SEQ ID NO 307
<211> LENGTH: 8
<212> TYPE: PRT
<213> ORGANISM: Artificial Sequence
<220> FEATURE:
<223> OTHER INFORMATION: Description of Artificial Sequence: Synthetic
      peptide
```

```
<400> SEQUENCE: 307

Ile Ser Gln Gly Gly Ser Tyr Thr
1               5

<210> SEQ ID NO 308
<211> LENGTH: 38
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 308

Tyr Tyr Pro Asp Ser Val Lys Gly Arg Phe Thr Ile Ser Arg Asp Asn
1               5                   10                  15

Ser Lys Asn Thr Leu Tyr Leu Gln Met Asn Ser Leu Arg Ala Glu Asp
            20                  25                  30

Thr Ala Val Tyr Tyr Cys
        35

<210> SEQ ID NO 309
<211> LENGTH: 17
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 309

Ser Arg Pro Ser Glu Arg Ser His Tyr Tyr Ala Thr Ser Gln Phe Ala
1               5                   10                  15

Tyr

<210> SEQ ID NO 310
<211> LENGTH: 11
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 310

Trp Gly Gln Gly Thr Leu Val Thr Val Ser Ser
1               5                   10

<210> SEQ ID NO 311
<211> LENGTH: 25
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 311

Glu Val Gln Leu Leu Glu Ser Gly Gly Gly Leu Val Gln Pro Gly Gly
1               5                   10                  15

Ser Leu Arg Leu Ser Cys Ala Ala Ser
            20                  25

<210> SEQ ID NO 312
<211> LENGTH: 8
<212> TYPE: PRT
<213> ORGANISM: Artificial Sequence
<220> FEATURE:
<223> OTHER INFORMATION: Description of Artificial Sequence: Synthetic
``` peptide

<400> SEQUENCE: 312

Gly Phe Thr Phe Ser Asn Tyr Ala
1               5

<210> SEQ ID NO 313
<211> LENGTH: 17
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 313

Met Ser Trp Val Arg Gln Ala Pro Gly Lys Gly Leu Glu Trp Val Ala
1               5                   10                  15

Thr

<210> SEQ ID NO 314
<211> LENGTH: 8
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 314

Ile Ser Asn Leu Gly Ser Tyr Thr
1               5

<210> SEQ ID NO 315
<211> LENGTH: 38
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 315

Tyr Tyr Pro Asp Ser Val Lys Gly Arg Phe Thr Ile Ser Arg Asp Asn
1               5                   10                  15

Ser Lys Asn Thr Leu Tyr Leu Gln Met Asn Ser Leu Arg Ala Glu Asp
            20                  25                  30

Thr Ala Val Tyr Tyr Cys
        35

<210> SEQ ID NO 316
<211> LENGTH: 17
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 316

Ser Arg Pro Ser Glu Arg Ser His Tyr Tyr Ala Thr Ser Gln Phe Ala
1               5                   10                  15

Tyr

<210> SEQ ID NO 317
<211> LENGTH: 11
<212> TYPE: PRT
<213> ORGANISM: Artificial Sequence
<220> FEATURE:

```
<223> OTHER INFORMATION: Description of Artificial Sequence: Synthetic
      peptide

<400> SEQUENCE: 317

Trp Gly Gln Gly Thr Leu Val Thr Val Ser Ser
1               5                   10

<210> SEQ ID NO 318
<211> LENGTH: 25
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 318

Glu Val Gln Leu Leu Glu Ser Gly Gly Gly Leu Val Gln Pro Gly Gly
1               5                   10                  15

Ser Leu Arg Leu Ser Cys Ala Ala Ser
            20                  25

<210> SEQ ID NO 319
<211> LENGTH: 8
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 319

Gly Phe Thr Phe Ser Asn Tyr Ala
1               5

<210> SEQ ID NO 320
<211> LENGTH: 17
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 320

Met Ser Trp Val Arg Gln Ala Pro Gly Lys Gly Leu Glu Trp Val Ala
1               5                   10                  15

Thr

<210> SEQ ID NO 321
<211> LENGTH: 8
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 321

Ile Ser Asn Ser Gly Ser Tyr Thr
1               5

<210> SEQ ID NO 322
<211> LENGTH: 38
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 322
```

```
Tyr Tyr Pro Asp Ser Val Lys Gly Arg Phe Thr Ile Ser Arg Asp Asn
1               5                   10                  15

Ser Lys Asn Thr Leu Tyr Leu Gln Met Asn Ser Leu Arg Ala Glu Asp
            20                  25                  30

Thr Ala Val Tyr Tyr Cys
        35

<210> SEQ ID NO 323
<211> LENGTH: 17
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 323

Ser Arg Pro Ser Glu Arg Ser His Tyr Tyr Ala Thr Ser Gln Phe Ala
1               5                   10                  15

Tyr

<210> SEQ ID NO 324
<211> LENGTH: 11
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 324

Trp Gly Gln Gly Thr Leu Val Thr Val Ser Ser
1               5                   10

<210> SEQ ID NO 325
<211> LENGTH: 25
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 325

Glu Val Gln Leu Leu Glu Ser Gly Gly Gly Leu Val Gln Pro Gly Gly
1               5                   10                  15

Ser Leu Arg Leu Ser Cys Ala Ala Ser
            20                  25

<210> SEQ ID NO 326
<211> LENGTH: 8
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 326

Gly Phe Thr Phe Ser Asn Tyr Ala
1               5

<210> SEQ ID NO 327
<211> LENGTH: 17
<212> TYPE: PRT
<213> ORGANISM: Artificial Sequence
<220> FEATURE:
<223> OTHER INFORMATION: Description of Artificial Sequence: Synthetic
      peptide
```

<400> SEQUENCE: 327

Met Ser Trp Val Arg Gln Ala Pro Gly Lys Gly Leu Glu Trp Val Ala
1               5                   10                  15

Thr

<210> SEQ ID NO 328
<211> LENGTH: 8
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 328

Ile Ser Asp Gly Gly Ser Tyr Thr
1               5

<210> SEQ ID NO 329
<211> LENGTH: 38
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 329

Tyr Tyr Pro Asp Ser Val Lys Gly Arg Phe Thr Ile Ser Arg Asp Asn
1               5                   10                  15

Ser Lys Asn Thr Leu Tyr Leu Gln Met Asn Ser Leu Arg Ala Glu Asp
            20                  25                  30

Thr Ala Val Tyr Tyr Cys
        35

<210> SEQ ID NO 330
<211> LENGTH: 17
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 330

Ser Arg Pro Ser Glu Arg Ser His Tyr Tyr Ala Thr Ser Gln Phe Ala
1               5                   10                  15

Tyr

<210> SEQ ID NO 331
<211> LENGTH: 11
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 331

Trp Gly Gln Gly Thr Leu Val Thr Val Ser Ser
1               5                   10

<210> SEQ ID NO 332
<211> LENGTH: 25
<212> TYPE: PRT
<213> ORGANISM: Artificial Sequence
<220> FEATURE:
<223> OTHER INFORMATION: Description of Artificial Sequence: Synthetic -continued

```
      peptide

<400> SEQUENCE: 332

Glu Val Gln Leu Leu Glu Ser Gly Gly Gly Leu Val Gln Pro Gly Gly
1               5                   10                  15

Ser Leu Arg Leu Ser Cys Ala Ala Ser
            20                  25

<210> SEQ ID NO 333
<211> LENGTH: 8
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 333

Gly Phe Thr Phe Ser Asn Tyr Ala
1               5

<210> SEQ ID NO 334
<211> LENGTH: 17
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 334

Met Ser Trp Val Arg Gln Ala Pro Gly Lys Gly Leu Glu Trp Val Ala
1               5                   10                  15

Thr

<210> SEQ ID NO 335
<211> LENGTH: 8
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 335

Ile Ser Asn Val Gly Ser Tyr Thr
1               5

<210> SEQ ID NO 336
<211> LENGTH: 38
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 336

Tyr Tyr Pro Asp Ser Val Lys Gly Arg Phe Thr Ile Ser Arg Asp Asn
1               5                   10                  15

Ser Lys Asn Thr Leu Tyr Leu Gln Met Asn Ser Leu Arg Ala Glu Asp
            20                  25                  30

Thr Ala Val Tyr Tyr Cys
        35

<210> SEQ ID NO 337
<211> LENGTH: 17
<212> TYPE: PRT
<213> ORGANISM: Artificial Sequence
```

<220> FEATURE:
<223> OTHER INFORMATION: Description of Artificial Sequence: Synthetic
      peptide

<400> SEQUENCE: 337

Ser Arg Pro Ser Glu Arg Ser His Tyr Tyr Ala Thr Ser Gln Phe Ala
1               5                   10                  15

Tyr

<210> SEQ ID NO 338
<211> LENGTH: 11
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 338

Trp Gly Gln Gly Thr Leu Val Thr Val Ser Ser
1               5                   10

<210> SEQ ID NO 339
<211> LENGTH: 26
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 339

Asp Ile Val Leu Thr Gln Ser Pro Gly Ser Leu Ser Ala Ser Val Gly
1               5                   10                  15

Asp Arg Val Thr Met Thr Cys Ser Ala Ser
            20                  25

<210> SEQ ID NO 340
<211> LENGTH: 5
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 340

Ser Ser Val Ser Tyr
1               5

<210> SEQ ID NO 341
<211> LENGTH: 17
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 341

Met His Trp Tyr Gln Gln Lys Pro Gly Thr Ser Pro Lys Arg Trp Ile
1               5                   10                  15

Tyr

<210> SEQ ID NO 342
<211> LENGTH: 3
<212> TYPE: PRT
<213> ORGANISM: Artificial Sequence
<220> FEATURE:
<223> OTHER INFORMATION: Description of Artificial Sequence: Synthetic peptide

<400> SEQUENCE: 342

Asp Thr Ser
1

<210> SEQ ID NO 343
<211> LENGTH: 36
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 343

Lys Leu Ala Ser Gly Val Pro Ala Arg Phe Ser Gly Ser Gly Ser Gly
1               5                   10                  15

Thr Ser Tyr Ser Leu Thr Ile Ser Ser Leu Gln Pro Glu Asp Ala Ala
            20                  25                  30

Thr Tyr Tyr Cys
            35

<210> SEQ ID NO 344
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 344

Gln Gln Trp Ser Ser Ser Pro Leu Thr
1               5

<210> SEQ ID NO 345
<211> LENGTH: 10
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 345

Phe Gly Ala Gly Thr Lys Val Glu Leu Lys
1               5                   10

<210> SEQ ID NO 346
<211> LENGTH: 26
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 346

Asp Ile Val Leu Thr Gln Ser Pro Ser Ser Leu Ser Ala Ser Val Gly
1               5                   10                  15

Asp Arg Val Thr Ile Thr Cys Ser Ala Ser
            20                  25

<210> SEQ ID NO 347
<211> LENGTH: 5
<212> TYPE: PRT
<213> ORGANISM: Artificial Sequence
<220> FEATURE:
<223> OTHER INFORMATION: Description of Artificial Sequence: Synthetic

```
                            peptide

<400> SEQUENCE: 347

Ser Ser Val Ser Tyr
1               5

<210> SEQ ID NO 348
<211> LENGTH: 17
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 348

Met His Trp Tyr Gln Gln Lys Pro Gly Thr Ser Pro Lys Arg Trp Ile
1               5                   10                  15

Tyr

<210> SEQ ID NO 349
<211> LENGTH: 3
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 349

Asp Thr Ser
1

<210> SEQ ID NO 350
<211> LENGTH: 36
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 350

Lys Leu Ala Ser Gly Val Pro Ala Arg Phe Ser Gly Ser Gly Ser Gly
1               5                   10                  15

Thr Ser Tyr Ser Leu Thr Ile Ser Ser Leu Gln Pro Glu Asp Ala Ala
            20                  25                  30

Thr Tyr Tyr Cys
        35

<210> SEQ ID NO 351
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 351

Gln Gln Trp Ser Ser Ser Pro Leu Thr
1               5

<210> SEQ ID NO 352
<211> LENGTH: 10
<212> TYPE: PRT
<213> ORGANISM: Artificial Sequence
<220> FEATURE:
<223> OTHER INFORMATION: Description of Artificial Sequence: Synthetic
      peptide
```

```
<400> SEQUENCE: 352

Phe Gly Ala Gly Thr Lys Val Glu Ile Lys
1               5                   10

<210> SEQ ID NO 353
<211> LENGTH: 26
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 353

Asp Ile Val Leu Thr Gln Ser Pro Ser Ser Leu Ser Ala Ser Val Gly
1               5                   10                  15

Asp Arg Val Thr Ile Thr Cys Ser Ala Ser
            20                  25

<210> SEQ ID NO 354
<211> LENGTH: 5
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 354

Ser Ser Val Ser Tyr
1               5

<210> SEQ ID NO 355
<211> LENGTH: 17
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 355

Met His Trp Tyr Gln Gln Lys Pro Gly Gln Ser Pro Lys Arg Trp Ile
1               5                   10                  15

Tyr

<210> SEQ ID NO 356
<211> LENGTH: 3
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 356

Asp Thr Ser
1

<210> SEQ ID NO 357
<211> LENGTH: 36
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 357

Lys Leu Ala Ser Gly Val Pro Ala Arg Phe Ser Gly Ser Gly Ser Gly
```

```
                1               5                  10                  15
Thr Ser Tyr Ser Leu Thr Ile Ser Ser Leu Gln Pro Glu Asp Ala Ala
                20                 25                 30
Thr Tyr Tyr Cys
        35

<210> SEQ ID NO 358
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 358

Gln Gln Trp Ser Ser Ser Pro Leu Thr
1               5

<210> SEQ ID NO 359
<211> LENGTH: 10
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 359

Phe Gly Ala Gly Thr Lys Val Glu Ile Lys
1               5                   10

<210> SEQ ID NO 360
<211> LENGTH: 26
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 360

Asp Ile Gln Leu Thr Gln Ser Pro Gly Ser Leu Ser Ala Ser Val Gly
1               5                   10                  15

Asp Arg Val Thr Met Thr Cys Ser Ala Ser
            20                  25

<210> SEQ ID NO 361
<211> LENGTH: 5
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 361

Ser Ser Val Ser Tyr
1               5

<210> SEQ ID NO 362
<211> LENGTH: 17
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 362

Met His Trp Tyr Gln Gln Lys Pro Gly Thr Ser Pro Lys Arg Trp Ile
```

```
1               5                   10                  15
Tyr

<210> SEQ ID NO 363
<211> LENGTH: 3
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 363

Asp Thr Ser
1

<210> SEQ ID NO 364
<211> LENGTH: 36
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 364

Lys Leu Ala Ser Gly Val Pro Ala Arg Phe Ser Gly Ser Gly Ser Gly
1               5                   10                  15

Thr Ser Tyr Ser Leu Thr Ile Ser Ser Leu Gln Pro Glu Asp Ala Ala
            20                  25                  30

Thr Tyr Tyr Cys
        35

<210> SEQ ID NO 365
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 365

Gln Gln Trp Ser Ser Ser Pro Leu Thr
1               5

<210> SEQ ID NO 366
<211> LENGTH: 10
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 366

Phe Gly Ala Gly Thr Lys Val Glu Leu Lys
1               5                   10

<210> SEQ ID NO 367
<211> LENGTH: 25
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 367

Glu Val Gln Leu Glu Glu Ser Gly Gly Gly Leu Val Lys Pro Gly Gly
1               5                   10                  15
```

Ser Leu Lys Leu Ser Cys Ala Ala Ser
            20                  25

<210> SEQ ID NO 368
<211> LENGTH: 8
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 368

Gly Phe Thr Phe Thr Ser Tyr Ala
1               5

<210> SEQ ID NO 369
<211> LENGTH: 17
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 369

Met Ser Trp Val Arg Gln Thr Pro Glu Lys Arg Leu Glu Trp Val Ala
1               5                   10                  15

Thr

<210> SEQ ID NO 370
<211> LENGTH: 8
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 370

Ile Ser His Gly Gly Thr Tyr Thr
1               5

<210> SEQ ID NO 371
<211> LENGTH: 38
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 371

Tyr Tyr Pro Asp Ser Val Lys Gly Arg Phe Thr Ile Ser Arg Asp Asn
1               5                   10                  15

Ala Lys Asn Thr Leu Tyr Leu Gln Met Ser Ser Leu Arg Ser Glu Asp
            20                  25                  30

Thr Ala Met Tyr Tyr Cys
        35

<210> SEQ ID NO 372
<211> LENGTH: 16
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 372

Ala Arg His Pro Ile Tyr Ser Gly Asn Tyr Gln Gly Tyr Phe Asp Tyr
1               5                   10                  15

<210> SEQ ID NO 373
<211> LENGTH: 11
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 373

Trp Gly Gln Gly Thr Thr Leu Thr Val Ser Ser
1               5                   10

<210> SEQ ID NO 374
<211> LENGTH: 26
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 374

Asp Ile Val Leu Thr Gln Ser Pro Ala Ile Met Ser Ala Ser Leu Gly
1               5                   10                  15

Glu Lys Val Thr Met Ser Cys Arg Ala Ser
            20                  25

<210> SEQ ID NO 375
<211> LENGTH: 5
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 375

Ser Gly Val Asn Tyr
1               5

<210> SEQ ID NO 376
<211> LENGTH: 17
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 376

Ile Tyr Trp Tyr Gln Gln Lys Ser Asp Ala Ser Pro Lys Leu Trp Ile
1               5                   10                  15

Tyr

<210> SEQ ID NO 377
<211> LENGTH: 3
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 377

Phe Thr Ser
1

```
<210> SEQ ID NO 378
<211> LENGTH: 36
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 378

Asn Leu Ala Pro Gly Val Pro Ala Arg Phe Ser Gly Ser Gly Ser Gly
1               5                   10                  15

Asn Ser Tyr Ser Leu Thr Ile Ser Ser Met Glu Gly Glu Asp Ala Ala
            20                  25                  30

Thr Tyr Tyr Cys
            35

<210> SEQ ID NO 379
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 379

Gln Gln Phe Thr Ser Ser Pro Tyr Thr
1               5

<210> SEQ ID NO 380
<211> LENGTH: 10
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 380

Phe Gly Gly Gly Thr Lys Leu Glu Ile Lys
1               5                   10

<210> SEQ ID NO 381
<211> LENGTH: 25
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 381

Glu Val Gln Leu Leu Glu Ser Gly Gly Gly Leu Val Gln Pro Gly Gly
1               5                   10                  15

Ser Leu Arg Leu Ser Cys Ala Ala Ser
            20                  25

<210> SEQ ID NO 382
<211> LENGTH: 8
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 382

Gly Phe Thr Phe Thr Ser Tyr Ala
1               5
```

```
<210> SEQ ID NO 383
<211> LENGTH: 17
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 383

Met Ser Trp Val Arg Gln Ala Pro Gly Lys Gly Leu Glu Trp Val Ala
1               5                   10                  15

Val

<210> SEQ ID NO 384
<211> LENGTH: 8
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 384

Ile Ser His Gly Gly Thr Tyr Thr
1               5

<210> SEQ ID NO 385
<211> LENGTH: 38
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 385

Tyr Tyr Ala Asp Ser Val Lys Gly Arg Phe Thr Ile Ser Arg Asp Asn
1               5                   10                  15

Ala Lys Asn Thr Leu Tyr Leu Gln Met Asn Ser Leu Arg Ala Glu Asp
            20                  25                  30

Thr Ala Val Tyr Tyr Cys
        35

<210> SEQ ID NO 386
<211> LENGTH: 16
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 386

Ala Arg His Pro Ile Tyr Ser Gly Asn Tyr Gln Gly Tyr Phe Asp Tyr
1               5                   10                  15

<210> SEQ ID NO 387
<211> LENGTH: 11
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 387

Trp Gly Gln Gly Thr Leu Val Thr Val Ser Ser
1               5                   10

<210> SEQ ID NO 388
```

```
<211> LENGTH: 26
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 388

Asp Ile Gln Leu Thr Gln Ser Pro Ser Phe Leu Ser Ala Ser Val Gly
1               5                   10                  15

Asp Arg Val Thr Ile Thr Cys Arg Ala Ser
            20                  25

<210> SEQ ID NO 389
<211> LENGTH: 5
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 389

Ser Gly Val Asn Tyr
1               5

<210> SEQ ID NO 390
<211> LENGTH: 17
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 390

Leu Ala Trp Tyr Gln Gln Lys Pro Gly Lys Ala Pro Lys Leu Trp Ile
1               5                   10                  15

Tyr

<210> SEQ ID NO 391
<211> LENGTH: 3
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 391

Phe Thr Ser
1

<210> SEQ ID NO 392
<211> LENGTH: 36
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 392

Thr Leu Gln Ser Gly Val Pro Ser Arg Phe Ser Gly Ser Gly Ser Gly
1               5                   10                  15

Asn Glu Tyr Thr Leu Thr Ile Ser Ser Leu Gln Pro Glu Asp Phe Ala
            20                  25                  30

Thr Tyr Tyr Cys
        35
```

<210> SEQ ID NO 393
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 393

Gln Gln Phe Thr Ser Ser Pro Tyr Thr
1               5

<210> SEQ ID NO 394
<211> LENGTH: 10
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 394

Phe Gly Gln Gly Thr Lys Leu Glu Ile Lys
1               5                   10

<210> SEQ ID NO 395
<211> LENGTH: 25
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 395

Glu Val Gln Leu Leu Glu Ser Gly Gly Gly Leu Val Gln Pro Gly Gly
1               5                   10                  15

Ser Leu Arg Leu Ser Cys Ala Ala Ser
            20                  25

<210> SEQ ID NO 396
<211> LENGTH: 8
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 396

Gly Phe Thr Phe Thr Ser Tyr Ala
1               5

<210> SEQ ID NO 397
<211> LENGTH: 17
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 397

Met Ser Trp Val Arg Gln Ala Pro Gly Lys Gly Leu Glu Trp Val Ala
1               5                   10                  15

Thr

<210> SEQ ID NO 398
<211> LENGTH: 8
<212> TYPE: PRT

```
<213> ORGANISM: Artificial Sequence
<220> FEATURE:
<223> OTHER INFORMATION: Description of Artificial Sequence: Synthetic
      peptide

<400> SEQUENCE: 398

Ile Ser His Gly Gly Thr Tyr Thr
1               5

<210> SEQ ID NO 399
<211> LENGTH: 38
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 399

Tyr Tyr Pro Asp Ser Val Lys Gly Arg Phe Thr Ile Ser Arg Asp Asn
1               5                   10                  15

Ala Lys Asn Thr Leu Tyr Leu Gln Met Asn Ser Leu Arg Ala Glu Asp
            20                  25                  30

Thr Ala Met Tyr Tyr Cys
        35

<210> SEQ ID NO 400
<211> LENGTH: 16
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 400

Ala Arg His Pro Ile Tyr Ser Gly Asn Tyr Gln Gly Tyr Phe Asp Tyr
1               5                   10                  15

<210> SEQ ID NO 401
<211> LENGTH: 11
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 401

Trp Gly Gln Gly Thr Leu Val Thr Val Ser Ser
1               5                   10

<210> SEQ ID NO 402
<211> LENGTH: 26
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 402

Asp Ile Gln Leu Thr Gln Ser Pro Ser Phe Leu Ser Ala Ser Val Gly
1               5                   10                  15

Asp Arg Val Thr Ile Thr Cys Arg Ala Ser
            20                  25

<210> SEQ ID NO 403
<211> LENGTH: 5
<212> TYPE: PRT
```

<213> ORGANISM: Artificial Sequence
<220> FEATURE:
<223> OTHER INFORMATION: Description of Artificial Sequence: Synthetic peptide

<400> SEQUENCE: 403

Ser Gly Val Asn Tyr
1               5

<210> SEQ ID NO 404
<211> LENGTH: 17
<212> TYPE: PRT
<213> ORGANISM: Artificial Sequence
<220> FEATURE:
<223> OTHER INFORMATION: Description of Artificial Sequence: Synthetic peptide

<400> SEQUENCE: 404

Ile Tyr Trp Tyr Gln Gln Lys Pro Gly Lys Ala Pro Lys Leu Trp Ile
1               5                   10                  15

Tyr

<210> SEQ ID NO 405
<211> LENGTH: 3
<212> TYPE: PRT
<213> ORGANISM: Artificial Sequence
<220> FEATURE:
<223> OTHER INFORMATION: Description of Artificial Sequence: Synthetic peptide

<400> SEQUENCE: 405

Phe Thr Ser
1

<210> SEQ ID NO 406
<211> LENGTH: 36
<212> TYPE: PRT
<213> ORGANISM: Artificial Sequence
<220> FEATURE:
<223> OTHER INFORMATION: Description of Artificial Sequence: Synthetic polypeptide

<400> SEQUENCE: 406

Asn Leu Ala Pro Gly Val Pro Ser Arg Phe Ser Gly Ser Gly Ser Gly
1               5                   10                  15

Asn Glu Tyr Thr Leu Thr Ile Ser Ser Leu Gln Pro Glu Asp Phe Ala
                20                  25                  30

Thr Tyr Tyr Cys
            35

<210> SEQ ID NO 407
<211> LENGTH: 9
<212> TYPE: PRT
<213> ORGANISM: Artificial Sequence
<220> FEATURE:
<223> OTHER INFORMATION: Description of Artificial Sequence: Synthetic peptide

<400> SEQUENCE: 407

Gln Gln Phe Thr Ser Ser Pro Tyr Thr
1               5

<210> SEQ ID NO 408
<211> LENGTH: 10
<212> TYPE: PRT
<213> ORGANISM: Artificial Sequence

```
<220> FEATURE:
<223> OTHER INFORMATION: Description of Artificial Sequence: Synthetic
      peptide

<400> SEQUENCE: 408

Phe Gly Gly Gly Thr Lys Leu Glu Ile Lys
1               5                   10

<210> SEQ ID NO 409
<211> LENGTH: 25
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 409

Glu Val Gln Leu Glu Glu Ser Gly Gly Gly Leu Val Gln Pro Gly Gly
1               5                   10                  15

Ser Leu Arg Leu Ser Cys Ala Ala Ser
            20                  25

<210> SEQ ID NO 410
<211> LENGTH: 8
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 410

Gly Phe Thr Phe Thr Ser Tyr Ala
1               5

<210> SEQ ID NO 411
<211> LENGTH: 17
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 411

Met Ser Trp Val Arg Gln Thr Pro Glu Lys Arg Leu Glu Trp Val Ala
1               5                   10                  15

Thr

<210> SEQ ID NO 412
<211> LENGTH: 8
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 412

Ile Ser His Gly Gly Thr Tyr Thr
1               5

<210> SEQ ID NO 413
<211> LENGTH: 38
<212> TYPE: PRT
<213> ORGANISM: Artificial Sequence
<220> FEATURE:
<223> OTHER INFORMATION: Description of Artificial Sequence: Synthetic
      polypeptide
```

```
<400> SEQUENCE: 413

Tyr Tyr Pro Asp Ser Val Lys Gly Arg Phe Thr Ile Ser Arg Asp Asn
1               5                   10                  15

Ala Lys Asn Thr Leu Tyr Leu Gln Met Asn Ser Leu Arg Ala Glu Asp
            20                  25                  30

Thr Ala Met Tyr Tyr Cys
        35

<210> SEQ ID NO 414
<211> LENGTH: 16
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 414

Ala Arg His Pro Ile Tyr Ser Gly Asn Tyr Gln Gly Tyr Phe Asp Tyr
1               5                   10                  15

<210> SEQ ID NO 415
<211> LENGTH: 11
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 415

Trp Gly Gln Gly Thr Thr Val Thr Val Ser Ser
1               5                   10

<210> SEQ ID NO 416
<211> LENGTH: 26
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 416

Asp Ile Gln Leu Thr Gln Ser Pro Ser Phe Leu Ser Ala Ser Val Gly
1               5                   10                  15

Asp Arg Val Thr Ile Thr Cys Arg Ala Ser
            20                  25

<210> SEQ ID NO 417
<211> LENGTH: 5
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 417

Ser Gly Val Asn Tyr
1               5

<210> SEQ ID NO 418
<211> LENGTH: 17
<212> TYPE: PRT
<213> ORGANISM: Artificial Sequence
<220> FEATURE:
<223> OTHER INFORMATION: Description of Artificial Sequence: Synthetic
      peptide
```

```
<400> SEQUENCE: 418

Ile Tyr Trp Tyr Gln Gln Lys Pro Asp Ala Ala Pro Lys Leu Trp Ile
1               5                   10                  15

Tyr

<210> SEQ ID NO 419
<211> LENGTH: 3
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 419

Phe Thr Ser
1

<210> SEQ ID NO 420
<211> LENGTH: 36
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 420

Asn Leu Ala Pro Gly Val Pro Ser Arg Phe Ser Gly Ser Gly Ser Gly
1               5                   10                  15

Asn Ser Tyr Thr Leu Thr Ile Ser Ser Leu Gln Pro Glu Asp Phe Ala
            20                  25                  30

Thr Tyr Tyr Cys
        35

<210> SEQ ID NO 421
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 421

Gln Gln Phe Thr Ser Ser Pro Tyr Thr
1               5

<210> SEQ ID NO 422
<211> LENGTH: 10
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 422

Phe Gly Gly Gly Thr Lys Leu Glu Ile Lys
1               5                   10

<210> SEQ ID NO 423
<211> LENGTH: 25
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 423
```

```
Glu Val Gln Leu Leu Glu Ser Gly Gly Gly Leu Val Gln Pro Gly Gly
1               5                   10                  15

Ser Leu Arg Leu Ser Cys Ala Ala Ser
            20                  25

<210> SEQ ID NO 424
<211> LENGTH: 8
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 424

Gly Phe Thr Phe Thr Ser Tyr Ala
1               5

<210> SEQ ID NO 425
<211> LENGTH: 17
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 425

Met Ser Trp Val Arg Gln Ala Pro Gly Lys Gly Leu Glu Trp Val Ala
1               5                   10                  15

Val

<210> SEQ ID NO 426
<211> LENGTH: 8
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 426

Ile Ser His Gly Gly Thr Tyr Thr
1               5

<210> SEQ ID NO 427
<211> LENGTH: 38
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 427

Tyr Tyr Pro Asp Ser Val Lys Gly Arg Phe Thr Ile Ser Arg Asp Asn
1               5                   10                  15

Ala Lys Asn Thr Leu Tyr Leu Gln Met Asn Ser Leu Arg Ala Glu Asp
            20                  25                  30

Thr Ala Met Tyr Tyr Cys
                35

<210> SEQ ID NO 428
<211> LENGTH: 16
<212> TYPE: PRT
<213> ORGANISM: Artificial Sequence
<220> FEATURE:
<223> OTHER INFORMATION: Description of Artificial Sequence: Synthetic
      peptide
```

```
<400> SEQUENCE: 428

Ala Arg His Pro Ile Tyr Ser Gly Asn Tyr Gln Gly Tyr Phe Asp Tyr
1               5                   10                  15

<210> SEQ ID NO 429
<211> LENGTH: 11
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 429

Trp Gly Gln Gly Thr Leu Val Thr Val Ser Ser
1               5                   10

<210> SEQ ID NO 430
<211> LENGTH: 25
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 430

Glu Val Gln Leu Leu Glu Ser Gly Gly Gly Leu Val Gln Pro Gly Gly
1               5                   10                  15

Ser Leu Arg Leu Ser Cys Ala Ala Ser
            20                  25

<210> SEQ ID NO 431
<211> LENGTH: 8
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 431

Gly Phe Thr Phe Thr Ser Tyr Ala
1               5

<210> SEQ ID NO 432
<211> LENGTH: 17
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 432

Met Ser Trp Val Arg Gln Ala Pro Gly Lys Gly Leu Glu Trp Val Ala
1               5                   10                  15

Thr

<210> SEQ ID NO 433
<211> LENGTH: 8
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 433

Ile Ser His Gly Gly Thr Tyr Thr
1               5
```

<210> SEQ ID NO 434
<211> LENGTH: 38
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 434

Tyr Tyr Ala Asp Ser Val Lys Gly Arg Phe Thr Ile Ser Arg Asp Asn
1               5                   10                  15

Ala Lys Asn Thr Leu Tyr Leu Gln Met Asn Ser Leu Arg Ala Glu Asp
            20                  25                  30

Thr Ala Met Tyr Tyr Cys
        35

<210> SEQ ID NO 435
<211> LENGTH: 16
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 435

Ala Arg His Pro Ile Tyr Ser Gly Asn Tyr Gln Gly Tyr Phe Asp Tyr
1               5                   10                  15

<210> SEQ ID NO 436
<211> LENGTH: 11
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 436

Trp Gly Gln Gly Thr Leu Val Thr Val Ser Ser
1               5                   10

<210> SEQ ID NO 437
<211> LENGTH: 25
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 437

Glu Val Gln Leu Leu Glu Ser Gly Gly Gly Leu Val Gln Pro Gly Gly
1               5                   10                  15

Ser Leu Arg Leu Ser Cys Ala Ala Ser
            20                  25

<210> SEQ ID NO 438
<211> LENGTH: 8
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 438

Gly Phe Thr Phe Thr Ser Tyr Ala

```
<210> SEQ ID NO 439
<211> LENGTH: 17
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 439

Met Ser Trp Val Arg Gln Ala Pro Gly Lys Gly Leu Glu Trp Val Ala
1               5                   10                  15

Thr

<210> SEQ ID NO 440
<211> LENGTH: 8
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 440

Ile Ser His Gly Gly Thr Tyr Thr
1               5

<210> SEQ ID NO 441
<211> LENGTH: 38
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 441

Tyr Tyr Pro Asp Ser Val Lys Gly Arg Phe Thr Ile Ser Arg Asp Asn
1               5                   10                  15

Ala Lys Asn Thr Leu Tyr Leu Gln Met Asn Ser Leu Arg Ala Glu Asp
            20                  25                  30

Thr Ala Val Tyr Tyr Cys
        35

<210> SEQ ID NO 442
<211> LENGTH: 16
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 442

Ala Arg His Pro Ile Tyr Ser Gly Asn Tyr Gln Gly Tyr Phe Asp Tyr
1               5                   10                  15

<210> SEQ ID NO 443
<211> LENGTH: 11
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 443

Trp Gly Gln Gly Thr Leu Val Thr Val Ser Ser
1               5                   10
```

<210> SEQ ID NO 444
<211> LENGTH: 26
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 444

Asp Ile Gln Leu Thr Gln Ser Pro Ser Phe Leu Ser Ala Ser Val Gly
1               5                   10                  15

Asp Arg Val Thr Ile Thr Cys Arg Ala Ser
            20                  25

<210> SEQ ID NO 445
<211> LENGTH: 5
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 445

Ser Gly Val Asn Tyr
1               5

<210> SEQ ID NO 446
<211> LENGTH: 17
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 446

Leu Tyr Trp Tyr Gln Gln Lys Pro Gly Lys Ala Pro Lys Leu Trp Ile
1               5                   10                  15

Tyr

<210> SEQ ID NO 447
<211> LENGTH: 3
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 447

Phe Thr Ser
1

<210> SEQ ID NO 448
<211> LENGTH: 36
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 448

Asn Leu Ala Pro Gly Val Pro Ser Arg Phe Ser Gly Ser Gly Ser Gly
1               5                   10                  15

Asn Glu Tyr Thr Leu Thr Ile Ser Ser Leu Gln Pro Glu Asp Phe Ala
            20                  25                  30

Thr Tyr Tyr Cys
        35

<210> SEQ ID NO 449
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 449

Gln Gln Phe Thr Ser Ser Pro Tyr Thr
1               5

<210> SEQ ID NO 450
<211> LENGTH: 10
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 450

Phe Gly Gly Gly Thr Lys Leu Glu Ile Lys
1               5                   10

<210> SEQ ID NO 451
<211> LENGTH: 26
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 451

Asp Ile Gln Leu Thr Gln Ser Pro Ser Phe Leu Ser Ala Ser Val Gly
1               5                   10                  15

Asp Arg Val Thr Ile Thr Cys Arg Ala Ser
            20                  25

<210> SEQ ID NO 452
<211> LENGTH: 5
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 452

Ser Gly Val Asn Tyr
1               5

<210> SEQ ID NO 453
<211> LENGTH: 17
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 453

Ile Ala Trp Tyr Gln Gln Lys Pro Gly Lys Ala Pro Lys Leu Trp Ile
1               5                   10                  15

Tyr

```
<210> SEQ ID NO 454
<211> LENGTH: 3
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 454

Phe Thr Ser
1

<210> SEQ ID NO 455
<211> LENGTH: 36
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 455

Asn Leu Ala Pro Gly Val Pro Ser Arg Phe Ser Gly Ser Gly Ser Gly
1               5                   10                  15

Asn Glu Tyr Thr Leu Thr Ile Ser Ser Leu Gln Pro Glu Asp Phe Ala
            20                  25                  30

Thr Tyr Tyr Cys
        35

<210> SEQ ID NO 456
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 456

Gln Gln Phe Thr Ser Ser Pro Tyr Thr
1               5

<210> SEQ ID NO 457
<211> LENGTH: 10
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 457

Phe Gly Gly Gly Thr Lys Leu Glu Ile Lys
1               5                   10

<210> SEQ ID NO 458
<211> LENGTH: 26
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 458

Asp Ile Gln Leu Thr Gln Ser Pro Ser Phe Leu Ser Ala Ser Val Gly
1               5                   10                  15

Asp Arg Val Thr Ile Thr Cys Arg Ala Ser
            20                  25
```

```
<210> SEQ ID NO 459
<211> LENGTH: 5
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 459

Ser Gly Val Asn Tyr
1               5

<210> SEQ ID NO 460
<211> LENGTH: 17
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 460

Ile Tyr Trp Tyr Gln Gln Lys Pro Gly Lys Ala Pro Lys Leu Trp Ile
1               5                   10                  15

Tyr

<210> SEQ ID NO 461
<211> LENGTH: 3
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 461

Phe Thr Ser
1

<210> SEQ ID NO 462
<211> LENGTH: 36
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 462

Thr Leu Ala Pro Gly Val Pro Ser Arg Phe Ser Gly Ser Gly Ser Gly
1               5                   10                  15

Asn Glu Tyr Thr Leu Thr Ile Ser Ser Leu Gln Pro Glu Asp Phe Ala
                20                  25                  30

Thr Tyr Tyr Cys
        35

<210> SEQ ID NO 463
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 463

Gln Gln Phe Thr Ser Ser Pro Tyr Thr
1               5

<210> SEQ ID NO 464
```

```
<211> LENGTH: 10
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 464

Phe Gly Gly Gly Thr Lys Leu Glu Ile Lys
1               5                   10

<210> SEQ ID NO 465
<211> LENGTH: 26
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 465

Asp Ile Gln Leu Thr Gln Ser Pro Ser Phe Leu Ser Ala Ser Val Gly
1               5                   10                  15
Asp Arg Val Thr Ile Thr Cys Arg Ala Ser
            20                  25

<210> SEQ ID NO 466
<211> LENGTH: 5
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 466

Ser Gly Val Asn Tyr
1               5

<210> SEQ ID NO 467
<211> LENGTH: 17
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 467

Ile Tyr Trp Tyr Gln Gln Lys Pro Gly Lys Ala Pro Lys Leu Trp Ile
1               5                   10                  15
Tyr

<210> SEQ ID NO 468
<211> LENGTH: 3
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 468

Phe Thr Ser
1

<210> SEQ ID NO 469
<211> LENGTH: 36
<212> TYPE: PRT
<213> ORGANISM: Artificial Sequence
<220> FEATURE:
```

<223> OTHER INFORMATION: Description of Artificial Sequence: Synthetic
      polypeptide

<400> SEQUENCE: 469

Asn Leu Gln Pro Gly Val Pro Ser Arg Phe Ser Gly Ser Gly Ser Gly
1               5                   10                  15

Asn Glu Tyr Thr Leu Thr Ile Ser Ser Leu Gln Pro Glu Asp Phe Ala
            20                  25                  30

Thr Tyr Tyr Cys
        35

<210> SEQ ID NO 470
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 470

Gln Gln Phe Thr Ser Ser Pro Tyr Thr
1               5

<210> SEQ ID NO 471
<211> LENGTH: 10
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 471

Phe Gly Gly Gly Thr Lys Leu Glu Ile Lys
1               5                   10

<210> SEQ ID NO 472
<211> LENGTH: 26
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 472

Asp Ile Gln Leu Thr Gln Ser Pro Ser Phe Leu Ser Ala Ser Val Gly
1               5                   10                  15

Asp Arg Val Thr Ile Thr Cys Arg Ala Ser
            20                  25

<210> SEQ ID NO 473
<211> LENGTH: 5
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 473

Ser Gly Val Asn Tyr
1               5

<210> SEQ ID NO 474
<211> LENGTH: 17
<212> TYPE: PRT
<213> ORGANISM: Artificial Sequence
<220> FEATURE:

<223> OTHER INFORMATION: Description of Artificial Sequence: Synthetic
      peptide

<400> SEQUENCE: 474

Ile Tyr Trp Tyr Gln Gln Lys Pro Gly Lys Ala Pro Lys Leu Trp Ile
1               5                   10                  15
Tyr

<210> SEQ ID NO 475
<211> LENGTH: 3
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 475

Phe Thr Ser
1

<210> SEQ ID NO 476
<211> LENGTH: 36
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 476

Asn Leu Ala Ser Gly Val Pro Ser Arg Phe Ser Gly Ser Gly Ser Gly
1               5                   10                  15

Asn Glu Tyr Thr Leu Thr Ile Ser Ser Leu Gln Pro Glu Asp Phe Ala
            20                  25                  30

Thr Tyr Tyr Cys
        35

<210> SEQ ID NO 477
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 477

Gln Gln Phe Thr Ser Ser Pro Tyr Thr
1               5

<210> SEQ ID NO 478
<211> LENGTH: 10
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 478

Phe Gly Gly Gly Thr Lys Leu Glu Ile Lys
1               5                   10

<210> SEQ ID NO 479
<211> LENGTH: 26
<212> TYPE: PRT
<213> ORGANISM: Artificial Sequence
<220> FEATURE:
<223> OTHER INFORMATION: Description of Artificial Sequence: Synthetic peptide

<400> SEQUENCE: 479

Asp Ile Gln Leu Thr Gln Ser Pro Ser Phe Leu Ser Ala Ser Val Gly
1               5                   10                  15

Asp Arg Val Thr Ile Thr Cys Arg Ala Ser
            20                  25

<210> SEQ ID NO 480
<211> LENGTH: 5
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 480

Ser Gly Val Asn Tyr
1               5

<210> SEQ ID NO 481
<211> LENGTH: 17
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 481

Ile Tyr Trp Tyr Gln Gln Lys Pro Gly Lys Ala Pro Lys Leu Trp Ile
1               5                   10                  15

Tyr

<210> SEQ ID NO 482
<211> LENGTH: 3
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 482

Phe Thr Ser
1

<210> SEQ ID NO 483
<211> LENGTH: 36
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 483

Asn Leu Ala Pro Gly Val Pro Ser Arg Phe Ser Gly Ser Gly Ser Gly
1               5                   10                  15

Asn Glu Tyr Thr Leu Thr Ile Ser Ser Leu Gln Pro Glu Asp Phe Ala
            20                  25                  30

Thr Tyr Tyr Cys
        35

<210> SEQ ID NO 484
<211> LENGTH: 9
<212> TYPE: PRT
<213> ORGANISM: Artificial Sequence

```
<220> FEATURE:
<223> OTHER INFORMATION: Description of Artificial Sequence: Synthetic
      peptide

<400> SEQUENCE: 484

Gln Gln Phe Thr Ser Ser Pro Tyr Thr
1               5

<210> SEQ ID NO 485
<211> LENGTH: 10
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 485

Phe Gly Gln Gly Thr Lys Leu Glu Ile Lys
1               5                   10

<210> SEQ ID NO 486
<211> LENGTH: 25
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 486

Glu Val Gln Leu Leu Glu Ser Gly Gly Gly Leu Val Gln Pro Gly Gly
1               5                   10                  15

Ser Leu Lys Leu Ser Cys Ala Ala Ser
            20                  25

<210> SEQ ID NO 487
<211> LENGTH: 8
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 487

Gly Phe Thr Phe Thr Ser Tyr Ala
1               5

<210> SEQ ID NO 488
<211> LENGTH: 17
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 488

Met Ser Trp Val Arg Gln Thr Pro Gly Lys Arg Leu Glu Trp Val Ala
1               5                   10                  15

Thr

<210> SEQ ID NO 489
<211> LENGTH: 8
<212> TYPE: PRT
<213> ORGANISM: Artificial Sequence
<220> FEATURE:
<223> OTHER INFORMATION: Description of Artificial Sequence: Synthetic
      peptide
```

```
<400> SEQUENCE: 489

Ile Ser His Gly Gly Thr Tyr Thr
1               5

<210> SEQ ID NO 490
<211> LENGTH: 38
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 490

Tyr Tyr Pro Asp Ser Val Lys Gly Arg Phe Thr Ile Ser Arg Asp Asn
1               5                   10                  15

Ser Lys Asn Thr Leu Tyr Leu Gln Met Ser Ser Leu Arg Ser Glu Asp
            20                  25                  30

Thr Ala Met Tyr Tyr Cys
        35

<210> SEQ ID NO 491
<211> LENGTH: 16
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 491

Ala Arg His Pro Ile Tyr Ser Gly Asn Tyr Gln Gly Tyr Phe Asp Tyr
1               5                   10                  15

<210> SEQ ID NO 492
<211> LENGTH: 11
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 492

Trp Gly Gln Gly Thr Thr Leu Thr Val Ser Ser
1               5                   10

<210> SEQ ID NO 493
<211> LENGTH: 25
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 493

Glu Val Gln Leu Leu Glu Ser Gly Gly Gly Leu Val Gln Pro Gly Gly
1               5                   10                  15

Ser Leu Lys Leu Ser Cys Ala Ala Ser
            20                  25

<210> SEQ ID NO 494
<211> LENGTH: 8
<212> TYPE: PRT
<213> ORGANISM: Artificial Sequence
<220> FEATURE:
<223> OTHER INFORMATION: Description of Artificial Sequence: Synthetic
      peptide
```

```
<400> SEQUENCE: 494

Gly Phe Thr Phe Thr Ser Tyr Ala
1               5

<210> SEQ ID NO 495
<211> LENGTH: 17
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 495

Met Ser Trp Val Arg Gln Ala Pro Gly Lys Gly Leu Glu Trp Val Ala
1               5                   10                  15

Thr

<210> SEQ ID NO 496
<211> LENGTH: 8
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 496

Ile Ser His Gly Gly Thr Tyr Thr
1               5

<210> SEQ ID NO 497
<211> LENGTH: 38
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 497

Tyr Tyr Pro Asp Ser Val Lys Gly Arg Phe Thr Ile Ser Arg Asp Asn
1               5                   10                  15

Ser Lys Asn Thr Leu Tyr Leu Gln Met Ser Ser Leu Arg Ala Glu Asp
            20                  25                  30

Thr Ala Val Tyr Tyr Cys
        35

<210> SEQ ID NO 498
<211> LENGTH: 16
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 498

Ala Arg His Pro Ile Tyr Ser Gly Asn Tyr Gln Gly Tyr Phe Asp Tyr
1               5                   10                  15

<210> SEQ ID NO 499
<211> LENGTH: 11
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 499
```

-continued

```
Trp Gly Gln Gly Thr Leu Val Thr Val Ser Ser
1               5                   10

<210> SEQ ID NO 500
<211> LENGTH: 25
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 500

Glu Val Gln Leu Leu Glu Ser Gly Gly Gly Leu Val Gln Pro Gly Gly
1               5                   10                  15

Ser Leu Lys Leu Ser Cys Ala Ala Ser
            20                  25

<210> SEQ ID NO 501
<211> LENGTH: 8
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 501

Gly Phe Thr Phe Thr Ser Tyr Ala
1               5

<210> SEQ ID NO 502
<211> LENGTH: 17
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 502

Met Ser Trp Val Arg Gln Thr Pro Gly Lys Arg Leu Glu Trp Val Ala
1               5                   10                  15

Thr

<210> SEQ ID NO 503
<211> LENGTH: 8
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 503

Ile Ser His Gly Gly Thr Tyr Thr
1               5

<210> SEQ ID NO 504
<211> LENGTH: 38
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 504

Tyr Tyr Pro Glu Ser Val Lys Gly Arg Phe Thr Ile Ser Arg Asp Gln
1               5                   10                  15
```

Ser Lys Asn Thr Leu Tyr Leu Gln Met Ser Ser Leu Arg Ser Glu Asp
            20                  25                  30

Thr Ala Val Tyr Tyr Cys
        35

<210> SEQ ID NO 505
<211> LENGTH: 16
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 505

Ala Arg His Pro Ile Tyr Ser Gly Asn Tyr Gln Gly Tyr Phe Asp Tyr
1               5                   10                  15

<210> SEQ ID NO 506
<211> LENGTH: 11
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 506

Trp Gly Gln Gly Thr Thr Leu Thr Val Ser Ser
1               5                   10

<210> SEQ ID NO 507
<211> LENGTH: 25
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 507

Glu Val Gln Leu Leu Glu Ser Gly Gly Gly Leu Val Gln Pro Gly Gly
1               5                   10                  15

Ser Leu Lys Leu Ser Cys Ala Ala Ser
            20                  25

<210> SEQ ID NO 508
<211> LENGTH: 8
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 508

Gly Phe Thr Phe Thr Ser Tyr Ala
1               5

<210> SEQ ID NO 509
<211> LENGTH: 17
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 509

Met Ser Trp Val Arg Gln Ala Pro Gly Lys Gly Leu Glu Trp Val Ala
1               5                   10                  15

Thr

```
<210> SEQ ID NO 510
<211> LENGTH: 8
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 510

Ile Ser His Gly Gly Thr Tyr Thr
1               5

<210> SEQ ID NO 511
<211> LENGTH: 38
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 511

Tyr Tyr Pro Glu Ser Val Lys Gly Arg Phe Thr Ile Ser Arg Asp Gln
1               5                   10                  15

Ser Lys Asn Thr Leu Tyr Leu Gln Met Ser Ser Leu Arg Ala Glu Asp
            20                  25                  30

Thr Ala Val Tyr Tyr Cys
        35

<210> SEQ ID NO 512
<211> LENGTH: 16
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 512

Ala Arg His Pro Ile Tyr Ser Gly Asn Tyr Gln Gly Tyr Phe Asp Tyr
1               5                   10                  15

<210> SEQ ID NO 513
<211> LENGTH: 11
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 513

Trp Gly Gln Gly Thr Leu Val Thr Val Ser Ser
1               5                   10

<210> SEQ ID NO 514
<211> LENGTH: 26
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 514

Asp Ile Gln Leu Thr Gln Ser Pro Ala Ile Met Ser Ala Ser Val Gly
1               5                   10                  15

Asp Arg Val Thr Met Ser Cys Arg Ala Ser
```

```
<210> SEQ ID NO 515
<211> LENGTH: 5
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 515

Ser Gly Val Asn Tyr
1               5

<210> SEQ ID NO 516
<211> LENGTH: 17
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 516

Ile Tyr Trp Tyr Gln Gln Lys Pro Gly Ala Ser Pro Lys Leu Trp Ile
1               5                   10                  15

Tyr

<210> SEQ ID NO 517
<211> LENGTH: 3
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 517

Phe Thr Ser
1

<210> SEQ ID NO 518
<211> LENGTH: 36
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 518

Asn Leu Ala Pro Gly Val Pro Ala Arg Phe Ser Gly Ser Gly Ser Gly
1               5                   10                  15

Asn Ser Tyr Ser Leu Thr Ile Ser Ser Met Gln Gly Glu Asp Ala Ala
                20                  25                  30

Thr Tyr Tyr Cys
            35

<210> SEQ ID NO 519
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 519

Gln Gln Phe Thr Ser Ser Pro Tyr Thr
1               5
```

<210> SEQ ID NO 520
<211> LENGTH: 10
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 520

Phe Gly Gly Gly Thr Lys Leu Glu Ile Lys
1               5                   10

<210> SEQ ID NO 521
<211> LENGTH: 26
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 521

Asp Ile Gln Leu Thr Gln Ser Pro Ala Ile Leu Ser Ala Ser Val Gly
1               5                   10                  15

Asp Arg Val Thr Ile Ser Cys Arg Ala Ser
            20                  25

<210> SEQ ID NO 522
<211> LENGTH: 5
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 522

Ser Gly Val Asn Tyr
1               5

<210> SEQ ID NO 523
<211> LENGTH: 17
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 523

Ile Tyr Trp Tyr Gln Gln Lys Pro Gly Gln Ser Pro Lys Leu Trp Ile
1               5                   10                  15

Tyr

<210> SEQ ID NO 524
<211> LENGTH: 3
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 524

Phe Thr Ser
1

<210> SEQ ID NO 525
<211> LENGTH: 36

```
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 525

Asn Leu Ala Pro Gly Val Pro Ala Arg Phe Ser Gly Ser Gly Ser Gly
1               5                   10                  15

Asn Ser Tyr Ser Leu Thr Ile Ser Ser Met Gln Gly Glu Asp Ala Ala
            20                  25                  30

Thr Tyr Tyr Cys
        35

<210> SEQ ID NO 526
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 526

Gln Gln Phe Thr Ser Ser Pro Tyr Thr
1               5

<210> SEQ ID NO 527
<211> LENGTH: 10
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 527

Phe Gly Gly Gly Thr Lys Leu Glu Ile Lys
1               5                   10

<210> SEQ ID NO 528
<211> LENGTH: 26
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 528

Asp Ile Gln Leu Thr Gln Ser Pro Ala Ile Leu Ser Ala Ser Val Gly
1               5                   10                  15

Asp Arg Val Thr Met Ser Cys Arg Ala Ser
            20                  25

<210> SEQ ID NO 529
<211> LENGTH: 5
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 529

Ser Gly Val Asn Tyr
1               5

<210> SEQ ID NO 530
<211> LENGTH: 17
```

```
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 530

Ile Tyr Trp Tyr Gln Gln Lys Pro Gly Ala Ser Pro Lys Leu Trp Ile
1               5                   10                  15

Tyr

<210> SEQ ID NO 531
<211> LENGTH: 3
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 531

Phe Thr Ser
1

<210> SEQ ID NO 532
<211> LENGTH: 36
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 532

Asn Leu Ala Pro Gly Val Pro Ala Arg Phe Ser Gly Ser Gly Ser Gly
1               5                   10                  15

Asn Ser Tyr Ser Leu Thr Ile Ser Ser Met Gln Gly Glu Asp Ala Ala
            20                  25                  30

Thr Tyr Tyr Cys
        35

<210> SEQ ID NO 533
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 533

Gln Gln Phe Thr Ser Ser Pro Tyr Thr
1               5

<210> SEQ ID NO 534
<211> LENGTH: 10
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 534

Phe Gly Gly Gly Thr Lys Leu Glu Ile Lys
1               5                   10

<210> SEQ ID NO 535
<211> LENGTH: 26
<212> TYPE: PRT
```

<213> ORGANISM: Artificial Sequence
<220> FEATURE:
<223> OTHER INFORMATION: Description of Artificial Sequence: Synthetic
      peptide

<400> SEQUENCE: 535

Asp Ile Gln Leu Thr Gln Ser Pro Ala Ile Leu Ser Ala Ser Val Gly
1               5                   10                  15
Asp Arg Val Thr Ile Ser Cys Arg Ala Ser
            20                  25

<210> SEQ ID NO 536
<211> LENGTH: 5
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 536

Ser Gly Val Asn Tyr
1               5

<210> SEQ ID NO 537
<211> LENGTH: 17
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 537

Ile Tyr Trp Tyr Gln Gln Lys Pro Gly Gln Ser Pro Lys Leu Trp Ile
1               5                   10                  15
Tyr

<210> SEQ ID NO 538
<211> LENGTH: 3
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 538

Phe Thr Ser
1

<210> SEQ ID NO 539
<211> LENGTH: 36
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 539

Asn Leu Ala Pro Gly Val Pro Ala Arg Phe Ser Gly Ser Gly Ser Gly
1               5                   10                  15
Asn Ser Tyr Ser Leu Thr Ile Ser Ser Met Gln Gly Glu Asp Ala Ala
            20                  25                  30
Thr Tyr Tyr Cys
        35

<210> SEQ ID NO 540

```
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 540

Gln Gln Phe Thr Ser Ser Pro Tyr Thr
1               5

<210> SEQ ID NO 541
<211> LENGTH: 10
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 541

Phe Gly Gly Gly Thr Lys Leu Glu Ile Lys
1               5                   10

<210> SEQ ID NO 542
<211> LENGTH: 25
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 542

Glu Val Lys Leu Glu Glu Ser Gly Pro Glu Val Val Arg Pro Gly Val
1               5                   10                  15

Ser Val Lys Ile Ser Cys Lys Gly Ser
            20                  25

<210> SEQ ID NO 543
<211> LENGTH: 8
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 543

Gly Tyr Thr Phe Thr Asp Tyr Ala
1               5

<210> SEQ ID NO 544
<211> LENGTH: 17
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 544

Met His Trp Val Lys Gln Ser His Ala Lys Ser Leu Glu Trp Ile Gly
1               5                   10                  15

Val

<210> SEQ ID NO 545
<211> LENGTH: 8
<212> TYPE: PRT
<213> ORGANISM: Artificial Sequence
<220> FEATURE:
```

<223> OTHER INFORMATION: Description of Artificial Sequence: Synthetic
      peptide

<400> SEQUENCE: 545

Ile Ser Thr Tyr Asn Gly Asn Thr
1               5

<210> SEQ ID NO 546
<211> LENGTH: 38
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 546

Lys Tyr Asn Gln Lys Phe Lys Gly Lys Ala Thr Met Thr Val Asp Lys
1               5                   10                  15

Ser Ser Ser Thr Ala Tyr Met Glu Leu Ala Arg Leu Thr Ser Glu Asp
            20                  25                  30

Ser Ala Ile Tyr Tyr Cys
        35

<210> SEQ ID NO 547
<211> LENGTH: 11
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 547

Ala Arg Phe Leu Ser Leu Arg Tyr Phe Asp Val
1               5                   10

<210> SEQ ID NO 548
<211> LENGTH: 11
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 548

Trp Gly Ala Gly Thr Thr Val Thr Val Ser Ser
1               5                   10

<210> SEQ ID NO 549
<211> LENGTH: 26
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 549

Asp Ile Val Leu Thr Gln Ser Pro Ala Ile Leu Ser Ala Pro Pro Gly
1               5                   10                  15

Glu Lys Val Thr Met Thr Cys Arg Ala Ser
            20                  25

<210> SEQ ID NO 550
<211> LENGTH: 5
<212> TYPE: PRT
<213> ORGANISM: Artificial Sequence
<220> FEATURE:

<223> OTHER INFORMATION: Description of Artificial Sequence: Synthetic
      peptide

<400> SEQUENCE: 550

Ser Ser Val Ile Tyr
1               5

<210> SEQ ID NO 551
<211> LENGTH: 17
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 551

Met Tyr Trp Tyr Gln Gln Lys Pro Gly Ser Ser Pro Lys Pro Trp Ile
1               5                   10                  15

Tyr

<210> SEQ ID NO 552
<211> LENGTH: 3
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 552

Ala Thr Ser
1

<210> SEQ ID NO 553
<211> LENGTH: 36
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 553

Lys Leu Ala Ser Gly Val Pro Val Arg Phe Ser Gly Ser Gly Ser Gly
1               5                   10                  15

Thr Ser Tyr Ser Leu Thr Ile Ser Arg Val Glu Ala Glu Asp Val Ala
            20                  25                  30

Thr Tyr Tyr Cys
        35

<210> SEQ ID NO 554
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 554

Gln Gln Trp Ser Ser Glu Pro Leu Thr
1               5

<210> SEQ ID NO 555
<211> LENGTH: 10
<212> TYPE: PRT
<213> ORGANISM: Artificial Sequence
<220> FEATURE:
<223> OTHER INFORMATION: Description of Artificial Sequence: Synthetic -continued peptide

<400> SEQUENCE: 555

Phe Gly Ala Gly Thr Lys Leu Glu Leu Lys
1               5                   10

<210> SEQ ID NO 556
<211> LENGTH: 25
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 556

Gln Val Lys Leu Val Gln Ser Gly Ala Glu Val Lys Lys Pro Gly Ala
1               5                   10                  15

Ser Val Lys Val Ser Cys Lys Ala Ser
            20                  25

<210> SEQ ID NO 557
<211> LENGTH: 8
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 557

Gly Tyr Thr Phe Thr Asp Tyr Ala
1               5

<210> SEQ ID NO 558
<211> LENGTH: 17
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 558

Met His Trp Val Arg Gln Ala Pro Gly Gln Arg Leu Glu Trp Ile Gly
1               5                   10                  15

Trp

<210> SEQ ID NO 559
<211> LENGTH: 8
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 559

Ile Ser Thr Tyr Asn Gly Asn Thr
1               5

<210> SEQ ID NO 560
<211> LENGTH: 38
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 560

```
Lys Tyr Ser Gln Lys Phe Gln Gly Arg Ala Thr Met Thr Val Asp Lys
1               5                   10                  15

Ser Ala Ser Thr Ala Tyr Met Glu Leu Ser Ser Leu Arg Ser Glu Asp
                20                  25                  30

Thr Ala Val Tyr Tyr Cys
            35

<210> SEQ ID NO 561
<211> LENGTH: 11
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 561

Ala Arg Phe Leu Ser Leu Arg Tyr Phe Asp Val
1               5                   10

<210> SEQ ID NO 562
<211> LENGTH: 11
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 562

Trp Gly Lys Gly Thr Thr Val Thr Val Ser Ser
1               5                   10

<210> SEQ ID NO 563
<211> LENGTH: 26
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 563

Asp Ile Gln Leu Thr Gln Ser Pro Ser Phe Leu Ser Ala Ser Val Gly
1               5                   10                  15

Asp Arg Val Thr Ile Thr Cys Arg Ala Ser
                20                  25

<210> SEQ ID NO 564
<211> LENGTH: 5
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 564

Ser Ser Val Ile Tyr
1               5

<210> SEQ ID NO 565
<211> LENGTH: 17
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 565
```

```
Leu Ala Trp Tyr Gln Gln Lys Pro Gly Lys Ala Pro Lys Pro Trp Ile
1               5                   10                  15

Tyr

<210> SEQ ID NO 566
<211> LENGTH: 3
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 566

Ala Thr Ser
1

<210> SEQ ID NO 567
<211> LENGTH: 36
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 567

Thr Leu Gln Ser Gly Val Pro Ser Arg Phe Ser Gly Ser Gly Ser Gly
1               5                   10                  15

Thr Glu Tyr Thr Leu Thr Ile Ser Ser Leu Gln Pro Glu Asp Phe Ala
            20                  25                  30

Thr Tyr Tyr Cys
        35

<210> SEQ ID NO 568
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 568

Gln Gln Trp Ser Ser Glu Pro Leu Thr
1               5

<210> SEQ ID NO 569
<211> LENGTH: 10
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 569

Phe Gly Gly Gly Thr Lys Val Glu Ile Lys
1               5                   10

<210> SEQ ID NO 570
<211> LENGTH: 25
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 570

Gln Val Lys Leu Val Gln Ser Gly Ala Glu Val Lys Lys Pro Gly Ala
1               5                   10                  15
```

```
                1               5                   10                  15
Ser Val Lys Val Ser Cys Lys Gly Ser
            20                  25

<210> SEQ ID NO 571
<211> LENGTH: 8
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 571

Gly Tyr Thr Phe Thr Asp Tyr Ala
1               5

<210> SEQ ID NO 572
<211> LENGTH: 17
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 572

Met His Trp Val Arg Gln Ala Pro Gly Gln Arg Leu Glu Trp Ile Gly
1               5                   10                  15

Val

<210> SEQ ID NO 573
<211> LENGTH: 8
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 573

Ile Ser Thr Tyr Asn Gly Asn Thr
1               5

<210> SEQ ID NO 574
<211> LENGTH: 38
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 574

Lys Tyr Asn Gln Lys Phe Gln Gly Arg Ala Thr Met Thr Val Asp Lys
1               5                   10                  15

Ser Ala Ser Thr Ala Tyr Met Glu Leu Ser Ser Leu Arg Ser Glu Asp
            20                  25                  30

Thr Ala Ile Tyr Tyr Cys
        35

<210> SEQ ID NO 575
<211> LENGTH: 11
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 575
```

Ala Arg Phe Leu Ser Leu Arg Tyr Phe Asp Val
1               5                   10

<210> SEQ ID NO 576
<211> LENGTH: 11
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 576

Trp Gly Ala Gly Thr Thr Val Thr Val Ser Ser
1               5                   10

<210> SEQ ID NO 577
<211> LENGTH: 26
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 577

Asp Ile Gln Leu Thr Gln Ser Pro Ser Phe Leu Ser Ala Ser Val Gly
1               5                   10                  15

Asp Arg Val Thr Ile Thr Cys Arg Ala Ser
            20                  25

<210> SEQ ID NO 578
<211> LENGTH: 5
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 578

Ser Ser Val Ile Tyr
1               5

<210> SEQ ID NO 579
<211> LENGTH: 17
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 579

Met Tyr Trp Tyr Gln Gln Lys Pro Gly Lys Ala Pro Lys Pro Trp Ile
1               5                   10                  15

Tyr

<210> SEQ ID NO 580
<211> LENGTH: 3
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 580

Ala Thr Ser
1

```
<210> SEQ ID NO 581
<211> LENGTH: 36
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 581

Lys Leu Ala Ser Gly Val Pro Ser Arg Phe Ser Gly Ser Gly Ser Gly
1               5                   10                  15

Thr Glu Tyr Thr Leu Thr Ile Ser Ser Leu Gln Pro Glu Asp Phe Ala
            20                  25                  30

Thr Tyr Tyr Cys
        35

<210> SEQ ID NO 582
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 582

Gln Gln Trp Ser Ser Glu Pro Leu Thr
1               5

<210> SEQ ID NO 583
<211> LENGTH: 10
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 583

Phe Gly Ala Gly Thr Lys Val Glu Ile Lys
1               5                   10

<210> SEQ ID NO 584
<211> LENGTH: 25
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 584

Gln Val Lys Leu Val Gln Ser Gly Pro Glu Val Lys Val Pro Gly Ala
1               5                   10                  15

Ser Val Lys Val Ser Cys Lys Gly Ser
            20                  25

<210> SEQ ID NO 585
<211> LENGTH: 8
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 585

Gly Tyr Thr Phe Thr Asp Tyr Ala
1               5
```

<210> SEQ ID NO 586
<211> LENGTH: 17
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 586

Met His Trp Val Arg Gln Ala Pro Gly Gln Ser Leu Glu Trp Ile Gly
1               5                   10                  15

Val

<210> SEQ ID NO 587
<211> LENGTH: 8
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 587

Ile Ser Thr Tyr Asn Gly Asn Thr
1               5

<210> SEQ ID NO 588
<211> LENGTH: 38
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 588

Lys Tyr Asn Gln Lys Phe Gln Gly Arg Ala Thr Met Thr Val Asp Lys
1               5                   10                  15

Ser Ala Ser Thr Ala Tyr Met Glu Leu Ser Arg Leu Arg Ser Glu Asp
            20                  25                  30

Thr Ala Ile Tyr Tyr Cys
        35

<210> SEQ ID NO 589
<211> LENGTH: 11
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 589

Ala Arg Phe Leu Ser Leu Arg Tyr Phe Asp Val
1               5                   10

<210> SEQ ID NO 590
<211> LENGTH: 11
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 590

Trp Gly Ala Gly Thr Thr Val Thr Val Ser Ser
1               5                   10

```
<210> SEQ ID NO 591
<211> LENGTH: 26
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 591

Asp Ile Gln Leu Thr Gln Ser Pro Ser Phe Leu Ser Ala Ser Pro Gly
1               5                   10                  15

Asp Arg Val Thr Ile Thr Cys Arg Ala Ser
            20                  25

<210> SEQ ID NO 592
<211> LENGTH: 5
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 592

Ser Ser Val Ile Tyr
1               5

<210> SEQ ID NO 593
<211> LENGTH: 17
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 593

Met Tyr Trp Tyr Gln Gln Lys Pro Gly Ser Ala Pro Lys Pro Trp Ile
1               5                   10                  15

Tyr

<210> SEQ ID NO 594
<211> LENGTH: 3
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 594

Ala Thr Ser
1

<210> SEQ ID NO 595
<211> LENGTH: 36
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 595

Lys Leu Ala Ser Gly Val Pro Val Arg Phe Ser Gly Ser Gly Ser Gly
1               5                   10                  15

Thr Ser Tyr Thr Leu Thr Ile Ser Arg Leu Gln Ala Glu Asp Phe Ala
            20                  25                  30

Thr Tyr Tyr Cys
            35
```

<210> SEQ ID NO 596
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 596

Gln Gln Trp Ser Ser Glu Pro Leu Thr
1               5

<210> SEQ ID NO 597
<211> LENGTH: 10
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 597

Phe Gly Ala Gly Thr Lys Val Glu Ile Lys
1               5                   10

<210> SEQ ID NO 598
<211> LENGTH: 357
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 598
gaggtgcagc tggaagagtc cggcggaggc ctggtgcagc ccaagggcag cctgaagctg      60
agctgtgccg ccagcggcat cagcttcaac gacgccgcca tgaactggat ccggcaggcc     120
cctggcgagg gcctggaatg ggtggcccgg atcagaagca agatcaacga ctacggcacc     180
cactacgccg ccagcgtgaa ggaccggttc accatcagcc gggacgacag ccagaatatc     240
ctgttcctgc agatgaacaa cctgaaaacc gaggacaccg gcatgtacta ctgcgtgatc     300
gacggctacg gcagcctggc ctactggggc cagggaaccc tggtgacagt gtccgcc       357

<210> SEQ ID NO 599
<211> LENGTH: 324
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 599
gacatcgtgc tgacccagag ccccgccatc atgagcagca gcctggcga gaaagtgacc       60 atgacctgcc gggccagcag cagcgtgatc agcagctacc tgcactggta tcagcagcgg     120
agcggcgcca gccccaagct gtggatctac agcaccagca gcctggccag cggcgtgcca     180
gccagatttt ctggcagcgg cagcggcacc tccttcagcc tgaccatcag cagcgtggaa     240
gccgaggacg ccgccaccta ctactgccag cagtacagcg ctacccct gaccttcgga      300 gccggcacca agctggaact gaag                                            324

<210> SEQ ID NO 600
<211> LENGTH: 357
<212> TYPE: DNA

<213> ORGANISM: Artificial Sequence
<220> FEATURE:
<223> OTHER INFORMATION: Description of Artificial Sequence: Synthetic
      polynucleotide

<400> SEQUENCE: 600
gaggtgcagc tggtggaaag cggcggagga ctggtgcagc tggcggcag cctgaagctg      60 tcttgtgccg ccagcggcat cagcttcaac gacgccgcca tgcactgggt gcgccaggcc    120
tctggcaagg gcctggaatg ggtggcccgg atcagaagca agatcaacga ctacggcacc    180
gcctacgccg ccagcgtgaa gggcagattc accatcagcc gggacgacag ccagaacacc    240
ctgtacctgc agatgaacag cctgaaaacc gaggacaccg ccgtgtacta ctgcgtgatc    300
gacggctacg gcagcctggc ctactggggc cagggaaccc tggtgacagt gtccagc       357

<210> SEQ ID NO 601
<211> LENGTH: 324
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 601
gagatcgtgc tgacccagag ccccgccacc ctgtctctga gccctggcga gagagccacc     60
ctgagctgca gagccagcag cagcgtgatc agcagctacc tggcctggta tcagcagaag   120
cccggccagg cccccagact gtggatctac agcaccagca ccggccac cggcatcccc    180 gccagatttt ctggcagcgg cagcggcacc gacttcaccc tgaccatcag cagcctggaa   240
cccgaggact tcgccaccta ctactgccag cagtacagcg gctacccct gaccttcggc    300 ggaggcacca aggtggaaat caag                                          324

<210> SEQ ID NO 602
<211> LENGTH: 357
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 602
gaggtgcagc tggtggaaag cggcggagga ctggtgcagc tggcggcag cctgaagctg      60 tcttgtgccg ccagcggcat cagcttcaac gacgccgcca tgaactggat ccggcaggcc   120
agcggcaagg gcctggaatg ggtggcccgg atcagaagca agatcaacga ctacggcacc   180
cactacgccg ccagcgtgaa gggccggttc accatcagcc gggacgacag ccagaacacc   240
ctgtacctgc agatgaacag cctgaaaacc gaggacaccg ccatgtacta ctgcgtgatc   300
gacggctacg gcagcctggc ctactggggc cagggaaccc tggtgacagt gtccagc       357

<210> SEQ ID NO 603
<211> LENGTH: 324
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 603
gagatcgtgc tgacccagag ccccgccacc ctgtctctga gccctggcga gagagccacc     60
ctgagctgca gagccagcag cagcgtgatc agcagctacc tgcactggta tcagcagaag   120

```
cccggccagg cccccagact gtggatctac agcaccagca gcctggccag cggcatcccc      180
gccagatttt ctggcagcgg cagcggcacc gacttcaccc tgaccatcag ctccctggaa      240
cccgaggact tcgccaccta ctactgccag cagtacagcg ctacccctg accttcgga       300 gccggcacca aggtggaaat caag                                              324

<210> SEQ ID NO 604
<211> LENGTH: 357
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 604
gaggtgcagc tggtggaaag cggcggaggc ctggtgcagc ccaagggcag cctgaagctg      60
agctgtgccg ccagcggcat cagcttcaac gacgccgcca tgaactggat ccggcaggcc      120
agcggcaagg gcctggaatg ggtggcccgg atcagaagca agatcaacga ctacggcacc      180
cactacgccg ccagcgtgaa ggaccggttc accatcagcc gggacgacag ccagaacatc      240
ctgtacctgc agatgaacaa cctgaaaacc gaggacaccg ccatgtacta ctgcgtgatc      300
gacggctacg gcagcctggc ctactggggc cagggaaccc tggtgacagt gtccagc         357

<210> SEQ ID NO 605
<211> LENGTH: 324
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 605
gagatcgtgc tgacccagag ccccgccatc ctgagcagct ctccaggcga gagagccacc      60
ctgagctgca gagccagcag cagcgtgatc agcagctacc tgcactggta tcagcagaag      120
cctggcgccg ctcccggct gtggatctac agcacaagca gcctggccag cggcatcccc       180
gccagatttt ctggcagcgg cagcggcacc agcttcaccc tgaccatcag cagcctggaa      240
gccgaggact tcgccaccta ctactgccag cagtacagcg ctacccctg accttcgga       300 gccggcacca aggtggaaat caag                                              324

<210> SEQ ID NO 606
<211> LENGTH: 369
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 606
gaagtgaagc tggaagagtc cggcggaggc ctggtgaaac ctggcggcag cctgaagctg      60
agctgcgccg ccagcggctt caccttcacc agctacgccc tgagctgggt cgccagacc      120 cccgagaaga gactgaatg ggtggccacc atcagccacg gcggcagcta cacctactac       180
cccgacagcg tgaagggccg gttcaccatc agcagagaca cgccaagaa caccctgaac      240 ctgcagatga gcagcctgcg gagcgaggac accgccatgt actactgcgc caggcacccc      300
ttctacagcg gcaactacca gggctacttc gactactggg gccagggcac cctgctgacc      360
gtgtcctct                                                               369
```

<210> SEQ ID NO 607
<211> LENGTH: 318
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 607
gacatcgtgc tgacccagag ccccgccatc atgagcgcca gcctgggcga gaaagtgacc    60
atgaactgcc gggccaacag cggcgtgaac tacatgtact ggtatcagca gaagtccgac   120
gccagcccca agctgtggat ctacttcacc agcaacctgg cccctggcgt gcccgccaga   180
ttttctggca gcggcagcgg caacagctac agcctgacca tcagcagcat ggaaggcgag   240
gacgccgcca cctactactg ccagcagttc accagcagcc cctacacctt cggcggaggc   300
accaagctgg aaatcaag                                                  318

<210> SEQ ID NO 608
<211> LENGTH: 369
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 608
gaggtgcagc tggaagagtc cggcggagga ctggtgcagc ctggcggcag cctgagactg    60
tcttgcgccg ccagcggctt caccttcacc agctacgcca tgagctgggt gcgccaggcc   120
cctggcaagg gactggaatg ggtggccgtg atcagccacg gcggcagcta cacctactac   180
gccgacagcg tgaagggccg gttcaccatc agccgggaca acagcaagaa caccctgtac   240
ctgcagatga acagcctgcg ggccgaggac accgccgtgt actactgcgc cagacacccc   300
ttctacagcg gcaactacca gggctacttc gactactggg gccagggcac cctggtgaca   360
gtgtccagc                                                           369

<210> SEQ ID NO 609
<211> LENGTH: 318
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 609
gacatccagc tgacccagag ccccagcttc ctgagcgcca gcgtgggcga cagagtgacc    60
atcacctgtc gggccagcag cggcgtgaac tacctggcct ggtatcagca gaagcccggc   120
aaggccccca agctgtggat ctacttcacc agcaccctgc agagcggcgt gcccagcaga   180
ttttctggca gcggcagcgg caacgagtac accctgacca tcagcagcct gcagttcgag   240
gacttcgcca cctactactg ccagcagttc accagcagcc cctacacctt cggccagggc   300
accaagctgg aaatcaag                                                  318

<210> SEQ ID NO 610
<211> LENGTH: 369
<212> TYPE: DNA
<213> ORGANISM: Artificial Sequence
<220> FEATURE:
<223> OTHER INFORMATION: Description of Artificial Sequence: Synthetic polynucleotide

<400> SEQUENCE: 610

| | |
|---|---|
| gaggtgcagc tggaagagtc cggcggagga ctggtgcagc ctggcggcag cctgagactg | 60 |
| tcttgcgccg ccagcggctt caccttcacc agctacgccc tgagctgggt gcgccaggcc | 120 |
| cctggcaaag gactggaatg ggtggccacc atcagccacg gcggcagcta cacctactac | 180 |
| cccgacagcg tgaagggccg gttcaccatc agcagagaca acagcaagaa caccctgtac | 240 |
| ctgcagatga acagcctgcg ggccgaggac accgccgtgt actactgcgc cagacacccc | 300 |
| ttctacagcg gcaactacca gggctacttc gactactggg gccagggcac cctggtgaca | 360 |
| gtgtccagc | 369 |

<210> SEQ ID NO 611
<211> LENGTH: 318
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 611

| | |
|---|---|
| gacatccagc tgacccagag ccccagcttc ctgagcgcca gcgtgggcga cagagtgacc | 60 |
| atcacctgtc gggccaacag cggcgtgaac tacatgtact ggtatcagca gaagcccggc | 120 |
| aaggccccca agctgtggat ctacttcacc agcaacctgg cccctggcgt gcccagcaga | 180 |
| ttttctggca gcggcagcgg caacgagtac accctgacca tcagcagcct gcagttcgag | 240 |
| gacttcgcca cctactactg ccagcagttc accagcagcc cctacacctt cggcggaggc | 300 |
| accaagctgg aaatcaag | 318 |

<210> SEQ ID NO 612
<211> LENGTH: 369
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 612

| | |
|---|---|
| gaggtgcagc tgctggaaag cggcggagga ctggtgcagc ctggcggcag cctgagactg | 60 |
| tcttgcgccg ccagcggctt caccttcacc agctacgccc tgagctgggt gcgccagacc | 120 |
| cccgagaaga gactggaatg ggtggccacc atcagccacg gcggcagcta cacctactac | 180 |
| cccgacagcg tgaagggccg gttcaccatc agcagagaca acagcaagaa caccctgaac | 240 |
| ctgcagatga gcagcctgcg ggccgaggac accgccgtgt actactgcgc caggcacccc | 300 |
| ttctacagcg gcaactacca gggctacttc gactactggg gccagggcac cctggtgaca | 360 |
| gtgtccagc | 369 |

<210> SEQ ID NO 613
<211> LENGTH: 318
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 613

| | |
|---|---|
| gacatccagc tgacccagag ccccagcttc ctgagcgcca gcgtgggcga cagagtgacc | 60 |

```
atcacctgtc gggccaacag cggcgtgaac tacatgtact ggtatcagca gaagcccgac    120
gccgctccca agctgtggat ctacttcacc agcaacctgg ccctggcgt gcccagcaga     180 ttttctggca gcggcagcgg caacagctac accctgacca tcagcagcct gcagttcgag    240
gacttcgcca cctactactg ccagcagttc accagcagcc cctacacctt cggcggaggc    300
accaagctgg aaatcaag                                                  318

<210> SEQ ID NO 614
<211> LENGTH: 372
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 614
gaagtgcagc tggaggagtc aggggagggc ttagtgaagc ctggagggtc cctaaaactc    60
tcctgtgcag cctctggatt cactttcagt aattatgcca tgtcttgggt tcgccagact    120
ccggataagc ggctggagtg ggtcgcaacc attagtaatg gtggtagtta cacctactat    180
ccagacactg tgaagggtcg cttcaccatc tccagagaca atgccaagaa caccctgtct    240
ctgcaaatga gcagtctgag gtctgaggac acggccatgt attactgttc aagaccctct    300
gagagatccc attactacgc tactagccag tttgcttact ggggccaagg gactctggtc    360
actgtctctg ca                                                        372

<210> SEQ ID NO 615
<211> LENGTH: 318
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 615
gacattgtgc tgacccagtc tccaggaatc atgtctgcat ctccagggga aaagtcacc     60 atgacctgca gtgccagctc aagtgtaagt tacatgcatt ggtaccagca gaagtcaggc    120
acctccccca aaagatggat ttatgacaca tccaaactgg cttctggagt ccctgctcgc    180
ttcagtggca gtgggtctgg gacctcttac tctctcacaa tcagcagcat ggaggctgaa    240
gatgctgcca cttattactg ccagcagtgg agtagtagcc cgctcacgtt cggtgctggg    300
accaaggtgg agctgaaa                                                  318

<210> SEQ ID NO 616
<211> LENGTH: 372
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 616
gaggtgcagc tgctggaaag cggcggagga ctggtgcagc ctggcggcag cctgagactg    60
tcttgcgccg ccagcggctt caccttcagc aactacgcca tgagctgggt gcgccaggcc    120
cctggcaagg gactggaatg ggtggccgtg atcagcaacg gcggcagcta cacctactac    180
gccgacagcg tgaagggccg gttcaccatc agcagggaca acagcaagaa caccctgtac    240
ctgcagatga acagcctgcg ggccgaggac accgccgtgt actactgcag ccggcccagc    300
```

```
gagcggagcc actactacgc caccagccag ttcgcctact ggggccaggg caccctggtg    360
acagtgtcca gc                                                        372

<210> SEQ ID NO 617
<211> LENGTH: 318
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 617
gagatcgtgc tgacccagag ccccgccacc ctgtctctga gccctggcga gagagccacc    60
ctgagctgca gagccagcag cagcgtgtcc tacctggcct ggtatcagca gaagcccggc   120
caggccccca gacggtggat ctacgacacc agcaaccggg ccaccggcat ccccgccaga   180
ttttctggca gcggcagcgg caccgactac accctgacca tcagcagcct ggaacccgag   240
gacttcgccg tgtactactg ccagcagtgg tccagcagcc cctgaccttc ggcggaggc    300 accaaggtgg aaatcaag                                                 318

<210> SEQ ID NO 618
<211> LENGTH: 372
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 618
gaggtgcagc tgctggaaag cggcggagga ctggtgcagc ctggcggcag cctgagactg    60
tcttgcgccg ccagcggctt caccttcagc aactacgcca tgagctgggt cgccaggcc   120 cctggcaagg gactggaatg ggtggccacc atcagcaacg gcggcagcta cacctactac   180
cccgacagcg tgaagggccg gttcaccatc agcagggaca cagcaagaa caccctgtac   240 ctgcagatga acagcctgcg ggccgaggac accgccgtgt actactgcag ccggcccagc   300
gagcggagcc actactacgc caccagccag ttcgcctact ggggccaggg caccctggtg   360
acagtgtcca gc                                                       372

<210> SEQ ID NO 619
<211> LENGTH: 318
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 619
gagatcgtgc tgacccagag ccccgccacc ctgtctctga gccctggcga gagagccacc    60
ctgagctgta gccagcag cagcgtgtcc tacatgcact ggtatcagca gaagcccggc    120
accgccccca gacggtggat ctacgatacc agcaagctgg ccagcggcat ccccgccaga   180
ttttctggca gcggcagcgg caccgactac accctgacca tcagcagcct ggaacccgag   240
gacttcgcca cctactactg ccagcagtgg tccagcagcc cctgaccttc ggagccggc    300 accaaggtgg aaatcaag                                                 318

<210> SEQ ID NO 620
<211> LENGTH: 372
<212> TYPE: DNA
```

<213> ORGANISM: Artificial Sequence
<220> FEATURE:
<223> OTHER INFORMATION: Description of Artificial Sequence: Synthetic
      polynucleotide

<400> SEQUENCE: 620
gaggtgcagc tggaagagtc cggcggagga ctggtgcagc ctggcggcag cctgagactg    60
tcttgcgccg ccagcggctt caccttcagc aactacgcca tgagctgggt gcgccagacc   120
cccgacaagc ggctggaatg ggtggccacc atcagcaacg gcggcagcta cacctactac   180
cccgacagcg tgaagggccg gttcaccatc agccgggaca acagcaagaa caccctgtac   240
ctgcagatga gcagcctgcg ggccgaggac accgccgtgt actactgcag ccggcccagc   300
gagcggagcc actactacgc caccagccag ttcgcctact ggggccaggg caccctggtg   360
acagtgtcca gc                                                       372

<210> SEQ ID NO 621
<211> LENGTH: 318
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 621
gagatcgtgc tgacccagag ccccgccatc ctgagcctgt ctccaggcga gagagccacc    60
ctgagctgca gcgccagcag cagcgtgtcc tacatgcact ggtatcagca gaagcccggc   120
caggccccca gacggtggat ctacgatacc agcaagctgg ccagcggcat ccccgccaga   180
ttttctggca gcggcagcgg caccagctac accctgacca tcagcagcct ggaagccgag   240
gacttcgcca cctactactg ccagcagtgg tccagcagcc ccctgacctt cggagccggc   300
accaaggtgg aaatcaag                                                 318

<210> SEQ ID NO 622
<211> LENGTH: 372
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 622
gaggtgcagc tggtggaaag cggcggaggc gtgaagaagc ctggcggcag cctgaagctg    60
agctgtgccg ccagcggctt caccttcagc aactacgcca tgagctgggt ccgacagacc   120
cccggcaagg gcctggaatg ggtggccacc atcagcaacg gcggcagcta cacctactac   180
cccgacagct tccagggccg gttcaccatc agccgggaca acgccaagag caccctgagc   240
ctgcagatgt ccagcctgaa gtccgaggac accgccatgt actactgcag ccggcccagc   300
gagcggagcc actactacgc caccagccag ttcgcctact ggggccaggg caccctggtc   360
accgtgtctg ct                                                       372

<210> SEQ ID NO 623
<211> LENGTH: 372
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 623
gaggtgcagc tggtggaaag cggcggaggc gtgaagaagc ctggcggcag cctgaagctg 60
agctgtgccg ccagcggctt caccttcagc aactacgcca tgagctgggt ccgacagacc 120
cccggcaagg gcctggaatg ggtggccacc atcagcaacg gcggcagcta cacctactac 180
cccgacagct tccagggccg gttcaccatc agccgggaca acgccaagag caccctgagc 240
ctgcagatgt ccagcctgaa ggccgaggac accgccatgt actactgcag ccggcccagc 300
gagcggagcc actactacgc caccagccag ttcgcctact ggggccaggg caccctggtc 360
accgtgtcct ct 372

<210> SEQ ID NO 624
<211> LENGTH: 372
<212> TYPE: DNA
<213> ORGANISM: Artificial Sequence
<220> FEATURE:
<223> OTHER INFORMATION: Description of Artificial Sequence: Synthetic
polynucleotide
<400> SEQUENCE: 624
gaggtgcagc tggtggaaag cggcggaggc gtgaagaagc ctggcggcag cctgaagctg 60
agctgtgccg ccagcggctt caccttcagc aactacgcca tgagctgggt ccgacagacc 120
cccggcaagg gcctggaatg ggtggccaca atcagccagg gcggcagcta cacctactac 180
cccgagagct tccagggccg gttcaccatc agccgggacc aggccaagag caccctgagc 240
ctgcagatgt ccagcctgaa gtccgaggac accgccatgt actactgcag ccggcccagc 300
gagcggagcc actactacgc caccagccag ttcgcctact ggggccaggg caccctggtc 360
accgtgtctg ct 372

<210> SEQ ID NO 625
<211> LENGTH: 372
<212> TYPE: DNA
<213> ORGANISM: Artificial Sequence
<220> FEATURE:
<223> OTHER INFORMATION: Description of Artificial Sequence: Synthetic
polynucleotide
<400> SEQUENCE: 625
gaggtgcagc tgctggaaag cggcggagga ctggtgcagc ctggcggcag cctgagactg 60
tcttgcgccg ccagcggctt caccttcagc aactacgcca tgagctgggt gcgccaggcc 120
cctggcaagg gactggaatg ggtggccacc atcagccagg gtggcagcta cacctactac 180
cccgacagcg tgaagggccg gttcaccatc agccgggaca acagcaagaa caccctgtac 240
ctgcagatga acagcctgcg ggccgaggac accgccgtgt actactgcag ccggcccagc 300
gagcggagcc actactacgc caccagccag ttcgcctact ggggccaggg caccctggtg 360
acagtgtcca gc 372

<210> SEQ ID NO 626
<211> LENGTH: 372
<212> TYPE: DNA
<213> ORGANISM: Artificial Sequence
<220> FEATURE:
<223> OTHER INFORMATION: Description of Artificial Sequence: Synthetic
polynucleotide
<400> SEQUENCE: 626
gaggtgcagc tgctggaaag cggcggagga ctggtgcagc ctggcggcag cctgagactg 60
tcttgcgccg ccagcggctt caccttcagc aactacgcca tgagctgggt gcgccaggcc 120

```
cctggcaagg gactggaatg ggtggccacc atcagcaatc tgggcagcta cacctactac    180
cccgacagcg tgaagggccg gttcaccatc agccgggaca cagcaagaa caccctgtac    240 ctgcagatga acagcctgcg ggccgaggac accgccgtgt actactgcag ccggcccagc    300
gagcggagcc actactacgc caccagccag ttcgcctact ggggccaggg caccctggtg    360
acagtgtcca gc                                                        372
```

<210> SEQ ID NO 627
<211> LENGTH: 372
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 627

```
gaggtgcagc tgctggaaag cggcggagga ctggtgcagc ctggcggcag cctgagactg     60
tcttgcgccg ccagcggctt caccttcagc aactacgcca tgagctgggt gcgccaggcc    120
cctggcaagg gactggaatg ggtggccacc atcagcaatt caggcagcta cacctactac    180
cccgacagcg tgaagggccg gttcaccatc agccgggaca cagcaagaa caccctgtac    240 ctgcagatga acagcctgcg ggccgaggac accgccgtgt actactgcag ccggcccagc    300
gagcggagcc actactacgc caccagccag ttcgcctact ggggccaggg caccctggtg    360
acagtgtcca gc                                                        372
```

<210> SEQ ID NO 628
<211> LENGTH: 372
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 628

```
gaggtgcagc tgctggaaag cggcggagga ctggtgcagc ctggcggcag cctgagactg     60
tcttgcgccg ccagcggctt caccttcagc aactacgcca tgagctgggt gcgccaggcc    120
cctggcaagg gactggaatg ggtggccacc atcagcgacg gtggcagcta cacctactac    180
cccgacagcg tgaagggccg gttcaccatc agccgggaca cagcaagaa caccctgtac    240 ctgcagatga acagcctgcg ggccgaggac accgccgtgt actactgcag ccggcccagc    300
gagcggagcc actactacgc caccagccag ttcgcctact ggggccaggg caccctggtg    360
acagtgtcca gc                                                        372
```

<210> SEQ ID NO 629
<211> LENGTH: 372
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 629

```
gaggtgcagc tgctggaaag cggcggagga ctggtgcagc ctggcggcag cctgagactg     60
tcttgcgccg ccagcggctt caccttcagc aactacgcca tgagctgggt gcgccaggcc    120
cctggcaagg gactggaatg ggtggccacc atcagcaatg tcggcagcta cacctactac    180
cccgacagcg tgaagggccg gttcaccatc agccgggaca cagcaagaa caccctgtac    240
```

```
ctgcagatga acagcctgcg ggccgaggac accgccgtgt actactgcag ccggcccagc      300
gagcggagcc actactacgc caccagccag ttcgcctact ggggccaggg caccctggtg      360
acagtgtcca gc                                                         372
```

<210> SEQ ID NO 630
<211> LENGTH: 318
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 630

```
gacatcgtgc tgacccagag ccccggcagc ctgtctgcca gcgtgggcga cagagtgacc       60
atgacctgca gcgccagcag cagcgtgtcc tacatgcact ggtatcagca gaagcccggc      120
accagcccca agcggtggat ctacgacacc agcaagctgg ccagcggcgt gcccgccaga      180
ttttctggca gcggcagcgg caccagctac agcctgacca tcagcagcct gcagcccgag      240
gacgccgcca cctactactg ccagcagtgg tccagcagcc cctgaccttt ggagccggc       300 accaaggtgg aactgaag                                                   318
```

<210> SEQ ID NO 631
<211> LENGTH: 318
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 631

```
gacatcgtgc tgacccagag ccccagcagc ctgagcgcca gcgtgggcga cagagtgacc       60
atcacctgta gcgccagcag cagcgtgtcc tacatgcact ggtatcagca gaagcccggc      120
accagcccca agcggtggat ctacgacacc agcaagctgg ccagcggcgt gcccgccaga      180
ttttctggca gcggcagcgg caccagctac agcctgacca tcagcagcct gcagcccgag      240
gacgccgcca cctactactg ccagcagtgg tccagcagcc cctgaccttt ggagccggc       300 accaaggtgg aaatcaag                                                   318
```

<210> SEQ ID NO 632
<211> LENGTH: 318
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 632

```
gacatcgtgc tgacccagag ccccagcagc ctgagcgcca gcgtgggcga cagagtgacc       60
atcacctgta gcgccagcag cagcgtgtcc tacatgcact ggtatcagca gaagcccggc      120
cagtccccca agcggtggat ctacgacacc agcaagctgg ccagcggcgt gcccgccaga      180
ttttctggca gcggcagcgg caccagctac agcctgacca tcagcagcct gcagcccgag      240
gacgccgcca cctactactg ccagcagtgg tccagcagcc cctgaccttt ggagccggc       300 accaaggtgg aaatcaag                                                   318
```

<210> SEQ ID NO 633
<211> LENGTH: 318

```
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 633
gacatccagc tgacccagag ccccggcagc ctgtctgcca gcgtgggcga cagagtgacc    60
atgacctgca gcgccagcag cagcgtgtcc tacatgcact ggtatcagca gaagcccggc   120
accagcccca gcggtggat ctacgacacc agcaagctgg ccagcggcgt gcccgccaga    180
ttttctggca gcggcagcgg caccagctac agcctgacca tcagcagcct gcagcccgag   240
gacgccgcca cctactactg ccagcagtgg tccagcagcc ccctgacctt ggagccggc    300 accaaggtgg aactgaag                                                 318

<210> SEQ ID NO 634
<211> LENGTH: 369
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 634
gaggttcagc tggaggagtc aggggggaggc ttagtgaagc ctggagggtc cctgaaactc   60
tcctgtgcag cctctggatt cactttcact agctatgcca tgtcttgggt tcgccagact  120
ccggagaaga ggctggagtg ggtcgcaacc attagtcatg gtggtactta cacctactat  180
ccagacagtg tgaagggacg attcaccatc tccagagaca atgccaagaa caccctgtac  240
ctgcaaatga gcagtctgag gtctgaggac acggccatgt attactgtgc aagacatcct  300
atctactctg gtaactacca gggatacttt gactactggg gccaaggcac cactctcaca  360
gtctcctca                                                           369

<210> SEQ ID NO 635
<211> LENGTH: 318
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 635
gacattgtgc tcacccagtc tccagcaatc atgtctgcat ctctagggga gaaggtcacc    60
atgagctgca gggccagctc aggtgtaaat tacatatact ggtaccagca gaagtcagat  120
gcctccccca aactatggat ttatttcaca tccaacctgg ctcctggagt cccagctcgc  180
ttcagtggca gtgggtctgg gaactcttat tctctcacaa tcagcagcat ggaggtgaa   240 gatgctgcca cttattactg ccagcagttt actagttccc cgtacacgtt cggaggggg   300 accaagctgg aaataaaa                                                 318

<210> SEQ ID NO 636
<211> LENGTH: 369
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 636
```

```
gaggtgcagc tgctggaaag cggcggagga ctggtgcagc ctggcggcag cctgagactg    60
tcttgcgccg ccagcggctt caccttcacc agctacgcca tgagctgggt gcgccaggcc   120
cctggcaagg gactggaatg ggtggccgtg atcagccacg gcggcaccta cacctactac   180
gccgacagcg tgaagggccg gttcaccatc agccgggaca cgccaagaa caccctgtac    240 ctgcagatga acagcctgcg ggccgaggac accgccgtgt actactgcgc cagacacccc   300
atctacagcg gcaactacca gggctacttc gactactggg gccagggcac cctggtgaca   360
gtgtccagc                                                           369

<210> SEQ ID NO 637
<211> LENGTH: 318
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 637
gacatccagc tgacccagag ccccagcttc ctgagcgcca gcgtgggcga cagagtgacc    60
atcacctgtc gggccagcag cggcgtgaac tacctggcct ggtatcagca gaagcccggc   120
aaggccccca agctgtggat ctacttcacc agcaccctgc agagcggcgt gcccagcaga   180
ttttctggca gcggcagcgg caacgagtac accctgacca tcagcagcct gcagcccgag   240
gacttcgcca cctactactg ccagcagttc accagcagcc cctacacctt cggccagggc   300
accaagctgg aaatcaag                                                 318

<210> SEQ ID NO 638
<211> LENGTH: 369
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 638
gaggtgcagc tgctggaaag cggcggagga ctggtgcagc ctggcggcag cctgagactg    60
tcttgcgccg ccagcggctt caccttcacc agctacgcca tgagctgggt gcgccaggcc   120
cctggcaagg gactggaatg ggtggccaca atcagccacg gcggcaccta cacctactac   180
cccgacagcg tgaagggccg gttcaccatc agccgggaca cgccaagaa caccctgtac    240 ctgcagatga acagcctgcg ggccgaggac accgccatgt actactgcgc cagacacccc   300
atctacagcg gcaactacca gggctacttc gactactggg gccagggcac cctggtgaca   360
gtgtccagc                                                           369

<210> SEQ ID NO 639
<211> LENGTH: 318
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 639
gacatccagc tgacccagag ccccagcttc ctgagcgcca gcgtgggcga cagagtgacc    60
atcacctgtc gggccagcag cggcgtgaac tacatctact ggtatcagca gaagcccggc   120
aaggccccca agctgtggat ctacttcacc agcaacctgg cccctggcgt gcccagcaga   180
```

```
ttttctggca gcggcagcgg caacgagtac accctgacca tcagcagcct gcagcccgag    240
gacttcgcca cctactactg ccagcagttc accagcagcc cctacacctt cggcggaggc    300
accaagctgg aaatcaag                                                  318
```

<210> SEQ ID NO 640
<211> LENGTH: 369
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 640

```
gaggtgcagc tggaagagtc cggcggagga ctggtgcagc ctggcggcag cctgagactg     60
tcttgcgccg ccagcggctt caccttcacc agctacgcca tgagctgggt gcgccagacc    120
cccgagaagc ggctggaatg gtggccaca atcagccacg gcggcaccta cacctactac    180
cccgacagcg tgaagggccg gttcaccatc agccgggaca cgccaagaa cccctgtac    240 ctgcagatga acagcctgcg ggccgaggac accgccatgt actactgcgc caggcacccc    300
atctacagcg gcaactacca gggctacttc gactactggg gccagggcac caccgtgacc    360
gtgtcctct                                                             369
```

<210> SEQ ID NO 641
<211> LENGTH: 318
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 641

```
gacatccagc tgacccagag ccccagcttc ctgagcgcca gcgtgggcga cagagtgacc     60
atcacctgtc gggccagcag cggcgtgaac tacatctact ggtatcagca gaagcccgac    120
gccgctccca agctgtggat ctacttcacc agcaacctgg cccctggcgt gcccagcaga    180
ttttctggca gcggcagcgg caacagctac accctgacca tcagcagcct gcagcccgag    240
gacttcgcca cctactactg ccagcagttc accagcagcc cctacacctt cggcggaggc    300
accaagctgg aaatcaag                                                  318
```

<210> SEQ ID NO 642
<211> LENGTH: 369
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 642

```
gaggtgcagc tgctggaaag cggcggagga ctggtgcagc ctggcggcag cctgagactg     60
tcttgcgccg ccagcggctt caccttcacc agctacgcca tgagctgggt gcgccaggcc    120
cctggcaagg gactggaatg gtggccgta atcagccacg gcggcaccta cacctactac    180
cccgacagcg tgaagggccg gttcaccatc agccgggaca cgccaagaa cccctgtac    240 ctgcagatga acagcctgcg ggccgaggac accgccatgt actactgcgc cagacacccc    300
atctacagcg gcaactacca gggctacttc gactactggg gccagggcac cctggtgaca    360
gtgtccagc                                                             369
```

<210> SEQ ID NO 643
<211> LENGTH: 369
<212> TYPE: DNA
<213> ORGANISM: Artificial Sequence
<220> FEATURE:
<223> OTHER INFORMATION: Description of Artificial Sequence: Synthetic polynucleotide

<400> SEQUENCE: 643

```
gaggtgcagc tgctggaaag cggcggagga ctggtgcagc ctggcggcag cctgagactg      60
tcttgcgccg ccagcggctt caccttcacc agctacgcca tgagctgggt gcgccaggcc     120
cctggcaagg gactggaatg ggtggccaca atcagccacg gcggcaccta cacctactac     180
gccgacagcg tgaagggccg gttcaccatc agccgggaca cgccaagaa caccctgtac      240
ctgcagatga acagcctgcg ggccgaggac accgccatgt actactgcgc cagacacccc     300
atctacagcg gcaactacca gggctacttc gactactggg gccagggcac cctggtgaca     360
gtgtccagc                                                              369
```

<210> SEQ ID NO 644
<211> LENGTH: 369
<212> TYPE: DNA
<213> ORGANISM: Artificial Sequence
<220> FEATURE:
<223> OTHER INFORMATION: Description of Artificial Sequence: Synthetic polynucleotide

<400> SEQUENCE: 644

```
gaggtgcagc tgctggaaag cggcggagga ctggtgcagc ctggcggcag cctgagactg      60
tcttgcgccg ccagcggctt caccttcacc agctacgcca tgagctgggt gcgccaggcc     120
cctggcaagg gactggaatg ggtggccaca atcagccacg gcggcaccta cacctactac     180
cccgacagcg tgaagggccg gttcaccatc agccgggaca cgccaagaa caccctgtac      240
ctgcaggtga acagcctgcg ggccgaggac accgccatgt actactgcgc cagacacccc     300
atctacagcg gcaactacca gggctacttc gactactggg gccagggcac cctggtgaca     360
gtgtccagc                                                              369
```

<210> SEQ ID NO 645
<211> LENGTH: 318
<212> TYPE: DNA
<213> ORGANISM: Artificial Sequence
<220> FEATURE:
<223> OTHER INFORMATION: Description of Artificial Sequence: Synthetic polynucleotide

<400> SEQUENCE: 645

```
gacatccagc tgacccagag ccccagcttc ctgagcgcca gcgtgggcga cagagtgacc      60
atcacctgtc gggccagcag cggcgtgaac tacctctact ggtatcagca gaagcccggc     120
aaggccccca gctgtggat ctacttcacc agcaacctgg ccctggcgt gcccagcaga       180
ttttctggca gcggcagcgg caacgagtac accctgacca tcagcagcct gcagcccgag     240
gacttcgcca cctactactg ccagcagttc accagcagcc ctacaccctt cggcggaggc     300
accaagctgg aaatcaag                                                    318
```

<210> SEQ ID NO 646
<211> LENGTH: 318
<212> TYPE: DNA
<213> ORGANISM: Artificial Sequence
<220> FEATURE:

<223> OTHER INFORMATION: Description of Artificial Sequence: Synthetic
polynucleotide

<400> SEQUENCE: 646

```
gacatccagc tgacccagag ccccagcttc ctgagcgcca gcgtgggcga cagagtgacc      60
atcacctgtc gggccagcag cggcgtgaac tacatcgcct ggtatcagca gaagcccggc     120
aaggccccca agctgtggat ctacttcacc agcaacctgg cccctggcgt gcccagcaga     180
ttttctggca gcggcagcgg caacgagtac accctgacca tcagcagcct gcagcccgag     240
gacttcgcca cctactactg ccagcagttc accagcagcc cctacacctt cggcggaggc     300
accaagctgg aaatcaag                                                   318
```

<210> SEQ ID NO 647
<211> LENGTH: 318
<212> TYPE: DNA
<213> ORGANISM: Artificial Sequence
<220> FEATURE:
<223> OTHER INFORMATION: Description of Artificial Sequence: Synthetic
polynucleotide

<400> SEQUENCE: 647

```
gacatccagc tgacccagag ccccagcttc ctgagcgcca gcgtgggcga cagagtgacc      60
atcacctgtc gggccagcag cggcgtgaac tacatctact ggtatcagca gaagcccggc     120
aaggccccca agctgtggat ctacttcacc agcaccctgg cccctggcgt gcccagcaga     180
ttttctggca gcggcagcgg caacgagtac accctgacca tcagcagcct gcagcccgag     240
gacttcgcca cctactactg ccagcagttc accagcagcc cctacacctt cggcggaggc     300
accaagctgg aaatcaag                                                   318
```

<210> SEQ ID NO 648
<211> LENGTH: 318
<212> TYPE: DNA
<213> ORGANISM: Artificial Sequence
<220> FEATURE:
<223> OTHER INFORMATION: Description of Artificial Sequence: Synthetic
polynucleotide

<400> SEQUENCE: 648

```
gacatccagc tgacccagag ccccagcttc ctgagcgcca gcgtgggcga cagagtgacc      60
atcacctgtc gggccagcag cggcgtgaac tacatctact ggtatcagca gaagcccggc     120
aaggccccca agctgtggat ctacttcacc agcaacctgc aacctggcgt gcccagcaga     180
ttttctggca gcggcagcgg caacgagtac accctgacca tcagcagcct gcagcccgag     240
gacttcgcca cctactactg ccagcagttc accagcagcc cctacacctt cggcggaggc     300
accaagctgg aaatcaag                                                   318
```

<210> SEQ ID NO 649
<211> LENGTH: 318
<212> TYPE: DNA
<213> ORGANISM: Artificial Sequence
<220> FEATURE:
<223> OTHER INFORMATION: Description of Artificial Sequence: Synthetic
polynucleotide

<400> SEQUENCE: 649

```
gacatccagc tgacccagag ccccagcttc ctgagcgcca gcgtgggcga cagagtgacc      60
atcacctgtc gggccagcag cggcgtgaac tacatctact ggtatcagca gaagcccggc     120
aaggccccca agctgtggat ctacttcacc agcaacctgg cctctggcgt gcccagcaga     180
```

```
tttctggca gcggcagcgg caacgagtac accctgacca tcagcagcct gcagcccgag    240
gacttcgcca cctactactg ccagcagttc accagcagcc cctacacctt cggcggaggc    300
accaagctgg aaatcaag                                                 318
```

<210> SEQ ID NO 650
<211> LENGTH: 318
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 650

```
gacatccagc tgacccagag ccccagcttc ctgagcgcca gcgtgggcga cagagtgacc    60
atcacctgtc gggccagcag cggcgtgaac tacatctact ggtatcagca gaagcccggc    120 aaggcccca agctgtggat ctacttcacc agcaacctgg ccctggcgt gcccagcaga    180 ttttctggca gcggcagcgg caacgagtac accctgacca tcagcagcct gcagcccgag    240
gacttcgcca cctactactg ccagcagttc accagcagcc cctacacctt cggccaaggc    300
accaagctgg aaatcaag                                                 318
```

<210> SEQ ID NO 651
<211> LENGTH: 354
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 651

```
gaagtgaagc tggaagagtc cggccctgag gtggtgcgcc tggcgtgtc cgtgaagatc    60 agctgcaagg gcagcggcta caccttcacc gactacgcca tgcactgggt gaaacagagc    120
cacgccaaga gcctggaatg gatcggcgtg atcagcacct acaacggcaa caccaagtac    180
aaccagaagt tcaagggcaa ggccaccatg accgtggaca gagcagcag caccgcctac    240 atggaactgg cccggctgac cagcgaggac agcgccatct actactgcgc ccggttcctg    300
agcctgcggt acttcgatgt gtggggagcc ggcaccaccg tgaccgtgtc tagc         354
```

<210> SEQ ID NO 652
<211> LENGTH: 318
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 652

```
gacatcgtgc tgacccagag ccccgccatc tgtctgccc cccctggcga gaaagtgacc    60
atgacctgcc gggccagcag cagcgtgatc tacatgtact ggtatcagca gaagcccggc    120
agcagcccca agccctggat ctacgccacc agcaagctgg ccagcggcgt gccagtgcgg    180
tttagcggca gcggctctgg caccagctac agcctgacca tcagccgggt ggaagccgag    240
gacgtggcca cctactactg ccagcagtgg tccagcgagc cctgaccttg cggagccggc    300
accaagctgg aactgaag                                                 318
```

<210> SEQ ID NO 653
<211> LENGTH: 354

<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 653
caggtgaaac tggtgcagtc tggcgccgaa gtgaagaaac ctggcgccag cgtgaaggtg      60
tcctgcaagg ccagcggcta caccttcacc gactacgcca tgcactgggt gcgccaggcc     120
cctggccaga gactggaatg gatcggctgg atcagcacct acaacggcaa caccaagtac     180
agccagaagt tccagggcag agccaccatg accgtggaca gagcgccag caccgcctac      240 atggaactga gcagcctgcg gagcgaggac accgccgtgt actactgcgc ccggttcctg     300
agcctgcggt acttcgacgt gtggggcaag ggcaccaccg tgaccgtgtc cagc           354

<210> SEQ ID NO 654
<211> LENGTH: 318
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 654
gacatccagc tgacccagag ccccagcttc ctgagcgcca gcgtgggcga cagagtgacc      60
atcacctgtc gggccagcag cagcgtgatc tacctggcct ggtatcagca gaagcccggc     120
aaggccccca agccctggat ctacgccacc agcacactgc agagcggcgt gcccagcaga     180
ttcagcggca gcggctctgg caccgagtac accctgacca tcagcagcct gcagcccgag     240
gacttcgcca cctactactg ccagcagtgg tccagcgagc ccctgacctt cggcggaggc     300
accaaggtgg aaatcaag                                                   318

<210> SEQ ID NO 655
<211> LENGTH: 354
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 655
caggtgaaac tggtgcagtc tggcgccgaa gtgaagaaac ctggcgccag cgtgaaggtg      60
tcctgcaagg gcagcggcta caccttcacc gactacgcca tgcactgggt gcgccaggcc     120
cctggccaga gactggaatg gatcggcgtg atcagcacct acaacggcaa caccaagtac     180
aaccagaagt tccagggcag agccaccatg accgtggaca gagcgccag caccgcctac      240 atggaactga gcagcctgcg gagcgaggac accgccatct actactgcgc ccggttcctg     300
agcctgcggt acttcgatgt gtggggagcc ggcaccaccg tgaccgtgtc tagc           354

<210> SEQ ID NO 656
<211> LENGTH: 318
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 656
gacatccagc tgacccagag ccccagcttc ctgagcgcca gcgtgggcga cagagtgacc      60

| | |
|---|---|
| atcacctgtc gggccagcag cagcgtgatc tacatgtact ggtatcagca gaagcccggc | 120 |
| aaggccccca agccctggat ctacgccacc agcaagctgg ccagcggcgt gcccagcaga | 180 |
| ttttctggca gcggcagcgg caccgagtac accctgacca tcagcagcct gcagcccgag | 240 |
| gacttcgcca cctactactg ccagcagtgg tccagcgagc ccctgacctt cggagccggc | 300 |
| accaaggtgg aaatcaag | 318 |

<210> SEQ ID NO 657
<211> LENGTH: 354
<212> TYPE: DNA
<213> ORGANISM: Artificial Sequence
<220> FEATURE:
<223> OTHER INFORMATION: Description of Artificial Sequence: Synthetic polynucleotide

<400> SEQUENCE: 657

| | |
|---|---|
| caggtgaaac tggtgcagag cggccctgaa gtgaaggtgc aggcgccag cgtgaaggtg | 60 |
| tcctgcaagg gcagcggcta caccttcacc gactacgcca tgcactgggt gcgccaggcc | 120 |
| cctggccaga gcctggaatg gatcggcgtg atcagcacct acaacggcaa caccaagtac | 180 |
| aaccagaagt tccagggcag agccaccatg accgtggaca gagcgccag caccgcctac | 240 |
| atggaactga gccggctgcg gagcgaggac accgccatct actactgcgc ccggttcctg | 300 |
| agcctgcggt acttcgatgt gtggggagcc ggcaccaccg tgaccgtgtc tagc | 354 |

<210> SEQ ID NO 658
<211> LENGTH: 318
<212> TYPE: DNA
<213> ORGANISM: Artificial Sequence
<220> FEATURE:
<223> OTHER INFORMATION: Description of Artificial Sequence: Synthetic polynucleotide

<400> SEQUENCE: 658

| | |
|---|---|
| gacatccagc tgacccagag ccccagcttc ctgagcgcca gcctggcga cagagtgacc | 60 |
| atcacctgtc gggccagcag cagcgtgatc tacatgtact ggtatcagca gaagcccggc | 120 |
| agcgccccca agccctggat ctacgccaca agcaagctgg ccagcggcgt gcccgtgcgg | 180 |
| tttagcggct ctggcagcgg caccagctac accctgacca tcagccggct gcaggccgag | 240 |
| gacttcgcca cctactactg ccagcagtgg tccagcgagc ccctgacctt cggagccggc | 300 |
| accaaggtgg aaatcaag | 318 |

<210> SEQ ID NO 659
<211> LENGTH: 113
<212> TYPE: PRT
<213> ORGANISM: Artificial Sequence
<220> FEATURE:
<223> OTHER INFORMATION: Description of Artificial Sequence: Synthetic polypeptide

<400> SEQUENCE: 659

```
Glu Val Gln Leu Leu Glu Ser Gly Gly Gly Leu Val Gln Pro Gly Gly
 1               5                  10                  15

Ser Leu Arg Leu Ser Cys Ala Ala Ser Gly Phe Thr Phe Ser Ser Tyr
            20                  25                  30

Ala Met Ser Trp Val Arg Gln Ala Pro Gly Lys Gly Leu Glu Trp Val
        35                  40                  45

Ser Val Ile Tyr Ser Gly Gly Ser Thr Tyr Tyr Ala Asp Ser Val
    50                  55                  60
```

```
Lys Gly Arg Phe Thr Ile Ser Arg Asp Asn Ser Lys Asn Thr Leu Tyr
 65                  70                  75                  80

Leu Gln Met Asn Ser Leu Arg Ala Glu Asp Thr Ala Val Tyr Tyr Cys
                 85                  90                  95

Ala Lys Tyr Phe Asp Tyr Trp Gly Gln Gly Thr Leu Val Thr Val Ser
            100                 105                 110

Ser

<210> SEQ ID NO 660
<211> LENGTH: 107
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 660

Glu Ile Val Leu Thr Gln Ser Pro Ala Thr Leu Ser Leu Ser Pro Gly
  1               5                  10                  15

Glu Arg Ala Thr Leu Ser Cys Arg Ala Ser Gln Ser Val Ser Ser Tyr
                 20                  25                  30

Leu Ala Trp Tyr Gln Gln Lys Pro Gly Gln Ala Pro Arg Leu Leu Ile
             35                  40                  45

Tyr Asp Ala Ser Asn Arg Ala Thr Gly Ile Pro Ala Arg Phe Ser Gly
 50                  55                  60

Ser Gly Ser Gly Thr Asp Phe Thr Leu Thr Ile Ser Ser Leu Glu Pro
 65                  70                  75                  80

Glu Asp Phe Ala Val Tyr Tyr Cys Gln Gln Arg Ser Asn Trp Pro Phe
                 85                  90                  95

Thr Phe Gly Thr Gly Thr Lys Leu Glu Ile Lys
            100                 105

<210> SEQ ID NO 661
<211> LENGTH: 115
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 661

Glu Val Gln Leu Val Glu Ser Gly Gly Gly Leu Val Gln Pro Gly Gly
  1               5                  10                  15

Ser Leu Lys Leu Ser Cys Ala Ala Ser Gly Phe Thr Phe Ser Gly Ser
                 20                  25                  30

Ala Met His Trp Val Arg Gln Ala Ser Gly Lys Gly Leu Glu Trp Val
             35                  40                  45

Gly Arg Ile Arg Ser Lys Ala Asn Ser Tyr Ala Thr Ala Tyr Ala Ala
 50                  55                  60

Ser Val Lys Gly Arg Phe Thr Ile Ser Arg Asp Asp Ser Lys Asn Thr
 65                  70                  75                  80

Ala Tyr Leu Gln Met Asn Ser Leu Lys Thr Glu Asp Thr Ala Val Tyr
                 85                  90                  95

Tyr Cys Thr Arg Tyr Phe Asp Tyr Trp Gly Gln Gly Thr Leu Val Thr
            100                 105                 110

Val Ser Ser
        115
```

<210> SEQ ID NO 662
<211> LENGTH: 107
<212> TYPE: PRT
<213> ORGANISM: Artificial Sequence
<220> FEATURE:
<223> OTHER INFORMATION: Description of Artificial Sequence: Synthetic polypeptide

<400> SEQUENCE: 662

```
Glu Ile Val Leu Thr Gln Ser Pro Ala Thr Leu Ser Leu Ser Pro Gly
1               5                   10                  15

Glu Arg Ala Thr Leu Ser Cys Arg Ala Ser Gln Ser Val Ser Ser Tyr
            20                  25                  30

Leu Ala Trp Tyr Gln Gln Lys Pro Gly Gln Ala Pro Arg Leu Leu Ile
        35                  40                  45

Tyr Asp Ala Ser Asn Arg Ala Thr Gly Ile Pro Ala Arg Phe Ser Gly
 50                  55                  60

Ser Gly Ser Gly Thr Asp Phe Thr Leu Thr Ile Ser Ser Leu Glu Pro
65                  70                  75                  80

Glu Asp Phe Ala Val Tyr Tyr Cys Gln Gln Arg Ser Asn Trp Pro Phe
                85                  90                  95

Thr Phe Gly Thr Gly Thr Lys Leu Glu Ile Lys
            100                 105
```

<210> SEQ ID NO 663
<211> LENGTH: 113
<212> TYPE: PRT
<213> ORGANISM: Artificial Sequence
<220> FEATURE:
<223> OTHER INFORMATION: Description of Artificial Sequence: Synthetic polypeptide

<400> SEQUENCE: 663

```
Glu Val Gln Leu Leu Glu Ser Gly Gly Gly Leu Val Gln Pro Gly Gly
1               5                   10                  15

Ser Leu Arg Leu Ser Cys Ala Ala Ser Gly Phe Thr Phe Ser Ser Tyr
            20                  25                  30

Ala Met Ser Trp Val Arg Gln Ala Pro Gly Lys Gly Leu Glu Trp Val
        35                  40                  45

Ser Val Ile Tyr Ser Gly Gly Ser Ser Thr Tyr Tyr Ala Asp Ser Val
 50                  55                  60

Lys Gly Arg Phe Thr Ile Ser Arg Asp Asn Ser Lys Asn Thr Leu Tyr
65                  70                  75                  80

Leu Gln Met Asn Ser Leu Arg Ala Glu Asp Thr Ala Val Tyr Tyr Cys
                85                  90                  95

Ala Lys Tyr Phe Asp Tyr Trp Gly Gln Gly Thr Leu Val Thr Val Ser
            100                 105                 110

Ser
```

<210> SEQ ID NO 664
<211> LENGTH: 107
<212> TYPE: PRT
<213> ORGANISM: Artificial Sequence
<220> FEATURE:
<223> OTHER INFORMATION: Description of Artificial Sequence: Synthetic polypeptide

<400> SEQUENCE: 664

```
Asp Ile Gln Leu Thr Gln Ser Pro Ser Phe Leu Ser Ala Ser Val Gly
1               5                   10                  15
```

```
Asp Arg Val Thr Ile Thr Cys Arg Ala Ser Gln Gly Ile Ser Ser Tyr
                20                  25                  30

Leu Ala Trp Tyr Gln Gln Lys Pro Gly Lys Ala Pro Lys Leu Leu Ile
         35                  40                  45

Tyr Ala Ala Ser Thr Leu Gln Ser Gly Val Pro Ser Arg Phe Ser Gly
     50                  55                  60

Ser Gly Ser Gly Thr Glu Phe Thr Leu Thr Ile Ser Ser Leu Gln Pro
65                  70                  75                  80

Glu Asp Phe Ala Thr Tyr Tyr Cys Gln Gln Leu Asn Ser Tyr Pro Tyr
                 85                  90                  95

Thr Phe Gly Gln Gly Thr Lys Leu Glu Ile Lys
            100                 105
```

<210> SEQ ID NO 665
<211> LENGTH: 115
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 665

```
Gln Val Gln Leu Val Gln Ser Gly Ala Glu Val Lys Lys Pro Gly Ala
1               5                   10                  15

Ser Val Lys Val Ser Cys Lys Ala Ser Gly Tyr Thr Phe Thr Ser Tyr
                20                  25                  30

Ala Met His Trp Val Arg Gln Ala Pro Gly Gln Arg Leu Glu Trp Met
         35                  40                  45

Gly Trp Ile Asn Ala Gly Asn Gly Asn Thr Lys Tyr Ser Gln Lys Phe
     50                  55                  60

Gln Gly Arg Val Thr Ile Thr Arg Asp Thr Ser Ala Ser Thr Ala Tyr
65                  70                  75                  80

Met Glu Leu Ser Ser Leu Arg Ser Glu Asp Thr Ala Val Tyr Tyr Cys
                 85                  90                  95

Ala Arg Tyr Trp Tyr Phe Asp Leu Trp Gly Arg Gly Thr Leu Val Thr
            100                 105                 110

Val Ser Ser
        115
```

<210> SEQ ID NO 666
<211> LENGTH: 107
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 666

```
Asp Ile Gln Leu Thr Gln Ser Pro Ser Phe Leu Ser Ala Ser Val Gly
1               5                   10                  15

Asp Arg Val Thr Ile Thr Cys Arg Ala Ser Gln Gly Ile Ser Ser Tyr
                20                  25                  30

Leu Ala Trp Tyr Gln Gln Lys Pro Gly Lys Ala Pro Lys Leu Leu Ile
         35                  40                  45

Tyr Ala Ala Ser Thr Leu Gln Ser Gly Val Pro Ser Arg Phe Ser Gly
     50                  55                  60

Ser Gly Ser Gly Thr Glu Phe Thr Leu Thr Ile Ser Ser Leu Gln Pro
65                  70                  75                  80
```

Glu Asp Phe Ala Thr Tyr Tyr Cys Gln Gln Leu Asn Ser Tyr Pro Phe
                85                  90                  95

Thr Phe Gly Thr Gly Thr Lys Leu Glu Ile Lys
            100                 105

<210> SEQ ID NO 667
<211> LENGTH: 113
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 667

Glu Val Gln Leu Leu Glu Ser Gly Gly Gly Leu Val Gln Pro Gly Gly
1               5                   10                  15

Ser Leu Arg Leu Ser Cys Ala Ala Ser Gly Phe Thr Phe Ser Ser Tyr
            20                  25                  30

Ala Met Ser Trp Val Arg Gln Ala Pro Gly Lys Gly Leu Glu Trp Val
        35                  40                  45

Ser Val Ile Tyr Ser Gly Gly Ser Ser Thr Tyr Tyr Ala Asp Ser Val
    50                  55                  60

Lys Gly Arg Phe Thr Ile Ser Arg Asp Asn Ser Lys Asn Thr Leu Tyr
65                  70                  75                  80

Leu Gln Met Asn Ser Leu Arg Ala Glu Asp Thr Ala Val Tyr Tyr Cys
                85                  90                  95

Ala Lys Tyr Phe Asp Tyr Trp Gly Gln Gly Thr Leu Val Thr Val Ser
            100                 105                 110

Ser

<210> SEQ ID NO 668
<211> LENGTH: 107
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 668

Asp Ile Gln Leu Thr Gln Ser Pro Ser Phe Leu Ser Ala Ser Val Gly
1               5                   10                  15

Asp Arg Val Thr Ile Thr Cys Arg Ala Ser Gln Gly Ile Ser Ser Tyr
            20                  25                  30

Leu Ala Trp Tyr Gln Gln Lys Pro Gly Lys Ala Pro Lys Leu Leu Ile
        35                  40                  45

Tyr Ala Ala Ser Thr Leu Gln Ser Gly Val Pro Ser Arg Phe Ser Gly
    50                  55                  60

Ser Gly Ser Gly Thr Glu Phe Thr Leu Thr Ile Ser Ser Leu Gln Pro
65                  70                  75                  80

Glu Asp Phe Ala Thr Tyr Tyr Cys Gln Gln Leu Asn Ser Tyr Pro Tyr
                85                  90                  95

Thr Phe Gly Gln Gly Thr Lys Leu Glu Ile Lys
            100                 105

<210> SEQ ID NO 669
<211> LENGTH: 107
<212> TYPE: PRT
<213> ORGANISM: Artificial Sequence
<220> FEATURE:
<223> OTHER INFORMATION: Description of Artificial Sequence: Synthetic polypeptide

<400> SEQUENCE: 669

Asp Ile Gln Met Thr Gln Ser Pro Ser Ser Leu Ser Ala Ser Val Gly
1               5                   10                  15

Asp Arg Val Thr Ile Thr Cys Gln Ala Ser Gln Asp Ile Ser Asn Tyr
            20                  25                  30

Leu Asn Trp Tyr Gln Gln Lys Pro Gly Lys Ala Pro Lys Leu Leu Ile
        35                  40                  45

Tyr Asp Ala Ser Asn Leu Glu Thr Gly Val Pro Ser Arg Phe Ser Gly
    50                  55                  60

Ser Gly Ser Gly Thr Asp Phe Thr Phe Thr Ile Ser Ser Leu Gln Pro
65                  70                  75                  80

Glu Asp Ile Ala Thr Tyr Tyr Cys Gln Gln Tyr Asp Asn Leu Pro Phe
                85                  90                  95

Thr Phe Gly Thr Gly Thr Lys Leu Glu Ile Lys
            100                 105

<210> SEQ ID NO 670
<211> LENGTH: 126
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 670

Gln Val Gln Val Val Gln Ser Gly Ala Glu Val Lys Lys Pro Gly Ala
1               5                   10                  15

Ser Val Lys Val Ser Cys Lys Thr Ser Gly Tyr Thr Phe Thr Gly Asn
            20                  25                  30

Tyr Ile His Trp Val Arg Gln Ala Pro Gly Gln Gly Leu Glu Trp Met
        35                  40                  45

Gly Trp Ile Asn Pro Asn Ser Gly Gly Thr Asn Phe Ala Gln Lys Phe
    50                  55                  60

Gln Gly Arg Val Thr Met Thr Arg Asp Thr Ser Ile Thr Thr Ala Tyr
65                  70                  75                  80

Met Val Leu Ser Arg Leu Arg Ser Asp Asp Thr Ala Val Tyr Tyr Cys
                85                  90                  95

Ala Arg Gly Gly Asn Asn Met Ile Val Val Ala Arg Gly Tyr Tyr Gly
            100                 105                 110

Met Asp Val Trp Gly Gln Gly Thr Thr Val Thr Val Ser Ser
        115                 120                 125

<210> SEQ ID NO 671
<211> LENGTH: 126
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 671

Gln Val Gln Val Val Gln Ser Gly Ala Glu Val Lys Lys Pro Gly Ala
1               5                   10                  15

Ser Val Lys Val Ser Cys Lys Ala Ser Gly Tyr Thr Phe Thr Gly Tyr
            20                  25                  30

Tyr Ile His Trp Val Arg Gln Ala Pro Gly Gln Gly Leu Glu Trp Met
        35                  40                  45

```
Gly Trp Ile Asn Pro Asp Ser Gly Gly Thr Asn Tyr Ala Gln Lys Phe
        50                  55                  60

Gln Gly Arg Val Thr Met Thr Arg Asp Thr Ser Ile Ser Thr Ala Tyr
 65                  70                  75                  80

Met Val Leu Asn Arg Leu Arg Ser Asp Asp Thr Ala Val Tyr Tyr Cys
                85                  90                  95

Ala Lys Gly Gly Ile Asn Met Ile Val Val Ala Arg Gly Tyr Tyr Gly
            100                 105                 110

Met Asp Val Trp Gly Gln Gly Thr Thr Val Thr Val Ser Ser
        115                 120                 125

<210> SEQ ID NO 672
<211> LENGTH: 106
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 672

Asp Ile Gln Met Thr Gln Ser Pro Ser Ser Leu Ser Ala Ser Val Gly
 1               5                  10                  15

Asp Arg Val Thr Ile Thr Cys Arg Ala Ser Gln Ser Ile Arg Tyr Leu
                20                  25                  30

Asn Trp Tyr Gln Gln Lys Pro Gly Lys Ala Pro Lys Leu Leu Ile Tyr
            35                  40                  45

Gly Ala Ser Ser Leu Gln Ser Gly Val Pro Ser Arg Phe Ser Gly Ser
        50                  55                  60

Gly Ser Gly Thr Glu Phe Thr Leu Thr Ile Ser Ser Leu Gln Pro Glu
 65                  70                  75                  80

Asp Phe Ala Thr Tyr Tyr Cys Gln Gln Ser Phe Arg Val Pro Ile Ser
                85                  90                  95

Phe Gly Gln Gly Thr Arg Leu Glu Ile Lys
            100                 105

<210> SEQ ID NO 673
<211> LENGTH: 107
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 673

Asp Ile Gln Met Thr Gln Ser Pro Ser Ser Leu Ser Ala Ser Val Gly
 1               5                  10                  15

Asp Arg Val Thr Ile Thr Cys Arg Thr Ser Gln Ser Ile Gly Arg Tyr
                20                  25                  30

Leu Asn Trp Tyr Gln Gln Lys Pro Gly Lys Ala Pro Lys Leu Leu Ile
            35                  40                  45

Tyr Gly Ala Ser Ser Leu Gln Ser Gly Val Pro Ser Arg Phe Ser Gly
        50                  55                  60
```

-continued

```
Ser Gly Ser Gly Thr Glu Phe Thr Phe Ile Ile Ser Ser Leu Gln Pro
 65              70                  75                  80

Glu Asp Phe Ala Thr Tyr Tyr Cys Gln Gln Ser Phe Arg Val Pro Ile
                 85                  90                  95

Thr Phe Gly Gln Gly Thr Arg Leu Glu Ile Lys
            100             105
```